United States Patent
Long et al.

(10) Patent No.: US 9,107,412 B2
(45) Date of Patent: Aug. 18, 2015

(54) FUNGICIDAL PYRAZOLES AND THEIR MIXTURES

(75) Inventors: Jeffrey Keith Long, Wilmington, DE (US); Vann Gregory, Newark, DE (US); Steven Gutteridge, Wilmington, DE (US); Andrew Edmund Taggi, Newark, DE (US); James Francis Bereznak, Newtown Square, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 83 days.

(21) Appl. No.: 13/812,304

(22) PCT Filed: Sep. 1, 2011

(86) PCT No.: PCT/US2011/050124
§ 371 (c)(1),
(2), (4) Date: Jan. 25, 2013

(87) PCT Pub. No.: WO2012/031061
PCT Pub. Date: Mar. 8, 2012

(65) Prior Publication Data
US 2013/0129839 A1    May 23, 2013

Related U.S. Application Data

(60) Provisional application No. 61/378,982, filed on Sep. 1, 2010, provisional application No. 61/416,346, filed on Nov. 23, 2010, provisional application No. 61/438,356, filed on Feb. 1, 2011, provisional application No. 61/510,137, filed on Jul. 21, 2011.

(51) Int. Cl.
  *A01N 43/56*   (2006.01)
  *A01N 43/48*   (2006.01)
  *A01N 43/40*   (2006.01)
  *A01N 43/42*   (2006.01)
  *A01N 43/50*   (2006.01)
  *A01N 43/54*   (2006.01)
  *A01N 43/653*  (2006.01)
  *A01N 43/78*   (2006.01)
  *A01N 43/84*   (2006.01)
  *A01N 43/90*   (2006.01)
  *A01N 59/20*   (2006.01)
  *C07D 231/38*  (2006.01)

(52) U.S. Cl.
  CPC .............. *A01N 43/56* (2013.01); *A01N 43/40* (2013.01); *A01N 43/42* (2013.01); *A01N 43/48* (2013.01); *A01N 43/50* (2013.01); *A01N 43/54* (2013.01); *A01N 43/653* (2013.01); *A01N 43/78* (2013.01); *A01N 43/84* (2013.01); *A01N 43/90* (2013.01); *A01N 59/20* (2013.01); *C07D 231/38* (2013.01)

(58) Field of Classification Search
  CPC ....... A01N 43/48; A01N 43/56; A01N 59/20; A01N 43/90; A01N 43/84; A01N 43/78; A01N 43/653; A01N 43/54; C07D 231/38
  USPC .......................................................... 424/633
  See application file for complete search history.

(56) References Cited

U.S. PATENT DOCUMENTS

| 5,849,778 A * | 12/1998 | Heil et al. .................... 514/403 |
| 2011/0319430 A1 | 12/2011 | Long et al. |
| 2014/0221448 A1 | 8/2014 | LONG, ET AL. |
| 2014/0235689 A1 | 8/2014 | KAR, MOUMITA |
| 2015/0018374 A1 | 1/2015 | TAGGI, ET AL. |

FOREIGN PATENT DOCUMENTS

| JP | 8208620 A | 8/1996 |
| WO | 9602138 A1 | 2/1996 |
| WO | 2004050650 A1 | 6/2004 |
| WO | 2004050651 A1 | 6/2004 |
| WO | 2007027842 A1 | 3/2007 |
| WO | 2009030469 A1 | 3/2009 |

(Continued)

OTHER PUBLICATIONS

International Search Report and Written Opinion of corresponding PCT/US2011/050124 mailed Mar. 7, 2013.

*Primary Examiner* — Sean Basquill
(74) *Attorney, Agent, or Firm* — Charlene Gross Sternberg

(57) ABSTRACT

Disclosed is a fungicidal composition comprising (a) at least one compound selected from the compounds of Formula 1, N-oxides, and salts thereof,

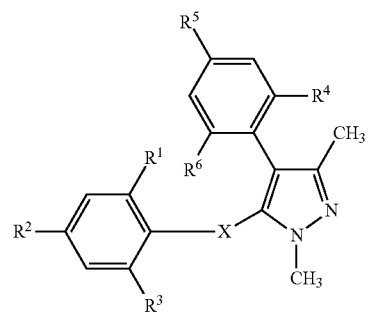

wherein $R^1$, $R^2$, $R^3$, $R^4$, $R^5$ and $R^6$ are as defined in the disclosure;
and (b) at least one additional fungicidal compound.
Also disclosed is a method for controlling plant diseases caused by fungal plant pathogens comprising applying to the plant or portion thereof, or to the plant seed, a fungicidally effective amount of a compound of Formula 1, an N-oxide, or salt thereof (e.g., as a component in the aforesaid composition). Also disclosed is a composition comprising: (a) at least one compound selected from the compounds of Formula 1 described above, N-oxides, and salts thereof; and at least one invertebrate pest control compound or agent.

26 Claims, No Drawings

(56) References Cited

FOREIGN PATENT DOCUMENTS

| | | | |
|---|---|---|---|
| WO | 2009137538 A2 | 11/2009 | |
| WO | 2009137651 A2 | 11/2009 | |
| WO | 2010101973 A1 | 9/2010 | |
| WO | WO2010/101973 | * 9/2010 | .......... C07D 231/12 |
| WO | 2012023143 A1 | 2/2012 | |
| WO | 2012024586 A1 | 2/2012 | |
| WO | 2012030922 A1 | 3/2012 | |
| WO | 2013116251 A2 | 8/2013 | |
| WO | 2013126283 A1 | 8/2013 | |
| WO | 2013192126 A1 | 12/2013 | |
| WO | 2014130241 A1 | 8/2014 | |
| WO | 2014130409 A2 | 8/2014 | |
| WO | 2014189753 A1 | 11/2014 | |

* cited by examiner

FUNGICIDAL PYRAZOLES AND THEIR MIXTURES

FIELD OF THE INVENTION

This invention relates to certain pyrazole derivatives, their N-oxides and salts, and to mixtures and compositions comprising such pyrazole derivatives and methods for using such pyrazole derivatives and their mixtures and compositions as fungicides.

BACKGROUND OF THE INVENTION

The control of plant diseases caused by fungal plant pathogens is extremely important in achieving high crop efficiency. Plant disease damage to ornamental, vegetable, field, cereal and fruit crops can cause significant reduction in productivity and thereby result in increased costs to the consumer. In addition to often being highly destructive, plant diseases can be difficult to control and may develop resistance to commercial fungicides. Many products are commercially available for these purposes, but the need continues for new fungicidal compounds which are more effective, less costly, less toxic, environmentally safer or have different sites of action. Besides introduction of new fungicides, combinations of fungicides are often used to facilitate disease control, to broaden spectrum of control and to retard resistance development. Furthermore, certain rare combinations of fungicides demonstrate a greater-than-additive (i.e. synergistic) effect to provide commercially important levels of plant disease control. The advantages of particular fungicide combinations are recognized in the art to vary, depending on such factors as the particular plant species and plant disease to be treated, and whether the plants are treated before or after infection with the fungal plant pathogen. Accordingly new advantageous combinations are needed to provide a variety of options to best satisfy particular plant disease control needs. Such combinations have now been discovered. JP08208620 discloses N-phenyl-pyrazolylamine derivatives as insecticides, herbicides and fungicides; however the fungicidal pyrazoles of the present invention and their mixtures are not disclosed in this publication.

SUMMARY OF THE INVENTION

This invention relates to a fungicidal composition (i.e. combination) comprising (a) at least one compound selected from the compounds of Formula 1 (including all stereoisomers), N-oxides, and salts thereof:

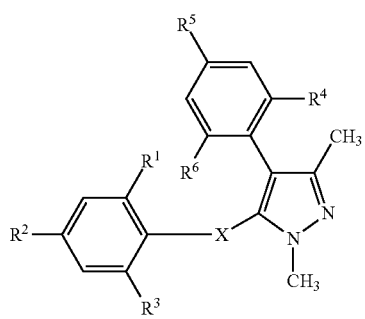

1 wherein
X is CHOH, O or NH;
R¹ is halogen or methyl;
R² is H, cyano, halogen or $C_1$-$C_2$ alkoxy;
R³ is H, halogen or methyl;
R⁴ is halogen;
R⁵ is H, cyano, halogen or $C_1$-$C_2$ alkoxy; and
R⁶ is H or halogen; and
(b) at least one additional fungicidal compound.

This invention also relates to a composition comprising: (a) at least one compound selected from the compounds of Formula 1 described above, N-oxides, and salts thereof; and at least one invertebrate pest control compound or agent.

This invention also relates to a composition comprising one of the aforesaid compositions comprising component (a) and at least one additional component selected from the group consisting of surfactants, solid diluents and liquid diluents.

This invention also relates to a method for controlling plant diseases caused by fungal plant pathogens comprising applying to the plant or portion thereof, or to the plant seed, a fungicidally effective amount of one of the aforesaid compositions.

The aforedescribed method can also be described as a method for protecting a plant or plant seed from diseases caused by fungal pathogens comprising applying a fungicidally effective amount of one of the aforesaid compositions to the plant (or portion thereof) or plant seed (directly or through the environment (e.g., growing medium) of the plant or plant seed).

This invention also relates to a compound of Formula 1 described above, or an N-oxide or salt thereof. This invention further relates to a fungicidal composition comprising a compound of Formula 1, or an N-oxide or salt thereof, and at least one additional component selected from the group consisting of surfactants, solid diluents and liquid diluents. This invention also further relates to a method for protecting a plant or plant seed from diseases caused by fungal pathogens comprising a fungicidally effective amount of a compound of Formula 1, or an N-oxide or salt thereof, to the plant or plant seed.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step, or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium (e.g., soil), such as roots, tubers, bulbs and corms, and also members growing above the growing medium, such as foliage (including stems and leaves), flowers, fruits and seeds.

As referred to herein, the term "seedling", used either alone or in a combination of words means a young plant developing from the embryo of a seed.

In the above recitations, the term "alkoxy" includes, for example, methoxy and ethoxy. The term "halogen" includes fluorine, chlorine, bromine or iodine.

The total number of carbon atoms in a substituent group is indicated by the "$C_i$-$C_j$" prefix where i and j are numbers from 1 to 2.

Compounds relevant to the compositions and methods of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds in the compositions of this invention may be present as a mixture of stereoisomers, individual stereoisomers or as an optically active form.

Synthetic methods for the preparation of N-oxides of heterocycles such as pyrazoles are very well known by one skilled in the art including the oxidation of heterocycles with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of Formula 1 alone and in mixtures are useful for control of plant diseases caused by fungal plant pathogens (i.e. are agriculturally suitable). The salts of the compounds of Formula 1 include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Accordingly, the present invention relates to mixtures of compounds selected from Formula 1, N-oxides and agriculturally suitable salts thereof.

Compounds selected from Formula 1, stereoisomers, tautomers, N-oxides, and salts thereof, typically exist in more than one form, and Formula 1 thus includes all crystalline and non-crystalline forms of the compounds that Formula 1 represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by Formula 1 can exhibit beneficial effects (e.g., suitability for preparation of useful formulations, improved biological performance) relative to another polymorph or a mixture of polymorphs of the same compound represented by Formula 1. Preparation and isolation of a particular polymorph of a compound represented by Formula 1 can be achieved by methods known to those skilled in the art including, for example, crystallization using selected solvents and temperatures.

As described in the Summary of the Invention, an aspect of the present invention is directed at a composition comprising (a) at least one compound selected from Formula 1, N-oxides, and salts thereof, with (b) at least one additional fungicidal compound. More particularly, Component (b) is selected from the group consisting of
  (b1) methyl benzimidazole carbamate (MBC) fungicides;
  (b2) dicarboximide fungicides;
  (b3) demethylation inhibitor (DMI) fungicides;
  (b4) phenylamide fungicides;
  (b5) amine/morpholine fungicides;
  (b6) phospholipid biosynthesis inhibitor fungicides;
  (b7) carboxamide fungicides;
  (b8) hydroxy(2-amino-)pyrimidine fungicides;
  (b9) anilinopyrimidine fungicides;
  (b10) N-phenyl carbamate fungicides;

(b11) quinone outside inhibitor (QoI) fungicides;
(b12) phenylpyrrole fungicides;
(b13) quinoline fungicides;
(b14) lipid peroxidation inhibitor fungicides;
(b15) melanin biosynthesis inhibitors-reductase (MBI-R) fungicides;
(b16) melanin biosynthesis inhibitors-dehydratase (MBI-D) fungicides;
(b17) hydroxyanilide fungicides;
(b18) squalene-epoxidase inhibitor fungicides;
(b19) polyoxin fungicides;
(b20) phenylurea fungicides;
(b21) quinone inside inhibitor (QiI) fungicides;
(b22) benzamide fungicides;
(b23) enopyranuronic acid antibiotic fungicides;
(b24) hexopyranosyl antibiotic fungicides;
(b25) glucopyranosyl antibiotic: protein synthesis fungicides;
(b26) glucopyranosyl antibiotic: trehalase and inositol biosynthesis fungicides;
(b27) cyanoacetamideoxime fungicides;
(b28) carbamate fungicides;
(b29) oxidative phosphorylation uncoupling fungicides;
(b30) organo tin fungicides;
(b31) carboxylic acid fungicides;
(b32) heteroaromatic fungicides;
(b33) phosphonate fungicides;
(b34) phthalamic acid fungicides;
(b35) benzotriazine fungicides;
(b36) benzene-sulfonamide fungicides;
(b37) pyridazinone fungicides;
(b38) thiophene-carboxamide fungicides;
(b39) pyrimidinamide fungicides;
(b40) carboxylic acid amide (CAA) fungicides;
(b41) tetracycline antibiotic fungicides;
(b42) thiocarbamate fungicides;
(b43) benzamide fungicides;
(b44) host plant defense induction fungicides;
(b45) multi-site contact activity fungicides;
(b46) fungicides other than fungicides of component (a) and components (b1) through (b45); and
salts of compounds of (b1) through (b46).

Of note are embodiments wherein component (b) comprises at least one fungicidal compound from each of two different groups selected from (b1) through (b46).

"Methyl benzimidazole carbamate (MBC) fungicides (b1)" (FRAC (Fungicide Resistance Action Committee) code 1) inhibit mitosis by binding to β-tubulin during microtubule assembly. Inhibition of microtubule assembly can disrupt cell division, transport within the cell and cell structure. Methyl benzimidazole carbamate fungicides include benzimidazole and thiophanate fungicides. The benzimidazoles include benomyl, carbendazim, fuberidazole and thiabendazole. The thiophanates include thiophanate and thiophanate-methyl.

"Dicarboximide fungicides (b2)" (FRAC code 2) are proposed to inhibit a lipid peroxidation in fungi through interference with NADH cytochrome c reductase. Examples include chlozolinate, iprodione, procymidone and vinclozolin.

"Demethylation inhibitor (DMI) fungicides (b3)" (FRAC code 3) inhibit C14-demethylase which plays a role in sterol production. Sterols, such as ergosterol, are needed for membrane structure and function, making them essential for the development of functional cell walls. Therefore, exposure to these fungicides result in abnormal growth and eventually death of sensitive fungi. DMI fungicides are divided between several chemical classes: azoles (including triazoles and imidazoles), pyrimidines, piperazines and pyridines. The triazoles include azaconazole, bitertanol, bromuconazole, cyproconazole, difenoconazole, diniconazole (including diniconazole-M), epoxiconazole, etaconazole, fenbuconazole, fluquinconazole, flusilazole, flutriafol, hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole and uniconazole. The imidazoles include clotrimazole, econazole, imazalil, isoconazole, miconazole, oxpoconazole, prochloraz, pefurazoate and triflumizole. The pyrimidines include fenarimol, nuarimol and triarimol. The piperazines include triforine. The pyridines include buthiobate and pyrifenox. Biochemical investigations have shown that all of the above mentioned fungicides are DMI fungicides as described by K. H. Kuck et al. in *Modern Selective Fungicides—Properties, Applications and Mechanisms of Action*, H. Lyr (Ed.), Gustav Fischer Verlag: New York, 1995, 205-258.

"Phenylamide fungicides (b4)" (FRAC code 4) are specific inhibitors of RNA polymerase in Oomycete fungi. Sensitive fungi exposed to these fungicides show a reduced capacity to incorporate uridine into rRNA. Growth and development in sensitive fungi is prevented by exposure to this class of fungicide. Phenylamide fungicides include acylalanine, oxazolidinone and butyrolactone fungicides. The acylalanines include benalaxyl, benalaxyl-M, furalaxyl, metalaxyl, metalaxyl-M (also known as mefenoxam). The oxazolidinones include oxadixyl. The butyrolactones include ofurace.

"Amine/morpholine fungicides (b5)" (FRAC code 5) inhibit two target sites within the sterol biosynthetic pathway, $\Delta^8 \rightarrow \Delta^7$ isomerase and $\Delta^{14}$ reductase. Sterols, such as ergosterol, are needed for membrane structure and function, making them essential for the development of functional cell walls. Therefore, exposure to these fungicides results in abnormal growth and eventually death of sensitive fungi. Amine/morpholine fungicides (also known as non-DMI sterol biosynthesis inhibitors) include morpholine, piperidine and spiroketal-amine fungicides. The morpholines include aldimorph, dodemorph, fenpropimorph, tridemorph and trimorphamide. The piperidines include fenpropidin and piperalin. The spiroketal-amines include spiroxamine.

"Phospholipid biosynthesis inhibitor fungicides (b6)" (FRAC code 6) inhibit growth of fungi by affecting phospholipid biosynthesis. Phospholipid biosynthesis fungicides include phosphorothiolate and dithiolane fungicides. The phosphorothiolates include edifenphos, iprobenfos and pyrazophos. The dithiolanes include isoprothiolane.

"Carboxamide fungicides (b7)" (FRAC code 7) inhibit Complex II (succinate dehydrogenase) fungal respiration by disrupting a key enzyme in the Krebs Cycle (TCA cycle) named succinate dehydrogenase. Inhibiting respiration prevents the fungus from making ATP, and thus inhibits growth and reproduction. Carboxamide fungicides include benzamide, furan carboxamide, oxathiin carboxamide, thiazole carboxamide, pyrazole carboxamide and pyridine carboxamide. The benzamides include benodanil, flutolanil and mepronil. The furan carboxamides include fenfuram. The oxathiin carboxamides include carboxin and oxycarboxin. The thiazole carboxamides include thifluzamide. The pyrazole carboxamides include bixafen, furametpyr, isopyrazam, fluxapyroxad, penthiopyrad, sedaxane (N-[2-(1S,2R)-[1,1'-bicyclopropyl]-2-ylphenyl]-3-(difluoromethyl)-1-methyl-1H-pyrazole-4-carboxamide) and penflufen (N-[2-(1,3-dimethylbutyl)phenyl]-5-fluoro-1,3-dimethyl-1H-pyrazole-4-carboxamide) (PCT Patent Publication WO 2003/010149). The pyridine carboxamides include boscalid.

"Hydroxy(2-amino-)pyrimidine fungicides (b8)" (FRAC code 8) inhibit nucleic acid synthesis by interfering with adenosine deaminase. Examples include bupirimate, dimethirimol and ethirimol.

"Anilinopyrimidine fungicides (b9)" (FRAC code 9) are proposed to inhibit biosynthesis of the amino acid methionine and to disrupt the secretion of hydrolytic enzymes that lyse plant cells during infection. Examples include cyprodinil, mepanipyrim and pyrimethanil.

"N-Phenyl carbamate fungicides (b10)" (FRAC code 10) inhibit mitosis by binding to β-tubulin and disrupting microtubule assembly. Inhibition of microtubule assembly can disrupt cell division, transport within the cell and cell structure. Examples include diethofencarb.

"Quinone outside inhibitor (QoI) fungicides (b11)" (FRAC code 11) inhibit Complex III mitochondrial respiration in fungi by affecting ubiquinol oxidase. Oxidation of ubiquinol is blocked at the "quinone outside" ($Q_o$) site of the cytochrome $bc_1$ complex, which is located in the inner mitochondrial membrane of fungi. Inhibiting mitochondrial respiration prevents normal fungal growth and development. Quinone outside inhibitor fungicides include methoxyacrylate, methoxycarbamate, oximinoacetate, oximinoacetamide and dihydrodioxazine fungicides (collectively also known as strobilurin fungicides), and oxazolidinedione, imidazolinone and benzylcarbamate fungicides. The methoxyacrylates include azoxystrobin, enestroburin (SYP-Z071) and picoxystrobin. The methoxycarbamates include pyraclostrobin and pyrametostrobin. The oximinoacetates include kresoxim-methyl, pyraoxystrobin and trifloxystrobin. The oximinoacetamides include dimoxystrobin, metominostrobin, orysastrobin and α-(methoxyimino)-N-methyl-2-[[[1-[3-(trifluoromethyl)phenyl]ethoxy]imino]methyl]benzeneacetamide.
The dihydrodioxazines include fluoxastrobin. The oxazolidinediones include famoxadone. The imidazolinones include fenamidone. The benzylcarbamates include pyribencarb.

"Phenylpyrrole fungicides (b12)" (FRAC code 12) inhibit a MAP protein kinase associated with osmotic signal transduction in fungi. Fenpiclonil and fludioxonil are examples of this fungicide class.

"Quinoline fungicides (b13)" (FRAC code 13) are proposed to inhibit signal transduction by affecting G-proteins in early cell signaling. They have been shown to interfere with germination and/or appressorium formation in fungi that cause powdery mildew diseases. Quinoxyfen is an example of this class of fungicide.

"Lipid peroxidation inhibitor fungicides (b14)" (FRAC code 14) are proposed to inhibit lipid peroxidation which affects membrane synthesis in fungi. Members of this class, such as etridiazole, may also affect other biological processes such as respiration and melanin biosynthesis. Lipid peroxidation fungicides include aromatic carbon and 1,2,4-thiadiazole fungicides. The aromatic carbons include biphenyl, chloroneb, dicloran, quintozene, tecnazene and tolclofos-methyl. The 1,2,4-thiadiazoles include etridiazole.

"Melanin biosynthesis inhibitors-reductase (MBI-R) fungicides (b15)" (FRAC code 16.1) inhibit the naphthal reduction step in melanin biosynthesis. Melanin is required for host plant infection by some fungi. Melanin biosynthesis inhibitors-reductase fungicides include isobenzofuranone, pyrroloquinolinone and triazolobenzothiazole fungicides. The isobenzofuranones include fthalide. The pyrroloquinolinones include pyroquilon. The triazolobenzothiazoles include tricyclazole.

"Melanin biosynthesis inhibitors-dehydratase (MBI-D) fungicides (b16)" (FRAC code 16.2) inhibit scytalone dehydratase in melanin biosynthesis. Melanin in required for host plant infection by some fungi. Melanin biosynthesis inhibitors-dehydratase fungicides include cyclopropanecarboxamide, carboxamide and propionamide fungicides. The cyclopropanecarboxamides include carpropamid. The carboxamides include diclocymet. The propionamides include fenoxanil.

"Hydroxyanilide fungicides (b17)" (FRAC code 17) inhibit C4-demethylase which plays a role in sterol production. Examples include fenhexamid.

"Squalene-epoxidase inhibitor fungicides (b18)" (FRAC code 18) inhibit squalene-epoxidase in ergosterol biosynthesis pathway. Sterols such as ergosterol are needed for membrane structure and function, making them essential for the development of functional cell walls. Therefore exposure to these fungicides result in abnormal growth and eventually death of sensitive fungi. Squalene-epoxidase inhibitor fungicides include thiocarbamate and allylamine fungicides. The thiocarbamates include pyributicarb. The allylamines include naftifine and terbinafine.

"Polyoxin fungicides (b19)" (FRAC code 19) inhibit chitin synthase. Examples include polyoxin.

"Phenylurea fungicides (b20)" (FRAC code 20) are proposed to affect cell division. Examples include pencycuron.

"Quinone inside inhibitor (QiI) fungicides (b21)" (FRAC code 21) inhibit Complex III mitochondrial respiration in fungi by affecting ubiquinol reductase. Reduction of ubiquinol is blocked at the "quinone inside" ($Q_i$) site of the cytochrome $bc_1$ complex, which is located in the inner mitochondrial membrane of fungi. Inhibiting mitochondrial respiration prevents normal fungal growth and development. Quinone inside inhibitor fungicides include cyanoimidazole and sulfamoyltriazole fungicides. The cyanoimidazoles include cyazofamid. The sulfamoyltriazoles include amisulbrom.

"Benzamide fungicides (b22)" (FRAC code 22) inhibit mitosis by binding to β-tubulin and disrupting microtubule assembly. Inhibition of microtubule assembly can disrupt cell division, transport within the cell and cell structure. Examples include zoxamide.

"Enopyranuronic acid antibiotic fungicides (b23)" (FRAC code 23) inhibit growth of fungi by affecting protein biosynthesis. Examples include blasticidin-S.

"Hexopyranosyl antibiotic fungicides (b24)" (FRAC code 24) inhibit growth of fungi by affecting protein biosynthesis. Examples include kasugamycin.

"Glucopyranosyl antibiotic: protein synthesis fungicides (b25)" (FRAC code 25) inhibit growth of fungi by affecting protein biosynthesis. Examples include streptomycin.

"Glucopyranosyl antibiotic: trehalase and inositol biosynthesis fungicides (b26)" (FRAC code 26) inhibit trehalase in inositol biosynthesis pathway. Examples include validamycin.

"Cyanoacetamideoxime fungicides (b27) (FRAC code 27) include cymoxanil.

"Carbamate fungicides (b28)" (FRAC code 28) are considered multi-site inhibitors of fungal growth. They are proposed to interfere with the synthesis of fatty acids in cell membranes, which then disrupts cell membrane permeability. Propamacarb, iodocarb, and prothiocarb are examples of this fungicide class.

"Oxidative phosphorylation uncoupling fungicides (b29)" (FRAC code 29) inhibit fungal respiration by uncoupling oxidative phosphorylation. Inhibiting respiration prevents normal fungal growth and development. This class includes 2,6-dinitroanilines such as fluazinam, pyrimidonehydrazones such as ferimzone and dinitrophenyl crotonates such as dinocap, meptyldinocap and binapacryl.

"Organo tin fungicides (b30)" (FRAC code 30) inhibit adenosine triphosphate (ATP) synthase in oxidative phosphorylation pathway. Examples include fentin acetate, fentin chloride and fentin hydroxide.

"Carboxylic acid fungicides (b31)" (FRAC code 31) inhibit growth of fungi by affecting deoxyribonucleic acid (DNA) topoisomerase type II (gyrase). Examples include oxolinic acid.

"Heteroaromatic fungicides (b32)" (FRAC code 32) are proposed to affect DNA/ribonucleic acid (RNA) synthesis. Heteroaromatic fungicides include isoxazole and isothiazolone fungicides. The isoxazoles include hymexazole and the isothiazolones include octhilinone.

"Phosphonate fungicides (b33)" (FRAC code 33) include phosphorous acid and its various salts, including fosetyl-aluminum.

"Phthalamic acid fungicides (b34)" (FRAC code 34) include teclofthalam.

"Benzotriazine fungicides (b35)" (FRAC code 35) include triazoxide.

"Benzene-sulfonamide fungicides (b36)" (FRAC code 36) include flusulfamide.

"Pyridazinone fungicides (b37)" (FRAC code 37) include diclomezine.

"Thiophene-carboxamide fungicides (b38)" (FRAC code 38) are proposed to affect ATP production. Examples include silthiofam.

"Pyrimidinamide fungicides (b39)" (FRAC code 39) inhibit growth of fungi by affecting phospholipid biosynthesis and include diflumetorim.

"Carboxylic acid amide (CAA) fungicides (b40)" (FRAC code 40) are proposed to inhibit phospholipid biosynthesis and cell wall deposition. Inhibition of these processes prevents growth and leads to death of the target fungus. Carboxylic acid amide fungicides include cinnamic acid amide, valinamide carbamate and mandelic acid amide fungicides. The cinnamic acid amides include dimethomorph and flumorph. The valinamide carbamates include benthiavalicarb, benthiavalicarb-isopropyl, iprovalicarb and valifenalate (valiphenal). The mandelic acid amides include mandipropamid, N-[2-[4-[[3-(4-chlorophenyl)-2-propyn-1-yl]oxy]-3-methoxyphenyl]ethyl]-3-methyl-2-[(methylsulfonyl)amino]butanamide and N-[2-[4-[[3-(4-chlorophenyl)-2-propyn-1-yl]oxy]-3-methoxyphenyl]-ethyl]-3-methyl-2-[(ethylsulfonyl)amino]butanamide.

"Tetracycline antibiotic fungicides (b41)" (FRAC code 41) inhibit growth of fungi by affecting complex 1 nicotinamide adenine dinucleotide (NADH) oxidoreductase. Examples include oxytetracycline.

"Thiocarbamate fungicides (b42)" (FRAC code 42) include methasulfocarb.

"Benzamide fungicides (b43)" (FRAC code 43) inhibit growth of fungi by delocalization of spectrin-like proteins. Examples include acylpicolide fungicides such as fluopicolide and fluopyram.

"Host plant defense induction fungicides (b44)" (FRAC code P) induce host plant defense mechanisms. Host plant defense induction fungicides include benzo-thiadiazole, benzisothiazole and thiadiazole-carboxamide fungicides. The benzo-thiadiazoles include acibenzolar-S-methyl. The benzisothiazoles include probenazole. The thiadiazole-carboxamides include tiadinil and isotianil.

"Multi-site contact fungicides (b45)" inhibit fungal growth through multiple sites of action and have contact/preventive activity. This class of fungicides includes: "copper fungicides (b45.1) (FRAC code M1)", "sulfur fungicides (b45.2) (FRAC code M2)", "dithiocarbamate fungicides (b45.3) (FRAC code M3)", "phthalimide fungicides (b45.4) (FRAC code M4)", "chloronitrile fungicides (b45.5) (FRAC code M5)", "sulfamide fungicides (b45.6) (FRAC code M6)", "guanidine fungicides (b45.7) (FRAC code M7)" "triazine fungicides (b45.8) (FRAC code M8)" and "quinone fungicides (b45.9) (FRAC code M9)". "Copper fungicides" are inorganic compounds containing copper, typically in the copper(II) oxidation state; examples include copper oxychloride, copper sulfate and copper hydroxide, including compositions such as Bordeaux mixture (tribasic copper sulfate). "Sulfur fungicides" are inorganic chemicals containing rings or chains of sulfur atoms; examples include elemental sulfur. "Dithiocarbamate fungicides" contain a dithiocarbamate molecular moiety; examples include mancozeb, metiram, propineb, ferbam, maneb, thiram, zineb and ziram. "Phthalimide fungicides" contain a phthalimide molecular moiety; examples include folpet, captan and captafol. "Chloronitrile fungicides" contain an aromatic ring substituted with chloro and cyano; examples include chlorothalonil. "Sulfamide fungicides" include dichlofluanid and tolylfluanid. "Guanidine fungicides" include dodine, guazatine and iminoctadine. "Triazine fungicides" include anilazine. "Quinone fungicides" include dithianon.

"Fungicides other than fungicides of component (a) and components (b1) through (b45); (b46)" include certain fungicides whose mode of action may be unknown. These include: (b46.1) "thiazole carboxamide fungicides" (FRAC code U5), (b46.2) "phenyl-acetamide fungicides" (FRAC code U6), (b46.3) "quinazolinone fungicides" (FRAC code U7), (b46.4) "benzophenone fungicides" (FRAC code U8) and (b46.5) "triazolopyrimidylamine fungicides" (FRAC code 45). The thiazole carboxamides include ethaboxam. The phenyl-acetamides include cyflufenamid and N-[[(cyclopropyl-methoxy)amino][6-(difluoromethoxy)-2,3-difluorophenyl]-methylene]benzeneacetamide. The quinazolinones include proquinazid and 2-butoxy-6-iodo-3-propyl-4H-1-benzopyran-4-one. The benzophenones include metrafenone and pyriofenone. The triazolopyrimidylamines include ametoctradin and are believed to inhibit Complex III mitochondrial respiration by binding to an unelucidated site on ubiquinone-cytochrome bc1 reductase. The (b46) class also includes bethoxazin, neo-asozin (ferric methanearsonate), fenpyrazamine, pyrrolnitrin, quinomethionate, tebufloquin, 2-[[2-fluoro-5-(trifluoromethyl)phenyl]thio]-2-[3-(2-methoxyphenyl)-2-thiazolidinylidene]acetonitrile, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]carbamate, 5-chloro-6-(2,4,6-trifluorophenyl)-7-(4-methylpiperidin-1-yl) [1,2,4]triazolo[1,5-a]pyrimidine, N-(4-chloro-2-nitrophenyl)-N-ethyl-4-methylbenzene-sulfonamide, N-[4-[4-chloro-3-(trifluoromethyl)phenoxy]-2,5-dimethylphenyl]-N-ethyl-N-methylmethanimidamide and 1-[(2-propenylthio)carbonyl]-2-(1-methylethyl)-4-(2-methylphenyl)-5-amino-1H-pyrazol-3-one.

"Fungicides other than fungicides of component (a) and components (b1) through (b45); (b46)" also include (b46.5) 6-quinolinyloxyacetamide compounds of Formula A1 and salts thereof

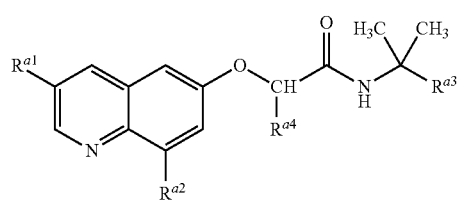

wherein
- $R^{a1}$ is halogen, $C_1$-$C_4$ alkoxy or $C_1$-$C_4$ alkynyl;
- $R^{a2}$ is H, halogen or $C_1$-$C_4$ alkyl;
- $R^{a3}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
- $R^{a4}$ is methyl or $Y^{a1}$—$R^{a5}$;
- $R^{a5}$ is $C_1$-$C_2$ alkyl; and
- $Y^{a1}$ is $CH_2$, O or S.

Compounds of Formula A1, their use as fungicides and methods of preparation are generally known; see, for example, PCT Patent Publications WO 2004/047538, WO 2004/108663, WO 2006/058699, WO 2006/058700, WO 2008/110355, WO 2009/030469, WO 2009/049716 and WO 2009/087098. Examples of compounds of Formula A1 include: 2-[(3-bromo-6-quinolinyl)oxy]-N-(1,1-dimethyl-2-butyn-1-yl)-2-(methylthio)acetamide, 2-[(3-ethynyl-6-quinolinyl)oxy]-N-[1-(hydroxymethyl)-1-methyl-2-propyn-1-yl]-2-(methyl-thio)acetamide, N-(1,1-dimethyl-2-butyn-1-yl)-2-[(3-ethynyl-6-quinolinyl)oxy]-2-(methyl-thio)acetamide, 2-[(3-bromo-8-methyl-6-quinolinyl)oxy]-N-(1,1-dimethyl-2-propyn-1-yl)-2-(methylthio)acetamide and 2-[(3-bromo-6-quinolinyl)oxy]-N-(1,1-dimethylethyl)-butanamide.

"Fungicides other than fungicides of component (a) and components (b1) through (b45); (b46)" also include (b46.6) N'-[4-[[3-[(4-chlorophenyl)methyl]-1,2,4-thiadiazol-5-yl]oxy]-2,5-dimethylphenyl]-N-ethyl-N-methylmethanimidamide, which is believed to inhibit C24-methyl transferase involved in biosynthesis of sterols.

In the embodiments of the present invention, including those described below, reference to Formula 1 includes N-oxides and salts thereof unless otherwise indicated, and reference to "a compound of Formula 1" includes the definitions of substituents specified in the Summary of the Invention unless further defined in the Embodiments.

Embodiment 1. The composition comprising components (a) and (b) described in the Summary of the Invention wherein in Formula 1, X is CHOH or NH.

Embodiment 2. The composition of Embodiment 1 wherein X is CHOH.

Embodiment 3. The composition of Embodiment 1 wherein X is NH.

Embodiment 4. The composition comprising components (a) and (b) described in the Summary of the Invention or any one of Embodiments 1 through 3 wherein in Formula 1, $R^1$ is halogen.

Embodiment 5. The composition of Embodiment 4 wherein $R^1$ is F, Cl or Br.

Embodiment 6. The composition of Embodiment 5 wherein $R^1$ is Cl or Br.

Embodiment 7. The composition comprising components (a) and (b) described in the Summary of the Invention or any one of Embodiments 1 through 6 wherein in Formula 1, $R^2$ is H, cyano, F, Cl, Br or $C_1$-$C_2$ alkoxy.

Embodiment 8. The composition of Embodiment 7 wherein $R^2$ is H, cyano, F, Cl, Br or methoxy.

Embodiment 9. The composition of Embodiment 8 wherein $R^2$ is cyano, F, Cl or methoxy.

Embodiment 10. The composition of Embodiment 9 wherein $R^2$ is F or Cl.

Embodiment 11. The composition of Embodiment 8 wherein $R^2$ is H.

Embodiment 12. The composition comprising components (a) and (b) described in the Summary of the Invention or any one of Embodiments 1 through 11 wherein in Formula 1, $R^3$ is H or halogen.

Embodiment 13. The composition of Embodiment 12 wherein $R^3$ is H, F, Cl or Br.

Embodiment 14. The composition of Embodiment 13 wherein $R^3$ is H, F or Cl.

Embodiment 15. The composition of Embodiment 14 wherein $R^3$ is H or F.

Embodiment 16. The composition comprising components (a) and (b) described in the Summary of the Invention or any one of Embodiments 1 through 11 wherein in Formula 1, $R^3$ is halogen or methyl.

Embodiment 17. The composition of Embodiment 16 wherein $R^3$ is halogen.

Embodiment 18. The composition of Embodiment 17 wherein $R^3$ is F, Cl or Br.

Embodiment 19. The composition of Embodiment 14 or 18 wherein $R^3$ is F or Cl.

Embodiment 20. The composition of Embodiment 15 or 19 wherein $R^3$ is F.

Embodiment 21. The composition comprising components (a) and (b) described in the Summary of the Invention or any one of Embodiments 1 through 20 wherein in Formula 1, $R^4$ is F, Cl or Br.

Embodiment 22. The composition of Embodiment 21 wherein $R^4$ is Cl or Br.

Embodiment 23. The composition comprising components (a) and (b) described in the Summary of the Invention or any one of Embodiments 1 through 22 wherein in Formula 1, $R^5$ is H, cyano, F, Cl, Br or $C_1$-$C_2$ alkoxy.

Embodiment 24. The composition of Embodiment 23 wherein $R^5$ is H, cyano, F, Cl or methoxy.

Embodiment 25. The composition of Embodiment 24 wherein $R^5$ is cyano, F, Cl or methoxy.

Embodiment 26. The composition of Embodiment 25 wherein $R^5$ is cyano or F.

Embodiment 27. The composition of Embodiment 26 wherein $R^5$ is cyano.

Embodiment 28. The composition of Embodiment 26 wherein $R^5$ is F.

Embodiment 29. The composition comprising components (a) and (b) described in the Summary of the Invention or any one of Embodiments 1 through 28 wherein in Formula 1, $R^6$ is H, F, Cl or Br.

Embodiment 30. The composition of Embodiment 29 wherein $R^6$ is H or F.

Embodiment 31. The composition of Embodiment 30 wherein $R^6$ is H.

Embodiment 32. The composition comprising components (a) and (b) described in the Summary of the Invention or any one of Embodiments 1 through 31 wherein in Formula 1, at most, only one of $R^2$ and $R^3$ is H (i.e. only one of $R^2$ and $R^3$ is H, or neither $R^2$ nor $R^3$ is H).

Embodiment 33. The composition of Embodiment 32 wherein $R^3$ is H (and $R^2$ is other than H).

Embodiment 34. The composition of Embodiment 32 wherein $R^2$ is H (and $R^3$ is other than H).

Embodiment 35. The composition of Embodiment 32 wherein both $R^2$ and $R^3$ are other than H.

Embodiment 36. The composition comprising components (a) and (b) described in the Summary of the Invention or any one of Embodiments 1 through 35 wherein in Formula 1, at most, only one of $R^5$ and $R^6$ is H (i.e. only one of $R^5$ and $R^6$ is H, or neither $R^5$ nor $R^6$ is H).

Embodiment 37. The composition of Embodiment 36 wherein $R^6$ is H (and $R^5$ is other than H).

Embodiment 38. The composition of Embodiment 36 wherein $R^5$ is H (and $R^6$ is other than H).

Embodiment 39. The composition of Embodiment 36 wherein both $R^5$ and $R^6$ are other than H.

Embodiment 40. The composition comprising components (a) and (b) described in the Summary of the Invention or any one of Embodiments 1 through 39 wherein in Formula 1, at most, only two of $R^2$, $R^3$, $R^4$ and $R^6$ are H.

Embodiment 41. The composition of Embodiment 40 wherein two of $R^2$, $R^3$, $R^4$ and $R^6$ are H.

Embodiment 42. The composition of Embodiment 40 wherein, at most, only one of $R^2$, $R^3$, $R^4$ and $R^6$ is H.

Embodiment 43. The composition of Embodiment 42 wherein one of $R^2$, $R^3$, $R^4$ and $R^6$ is H.

Embodiment 44. The composition comprising components (a) and (b) described in the Summary of the Invention or any one of Embodiments 1 through 43 wherein component (a) does not comprise an N-oxide of a compound of Formula 1.

Embodiment 45. The composition comprising components (a) and (b) described in the Summary of the Invention or any one of Embodiments 1 through 44 wherein component (a) comprises a compound selected from the group consisting of N,4-bis(2-chloro-4-fluorophenyl)-1,3-dimethyl-1H-pyrazol-5-amine (Compound 47),
N-(2-bromo-4,6-difluorophenyl)-4-(2,4-difluorophenyl)-1,3-dimethyl-1H-pyrazol-5-amine (Compound 143),
N-(2-bromo-4,6-difluorophenyl)-4-(2-bromo-4-fluorophenyl)-1,3-dimethyl-1H-pyrazol-5-amine (Compound 195),
N-(2-bromo-4,6-difluorophenyl)-4-(2-chloro-4-fluorophenyl)-1,3-dimethyl-1H-pyrazol-5-amine (Compound 144),
N-(4-chloro-2,6-difluorophenyl)-4-(2-chloro-4-fluorophenyl)-1,3-dimethyl-1H-pyrazole-5-amine (Compound 81),
4-[5-[(4-chloro-2-fluorophenyl)amino]-1,3-dimethyl-1H-pyrazol-4-yl]-3,5-difluorobenzonitrile (Compound 40),
N-(2-chloro-4,6-difluorophenyl)-4-(2-chloro-4-fluorophenyl)-1,3-dimethyl-1H-pyrazol-5-amine (Compound 82),
4-[5-[(2-chloro-4,6-difluorophenyl)amino]-1,3-dimethyl-1H-pyrazol-4-yl]-3-fluorobenzonitrile (Compound 238),
4-[[4-(2-chloro-4-fluorophenyl)-1,3-dimethyl-1H-pyrazol-5-yl]oxy]-3,5-difluorobenzonitrile (Compound 13),
4-(2-chloro-4-fluorophenyl)-N-(2,4-dichloro-6-fluorophenyl)-1,3-dimethyl-1H-pyrazol-5-amine (Compound 136),
4-(2-chloro-4-fluorophenyl)-N-(2,6-difluoro-4-methoxyphenyl)-1,3-dimethyl-1H-pyrazol-5-amine (Compound 3),
4-(2-chloro-4-fluorophenyl)-α-(2,4-difluorophenyl)-1,3-dimethyl-1H-pyrazole-5-methanol (Compound 122),
N-(2,4-dichloro-6-fluorophenyl)-4-(2,4-difluorophenyl)-1,3-dimethyl-1H-pyrazol-5-amine (Compound 161),
4-(2,4-dichlorophenyl)-N-(2,4-difluorophenyl)-1,3-dimethyl-1H-pyrazol-5-amine (Compound 17),
4-(2,6-difluoro-4-methoxyphenyl)-1,3-dimethyl-N-(2,4,6-trifluorophenyl)-1H-pyrazol-5-amine (Compound 7),
4-[[1,3-dimethyl-4-(2,4,6-trifluorophenyl)-1H-pyrazol-5-yl]oxy]-3,5-difluorobenzonitrile (Compound 8),
4-(2-chloro-4-fluorophenyl)-N-(2-chloro-6-fluorophenyl)-1,3-dimethyl-1H-pyrazol-5-amine (Compound 239),
4-(2-bromo-4-fluorophenyl)-N-(2-chloro-6-fluorophenyl)-1,3-dimethyl-1H-pyrazol-5 amine (Compound 240),
N-(2-bromo-6-fluorophenyl)-4-(2-chloro-4-fluorophenyl)-1,3-dimethyl-1H-pyrazol-5-amine (Compound 241),
4-(2-bromo-4-fluorophenyl)-N-(2-bromo-6-fluorophenyl)-1,3-dimethyl-1H-pyrazol-5-amine (Compound 244),
N-(2-bromo-6-fluorophenyl)-4-(2,4-difluorophenyl)-1,3-dimethyl-1H-pyrazol-5-amine (Compound 245),
N-(2-bromo-6-fluorophenyl)-4-(2,6-difluorophenyl)-1,3-dimethyl-1H-pyrazol-5-amine (Compound 247),
4-(2-chloro-4-fluorophenyl)-N-(2-fluoro-6-methylphenyl)-1,3-dimethyl-1H-pyrazol-5-amine (Compound 252),
4-(2-chloro-4-fluorophenyl)-N-(2-chloro-6-methylphenyl)-1,3-dimethyl-1H-pyrazol-5-amine (Compound 253),
N-(2-bromo-6-methylphenyl)-4-(2-chloro-4-fluorophenyl)-1,3-dimethyl-1H-pyrazol-5-amine (Compound 254),
N-(2-chloro-6-methylphenyl)-4-(2-fluoro-4-methoxyphenyl)-1,3-dimethyl-1H-pyrazol-5-amine (Compound 257),
N-(2-bromo-6-methylphenyl)-4-(2-fluoro-4-methoxyphenyl)-1,3-dimethyl-1H-pyrazol-5-amine (Compound 258),
4-(2-fluoro-4-methoxyphenyl)-N-(2-fluoro-6-methylphenyl)-1,3-dimethyl-1H-pyrazol-5-amine (Compound 259),
N-(2-chloro-6-fluorophenyl)-4-(2-fluoro-4-methoxyphenyl)-1,3-dimethyl-1H-pyrazol-5-amine (Compound 260),
N-(2-bromo-6-fluorophenyl)-4-(2-fluoro-4-methoxyphenyl)-1,3-dimethyl-1H-pyrazol-5-amine (Compound 261),
4-(2-chloro-4-methoxyphenyl)-N-(2-chloro-6-methylphenyl)-1,3-dimethyl-1H-pyrazol-5-amine (Compound 262),
N-(2-bromo-6-methylphenyl)-4-(2-chloro-4-methoxyphenyl)-1,3-dimethyl-1H-pyrazol-5-amine (Compound 263),
N-(2-bromo-6-methylphenyl)-4-(2-chloro-4-methoxyphenyl)-1,3-dimethyl-1H-pyrazol-5-amine (Compound 264),
N-(2-bromo-6-methylphenyl)-4-(2,4-difluorophenyl)-1,3-dimethyl-1H-pyrazol-5-amine (Compound 265),
4-(2-bromo-4-fluorophenyl)-N-(2-bromo-6-methylphenyl)-1,3-dimethyl-1H-pyrazol-5-amine (Compound 266),
4-(2-bromo-4-fluorophenyl)-N-(2-fluoro-6-methylphenyl)-1,3-dimethyl-1H-pyrazol-5-amine (Compound 267),
4-(2,4-difluorophenyl)-N-(2-fluoro-6-methylphenyl)-1,3-dimethyl-1H-pyrazol-5-amine (Compound 268),
N-(2-chloro-6-methylphenyl)-4-(2,4-difluorophenyl)-1,3-dimethyl-1H-pyrazol-5-amine (Compound 269),
4-(2,4-difluorophenyl)-N-(2,6-dimethylphenyl)-1,3-dimethyl-1H-pyrazol-5-amine (Compound 270),
4-(2-chloro-4-fluorophenyl)-N-(2,6-dimethylphenyl)-1,3-dimethyl-1H-pyrazol-5-amine (Compound 271),
N-(2-bromo-6-fluorophenyl)-4-(2-chloro-4-methoxyphenyl)-1,3-dimethyl-1H-pyrazol-5-amine (Compound 273),
N-(2-chloro-6-fluorophenyl)-4-(2,4-difluorophenyl)-1,3-dimethyl-1H-pyrazol-5-amine (Compound 275), and
4-(2-bromo-4-fluorophenyl)-N-(2-chloro-6-methylphenyl)-1,3-dimethyl-1H-pyrazol-5-amine (Compound 276).

(to the extent that the compounds of the group are within the scope of the parent Embodiment).

Embodiment 46. The composition of Embodiment 45 wherein component (a) comprises a compound selected from the group consisting of Compounds 3, 7, 8, 13, 17, 40, 47, 81, 82, 122, 136, 143, 144, 161, 195, 238, 239, 240 and 241.

Embodiment 47. The composition of Embodiment 46 wherein component (a) comprises a compound selected from the group consisting of Compounds 3, 7, 8, 13, 17, 40, 47, 81, 82, 122, 136, 143, 144, 161, 195 and 238.

Embodiment 48. The composition of Embodiment 45 wherein component (a) comprises a compound selected from the group consisting of Compounds 239, 240, 241, 244, 245, 247, 252, 253, 254, 257, 258, 259, 260, 261, 262, 263, 264, 265, 266, 267, 268, 269, 270, 271, 273, 275 and 276.

Embodiment 49. The composition of Embodiment 48 wherein component (a) comprises a compound selected from the group consisting of Compounds 239, 240 and 241.

Embodiment 50. The composition of Embodiment 45 wherein component (a) comprises a compound selected from the group consisting of Compound 195 and Compound 238.

Embodiment 51. The composition comprising components (a) and (b) described in the Summary of the Invention or any one of Embodiments 1 through 50, provided that when component (a) consists of a compound selected from the group consisting of 4-(2-chloro-4-fluorophenyl)-1,3-dimethyl-N-(2,4,6-trifluorophenyl)-1H-pyrazol-5-amine (Compound 4),
4-(2,6-difluoro-4-methoxyphenyl)-N-(2,4-difluorophenyl)-1,3-dimethyl-1H-pyrazol-5-amine (Compound 6),
4-(2,6-difluoro-4-methoxyphenyl)-1,3-dimethyl-N-(2,4,6-trifluorophenyl)-1H-pyrazol-5-amine (Compound 7),
4-(2,4-difluorophenyl)-1,3-dimethyl-N-(2,4,6-trifluorophenyl)-1H-pyrazol-5-amine (Compound II),
4-[[4-(2-chloro-4-fluorophenyl)-1,3-dimethyl-1H-pyrazol-5-yl]oxy]-3,5-difluorobenzonitrile (Compound 13),
4-[[4-(2,6-difluorophenyl)-1,3-dimethyl-1H-pyrazol-5-yl]oxy]-3-fluorobenzonitrile (Compound 130),
4-(2-chloro-4-fluorophenyl)-N-(2,6-difluorophenyl)-1,3-dimethyl-1H-pyrazol-5-amine (Compound 46),
4-[[4-(2-chloro-4-fluorophenyl)-1,3-dimethyl-1H-pyrazol-5-yl]oxy]-3-fluorobenzonitrile (Compound 33),
3-chloro-4-[[4-(2,6-difluorophenyl)-1,3-dimethyl-1H-pyrazol-5-yl]oxy]benzonitrile (Compound 127),
4-(2-chloro-4-fluorophenyl)-α-(2,4-difluorophenyl)-1,3-dimethyl-1H-pyrazole-5-methanol (Compound 122),
N,4-bis(2-chloro-4-fluorophenyl)-1,3-dimethyl-1H-pyrazol-5-amine (Compound 47),
N-(2-chloro-4-fluorophenyl)-4-(2-chloro-6-fluorophenyl)-1,3-dimethyl-1H-pyrazol-5-amine (Compound 58),
N-(2-chloro-4,6-difluorophenyl)-4-(2,6-difluorophenyl)-1,3-dimethyl-1H-pyrazol-5-amine (Compound 86),
N-(2-chloro-4,6-difluorophenyl)-4-(2,4-difluorophenyl)-1,3-dimethyl-1H-pyrazol-5-amine (Compound 117),
N-(4-chloro-2,6-difluorophenyl)-4-(2,6-difluorophenyl)-1,3-dimethyl-1H-pyrazol-5-amine (Compound 121),
N-(4-chloro-2,6-difluorophenyl)-4-(2,4-difluorophenyl)-1,3-dimethyl-1H-pyrazol-5-amine (Compound 126),
3-chloro-4-[[4-(2-chloro-4-fluorophenyl)-1,3-dimethyl-1H-pyrazol-5-yl]oxy]benzonitrile (Compound 37),
4-[[4-(2-chloro-4-fluorophenyl)-1,3-dimethyl-1H-pyrazol-5-yl]amino]-3,5-difluorobenzonitrile (Compound 25),
N-(2-chloro-4-fluorophenyl)-4-(2,6-difluoro-4-methoxyphenyl)-1,3-dimethyl-1H-pyrazol-5-amine (Compound 23),
α,4-bis(2-chloro-4-fluorophenyl)-1,3-dimethyl-1H-pyrazole-5-methanol (Compound 123),
N-(4-chloro-2,6-difluorophenyl)-4-(2-chloro-4-fluorophenyl)-1,3-dimethyl-1H-pyrazole-5-amine (Compound 81),
N-(2-chloro-4,6-difluorophenyl)-4-(2-chloro-4-fluorophenyl)-1,3-dimethyl-1H-pyrazol-5-amine (Compound 82),
N-(2,6-dichloro-4-fluorophenyl)-4-(2,4-difluorophenyl)-1,3-dimethyl-1H-pyrazol-5-amine (Compound 137),
3-chloro-4-[5-[(2-chloro-4,6-difluorophenyl)amino]-1,3-dimethyl-1H-pyrazol-4-yl]benzonitrile (Compound 108),
3-chloro-4-[5-[(4-chloro-2,6-difluorophenyl)amino]-1,3-dimethyl-1H-pyrazol-4-yl]benzonitrile (Compound III),
N-(2-bromo-4-fluorophenyl)-4-(2,4-difluorophenyl)-1,3-dimethyl-1H-pyrazol-5-amine (Compound 118),
4-(2-chloro-4-fluorophenyl)-N-(2,4-dichloro-6-fluorophenyl)-1,3-dimethyl-1H-pyrazol-5-amine (Compound 136),
4-(2-chloro-4-fluorophenyl)-N-(2,6-dichloro-4-fluorophenyl)-1,3-dimethyl-1H-pyrazol-5-amine (Compound 138),
4-[[4-(2-bromo-4-fluorophenyl)-1,3-dimethyl-1H-pyrazol-5-yl]oxy]-3-fluorobenzonitrile (Compound 79),
N-(2-bromo-4-fluorophenyl)-4-(2-chloro-4-fluorophenyl)-1,3-dimethyl-1H-pyrazol-5-amine (Compound 73),
4-(2-bromo-4-fluorophenyl)-1,3-dimethyl-N-(2,4,6-trifluorophenyl)-1H-pyrazol-5-amine (Compound 74),
N-(4-bromo-2,6-difluorophenyl)-4-(2,4-difluorophenyl)-1,3-dimethyl-1H-pyrazol-5-amine (Compound 133),
4-[[4-(2-bromo-4-fluorophenyl)-1,3-dimethyl-1H-pyrazol-5-yl]oxy]-3,5-difluorobenzonitrile (Compound 65),
4-(2-bromo-4-fluorophenyl)-N-(2-chloro-4,6-difluorophenyl)-1,3-dimethyl-1H-pyrazol-5-amine (Compound 84),
4-(2-bromo-4-fluorophenyl)-N-(4-chloro-2,6-difluorophenyl)-1,3-dimethyl-1H-pyrazol-5-amine (Compound 129),
N-(4-bromo-2,6-difluorophenyl)-4-(2-chloro-4-fluorophenyl)-1,3-dimethyl-1H-pyrazol-5-amine (Compound 134),
3-bromo-4-[[4-(2,4-difluorophenyl)-1,3-dimethyl-1H-pyrazol-5-yl]oxy]benzonitrile (Compound 139),
3-chloro-4-[[4-(2,4-difluorophenyl)-1,3-dimethyl-1H-pyrazol-5-yl]oxy]benzonitrile (Compound 140),
N-(2,4-dichloro-6-fluorophenyl)-4-(2,4-difluorophenyl)-1,3-dimethyl-1H-pyrazol-5-amine (Compound 141),
N-(2,6-dichloro-4-fluorophenyl)-4-(2,6-difluorophenyl)-1,3-dimethyl-1H-pyrazol-5-amine (Compound 142),
N-(2-bromo-4,6-difluorophenyl)-4-(2,4-difluorophenyl)-1,3-dimethyl-1H-pyrazol-5-amine (Compound 143),
N-(2-bromo-4,6-difluorophenyl)-4-(2-chloro-4-fluorophenyl)-1,3-dimethyl-1H-pyrazol-5-amine (Compound 144),
N-(4-bromo-2,6-difluorophenyl)-4-(2,6-difluorophenyl)-1,3-dimethyl-1H-pyrazol-5-amine (Compound 145),
N-(2-bromo-4,6-difluorophenyl)-4-(2,6-difluorophenyl)-1,3-dimethyl-1H-pyrazol-5-amine (Compound 146),
N-(2-bromo-4,6-difluorophenyl)-4-(2-chloro-6-fluorophenyl)-1,3-dimethyl-1H-pyrazol-5-amine (Compound 147),
α-(4-chloro-2,6-difluorophenyl)-4-(2-chloro-4-fluorophenyl)-1,3-dimethyl-1H-pyrazole-5-methanol (Compound 148),
4-[5-[(2-chloro-4,6-difluorophenyl)amino]-1,3-dimethyl-1H-pyrazol-4-yl]-3-fluorobenzonitrile (Compound 238),
4-[5-[(4-chloro-2,6-difluorophenyl)amino]-1,3-dimethyl-1H-pyrazol-4-yl]-3-fluorobenzonitrile (Compound 150),
α-(2-chloro-4,6-difluorophenyl)-4-(2-chloro-4-fluorophenyl)-1,3-dimethyl-1H-pyrazole-5-methanol (Compound 151),
α-(2-bromo-4-fluorophenyl)-4-(2,4-difluorophenyl)-1,3-dimethyl-1H-pyrazole-5-methanol (Compound 152), and
α-(2-bromo-4-fluorophenyl)-4-(2-chloro-4-fluorophenyl)-1,3-dimethyl-1H-pyrazole-5-methanol (Compound 153), then component (b) comprises at least two fungicidal compounds, and (1) when component (b) consists of a binary combination of two fungicidal compounds, wherein one of the fungicidal compounds is cyproconazole, difenconazole, epoxiconazole, metconazole, myclobutanil, prothioconazole or tebuconazole then the other fungicidal compound is other than azoxystrobin, bixafen, boscalid, cyflufenamid, fluopyram, isopyrazam, kresoxim-methyl, metrafenone, penthiopyrad, picoxystrobin, proquinazid, pyraclostrobin, quinoxyfen, sedaxane or trifloxystrobin, and (2) when component (b) consists as a ternary combination of three fungicidal compounds, wherein one of the fungicidal compounds is cyproconazole, difenconazole, epoxiconazole, metconazole, myclobutanil, prothioconazole or tebuconazole, and another of the fungicidal compounds is picoxystrobin or trifloxystrobin, then the third fungicidal compound is other than proquinazid.

Embodiments of this invention, including Embodiments 1-51 above as well as any other embodiments described herein, can be combined in any manner, and the descriptions of variables in the embodiments pertain not only to the compositions comprising compounds of Formula 1 with at least one other fungicidal compound but also to compositions comprising compounds of Formula 1 with at least one invertebrate pest control compound or agent, and also to the compounds of Formula 1 and their compositions, and also to the starting compounds and intermediate compounds useful for preparing the compounds of Formula 1. In addition, embodiments of this invention, including Embodiments 1-51 above as well as any other embodiments described herein, and any combination thereof, pertain to the methods of the present invention. Therefore of note as a further embodiment is the composition disclosed above comprising (a) at least one compound selected from the compounds of Formula 1 described above, N-oxides, and salts thereof; and at least one invertebrate pest control compound or agent, provided that when component (a) is consists of a compound selected from the group listed in Embodiment 51, then the composition comprises at least two invertebrate pest control compounds or agents, or at least one additional fungicidal compound (i.e. fungicidal compound in addition to the Formula 1 compound).

Combinations of Embodiments 1-51 are illustrated by:

Embodiment A1. The composition comprising components (a) and (b) described in the Summary of the Invention wherein component (a) comprises a compound of Formula 1 or salt thereof, wherein in Formula 1,
at most, only one of $R^2$ and $R^3$ is H; and
at most, only one of $R^5$ and $R^6$ is H.

Embodiment A2. The composition of Embodiment A1 wherein in Formula 1,
$R^1$ is F, Cl or Br;
$R^2$ is H, cyano, F, Cl, Br or methoxy;
$R^3$ is H, F or Cl;
$R^4$ is F, Cl or Br;
$R^5$ is H, cyano, F, Cl or methoxy; and
$R^6$ is H or F.

Embodiment A3. The composition of Embodiment A2 wherein in Formula 1,
$R^3$ is H or F; and
$R^5$ is cyano, F, Cl or methoxy.

Embodiment A4. The composition of Embodiment A3 wherein component (a) comprises a compound selected from the group consisting of: Compound 3, Compound 7, Compound 8, Compound 13, Compound 17, Compound 40, Compound 47, Compound 81, Compound 82, Compound 122, Compound 136, Compound 143, Compound 144, Compound 161, Compound 195, Compound 238, Compound 239, Compound 240 and Compound 241.

Embodiment A5. The composition of Embodiment A4 wherein component (a) comprises a compound selected from the group consisting of: Compound 3, Compound 7, Compound 8, Compound 13, Compound 17, Compound 40, Compound 47, Compound 81, Compound 82, Compound 122, Compound 136, Compound 143, Compound 144, Compound 161, Compound 195 and Compound 238.

Embodiment A6. The composition comprising components (a) and (b) described in the Summary of the Invention wherein component (a) comprises a compound of Formula 1 or salt thereof, wherein in Formula 1,
X is NH;
$R^1$ is halogen or methyl;
$R^2$ is H;
$R^3$ is halogen or methyl;
$R^4$ is halogen;
$R^5$ is H, cyano, halogen or $C_1$-$C_2$ alkoxy; and
$R^6$ is H or halogen;
provided that when $R^1$ is F, then $R^3$ is Cl, and when $R^1$ is Cl, then $R^3$ is F.

Embodiment A7. The composition of Embodiment A6 wherein in Formula 1,
$R^3$ is F or Cl.

Embodiment A8. The composition of Embodiment A7 wherein in Formula 1,
$R^1$ is Cl or Br; and
$R^3$ is F.

Embodiment A9. The composition of any one of Embodiments A6 through A8 wherein in Formula 1, at most, only one of $R^5$ and $R^6$ is H.

Embodiment A10. The composition of Embodiment A9 wherein in Formula 1,
$R^4$ is F, Cl or Br;
$R^5$ is H, cyano, F, Cl or methoxy; and
$R^6$ is H or F.

Embodiment A11. The composition of Embodiment A10 wherein in Formula 1,
$R^5$ is cyano, F, Cl or methoxy.

Embodiment A12. The composition of Embodiment A6 wherein component (a) comprises a compound selected from the group consisting of: Compound 239, Compound 240, and Compound 241.

Embodiment B1. The composition described in the Summary of the Invention (including but not limited to the composition of any one of Embodiments 1 through 51 and A1 through A12) wherein component (b) includes at least one compound selected from (b1) methyl benzimidazole carbamate fungicides such as benomyl, carbendazim and thiophanate-methyl.

Embodiment B2. The composition described in the Summary of the Invention (including but not limited to the composition of any one of Embodiments 1 through 51 and A1 through A12) wherein component (b) includes at least one compound selected from (b2) dicarboximide fungicides such as procymidone, iprodione and vinclozolin.

Embodiment B3. The composition described in the Summary of the Invention (including but not limited to the composition of any one of Embodiments 1 through 51 and A1 through A12) wherein component (b) includes at least one compound selected from (b3) demethylation inhibitor fungicides such as epoxiconazole, fluquinconazole, triadimenol, simeconazole, ipconazole, triforine, cyproconazole, difenconazole, flusilazole, flutriafol, metconazole, myclobutanil, prochloraz, propiconazole, prothioconazole, tebuconazole and tetraconazole.

Embodiment B4. The composition described in the Summary of the Invention (including but not limited to the composition of any one of Embodiments 1 through 51 and A1 through A12) wherein component (b) includes at least one compound selected from (b4) phenylamide fungicides such as metalaxyl, metalaxyl-M, benalaxyl, benalaxyl-M, furalaxyl, ofurace and oxadixyl.

Embodiment B5. The composition described in the Summary of the Invention (including but not limited to the composition of any one of Embodiments 1 through 51 and A1 through A12) wherein component (b) includes at least one compound selected from (b5) amine/morpholine fungicides such as aldimorph, dodemorph, fenpropimorph, tridemorph, trimorphamide, fenpropidin, piperalin and spiroxamine.

Embodiment B6. The composition described in the Summary of the Invention (including but not limited to the composition of any one of Embodiments 1 through 51 and A1 through A12) wherein component (b) includes at least one compound selected from (b6) phospholipid biosynthesis inhibitor fungicides such as edifenphos and isoprothiolane.

Embodiment B7. The composition described in the Summary of the Invention (including but not limited to the composition of any one of Embodiments 1 through 51 and A1 through A12) wherein component (b) includes at least one compound selected from (b7) carboxamide fungicides such as bixafen, boscalid, carboxin, isopyrazam, oxycarboxin, penflufen and penthiopyrad.

Embodiment B8. The composition described in the Summary of the Invention (including but not limited to the composition of any one of Embodiments 1 through 51 and A1 through A12) wherein component (b) includes at least one compound selected from (b8) hydroxy(2-amino-)pyrimidine fungicides such as ethirimol.

Embodiment B9. The composition described in the Summary of the Invention (including but not limited to the composition of any one of Embodiments 1 through 51 and A1 through A12) wherein component (b) includes at least one compound selected from (b9) anilinopyrimidine fungicides such as cyprodinil.

Embodiment B10. The composition described in the Summary of the Invention (including but not limited to the composition of any one of Embodiments 1 through 51 and A1 through A12) wherein component (b) includes at least one compound selected from (b10) N-phenyl carbamate fungicides such as diethofencarb.

Embodiment B11. The composition described in the Summary of the Invention (including but not limited to the composition of any one of Embodiments 1 through 51 and A1 through A12) wherein component (b) includes at least one compound selected from (b11) quinone outside inhibitor fungicides such as azoxystrobin, pyraclostrobin, pyrametostrobin, kresoxim-methyl, trifloxystrobin, picoxystrobin, pyraoxystrobin, pyribencarb, famoxadone, fenamidone, discostrobin, enestrobin, dimoxystrobin, metominostrobin, orysastrobin and fluoxastrobin.

Embodiment B12. The composition described in the Summary of the Invention (including but not limited to the composition of any one of Embodiments 1 through 51 and A1 through A12) wherein component (b) includes at least one compound selected from (b12) phenylpyrrole fungicides compound such as fenpiclonil and fludioxonil.

Embodiment B13. The composition described in the Summary of the Invention (including but not limited to the composition of any one of Embodiments 1 through 51 and A1 through A12) wherein component (b) includes at least one compound selected from (b13) quinoline fungicides such as quinoxyfen.

Embodiment B14. The composition described in the Summary of the Invention (including but not limited to the composition of any one of Embodiments 1 through 51 and A1 through A12) wherein component (b) includes at least one compound selected from (b14) lipid peroxidation inhibitor fungicides such as chloroneb.

Embodiment B15. The composition described in the Summary of the Invention (including but not limited to the composition of any one of Embodiments 1 through 51 and A1 through A12) wherein component (b) includes at least one compound selected from (b15) melanin biosynthesis inhibitors-reductase fungicides such as pyroquilon and tricyclazole.

Embodiment B16. The composition described in the Summary of the Invention (including but not limited to the composition of any one of Embodiments 1 through 51 and A1 through A12) wherein component (b) includes at least one compound selected from (b16) melanin biosynthesis inhibitors-dehydratase fungicides such as carpropamid.

Embodiment B17. The composition described in the Summary of the Invention (including but not limited to the composition of any one of Embodiments 1 through 51 and A1 through A12) wherein component (b) includes at least one compound selected from (b17) hydroxyanilide fungicides such as fenhexamid.

Embodiment B18. The composition described in the Summary of the Invention (including but not limited to the composition of any one of Embodiments 1 through 51 and A1 through A12) wherein component (b) includes at least one compound selected from (b18) squalene-epoxidase inhibitor fungicides such as pyributicarb.

Embodiment B19. The composition described in the Summary of the Invention (including but not limited to the composition of any one of Embodiments 1 through 51 and A1 through A12) wherein component (b) includes at least one compound selected from (b19) polyoxin fungicides such as polyoxin.

Embodiment B20. The composition described in the Summary of the Invention (including but not limited to the composition of any one of Embodiments 1 through 51 and A1 through A12) wherein component (b) includes at least one compound selected from (b20) phenylurea fungicides such as pencycuron.

Embodiment B21. The composition described in the Summary of the Invention (including but not limited to the composition of any one of Embodiments 1 through 51 and A1 through A12) wherein component (b) includes at least one compound selected from (b21) quinone inside inhibitor fungicides such as cyazofamid and amisulbrom.

Embodiment B22. The composition described in the Summary of the Invention (including but not limited to the composition of any one of Embodiments 1 through 51 and A1 through A12) wherein component (b) includes at least one compound selected from (b22) benzamide fungicides such as zoxamide.

Embodiment B23. The composition described in the Summary of the Invention (including but not limited to the composition of any one of Embodiments 1 through 51 and A1 through A12) wherein component (b) includes at least one compound selected from (b23) enopyranuronic acid antibiotic fungicides such as blasticidin-S.

Embodiment B24. The composition described in the Summary of the Invention (including but not limited to the composition of any one of Embodiments 1 through 51 and A1 through A12) wherein component (b) includes at least one compound selected from (b24) hexopyranosyl antibiotic fungicides such as kasugamycin.

Embodiment B25. The composition described in the Summary of the Invention (including but not limited to the composition of any one of Embodiments 1 through 51 and A1 through A12) wherein component (b) includes at least one compound selected from (b25) glucopyranosyl antibiotic: protein synthesis fungicides such as streptomycin.

Embodiment B26. The composition described in the Summary of the Invention (including but not limited to the composition of any one of Embodiments 1 through 51 and A1 through A12) wherein component (b) includes at least one compound selected from (b26) glucopyranosyl antibiotic: trehalase and inositol biosynthesis fungicides such as validamycin.

Embodiment B27. The composition described in the Summary of the Invention (including but not limited to the composition of any one of Embodiments 1 through 51 and A1 through A12) wherein component (b) includes at least one compound selected from (b27) cyanoacetylamideoxime fungicides such as cymoxanil.

Embodiment B28. The composition described in the Summary of the Invention (including but not limited to the composition of any one of Embodiments 1 through 51 and A1 through A12) wherein component (b) includes at least one compound selected from (b28) carbamate fungicides such as propamacarb, prothiocarb and iodocarb.

Embodiment B29. The composition described in the Summary of the Invention (including but not limited to the composition of any one of Embodiments 1 through 51 and A1 through A12) wherein component (b) includes at least one compound selected from (b29) oxidative phosphorylation uncoupling fungicides such as fluazinam, binapacryl, ferimzone, meptyldinocap and dinocap.

Embodiment B30. The composition described in the Summary of the Invention (including but not limited to the composition of any one of Embodiments 1 through 51 and A1 through A12) wherein component (b) includes at least one compound selected from (b30) organo tin fungicides such as fentin acetate.

Embodiment B31. The composition described in the Summary of the Invention (including but not limited to the composition of any one of Embodiments 1 through 51 and A1 through A12) wherein component (b) includes at least one compound selected from (b31) carboxylic acid fungicides such as oxolinic acid.

Embodiment B32. The composition described in the Summary of the Invention (including but not limited to the composition of any one of Embodiments 1 through 51 and A1 through A12) wherein component (b) includes at least one compound selected from (b32) heteroaromatic fungicides such as hymexazole.

Embodiment B33. The composition described in the Summary of the Invention (including but not limited to the composition of any one of Embodiments 1 through 51 and A1 through A12) wherein component (b) includes at least one compound selected from (b33) phosphonate fungicides such as phosphorous acid and its various salts, including fosetyl-aluminum.

Embodiment B34. The composition described in the Summary of the Invention (including but not limited to the composition of any one of Embodiments 1 through 51 and A1 through A12) wherein component (b) includes at least one compound selected from (b34) phthalamic acid fungicides such as teclofthalam.

Embodiment B35. The composition described in the Summary of the Invention (including but not limited to the composition of any one of Embodiments 1 through 51 and A1 through A12) wherein component (b) includes at least one compound selected from (b35) benzotriazine fungicides such as triazoxide.

Embodiment B36. The composition described in the Summary of the Invention (including but not limited to the composition of any one of Embodiments 1 through 51 and A1 through A12) wherein component (b) includes at least one compound selected from (b36) benzene-sulfonamide fungicides such as flusulfamide.

Embodiment B37. The composition described in the Summary of the Invention (including but not limited to the composition of any one of Embodiments 1 through 51 and A1 through A12) wherein component (b) includes at least one compound selected from (b37) pyridazinone fungicides such as diclomezine.

Embodiment B38. The composition described in the Summary of the Invention (including but not limited to the composition of any one of Embodiments 1 through 51 and A1 through A12) wherein component (b) includes at least one compound selected from (b38) thiophene-carboxamide fungicides such as silthiofam.

Embodiment B39. The composition described in the Summary of the Invention (including but not limited to the composition of any one of Embodiments 1 through 51 and A1 through A12) wherein component (b) includes at least one compound selected from (b39) pyrimidinamide fungicides such as diflumetorim.

Embodiment B40. The composition described in the Summary of the Invention (including but not limited to the composition of any one of Embodiments 1 through 51 and A1 through A12) wherein component (b) includes at least one compound selected from (b40) carboxylic acid amide fungicides such as dimethomorph, benthiavalicarb, benthiavalicarb-isopropyl, iprovalicarb, valifenalate, mandipropamid and flumorph.

Embodiment B41. The composition described in the Summary of the Invention (including but not limited to the composition of any one of Embodiments 1 through 51 and A1 through A12) wherein component (b) includes at least one compound selected from (b41) tetracycline antibiotic fungicides such as oxytetracycline.

Embodiment B42. The composition described in the Summary of the Invention (including but not limited to the composition of any one of Embodiments 1 through 51 and A1 through A12) wherein component (b) includes at least one compound selected from (b42) thiocarbamate fungicides such as methasulfocarb.

Embodiment B43. The composition described in the Summary of the Invention (including but not limited to the composition of any one of Embodiments 1 through 51 and A1 through A12) wherein component (b) includes at least one compound selected from (b43) benzamide fungicides such as fluopicolide and fluopyram.

Embodiment B44. The composition described in the Summary of the Invention (including but not limited to the composition of any one of Embodiments 1 through 51 and A1 through A12) wherein component (b) includes at least one compound selected from (b44) host plant defense induction fungicides such as acibenzolar-S-methyl.

Embodiment B45. The composition described in the Summary of the Invention (including but not limited to the composition of any one of Embodiments 1 through 51 and A1 through A12) wherein component (b) includes at least one compound selected from (b45) multi-site contact fungicides such as copper oxychloride, copper sulfate, copper hydroxide, Bordeaux composition (tribasic copper sulfide), elemental sulfur, mancozeb, metiram, propineb, ferbam, maneb, thiram, zineb, ziram, folpet, captan, captafol and chlorothalonil.

Embodiment B46. The composition described in the Summary of the Invention (including but not limited to the composition of any one of Embodiments 1 through 51 and A1 through A12) wherein component (b) includes at least one compound selected from (b46) fungicides other than fungicides of component (a) and components (b1) through (b45), such as ethaboxam, cyflufenamid, proquinazid, metrafenone, pyriofenone, ametoctradin, bethoxazin, neo-asozin, fenpyrazamine, pyrrolnitrin, quinomethionate, tebufloquin, 5-chloro-6-(2,4,6-trifluorophenyl)-7-(4-methylpiperidin-1-yl)[1,2,4]triazolo[1,5-c]pyrimidine (BAS600), 2-butoxy-6-iodo-3-propyl-4H-1-benzopyran-4-one, 3-[5-(4-chlorophenyl)-2,3-dimethyl-3-isoxazolidinyl]pyridine (SYP-Z048), 4-fluorophenyl N-[1-[[[1-(4-cyanophenyl)ethyl]sulfonyl]methyl]propyl]carbamate (XR-539), N-[[(cyclopropylmethoxy)amino][6-(difluoromethoxy)-2,3-difluorophenyl]methylene]benzeneacetamide, N-[4-[4-chloro-3-(trifluoromethyl)phenoxy]-2,5-dimethylphenyl]-N-ethyl-N-methylmethanimidamide, 2-[[2-fluoro-5-(trifluoromethyl)phenyl]thio]-2-[3-(2-methoxyphenyl)-2-thiazolidinylidene]acetonitrile (OK-5203), N-(4-chloro-2-nitrophenyl)-N-ethyl-4-methylbenzenesulfonamide (TF-991) and 1-[(2-propenylthio) carbonyl]-2-(1-methylethyl)-4-(2-methylphenyl)-5-amino-1H-pyrazol-3-one.

Embodiment B47. The composition described in the Summary of the Invention (including but not limited to the composition of any one of Embodiments 1 through 51 and A1 through A12) wherein component (b) includes at least one fungicidal compound (fungicide) selected from the group consisting of azoxystrobin, kresoxim-methyl, trifloxystrobin, pyraclostrobin, pyraoxystrobin, pyrametostrobin, picoxystrobin, dimoxystrobin, metominostrobin-/fenominostrobin, carbendazim, chlorothalonil, quinoxyfen, metrafenone, pyriofenone, cyflufenamid, fenpropidin, fenpropimorph, bromuconazole, cyproconazole, difenoconazole, epoxiconazole, fenbuconazole, flusilazole, hexaconazole, ipconazole, metconazole, myclobutanil, penconazole, propiconazole, proquinazid, prothioconazole, tebuconazole, triticonazole, famoxadone, prochloraz, penthiopyrad and boscalid (nicobifen).

Embodiment B48. The composition of Embodiment B47 wherein component (b) includes at least one compound selected from the group consisting of azoxystrobin, kresoxim-methyl, trifloxystrobin, pyraclostrobin, pyrametostrobin, pyraoxystrobin, picoxystrobin, dimoxystrobin, metominostrobin-/fenominostrobin, quinoxyfen, metrafenone, pyriofenone, cyflufenamid, fenpropidin, fenpropimorph, cyproconazole, difenoconazole, epoxiconazole, flusilazole, metconazole, myclobutanil, propiconazole, proquinazid, prothioconazole, tebuconazole, triticonazole, famoxadone and penthiopyrad.

Embodiment B49. The composition described in the Summary of the Invention (including but not limited to the composition of any one of Embodiments 1 through 51 and A1 through A12) wherein component (b) includes at least one fungicidal compound selected from compounds of Formula A1 and salts thereof, wherein Formula A1 and substituents thereon are as disclosed herein for the (b46.5) class of 6-quinolinyloxyacetamide compounds.

Embodiment B50. The composition of Embodiment B49 wherein component (b) includes at least one fungicidal compound selected from the group consisting of 2-[(3-bromo-6-quinolinyl)oxy]-N-(1,1-dimethyl-2-butyn-1-yl)-2-(methylthio)-acetamide, N-(1,1-dimethyl-2-butyn-1-yl)-2-[(3-ethynyl-6-quinolinyl)oxy]-2-(methylthio)acetamide, 2-[(3-bromo-8-methyl-6-quinolinyl)oxy]-N-(1,1-dimethyl-2-propyn-1-yl)-2-(methylthio)acetamide and 2-[(3-bromo-6-quinolinyl) oxy]-N-(1,1-dimethylethyl)butanamide.

Of note is the composition of any one of the embodiments described herein, including Embodiments 1 through 51, A1 through A12, and B1 through B50, wherein reference to Formula 1 includes salts thereof but not N-oxides thereof; therefore the phrase "a compound of Formula 1" can be replaced by the phrase "a compound of Formula 1 or a salt thereof". In this composition of note, component (a) comprises a compound of Formula 1 or a salt thereof.

Also noteworthy as embodiments are fungicidal compositions of the present invention comprising a fungicidally effective amount of a composition of Embodiments 1 to 51, A1 to A12, and B1 to B50 and at least one additional component selected from the group consisting of surfactants, solid diluents and liquid diluents.

Embodiments of the invention further include methods for controlling plant diseases caused by fungal plant pathogens comprising applying to the plant or portion thereof, or to the plant seed or seedling, a fungicidally effective amount of a composition any one of Embodiments 1 to 51, A1 to A12, and B1 to B50 (e.g., as a composition including formulation ingredients as described herein). Embodiments of the invention also include methods for protecting a plant or plant seed from diseases caused by fungal pathogens comprising applying a fungicidally effective amount of a composition of any one of Embodiments 1 to 51, A1 to A12, and B1 to B50 to the plant or plant seed.

Some embodiments of the invention involve control of a plant disease or protection from a plant disease that primarily afflicts plant foliage and/or applying the composition of the invention to plant foliage (i.e. plants instead of seeds). The preferred methods of use include those involving the above preferred compositions; and the diseases controlled with particular effectiveness include plant diseases caused by fungal plant pathogens.

Combinations of fungicides used in accordance with this invention can facilitate disease control and retard resistance development.

Method embodiments further include:

Embodiment C1. A method for protecting a plant from a disease selected from powdery mildew, rust and *Septoria* diseases comprising applying to the plant a fungicidally effective amount of the composition comprising components (a) and (b) described in the Summary of the Invention or any one of Embodiments 1 through 51.

Embodiment C2. The method of Embodiment C1 wherein the disease is a powdery mildew disease and component (b) of the composition includes at least one fungicidal compound selected from (b4) demethylation inhibitor (DMI) fungicides, (b11) quinine outside inhibitor (QoI) fungicides, and (b46.4) proquinazid.

Embodiment C3. The method of Embodiment C2 wherein the disease is wheat powdery mildew.

Embodiment C4. The method of Embodiment C2 or C3 wherein component (b) includes at least one fungicidal compound selected from (b4) DMI fungicides.

Embodiment C5. The method of Embodiment C4 wherein component (b) includes at least one fungicidal compound selected from the group consisting of cyproconazole, difenoconazole, epoxiconazole, myclobutanil, prothioconazole and tetraconazole.

Embodiment C6. The method of Embodiment C5 wherein component (b) includes at least one fungicidal compound selected from the group consisting of cyproconazole, difenoconazole and prothioconazole.

Embodiment C7. The method of Embodiment C2 or C3 wherein component (b) includes at least one fungicidal compound selected from (b11) QoI fungicides.

Embodiment C8. The method of Embodiment C7 wherein component (b) includes at least one fungicidal compound selected from the group consisting of azoxystrobin, picoxystrobin and pyraclostrobin.

Embodiment C9. The method of Embodiment C2 or C3 wherein component (b) includes (b46.4) proquinazid.

Embodiment C10. The method of Embodiment C1 wherein the disease is a rust disease and component (b) of the composition includes fenpropimorph.

Embodiment C11. The method of Embodiment C10 wherein the disease is wheat leaf rust.

Embodiment C12. The method of Embodiment C1 wherein the disease is a *Septoria* disease and component (b) of the composition includes at least one fungicidal compound selected from the group consisting of epoxiconazole, metalaxyl (including metalaxyl-M), iprovalicarb and fenpropimorph.

Embodiment C13. The method of Embodiment C12 wherein the disease is wheat leaf blotch.

Embodiment C14. A method for protecting a plant from a *Septoria* disease comprising applying to the plant a fungicidally effective amount of the composition of Embodiment B49 or B50.

Embodiment C15. The method of Embodiment C14 wherein the disease is caused by *Septoria tritici*.

Embodiment C16. The method of Embodiment C14 or C15 wherein the disease is wheat leaf blotch.

Embodiment C17. The method of any one of Embodiments C1 through C16 wherein components (a) and (b) are applied in synergistically effective amounts (and in a synergistic ratio relative to each other).

Of note are embodiments that are counterparts of Embodiments C1 through C17 relating to a method for controlling plant diseases caused by fungal plant pathogens comprising applying to the plant or portion thereof, a fungicidally effective amount of a fungicidal composition of the invention.

As noted in the Summary of the Invention, this invention also relates to a compound of Formula 1, or an N-oxide or salt thereof. Also already noted is that the embodiments of this invention, including Embodiments 1-51, relate also to compounds of Formula 1. Accordingly, combinations of Embodiments 1-51 are further illustrated by:

Embodiment D1. A compound of Formula 1, or an N-oxide or salt thereof, wherein
X is NH;
$R^1$ is halogen or methyl;
$R^2$ is H;
$R^3$ is halogen or methyl;
$R^4$ is halogen;
$R^5$ is H, cyano, halogen or $C_1$-$C_2$ alkoxy; and
$R^6$ is H or halogen;
provided that when $R^1$ is F, then $R^3$ is Cl, and when $R^1$ is Cl, then $R^3$ is F.

Embodiment D2. A compound of Embodiment D1 wherein
$R^3$ is F or Cl.

Embodiment D3. A compound of Embodiment D2 wherein
$R^1$ is Cl or Br; and
$R^3$ is F.

Embodiment D4. A compound of any one of Embodiments D1 through D4 wherein, at most, only one of $R^5$ and $R^6$ is H.

Embodiment D5. A compound of Embodiment D4 wherein
$R^4$ is F, Cl or Br;
$R^5$ is H, cyano, F, Cl or methoxy; and
$R^6$ is H or F.

Embodiment D6. A compound of Embodiment D5 wherein
$R^5$ is cyano, F, Cl or methoxy.

Embodiment D7. A compound of any one of Embodiments D1 through D6 wherein the compound is other than in the form of an N-oxide (i.e. is in the form of Formula 1 or a salt thereof).

Embodiment D8. A compound of Embodiment D1 selected from the group consisting of:
4-(2-chloro-4-fluorophenyl)-N-(2-chloro-6-fluorophenyl)-1,3-dimethyl-1H-pyrazol-5-amine (Compound 239),
4-(2-bromo-4-fluorophenyl)-N-(2-chloro-6-fluorophenyl)-1,3-dimethyl-1H-pyrazol-5 amine (Compound 240), and
N-(2-bromo-6-fluorophenyl)-4-(2-chloro-4-fluorophenyl)-1,3-dimethyl-1H-pyrazol-5-amine (Compound 241).

Additional embodiments include a fungicidal composition comprising: (1) a compound of any one of Embodiments D1 through D8; and (2) at least one additional component selected from the group consisting of surfactants, solid diluents and liquid diluents. Additional embodiments also include a method for protecting a plant or plant seed from diseases caused by fungal pathogens comprising applying a fungicidally effective amount of the compound of any one of Embodiments D1 through D8 to the plant (or portion thereof) or plant seed (directly or through the environment (e.g., growing medium) of the plant or plant seed). Of note are embodiments relating to a method for controlling plant diseases caused by fungal plant pathogens comprising applying to the plant or portion thereof, a fungicidally effective amount of a compound of any one of Embodiments D1 through D8.

One or more of the following methods and variations as described in Schemes 1-17 can be used to prepare the compounds of Formula 1. The definitions of $R^1$, $R^2$, $R^3$, $R^4$, $R^5$ and $R^6$ in the compounds of Formulae 1-26 below are as defined above in the Summary of the Invention unless otherwise noted. Formulae 1a and 1b are various subsets of Formula 1; Formulae 4a and 4b are various subsets of Formula 4; Formulae 6a and 6b are various subsets of Formula 6; Formula 11a is a subset of Formula 11; and Formula 23a is a subset of Formula 23. Substituents for each subset formula are as defined for its parent formula unless otherwise noted.

As shown in Scheme 1, compounds of Formula 1 in which X is NH can be prepared by the reaction of 1H-pyrazole compounds of Formula 2 with various methylating agents (e.g., Formula 3), such as iodomethane, methyl sulfonates (e.g., methyl mesylate (OMs) or tosylate (OTs)) or trimethyl phosphate, preferably in the presence of an organic or inorganic base such as 1,8-diazabicyclo[5.4.0]undec-7-ene, potassium carbonate or potassium hydroxide, and in a solvent such as N,N-dimethylformamide (DMF), tetrahydrofuran (THF), toluene or water.

Scheme 1

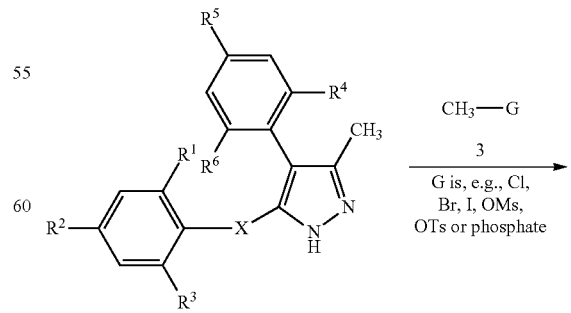

2

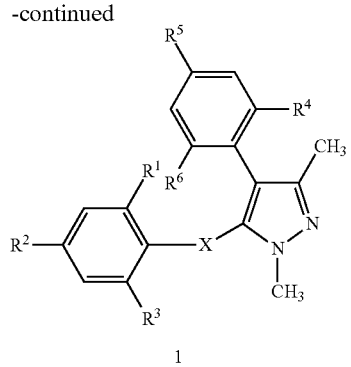

1

X is NH

As is shown in Scheme 2, compounds of Formula 1 can be prepared by the reaction of compounds of Formula 4 (i.e. 5-aminopyrazoles for X being NH, or 5-hydroxypyrazoles (5-pyrazolones) for X being O, with aromatic compounds of Formula 5 containing a leaving group G (i.e. halogen or (halo)alkylsulfonate), optionally in the presence of a metal catalyst, and generally in the presence of a base and a polar aprotic solvent such as N,N-dimethylformamide or dimethyl sulfoxide. For example, compounds of Formula 5 wherein the benzene ring contains electron-withdrawing substituents react by direct displacement of the leaving group G from the ring to provide compounds of Formula 1. The method of Scheme 2 is illustrated by Step D of Synthesis Example 6. Compounds of Formula 5 are commercially available or their preparation is known in the art.

Scheme 2

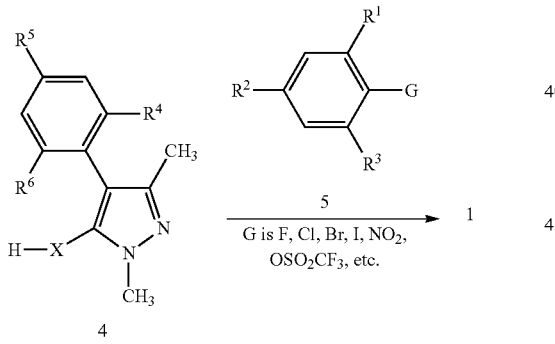

4

X is NH or O

For reactions according to the method of Scheme 2 of a compound of Formula 4 wherein X is O or NH with a compound of Formula 5 wherein the aromatic ring lacks sufficiently electron-withdrawing substituents, or to improve reaction rate, yield or product purity, the use of a metal catalyst (e.g., metal or metal salt) in amounts ranging from catalytic up to superstoichiometric can facilitate the desired reaction. Typically for these conditions, G is Br or I or a sulfonate such as $OS(O)_2CF_3$ or $OS(O)_2(CF_2)_3CF_3$. For example, copper salt complexes (e.g., CuI with N,N'-dimethylethylenediamine, proline or bipyridyl), palladium complexes (e.g., tris (dibenzylideneacetone)dipalladium(0)) or palladium salts (e.g., palladium acetate) with ligands such as 4,5-bis(diphenylphosphino)-9,9-dimethylxanthene (i.e. "Xantphos"), 2-dicyclohexylphosphino-2',4',6'-triisopropylbiphenyl (i.e.

"Xphos") or 2,2'-bis(diphenylphosphino)-1,1'-binaphthalene (i.e. "BINAP"), in the presence of a base such as potassium carbonate, cesium carbonate, sodium phenoxide or sodium tert-butoxide, in a solvent such as N,N-dimethylformamide, 1,2-dimethoxyethane, dimethyl sulfoxide, 1,4-dioxane or toluene, optionally mixed with alcohols such as ethanol, can be used. Alternatively as illustrated in Scheme 3, compounds of Formula 1a (i.e. Formula 1 in which X is NH) can be prepared by reaction of compounds of Formula 6 (i.e. 5-bromopyrazoles or other pyrazoles substituted at the 5-position with a leaving group) with compounds of Formula 7 under metal-catalyzed conditions similar to those described above for Scheme 2. The method of Scheme 3 is illustrated by Step C of Synthesis Example 1 and Step E of Synthesis Example 2. Compounds of Formula 7 are commercially available or their preparation is known in the art.

Scheme 3

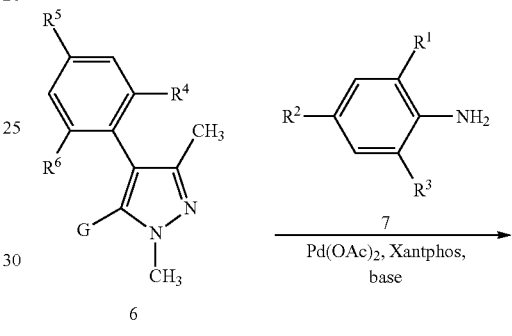

6

G is Br, I, $OSO_2C_4F_9$, etc.

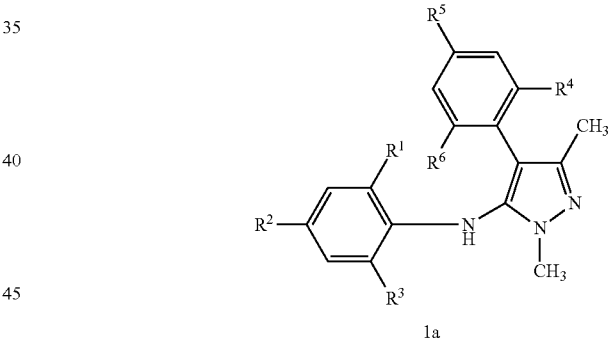

1a

As shown in Scheme 4, compounds of Formula 6 wherein G is Br or I can be prepared by reaction of 5-aminopyrazoles of Formula 4a (i.e. Formula 4 wherein X is NH) under diazotization conditions either in the presence of, or followed by combination with, copper salts containing bromide or iodide. For example, addition of tert-butyl nitrite to a solution of a 5-aminopyrazole of Formula 4a in the presence of $CuBr_2$ in a solvent such as acetonitrile provides the corresponding 5-bromopyrazole of Formula 6. Likewise, a 5-aminopyrazole of Formula 4a can be converted to a diazonium salt and then to a corresponding 5-halopyrazole of Formula 6 by treatment with sodium nitrite in solvents such as water, acetic acid or trifluoroacetic acid, in the presence of a mineral acid typically containing the same halide atom (such as aqueous HI solution for G being I), followed by treatment with the corresponding copper(I) or copper(II) salt according to general procedures well known to those skilled in the art. The method of Scheme 4 is illustrated by Step B of Synthesis Example 1 and Step D of Synthesis Example 2.

Scheme 4

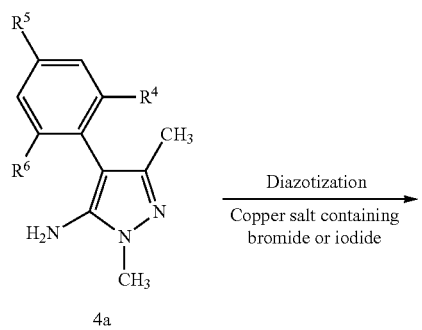

4a

As shown in Scheme 5, 5-bromopyrazoles of Formula 6a (i.e. Formula 6 wherein G is Br) can be prepared by reacting 5-hydroxypyrazoles of Formula 4b (i.e. Formula 4 wherein X is O) with phosphorus tribromide as described in *Tetrahedron Lett.* 2000, 41(24), 4713.

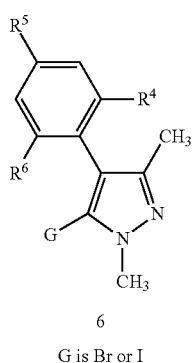

6

G is Br or I

Scheme 5

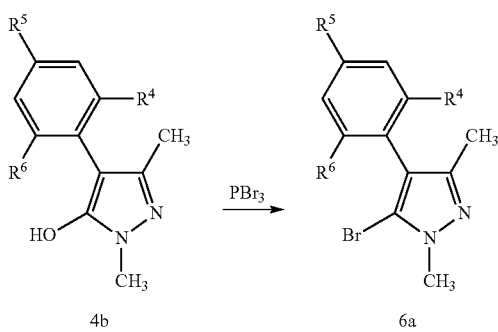

As shown in Scheme 6, 5-hydroxypyrazoles of Formula 4b can also be used to prepare 5-fluoroalkylsulfonyl (e.g., 5-trifluoromethanesulfonyl, 5-nonafluorobutylsulfonyl)pyrazoles of Formula 6b (i.e. Formula 6 wherein G is fluoroalkylsulfonyl) as described in *Synlett* 2004, 5, 795.

Scheme 6

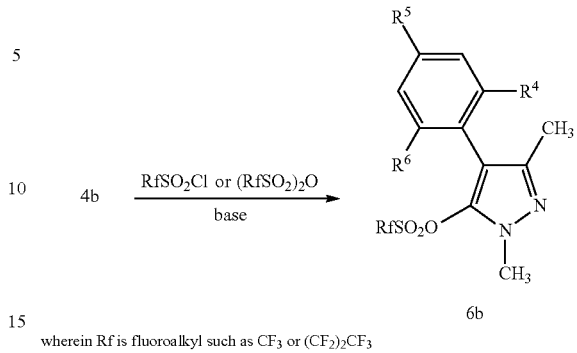

wherein Rf is fluoroalkyl such as $CF_3$ or $(CF_2)_2CF_3$

As shown in Scheme 7, compounds of Formula 1 can be prepared by reaction of 4-bromo or iodo pyrazoles of Formula 10 wherein X is O or NH with organometallic compounds of Formula 11 under transition-metal-catalyzed cross-coupling reaction conditions. Reaction of a 4-bromo or iodo pyrazole of Formula 10 with a boronic acid, trialkyltin, zinc or organomagnesium reagent of Formula 11 in the presence of a palladium or nickel catalyst having appropriate ligands (e.g., triphenylphosphine ($PPh_3$), dibenzylideneacetone (dba), dicyclohexyl(2',6'-dimethoxy[1,1'-biphenyl]-2-yl)phosphine (SPhos)) and a base, if needed, affords the corresponding compound of Formula 1. For example, a substituted aryl boronic acid or derivative e.g., Formula 11 wherein M is $B(OH)_2$, $B(OC(CH_3)_2C(CH_3)_2O))$ or $B(O-i-Pr)_3/Li.$, reacts with a 4-bromo- or 4-iodopyrazole of Formula 10 in the presence of dichlorobis(triphenylphosphine) palladium(II) and aqueous base such as sodium carbonate or potassium hydroxide, in solvents such as 1,4-dioxane, 1,2-dimethoxyethane, toluene or ethyl alcohol, or under anhydrous conditions with a ligand such as phosphine oxide or phosphite ligand (e.g., diphenylphosphine oxide) and potassium fluoride in a solvent such as 1,4-dioxane (see *Angewandte Chemie, International Edition* 2008, 47(25), 4695-4698) to provide the corresponding compound of Formula 1. The method of Scheme 7 is illustrated by Step C of present Synthesis Example 3.

Scheme 7

As illustrated in Scheme 8, compounds of Formula 4a (i.e. Formula 4 wherein X is NH) can be prepared by reacting compounds of Formula 12 with compounds of Formula 11a (e.g., compounds of Formula 11 wherein M is B(OH)$_2$) using transition-metal-catalyzed cross-coupling reaction conditions as described for the method of Scheme 7.

14 wherein X is NH can be prepared by methods known in the art. Furthermore, the compound of Formula 14 wherein X is NH is commercially available.

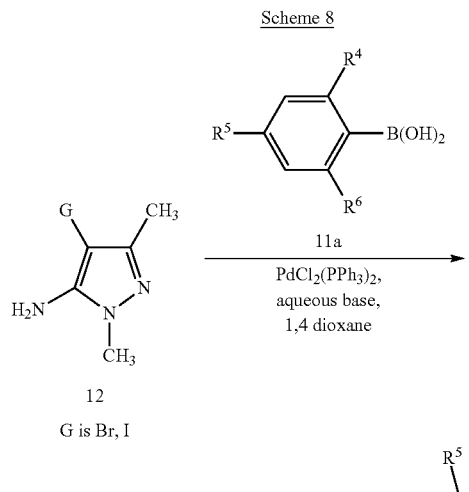

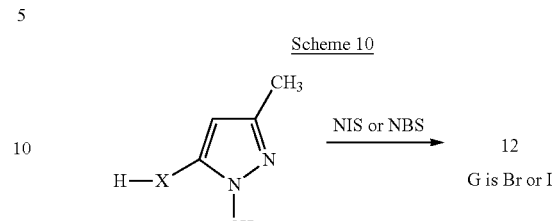

As shown in Scheme 11, compounds of Formula 13 wherein X is O or NH can be prepared from corresponding compounds of Formula 14 by procedures analogous to those used for the method of Scheme 2. The method of Scheme 11 is illustrated by Step A of Synthesis Example 3. Compounds of Formula 14 are commercially available or can be prepared by methods known in the art.

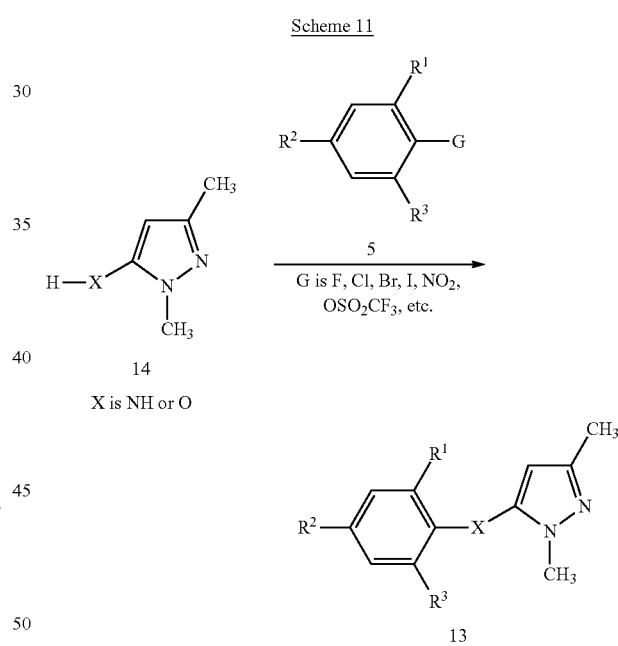

As illustrated in Scheme 9, pyrazoles of Formula 10 wherein X is O or NH and G is Br or I are readily prepared by the reaction of pyrazoles unsubstituted at the 4-position (Formula 13) with halogenating reagents such as bromine, sodium bromite, N-bromosuccinimide (NBS) or N-iodosuccinimide (NIS), in solvents such as acetic acid, acetonitrile, N,N-dimethylformamide, N,N-dimethylacetamide or 1,4-dioxane, or a mixture of water with the aforementioned solvents, at temperatures ranging from ambient to the boiling point of the solvent. The method of Scheme 9 is illustrated by Step B of Synthesis Example 3.

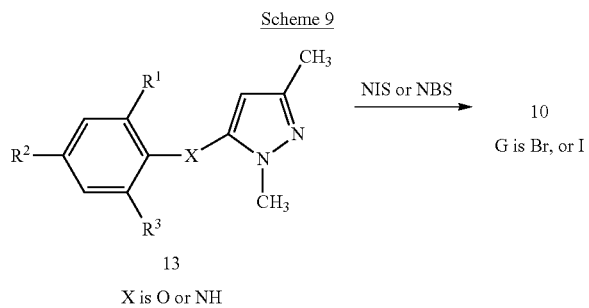

As illustrated in Scheme 10, using reaction conditions similar to those for the method of Scheme 9, the pyrazole of Formula 14 wherein X is NH can be converted into intermediates 12 which are useful for preparing compounds of Formula 4a as depicted in Scheme 8. The compound of Formula As shown in Scheme 12, compounds of Formula 1b (i.e. Formula 1 wherein X is CHOH), can be prepared by treatment of compounds of Formula 6 with an organometallic reagent (i.e. Formula 15) such as an alkyllithium, preferably n-butyllithium, or an alkylmagnesium reagent, preferably isopropylmagnesium chloride (optionally complexed with lithium chloride), followed by the addition of a substituted benzaldehyde of Formula 16. This method of Scheme 12 is illustrated by Synthesis Example 5. Alternatively, compounds of Formula 1b can be prepared by reduction of ketones of Formula 19 using standard methods well known in the art (e.g., sodium borohydride in methanol or methanol). Ketones of Formula 19 can be prepared by reaction of the same metalated pyrazole derivative of the compound of Formula 6 with carbon electrophiles of Formula 17 or 18. Reaction temperatures can range from −90° C. to the boiling point of the reaction solvent; temperatures of −78° C. to ambient temperature are generally preferred, with temperatures of −78 to −10° C. preferred when an alkyllithium reagent is used, and −20° C. to ambient temperature preferred with use of alkylmagnesium reagents. A variety of solvents are useful, such as toluene, ethyl ether, tetrahydrofuran or dimethoxymethane; anhydrous tetrahydrofuran is preferred. A second metallic component, such as zinc chloride, zinc bromide or a monovalent copper salt, such as copper(I) iodide or copper(I) cyanide, can advantageously be added before the electrophile in cases in which the electrophile is a compound of Formula 18. The carbonyl intermediates of Formula 16, 17 and 18 are commercially available or can be prepared by methods known in the art.

Scheme 12

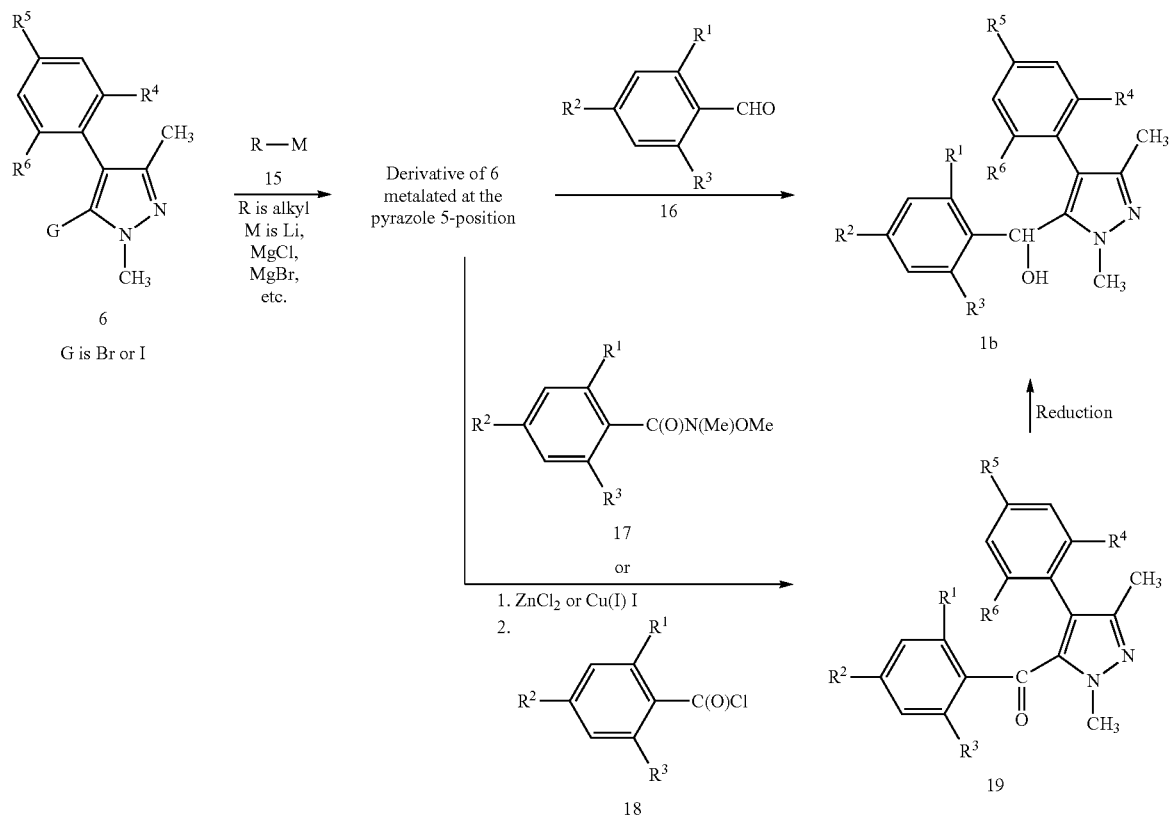

It will be recognized by one skilled in the art that reactions analogous to those shown in Scheme 12 can also be utilized with pyrazoles lacking a substituent in the 4 position, thus affording certain compounds of Formula 13 that are useful in the method outlined in Scheme 9.

General methods useful for preparing 5-aminopyrazoles of Formula 4a are well known in the art; see, for example, *Journal für Praktische Chemie (Leipzig)* 1911, 83, 171 and *J. Am. Chem. Soc.* 1954, 76, 501. Such a method is illustrated in Scheme 13. The method of Scheme 13 is illustrated by Step A of present Synthesis Example 1 and Step C of present Synthesis Example 2.

Scheme 13

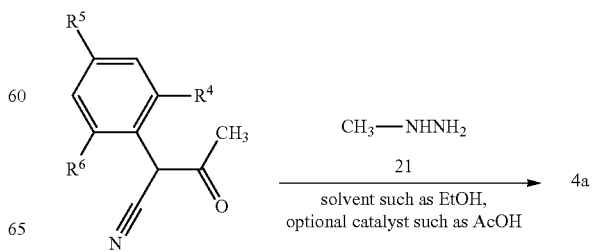

Similarly, general methods useful for preparing 5-hydroxypyrazoles of Formula 4b are well known in the art; see, for example, *Annalen der Chemie* 1924, 436, 88. Such a method is illustrated in Scheme 14. The method of Scheme 14 is illustrated by Step C of present Synthesis Example 6.

Scheme 14

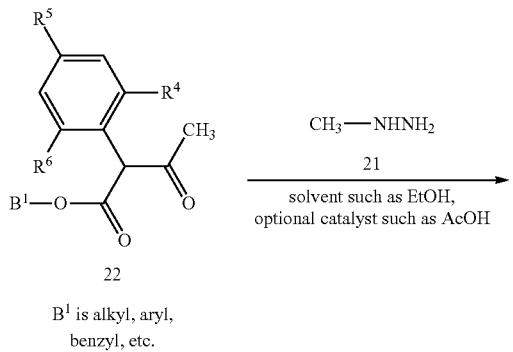

B¹ is alkyl, aryl, benzyl, etc.

As shown in Scheme 15, compounds of Formula 1a (i.e. Formula 1 wherein X is NH) can be prepared by condensing compounds of Formula 23 with methylhydrazine (Formula 21) in a solvent such as ethanol or methanol and optionally in the presence of an acid or base catalyst such as acetic acid, piperidine or sodium methoxide, according to general procedures known in the art. The method of Scheme 15 is illustrated by Step B of Synthesis Example 4, and Step C of Synthesis Example 7.

Scheme 15

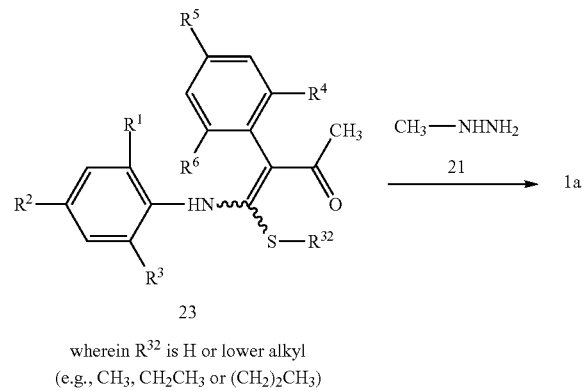

wherein $R^{32}$ is H or lower alkyl
(e.g., $CH_3$, $CH_2CH_3$ or $(CH_2)_2CH_3$)

In a manner analogous to the method of Scheme 15, compounds of Formula 2 wherein X is NH can be similarly prepared by condensing compounds of Formula 23 with hydrazine. This method is described in *Chemistry of Heterocyclic Compounds* 2005, 41(1), 105-110.

As shown in Scheme 16, compounds of Formula 23 (wherein, $R^{32}$ is H or lower alkyl such as $CH_3$, $CH_2CH_3$ or $(CH_2)_2CH_3$) can be prepared by reaction of corresponding ketene dithioacetal compounds of Formula 24 with compounds of Formula 7 optionally in the presence of a base, such as sodium hydride or ethylmagnesium chloride, in solvents such as toluene, tetrahydrofuran or dimethoxymethane, at temperatures ranging from −10° C. to the boiling point of the solvent. See, for example, *J. Heterocycl. Chem.* 1975, 12(1), 139. Methods useful for preparing compounds of Formula 24 are known in the art.

Scheme 16

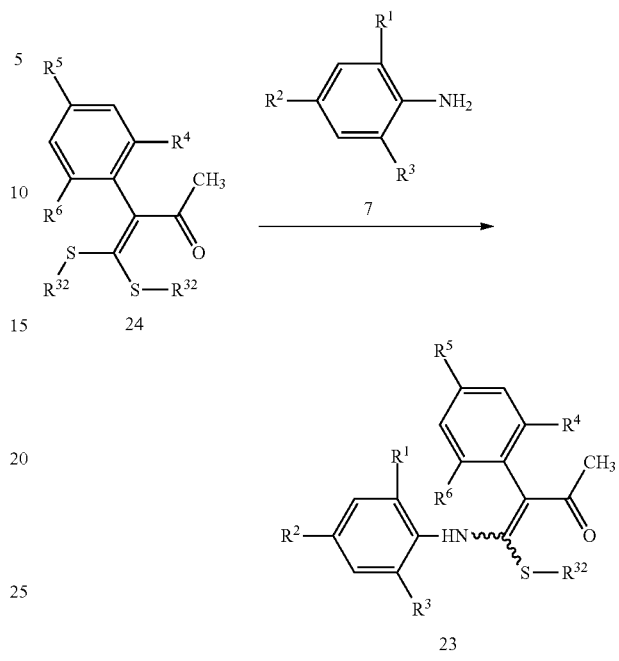

wherein $R^{32}$ is H or lower alkyl (e.g., $CH_3$, $CH_2CH_3$ or $(CH_2)_2CH_3$)

As shown in Scheme 17, compounds of Formula 23a (i.e. tautomer of Formula 23 wherein $R^{32}$ is H) can be prepared by reaction of corresponding isothiocyanate compounds of Formula 25 with arylacetone compounds of Formula 26; see, for example, *Zhurnal Organicheskoi Khimii* 1982, 18(12), 2501. Bases useful for this reaction include sodium hydride, alkoxide bases (e.g., potassium tert-butoxide or sodium ethoxide), potassium hydroxide, sodium hydroxide, potassium carbonate, or amine bases (e.g., triethylamine or N,N-diisopropylethylamine). A variety of solvents are useful, such as tetrahydrofuran, ether, toluene, N,N-dimethylformamide, alcohols (e.g., ethanol), esters (e.g., ethyl acetate or isopropyl acetate), or mixtures thereof. Solvents are chosen for compatibility with the base selected, as is well-known in the art. Reaction temperatures can range from −78° C. to the boiling point of the solvent. One useful mixture of base and solvent is potassium tert-butoxide in tetrahydrofuran, to which at −70 to 0° C. is added a solution of an isothiocyanate of Formula 25 and a carbonyl compound of Formula 26, which are either combined into one solution, or added separately, preferably by addition of the carbonyl compound followed by addition of the isothiocyanate. The method of Scheme 17 is illustrated by Step A of Synthesis Example 4, and Step C of Synthesis Example 7.

Scheme 17

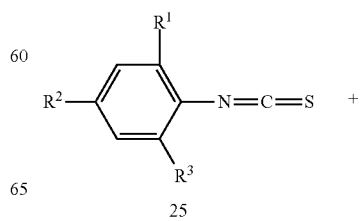

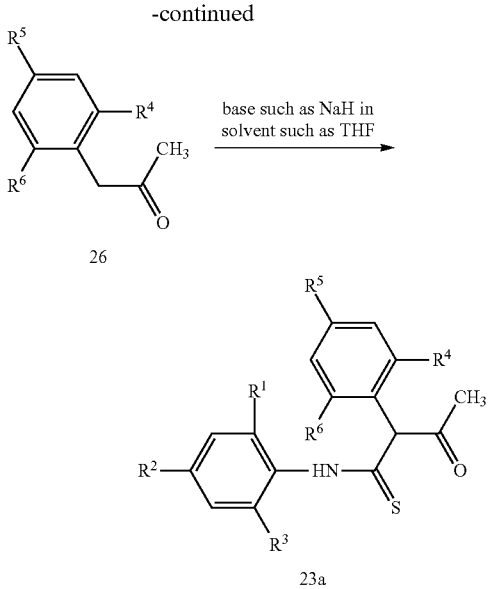

Ketothioamides of Formula 23a can be also be prepared by allowing the corresponding ketoamides to react with sulfurizing agents such as Lawesson's reagent or $P_2S_5$; see, for example, *Helv. Chim. Act.* 1998, 81(7), 1207.

It is recognized by one skilled in the art that various functional groups can be converted into others to provide different compounds of Formula 1. For example, intermediates for the preparation of compounds of Formula 1 may contain aromatic nitro groups, which can be reduced to amino groups, and then be converted via reactions well known in the art such as the Sandmeyer reaction, to various halides, providing compounds of Formula 1. By similar known reactions, aromatic amines (anilines) can be converted via diazonium salts to phenols, which can then be alkylated to prepare compounds of Formula 1 with alkoxy substituents. Likewise, aromatic halides such as bromides or iodides prepared via the Sandmeyer reaction can react with alcohols under copper-catalyzed conditions, such as the Ullmann reaction or known modifications thereof, to provide compounds of Formula 1 that contain alkoxy substituents. Additionally, some halogen groups, such as fluorine or chlorine, can be displaced with alcohols under basic conditions to provide compounds of Formula 1 containing the corresponding alkoxy substituents.

The above reactions can also in many cases be performed in alternate sequence, such as the preparation of 1H pyrazoles for use in the reaction in Scheme 2 by reactions illustrated later for the general preparation of substituted pyrazoles.

It is recognized that some reagents and reaction conditions described above for preparing compounds of Formula 1 may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Groups in Organic Synthesis,* 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula 1. One skilled in the art will also recognize that it may be necessary to perform a combination of the steps illustrated in the above schemes in an order other than that implied by the particular sequence presented to prepare the compounds of Formula 1. One skilled in the art will also recognize that compounds of Formula 1 and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps. Percentages are by weight except for chromatographic solvent mixtures or where otherwise indicated. Parts and percentages for chromatographic solvent mixtures are by volume unless otherwise indicated. $^1$H NMR spectra are reported in ppm downfield from tetramethylsilane in $CDCl_3$ unless otherwise noted; "s" means singlet, "m" means multiplet, "br s" means broad singlet. Mass spectra (MS) are reported as the molecular weight of the highest isotopic abundance parent ion (M+1) formed by addition of H$^+$ (molecular weight of 1) to the molecule, observed by mass spectrometry using atmospheric pressure chemical ionization (AP$^+$) where "amu" stands for atomic mass units. The presence of molecular ions containing one or more higher atomic weight isotopes of lower abundance (e.g., $^{37}$Cl, $^{81}$Br) is not reported. "LC/MS" refers the combination of physical separation of chemical compounds by liquid chromatography and mass analysis of the separated compounds by mass spectrometry.

Synthesis Example 1

Preparation of 4-(2-Chloro-4-fluorophenyl)-N-(2,6-difluoro-4-methoxyphenyl)-1,3-dimethyl-1H-pyrazol-5-amine (Compound 3)

Step A: Preparation of 4-[2-chloro-4-fluorophenyl]-1,3-dimethyl-1H-pyrazol-5-amine A suspension of dry, solid sodium ethoxide (Aldrich, 10.2 g, 150 mmol) in a mixture of xylenes (60 mL) and anhydrous ethanol (25 mL) was stirred at 70° C., and a solution of 2-chloro-4-fluorobenzeneacetonitrile (16.96 g, 100 mmol) in a mixture of ethyl acetate (30 mL) and ethanol (5 mL) was added dropwise to the hot reaction mixture over 20 minutes. The reaction mixture was heated at 75-78° C. for 3 h and then allowed to cool. Water (50 mL) was added to dissolve solids. The mixture was extracted once with ethyl acetate, and the extract was discarded. The aqueous phase was acidified to pH 2 by addition of 1 N aqueous hydrochloric acid, and then extracted with ethyl acetate (50 mL). The ethyl acetate phase was dried (MgSO$_4$) and evaporated to provide the intermediate product α-acetyl-2-chloro-4-fluorobenzeneacetonitrile as a solid (14.8 g).

A portion of the product obtained above (4.61 g, 21.8 mmol) was stirred in ethanol (15 mL), and glacial acetic acid (3 mL) and methylhydrazine (1.17 mL, 21.8 mol) were added. This reaction mixture was stirred and heated at overnight at reflux. The reaction mixture was then concentrated under reduced pressure, and the resultant residue was triturated with ethyl acetate. The resultant solids were collected on a glass frit and dried in air to afford the title compound as a white solid (2.42 g).

$^1$H NMR δ 7.2-7.3 (m, 2H), 7.0 (m, 1H), 3.7 (s, 3H), 3.4 (br s, 2H), 2.1 (s, 3H). MS: 240 amu (AP$^+$).

Step B: Preparation of 5-Bromo-4-(2-chloro-4-fluorophenyl)-1,3-dimethyl-1H-pyrazole Copper(II) bromide (3.94 g, 17.7 mmol) was added to a solution of 4-[2-chloro-4-fluorophenyl]-1,3-dimethyl-1H-pyrazol-5-amine (i.e. the product of Step A) (2.4 g, 10 mmol) in acetonitrile (50 mL), and the mixture was stirred and cooled in an ice-water bath while tert-butyl nitrite (90% technical grade, 2.33 mL, 17.7 mmol) was added dropwise over 5 min. The reaction mixture was allowed to warm slowly to ambient temperature. Aqueous HCl solution (20 mL) was added, and then ethyl acetate was added (20 mL). This mixture was filtered through a 2-cm pad of Celite® diatomaceous filter aid. The filter pad was washed with ethyl acetate (20 mL), and the phases were separated. The organic phase was washed with 1.0 N aqueous hydrochloric acid solution and brine, dried over MgSO$_4$, and concentrated to leave the title compound as an orange-brown semisolid (2.8 g).

$^1$H NMR δ 7.18-7.25 (m, 2H), 7.04 (m, 1H), 3.89 (s, 3H), 2.14 (s, 3H).

Step C: Preparation of 4-(2-Chloro-4-fluorophenyl)-N-(2,6-difluoro-4-methoxyphenyl)-1,3-dimethyl-1H-pyrazol-5-amine 5-Bromo-4-(2-chloro-4-fluorophenyl)-1,3-dimethyl-1H-pyrazole (i.e. the product of Step B) (0.20 g, 0.66 mmol), palladium(II) acetate (15 mg, 0.066 mmol), 4,5-bis(diphenylphosphino)-9,9-dimethylxanthene (76 mg, 0.13 mmol) and powdered potassium carbonate (1.8 g, 13 mmol) were combined in anhydrous 1,4-dioxane (3 mL), and the mixture was sparged with a subsurface stream of N$_2$ gas for 10 min. 2,6-Difluoro-4-methoxyaniline (0.22 g, 1.3 mmol) was added in one portion, and the reaction mixture was heated at reflux for 22 h. The reaction mixture was filtered through Celite® diatomaceous filter aid, and the filter pad was washed with ethyl acetate (20 mL). The filtrate was washed with water (10 mL) and brine (10 mL), dried over MgSO$_4$, and concentrated to leave a semisolid residue. This residue was purified by column chromatography through 5 g of silica gel eluted with a gradient of hexanes/ethyl acetate (20:1 to 1:3) to give the title compound as a light-brown solid (48 mg).

$^1$H NMR δ 7.0-7.1 (m, 2H), 6.85 (m, 1H), 6.26 (m, 2H), 4.84 (br s, 1H), 3.78 (s, 3H), 3.66 (s, 3H), 2.08 (s, 3H). MS: 382 amu (AP$^+$).

Synthesis Example 2

Preparation of 4-(2,6-Difluoro-4-methoxyphenyl)-1,3-dimethyl-N-(2,4,6-trifluorophenyl)-1H-pyrazol-5-amine (Compound 7)

Step A: Preparation of 2,6-Difluoro-4-methoxybenzeneacetonitrile

A solution of KCN (0.88 g, 13 mmol) dissolved in water (2 mL) was added dropwise to a water-bath-cooled solution of 2,6-difluoro-4-methoxybenzyl bromide (2.50 g, 10.5 mmol) in N,N-dimethylformamide (10 mL). The reaction mixture was stirred for 20 min. Water was added (20 mL) and then the reaction mixture was poured into saturated aqueous NaHCO$_3$ solution (20 mL) and extracted with ether (50 mL). The organic phase was washed with water (5×25 mL), dried over MgSO$_4$, and concentrated to give an oil, which crystallized on standing to provide the title compound as a white solid (1.9 g).

$^1$H NMR δ 6.50 (m, 2H), 3.80 (s, 3H), 3.65 (s, 2H).

Step B: Preparation of α-Acetyl-2,6-difluoro-4-methoxybenzeneacetonitrile

Solid sodium ethoxide (4.7 g, 66 mmol) was stirred in a mixture of xylene (20 mL) and ethanol (10 mL) and heated to 50° C. A solution of 2,6-difluoro-4-methoxybenzeneacetonitrile (i.e. the product of Step A) (8.0 g, 44 mmol) in ethyl acetate (10.4 mL) was added dropwise. The reaction mixture was heated at 50° C. for 4 h and then allowed to cool to ambient temperature. The reaction mixture was poured into water (100 mL) and extracted with ethyl acetate (25 mL). The aqueous phase was acidified with 3 N aqueous HCl to pH 4 and extracted with ethyl acetate (100 mL). This organic phase was washed with water (50 mL), brine (50 mL), then dried over MgSO$_4$, and concentrated to leave the title compound as a tan semisolid (8.0 g).

$^1$H NMR δ 6.56 (m, 2H), 4.86 (s, 1H), 3.83 (s, 3H), 2.40 (s, 3H).

Step C: Preparation of 4-(2,6-Difluoro-4-methoxyphenyl)-1,3-dimethyl-1H-pyrazole-5-amine α-Acetyl-2,6-difluoro-4-methoxybenzeneacetonitrile (i.e. the product of Step B) (8.03 g, 35.7 mmol) and acetic acid (5 mL) were stirred in ethanol (35 mL), and methylhydrazine (1.91 mL, 35.7 mmol) was added. The reaction mixture was heated at reflux for 16 h, cooled, and then poured into water (100 mL). The resulting mixture was extracted with ethyl acetate (100 mL). The organic phase was washed with 1 N aqueous NaOH (50 mL) and then brine (50 mL), dried over MgSO$_4$, and concentrated to leave a solid. The solid was dissolved in methanol, and the resulting solution was warmed to 45° C. Water (25 mL) was added dropwise, and the mixture was allowed to cool. The precipitate was collected on a glass frit to give the title compound as a white solid (3.88 g).

$^1$H NMR δ 6.55 (m, 2H), 3.81 (s, 3H), 3.67 (s, 3H), 3.43 (br s, 2H), 2.09 (s, 3H).

Step D: Preparation of 5-Bromo-4-(2,6-difluoro-4-methoxyphenyl)-1,3-dimethyl-1H-pyrazole Copper(II) bromide (3.81 g, 16.9 mmol) was added to a solution of 4-(2,6-difluoro-4-methoxyphenyl)-1,3-dimethyl-1H-pyrazole-5-amine (i.e. the product of Step C) (3.88 g, 15.4 mmol) in acetonitrile (50 mL), and the mixture was stirred and cooled in an ice-water bath while tert-butyl nitrite (90% technical grade, 3.54 mL, 26.9 mmol) was added dropwise over 5 min. The reaction mixture was allowed to warm slowly to ambient temperature. Aqueous hydrochloric acid solution (25 mL) was added, then ethyl acetate (25 mL) was added, and the resulting mixture was filtered through a 2-cm pad of Celite® diatomaceous filter aid. The filter pad was washed with ethyl acetate (50 mL), and the phases were separated. The organic phase was washed with 1 N aqueous HCl solution (25 mL) and brine (25 mL), dried over MgSO$_4$, and concentrated. The residue was purified by column chromatography through 24 g of silica gel eluted with a gradient of hexanes/ethyl acetate (9:1 to 1:1) to give the title compound as a white solid (3.25 g).

¹H NMR δ 6.54 (m, 2H), 3.88 (s, 3H), 3.83 (s, 3H), 2.16 (s, 3H).

Step E: Preparation of 4-(2,6-Difluoro-4-methoxyphenyl)-1,3-dimethyl-N-(2,4,6-trifluorophenyl)-1H-pyrazol-5-amine 5-Bromo-4-(2,6-difluoro-4-methoxyphenyl)-1,3-dimethyl-1H-pyrazole (i.e. the product of Step D) (0.30 g, 0.94 mmol), palladium(II) acetate (20 mg, 0.090 mmol), 4,5-bis(diphenylphosphino)-9,9-dimethylxanthene (0.11 g, 0.19 mmol) and powdered potassium carbonate (2.6 g, 19 mmol) were combined in anhydrous 1,4-dioxane (4 mL), and the resulting mixture was sparged with a subsurface stream of $N_2$ gas for 10 min. 2,4,6-Trifluoroaniline (0.28 g, 1.9 mmol) was added in one portion, and the reaction mixture was heated at reflux under nitrogen for 22 h. The reaction mixture was cooled, then filtered through Celite® diatomaceous filter aid. The filter pad was washed with ethyl acetate (20 mL), and the filtrate was washed with water (10 mL) and brine (10 mL), dried over $MgSO_4$, and concentrated to leave a semisolid residue. The residue was purified by column chromatography through 12 g of silica gel eluted with a gradient of hexanes/ethyl acetate (20:1 to 1:3) to give the title compound as a semisolid (73 mg).
¹H NMR (acetone-$d_6$) δ 6.84 (br s, 1H), 6.68 (m, 2H), 6.43 (m, 2H), 3.77 (s, 3H), 3.75 (s, 3H), 1.99 (s, 3H). MS: 384 amu (AP⁺).

Synthesis Example 3

Preparation of 4-[[4-(2-Chloro-4-fluorophenyl)-1,3-dimethyl-1H-pyrazol-5-yl]oxy]-3,5-difluorobenzonitrile (Compound 13)

Step A: Preparation of 4-[(1,3-Dimethyl-1H-pyrazol-5-yl)oxy]-3,5-difluorobenzonitrile Potassium carbonate (1.38 g, 10 mmol) was added to a solution of 2,4-dihydro-2,5-dimethyl-3H-pyrazol-3-one (0.70 g, 6.3 mmol) in N,N-dimethylformamide (15 mL). 3,4,5-Trifluorobenzonitrile (0.94 g, 6.0 mmol) was added, and the reaction mixture was heated at 75° C. under a nitrogen atmosphere for 16 h, then allowed to cool. The reaction mixture was partitioned between water (60 mL) and ethyl acetate (30 mL). The organic phase was washed with water (2×30 mL) and brine (30 mL), dried over $MgSO_4$, and concentrated to give the title compound as a yellow oil (1.38 g).
¹H NMR δ 7.36 (m, 2H), 5.24 (s, 1H), 3.78 (s, 3H), 2.16 (s, 3H).

Step B: Preparation of 3,5-Difluoro-4-[(4-iodo-1,3-dimethyl-1H-pyrazol-5-yl)oxy]benzonitrile A solution of 4-[(1,3-dimethyl-1H-pyrazol-5-yl)oxy]-3,5-difluorobenzonitrile (i.e. the product of Step A) (1.38 g, 5.5 mmol) in acetonitrile (20 mL) was stirred at ambient temperature, and N-iodosuccinimide (1.35 g, 6.0 mmol) was added in one portion. The reaction mixture was heated at reflux for 2 h, cooled, and then poured into water (40 mL). The resulting mixture was extracted with ethyl acetate (40 mL). The organic phase was washed with water (20 mL) and saturated aqueous $NaHCO_3$ solution (20 mL), dried over $MgSO_4$, and concentrated under reduced pressure to give the title compound as a tan solid (2.1 g).
¹H NMR (acetone-$d_6$) δ 7.80 (m, 2H), 3.82 (s, 3H), 2.09 (s, 3H). MS: 376 amu (AP⁺).

Step C: Preparation of 4-[[4-(2-Chloro-4-fluorophenyl)-1,3-dimethyl-1H-pyrazol-5-yl]oxy]-3,5-difluorobenzonitrile To a solution of 3,5-difluoro-4-[(4-iodo-1,3-dimethyl-1H-pyrazol-5-yl)oxy]-benzonitrile (i.e. the product of Step B) (1.0 g, 2.67 mmol) in 1,4-dioxane (6 mL) was added 2-chloro-4-fluorobenzeneboronic acid (alternatively named B-(2-chloro-4-fluorophenyl)-boronic acid) (0.93 g, 5.33 mmol), dichloro(bis)triphenylphosphine palladium(II) (alternatively named bis(triphenylphosphine)palladium(II) dichloride) (93 mg, 0.13 mmol), potassium carbonate (0.74 g, 5.33 mmol), and water (4 mL). The resulting mixture was heated at reflux for 5 h, allowed to cool, and partitioned between water (20 mL) and ethyl acetate (20 mL). The organic layer was dried over $MgSO_4$ and concentrated. The residue was purified by chromatography on silica gel with a gradient of hexanes/ethyl acetate to obtain the title compound as an off-white solid (110 mg).
¹H NMR δ 7.00-7.09 (m, 3H), 6.97 (m, 1H), 6.86 (m, 1H), 3.85 (s, 3H), 2.02 (s, 3H).

Synthesis Example 4

Preparation of 4-(2,4-Dichlorophenyl)-N-(2,4-difluorophenyl)-1,3-dimethyl-1H-pyrazol-5-amine (Compound 17)

Step A: Preparation of α-Acetyl-2,4-dichloro-N-(2,4-difluorophenyl)benzeneethanethioamide 2,4-Difluorophenyl isothiocyanate (0.27 mL, 2.0 mmol) was added to a stirred suspension of sodium hydride (60% in mineral oil) (112 mg, 2.8 mmol) in anhydrous tetrahydrofuran (4 mL) cooled in an ice-water bath under a nitrogen atmosphere. A solution of 1-(2,4-dichlorophenyl)-2-propanone (570 mg, 2.8 mmol) in tetrahydrofuran (4 mL) was added dropwise over 5 min. The resultant yellow solution was stirred at 5-10° C. for 1 h. Water (10 mL) was carefully added, and the reaction mixture was extracted with ethyl acetate (10 mL). The aqueous phase was acidified to pH 3 with 1 N aqueous HCl, then extracted with ethyl acetate (20 mL). The organic extract was washed with water (10 mL) and brine (10 mL), dried over $MgSO_4$, and concentrated to leave a solid. The solid was triturated with hexanes/ethyl acetate (2:1), collected on a glass frit, and air-dried to give the title compound as a white solid (240 mg). MS: 373 amu (AP⁺).

Step B: Preparation of 4-(2,4-Dichlorophenyl)-N-(2,4-difluorophenyl)-1,3-dimethyl-1H-pyrazol-5-amine Acetic acid (50 μL) and methylhydrazine (41 μL) were added to a stirred suspension of α-acetyl-2,4-dichloro-N-(2,4-difluorophenyl)benzeneethanethioamide (238 mg, 0.64 mmol) in ethanol (4 mL). The reaction mixture was heated at reflux for 2 h and allowed to cool. Then the reaction mixture was diluted with ethyl acetate (10 mL) and washed with 1 N aqueous NaOH (10 mL), water (10 mL) and brine (10 mL), dried over $MgSO_4$, and concentrated to leave a solid residue. The residue was purified by column chromatography on 5 g of silica gel with a gradient of hexanes/ethyl acetate (2:1 to 1:1) to give the title compound as a solid (170 mg).

¹H NMR δ 7.43 (s, 1H), 7.19 (m, 1H), 7.07 (m, 1H), 6.78 (m, 1H), 6.62 (m, 1H), 6.37 (m, 1H), 5.22 (br s, 1H), 3.70 (s, 3H), 2.18 (s, 3H). MS: 368 amu (AP⁺).

Synthesis Example 5

Preparation of 4-(2-Chloro-4-fluorophenyl)-α-(2,4-difluorophenyl)-1,3-dimethyl-1H-pyrazole-5-methanol (Compound 122)

5-Bromo-4-(2-chloro-4-fluorophenyl)-1,3-dimethyl-1H-pyrazole (i.e. the product of Synthesis Example 1, Step B) (0.25 g, 0.82 mmol) was dissolved in anhydrous tetrahydrofuran (12 mL), and the mixture was cooled in a dry ice/acetone bath under a nitrogen atmosphere. A hexane solution of n-butyllithium (2.0 M, 0.49 mL, 0.98 mmol) was added dropwise over 5 minutes. After 15 minutes, a solution of 2,4-difluorobenzaldehyde (0.09 mL, 0.82 mmol) in anhydrous tetrahydrofuran (3 mL) was added slowly dropwise, causing the dark red-colored solution to lighten to a yellow color. After 45 minutes, the reaction mixture was quenched by the addition of saturated aqueous NH₄Cl solution (~20 mL) and allowed to warm to ambient temperature. This mixture was extracted with ethyl acetate, and the organic phase was washed with saturated aqueous NH₄Cl solution (25 mL) and with brine, dried over Na₂SO₄, and concentrated to leave a viscous residue. This residue was purified by column chromatography through silica gel eluted with a gradient of ethyl acetate in hexane (7% to 10%) to give the title compound as a white semi-solid (109 mg).

¹H NMR δ 7.5 (m, 1H), 7.1 (m, 2H), 7.0 (m, 1H), 6.85 (m, 2H), 6.0 (br s, 1H), 5.9 (s, 1H), 3.8 (s, 3H), 2.1 (s, 3H). MS: 367 amu (AP⁺).

Synthesis Example 6

Preparation of 4-[[1,3-Dimethyl-4-(2,4,6-trifluorophenyl)-1H-pyrazol-5-yl]oxy]-3,5-difluorobenzonitrile (Compound 8)

Step A: Preparation of Methyl 2,4,6-trifluorobenzeneacetate

A solution of 2,4,6-trifluorobenzeneacetic acid (5.00 g, 26.3 mmol) in methanol (25 mL) was stirred at ambient temperature, and thionyl chloride (6 mL, ~3 eq.) was added dropwise, causing the temperature of the reaction mixture to reach 60° C. The reaction mixture was allowed to cool to ambient temperature and was stirred for 3 h. Water (25 mL) was added with ice cooling. The mixture was extracted with ethyl acetate (2×100 mL). The combined organic phases were sequentially washed with water (2×), saturated aqueous sodium bicarbonate solution and brine, and then dried (MgSO₄). Concentration provided the title compound as a clear oil (5.38 g).

¹H NMR δ 6.68 (m, 2H), 3.72 (s, 3H), 3.66 (s, 2H).

Step B: Preparation of Methyl α-acetyl-2,4,6-trifluorobenzeneacetate

To a commercially obtained tetrahydrofuran solution of lithium bis(trimethyl-silyl)amide (1.0 M, 21.0 mL) stirred under a nitrogen atmosphere and cooled to an internal temperature of −65° C., was added dropwise over 30 minutes a solution of methyl 2,4,6-trifluorobenzeneacetate (i.e. the product of Step A) (2.04 g, 10.0 mmol) dissolved in dry tetrahydrofuran (10 mL). The reaction mixture was stirred for an additional 30 minutes, and then while maintaining the −65° C. temperature, a solution of freshly distilled acetyl chloride (0.80 mL, 11 mmol) in dry tetrahydrofuran (3 mL) was added dropwise. The reaction mixture was allowed to warm slowly to ambient temperature, and then water (30 mL) was added. The resultant mixture was extracted with ethyl acetate (60 mL). The aqueous phase was acidified with 1 N hydrochloric acid and extracted with ethyl acetate (60 mL). Only the first ethyl acetate extract was retained, because thin layer chromatographic analysis showed the second extract to contain apparent polar impurities besides additional desired product. The first ethyl acetate extract was further sequentially washed with 1 N hydrochloric acid, water and brine, dried (MgSO₄), and concentrated to provide the title compound as a clear oil (1.86 g).

¹H NMR δ 6.69 (m, 2H), 3.7 (m, 1H and s, 3H), 1.87 (s, 3H); minor resonances at 13.2 ppm and 4.9 ppm indicated presence of enolic tautomer.

Step C: Preparation of 1,3-Dimethyl-4-(2,4,6-trifluorophenyl)-1H-pyrazol-5-ol

To a solution of methyl α-acetyl-2,4,6-trifluorobenzeneacetate (i.e. the product of Step B) (2.46 g, 10.0 mmol) in methanol (15 mL) was added methylhydrazine (0.665 mL, 12.5 mmol), and the mixture was stirred at ambient temperature over 3 days. Aqueous citric acid solution (1 M, 10 mL) was added, and then water (50 mL) was added. The mixture was extracted with ethyl acetate (2×50 mL). The combined ethyl acetate extracts were sequentially washed with water and brine, dried (MgSO₄), and concentrated to leave a yellow solid. This solid was suspended in a small volume of ethyl acetate (~5 mL), an equal volume of hexanes was gradually added, and the suspension was stirred for 30 minutes. The solid component was collected on a glass frit, washed with small portions of ethyl acetate/hexanes (1:1 and 1:2 v:v), and allowed to dry in air to provide a white solid (1.02 g). Evaporation of the mother liquor and treatment of the resultant residue with small volumes of ethyl acetate and hexanes as already described provided an additional 0.13 g of solid containing the title compound (1.15 g total). Analysis of the combined solids by LC/MS showed a primary component of mass 242 (AP⁺) and a minor component, eluting later by reverse-phase LC, also having a mass of 242 (AP⁺), thus being a regioisomer of the title compound. The apparent ratio of components was 94:6.

¹H NMR (acetone-d₆) δ 6.95 (m, 2H), 3.52 (s, 3H), 1.98 (s, 3H); 5-hydroxy resonance was not observed in this solvent.

Step D: Preparation of 4-[[1,3-Dimethyl-4-(2,4,6-trifluorophenyl)-1H-pyrazol-5-yl]oxy]-3,5-difluorobenzonitrile A solution of 1,3-dimethyl-4-(2,4,6-trifluorophenyl)-1H-pyrazol-5-ol (i.e. the product of Step C) (104 mg, 0.43 mmol) in anhydrous N,N-dimethylformamide (2.5 mL) was cooled in an ice-water bath under a nitrogen atmosphere, and sodium hydride (60% suspension in mineral oil, 20 mg, 0.46 mmol) was added in one portion. After 15 minutes, 3,4,5-trifluorobenzonitrile (101 mg, 0.64 mmol) was added in one portion. The reaction mixture was allowed to reach ambient temperature, and then it was heated at 40° C. for 2.5 h. Water (~10 mL) was added, and the mixture was extracted with ethyl acetate (2×~10 mL). The combined ethyl acetate extracts were sequentially washed with water (3×10 mL) and brine, dried (MgSO₄), and concentrated under reduced pressure. Chromatography on silica gel (5 g), eluting with a 2:1 mixture of hexanes-ethyl acetate, afforded a product (51 mg) containing the title compound in a 92:8 mixture with its regioisomer.

$^1$H NMR δ 7.1 (m, 2H), 6.5-6.6 (m, 2H), 3.85 (s, 3H), 2.05 (s, 3H). MS: 380 amu (AP$^+$).

Synthesis Example 7

Preparation of 4-(2-Bromo-4-fluorophenyl)-N-(2-chloro-6-fluorophenyl)-1,3-dimethyl-1H-pyrazol-5-amine (Compound 240)

Step A: Preparation of 1-(2-Bromo-4-fluorophenyl)-2-propanone

A solution of sodium methoxide in methanol (25%, 34 mL, 157 mmol) was combined with toluene (200 mL). The methanol was then distilled off at 90° C. using a Dean-Stark trap. After the solution was cooled to 70° C., 2-bromo-4-fluorobenzeneacetonitrile (21.4 g, 100 mmol) dissolved in ethyl acetate (40 mL) was added from a dropping funnel over 20 min with mechanical stirring. At this point additional toluene (150 mL) was added to facilitate stirring of a voluminous light pink precipitate. The reaction mixture was poured into water, and the organic phase was separated. The aqueous phase was acidified and extracted with ethyl acetate. The ethyl acetate phase was dried and concentrated under reduced pressure to provide the intermediate compound α-acetyl-2-bromo-4-fluorobenzeneacetonitrile as a crude oil.

The crude oil was dissolved in sulfuric acid (60%, 170 mL) and refluxed for 6.5 h. The reaction mixture was then extracted with hexanes (2×100 mL), and the combined hexane extracts were washed with water and brine, dried (MgSO$_4$) and concentrated under reduced pressure to yield the title compound as a yellow oil (14.7 g), which was used without further purification in Step C.

$^1$H NMR δ 7.33 (m, 1H), 7.18 (m, 1H), 7.01 (m, 1H), 3.85 (s, 2H), 2.23 (s, 3H).

Step B: Preparation of 1-Chloro-3-fluoro-2-isothiocyanatobenzene

To a solution of 2-chloro-6-fluorobenzenamine (5.0 g, 34 mmol) in chlorobenzene (52 mL) was added carbonothioic dichloride (thiophosgene) (5.1 g, 45 mmol) and DMF (0.27 mL). The reaction mixture was refluxed for 2 h and then concentrated to leave the title compound as a brown oil (6.15 g), which was used in Step C without further purification.

$^1$H NMR δ 7.18 (m, 2H), 7.07 (m, 1H).

Step C: Preparation of 4-(2-Bromo-4-fluorophenyl)-N-(2-chloro-6-fluorophenyl)-1,3-dimethyl-1H-pyrazol-5-amine To a solution of potassium tert-butoxide (0.41 g, 3.3 mmol) in THF (20 mL) at 0° C. was added a solution of 1-(2-bromo-4-fluorophenyl)-2-propanone (i.e. the product of Step A) (0.70 g, 3.0 mmol) in THF (10 mL) over 5 minutes. Stirring was continued for 1 h and then the temperature was reduced to −10° C. A solution of 1-chloro-3-fluoro-2-isothiocyanatobenzene (i.e. the product of Step B) (0.57 g, 3.0 mmol) in THF (10 mL) was added over 6 minutes, and stirring was continued for 15 minutes. Iodomethane (0.54 g, 3.8 mmol) was added, and the cooling bath was removed to provide a reaction mixture containing the intermediate compound α-acetyl-2-bromo-N-(2-chloro-6-fluorophenyl)-4-fluorobenzeneethanethioamide. After 5 min, water (0.2 mL, 11 mmol), glacial acetic acid (0.53 mL, 9.1 mmol) and methylhydrazine (0.81 mL, 15 mmol) were added in rapid succession, and the reaction mixture was heated to reflux for 6 h. The crude reaction mixture was then concentrated under reduced pressure and purified by MPLC (0 to 100% ethyl acetate in hexanes as eluent) to provide the title product, a compound of the present invention, as an off-white solid (0.55 g).

$^1$H NMR δ 7.24 (m, 1H), 7.04 (m, 1H), 6.95 (m, 1H), 6.87 (m, 1H), 6.78 (m, 1H), 6.68 (m, 1H), 5.45 (d, 1H), 3.80 (s, 3H), 2.10 (s, 3H).

By the procedures described herein together with methods known in the art, the compounds disclosed in the Tables that follow can be prepared. The following abbreviations are used in the Tables which follow: Me means methyl, MeO means methoxy, EtO means ethoxy, and CN means cyano. Because of symmetry, $R^1$ can be interchanged with $R^3$, and $R^4$ can be interchanged with $R^6$, if allowed by the definitions of $R^1$, $R^3$, $R^4$ and $R^6$.

TABLE 1

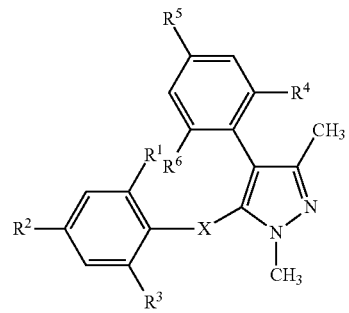

| $R^1$ | $R^2$ | $R^3$ | $R^1$ | $R^2$ | $R^3$ |
|---|---|---|---|---|---|
| F | H | H | F | H | F |
| F | F | H | F | F | F |
| F | CN | F | F | MeO | F |
| F | EtO | F | F | Cl | H |
| F | Cl | Cl | F | H | Cl |
| F | Br | H | F | H | Br |
| F | Cl | F | F | Br | F |
| F | I | H | F | F | I |
| F | I | F | F | CN | H |
| F | MeO | H | F | EtO | H |
| Cl | H | H | Cl | H | Cl |
| Cl | Cl | H | Cl | Cl | Cl |
| Cl | CN | Cl | Cl | MeO | Cl |
| Cl | EtO | Cl | Cl | F | H |
| Cl | F | F | Cl | F | Cl |
| Cl | Br | H | Cl | H | Br |
| Cl | Br | Br | Cl | Br | Cl |
| Cl | I | H | Cl | CN | H |
| Cl | MeO | H | Cl | EtO | H |
| Br | H | H | Br | F | H |
| Br | Cl | H | Br | Br | H |
| Br | F | F | Br | Br | F |
| Br | Cl | F | Br | F | Cl |
| Br | Cl | Cl | Br | F | Br |
| Br | CN | Br | Br | MeO | Br |
| Br | EtO | Br | Br | CN | H |
| Br | MeO | H | Br | EtO | H |
| Br | I | H | I | H | H |
| I | F | H | I | F | F |
| I | Cl | F | I | Cl | Cl |
| Br | H | Cl | Br | H | Br |
| I | H | F | I | H | Cl |
| Me | H | H | Me | H | F |
| Me | F | H | Me | F | F |
| Me | CN | F | Me | MeO | F |
| Me | EtO | F | Me | Cl | H |
| Me | Cl | Cl | Me | H | Cl |
| Me | Br | H | Me | H | Br |
| Me | Cl | F | Me | Br | F |

TABLE 1-continued

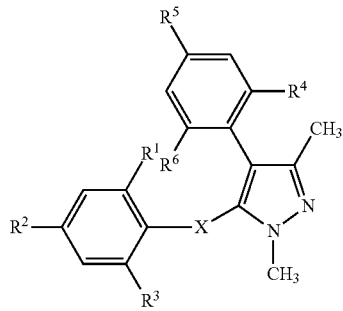

| $R^1$ | $R^2$ | $R^3$ | $R^1$ | $R^2$ | $R^3$ |
|---|---|---|---|---|---|
| Me | I | H | Me | F | I |
| Me | I | F | Me | CN | H |
| Me | MeO | H | Me | EtO | H |
| Me | H | Me | Me | Cl | Me |

$R^4$ is F, $R^5$ is H, $R^6$ is H, and X is NH.

The present disclosure also includes Tables 2 through 180, each of which is constructed the same as Table 1 above, except that the row heading in Table 1 (i.e. "$R^4$ is F, $R^5$ is H, $R^6$ is H, and X is NH.") is replaced with the respective row heading shown below. For Example, in Table 2 the row heading is "$R^4$ is F, $R^5$ is H, $R^6$ is F, and X is NH.", and $R^4$, $R^5$, and $R^6$ are as defined in Table 1 above. Thus, the first entry in Table 2 specifically discloses 4-(2,6-difluorophenyl)-N-(2-fluorophenyl)-1,3-dimethyl-1H-pyrazol-5-amine).

| Table | Row Heading |
|---|---|
| 2 | $R^4$ is F, $R^5$ is H, $R^6$ is F, and X is NH. |
| 3 | $R^4$ is F, $R^5$ is H, $R^6$ is Cl, and X is NH. |
| 4 | $R^4$ is F, $R^5$ is H, $R^6$ is Br, and X is NH. |
| 5 | $R^4$ is F, $R^5$ is Br, $R^6$ is H, and X is NH. |
| 6 | $R^4$ is F, $R^5$ is Br, $R^6$ is F, and X is NH. |
| 7 | $R^4$ is F, $R^5$ is Cl, $R^6$ is Cl, and X is NH. |
| 8 | $R^4$ is F, $R^5$ is Cl, $R^6$ is F, and X is NH. |
| 9 | $R^4$ is F, $R^5$ is Cl, $R^6$ is H, and X is NH. |
| 10 | $R^4$ is F, $R^5$ is —CN, $R^6$ is F, and X is NH. |
| 11 | $R^4$ is F, $R^5$ is —CN, $R^6$ is H, and X is NH. |
| 12 | $R^4$ is F, $R^5$ is F, $R^6$ is H, and X is NH. |
| 13 | $R^4$ is F, $R^5$ is F, $R^6$ is F, and X is NH. |
| 14 | $R^4$ is F, $R^5$ is F, $R^6$ is I, and X is NH. |
| 15 | $R^4$ is F, $R^5$ is I, $R^6$ is H, and X is NH. |
| 16 | $R^4$ is F, $R^5$ is I, $R^6$ is F, and X is NH. |
| 17 | $R^4$ is F, $R^5$ is EtO, $R^6$ is F, and X is NH. |
| 18 | $R^4$ is F, $R^5$ is EtO, $R^6$ is H, and X is NH. |
| 19 | $R^4$ is F, $R^5$ is MeO, $R^6$ is F, and X is NH. |
| 20 | $R^4$ is F, $R^5$ is MeO, $R^6$ is H, and X is NH. |
| 21 | $R^4$ is Cl, $R^5$ is H, $R^6$ is H, and X is NH. |
| 22 | $R^4$ is Cl, $R^5$ is H, $R^6$ is Cl, and X is NH. |
| 23 | $R^4$ is Cl, $R^5$ is H, $R^6$ is Br, and X is NH. |
| 24 | $R^4$ is Cl, $R^5$ is Br, $R^6$ is H, and X is NH. |
| 25 | $R^4$ is Cl, $R^5$ is Br, $R^6$ is Br, and X is NH. |
| 26 | $R^4$ is Cl, $R^5$ is Br, $R^6$ is Cl, and X is NH. |
| 27 | $R^4$ is Cl, $R^5$ is Cl, $R^6$ is H, and X is NH. |
| 28 | $R^4$ is Cl, $R^5$ is Cl, $R^6$ is Cl, and X is NH. |
| 29 | $R^4$ is Cl, $R^5$ is —CN, $R^6$ is Cl, and X is NH. |
| 30 | $R^4$ is Cl, $R^5$ is —CN, $R^6$ is H, and X is NH. |
| 31 | $R^4$ is Cl, $R^5$ is F, $R^6$ is F, and X is NH. |
| 32 | $R^4$ is Cl, $R^5$ is F, $R^6$ is H, and X is NH. |
| 33 | $R^4$ is Cl, $R^5$ is F, $R^6$ is Cl, and X is NH. |
| 34 | $R^4$ is Cl, $R^5$ is I, $R^6$ is H, and X is NH. |
| 35 | $R^4$ is Cl, $R^5$ is EtO, $R^6$ is Cl, and X is NH. |
| 36 | $R^4$ is Cl, $R^5$ is EtO, $R^6$ is H, and X is NH. |
| 37 | $R^4$ is Cl, $R^5$ is MeO, $R^6$ is Cl, and X is NH. |
| 38 | $R^4$ is Cl, $R^5$ is MeO, $R^6$ is H, and X is NH. |
| 39 | $R^4$ is Br, $R^5$ is H, $R^6$ is H, and X is NH. |

-continued

| Table | Row Heading |
|---|---|
| 40 | $R^4$ is Br, $R^5$ is Br, $R^6$ is H, and X is NH. |
| 41 | $R^4$ is Br, $R^5$ is Br, $R^6$ is F, and X is NH. |
| 42 | $R^4$ is Br, $R^5$ is Cl, $R^6$ is H, and X is NH. |
| 43 | $R^4$ is Br, $R^5$ is Cl, $R^6$ is F, and X is NH. |
| 44 | $R^4$ is Br, $R^5$ is Cl, $R^6$ is Cl, and X is NH. |
| 45 | $R^4$ is Br, $R^5$ is —CN, $R^6$ is Br, and X is NH. |
| 46 | $R^4$ is Br, $R^5$ is —CN, $R^6$ is H, and X is NH. |
| 47 | $R^4$ is Br, $R^5$ is F, $R^6$ is F, and X is NH. |
| 48 | $R^4$ is Br, $R^5$ is F, $R^6$ is H, and X is NH. |
| 49 | $R^4$ is Br, $R^5$ is F, $R^6$ is Cl, and X is NH. |
| 50 | $R^4$ is Br, $R^5$ is F, $R^6$ is Br, and X is NH. |
| 51 | $R^4$ is Br, $R^5$ is I, $R^6$ is H, and X is NH. |
| 52 | $R^4$ is Br, $R^5$ is EtO, $R^6$ is Br, and X is NH. |
| 53 | $R^4$ is Br, $R^5$ is EtO, $R^6$ is H, and X is NH. |
| 54 | $R^4$ is Br, $R^5$ is MeO, $R^6$ is Br, and X is NH. |
| 55 | $R^4$ is Br, $R^5$ is MeO, $R^6$ is H, and X is NH. |
| 56 | $R^4$ is I, $R^5$ is H, $R^6$ is H, and X is NH. |
| 57 | $R^4$ is I, $R^5$ is Cl, $R^6$ is F, and X is NH. |
| 58 | $R^4$ is I, $R^5$ is Cl, $R^6$ is Cl, and X is NH. |
| 59 | $R^4$ is I, $R^5$ is F, $R^6$ is H, and X is NH. |
| 60 | $R^4$ is I, $R^5$ is F, $R^6$ is F, and X is NH. |
| 61 | $R^4$ is F, $R^5$ is H, $R^6$ is H, and X is O. |
| 62 | $R^4$ is F, $R^5$ is H, $R^6$ is F, and X is O. |
| 63 | $R^4$ is F, $R^5$ is H, $R^6$ is Cl, and X is O. |
| 64 | $R^4$ is F, $R^5$ is H, $R^6$ is Br, and X is O. |
| 65 | $R^4$ is F, $R^5$ is Br, $R^6$ is H, and X is O. |
| 66 | $R^4$ is F, $R^5$ is Br, $R^6$ is F, and X is O. |
| 67 | $R^4$ is F, $R^5$ is Cl, $R^6$ is Cl, and X is O. |
| 68 | $R^4$ is F, $R^5$ is Cl, $R^6$ is F, and X is O. |
| 69 | $R^4$ is F, $R^5$ is Cl, $R^6$ is H, and X is O. |
| 70 | $R^4$ is F, $R^5$ is CN, $R^6$ is F, and X is O. |
| 71 | $R^4$ is F, $R^5$ is CN, $R^6$ is H, and X is O. |
| 72 | $R^4$ is F, $R^5$ is F, $R^6$ is H, and X is O. |
| 73 | $R^4$ is F, $R^5$ is F, $R^6$ is F, and X is O. |
| 74 | $R^4$ is F, $R^5$ is F, $R^6$ is I, and X is O. |
| 75 | $R^4$ is F, $R^5$ is I, $R^6$ is H, and X is O. |
| 76 | $R^4$ is F, $R^5$ is I, $R^6$ is F, and X is O. |
| 77 | $R^4$ is F, $R^5$ is EtO, $R^6$ is F, and X is O. |
| 78 | $R^4$ is F, $R^5$ is EtO, $R^6$ is H, and X is O. |
| 79 | $R^4$ is F, $R^5$ is MeO, $R^6$ is F, and X is O. |
| 80 | $R^4$ is F, $R^5$ is MeO, $R^6$ is H, and X is O. |
| 81 | $R^4$ is Cl, $R^5$ is H, $R^6$ is H, and X is O. |
| 82 | $R^4$ is Cl, $R^5$ is H, $R^6$ is Cl, and X is O. |
| 83 | $R^4$ is Cl, $R^5$ is H, $R^6$ is Br, and X is O. |
| 84 | $R^4$ is Cl, $R^5$ is Br, $R^6$ is H, and X is O. |
| 85 | $R^4$ is Cl, $R^5$ is Br, $R^6$ is Br, and X is O. |
| 86 | $R^4$ is Cl, $R^5$ is Br, $R^6$ is Cl, and X is O. |
| 87 | $R^4$ is Cl, $R^5$ is Cl, $R^6$ is H, and X is O. |
| 88 | $R^4$ is Cl, $R^5$ is Cl, $R^6$ is Cl, and X is O. |
| 89 | $R^4$ is Cl, $R^5$ is CN, $R^6$ is Cl, and X is O. |
| 90 | $R^4$ is Cl, $R^5$ is CN, $R^6$ is H, and X is O. |
| 91 | $R^4$ is Cl, $R^5$ is F, $R^6$ is F, and X is O. |
| 92 | $R^4$ is Cl, $R^5$ is F, $R^6$ is H, and X is O. |
| 93 | $R^4$ is Cl, $R^5$ is F, $R^6$ is Cl, and X is O. |
| 94 | $R^4$ is Cl, $R^5$ is I, $R^6$ is H, and X is O. |
| 95 | $R^4$ is Cl, $R^5$ is EtO, $R^6$ is Cl, and X is O. |
| 96 | $R^4$ is Cl, $R^5$ is EtO, $R^6$ is H, and X is O. |
| 97 | $R^4$ is Cl, $R^5$ is MeO, $R^6$ is Cl, and X is O. |
| 98 | $R^4$ is Cl, $R^5$ is MeO, $R^6$ is H, and X is O. |
| 99 | $R^4$ is Br, $R^5$ is H, $R^6$ is H, and X is O. |
| 100 | $R^4$ is Br, $R^5$ is Br, $R^6$ is H, and X is O. |
| 101 | $R^4$ is Br, $R^5$ is Br, $R^6$ is F, and X is O. |
| 102 | $R^4$ is Br, $R^5$ is Cl, $R^6$ is H, and X is O. |
| 103 | $R^4$ is Br, $R^5$ is Cl, $R^6$ is F, and X is O. |
| 104 | $R^4$ is Br, $R^5$ is Cl, $R^6$ is Cl, and X is O. |
| 105 | $R^4$ is Br, $R^5$ is CN, $R^6$ is Br, and X is O. |
| 106 | $R^4$ is Br, $R^5$ is CN, $R^6$ is H, and X is O. |
| 107 | $R^4$ is Br, $R^5$ is F, $R^6$ is F, and X is O. |
| 108 | $R^4$ is Br, $R^5$ is F, $R^6$ is H, and X is O. |
| 109 | $R^4$ is Br, $R^5$ is F, $R^6$ is Cl, and X is O. |
| 110 | $R^4$ is Br, $R^5$ is F, $R^6$ is Br, and X is O. |
| 111 | $R^4$ is Br, $R^5$ is I, $R^6$ is H, and X is O. |
| 112 | $R^4$ is Br, $R^5$ is EtO, $R^6$ is Br, and X is O. |
| 113 | $R^4$ is Br, $R^5$ is EtO, $R^6$ is H, and X is O. |

-continued

| Table | Row Heading |
|---|---|
| 114 | $R^4$ is Br, $R^5$ is MeO, $R^6$ is Br, and X is O. |
| 115 | $R^4$ is Br, $R^5$ is MeO, $R^6$ is H, and X is O. |
| 116 | $R^4$ is I, $R^5$ is H, $R^6$ is H, and X is O. |
| 117 | $R^4$ is I, $R^5$ is Cl, $R^6$ is F, and X is O. |
| 118 | $R^4$ is I, $R^5$ is Cl, $R^6$ is Cl, and X is O. |
| 119 | $R^4$ is I, $R^5$ is F, $R^6$ is H, and X is O. |
| 120 | $R^4$ is I, $R^5$ is F, $R^6$ is F, and X is O. |
| 121 | $R^4$ is F, $R^5$ is H, $R^6$ is H, and X is CHOH. |
| 122 | $R^4$ is F, $R^5$ is H, $R^6$ is F, and X is CHOH. |
| 123 | $R^4$ is F, $R^5$ is H, $R^6$ is Cl, and X is CHOH. |
| 124 | $R^4$ is F, $R^5$ is H, $R^6$ is Br, and X is CHOH. |
| 125 | $R^4$ is F, $R^5$ is Br, $R^6$ is H, and X is CHOH. |
| 126 | $R^4$ is F, $R^5$ is Br, $R^6$ is F, and X is CHOH. |
| 127 | $R^4$ is F, $R^5$ is Cl, $R^6$ is Cl, and X is CHOH. |
| 128 | $R^4$ is F, $R^5$ is Cl, $R^6$ is F, and X is CHOH. |
| 129 | $R^4$ is F, $R^5$ is Cl, $R^6$ is H, and X is CHOH. |
| 130 | $R^4$ is F, $R^5$ is CN, $R^6$ is F, and X is CHOH. |
| 131 | $R^4$ is F, $R^5$ is CN, $R^6$ is H, and X is CHOH. |
| 132 | $R^4$ is F, $R^5$ is F, $R^6$ is H, and X is CHOH. |
| 133 | $R^4$ is F, $R^5$ is F, $R^6$ is F, and X is CHOH. |
| 134 | $R^4$ is F, $R^5$ is F, $R^6$ is I, and X is CHOH. |
| 135 | $R^4$ is F, $R^5$ is I, $R^6$ is H, and X is CHOH. |
| 136 | $R^4$ is F, $R^5$ is I, $R^6$ is F, and X is CHOH. |
| 137 | $R^4$ is F, $R^5$ is EtO, $R^6$ is F, and X is CHOH. |
| 138 | $R^4$ is F, $R^5$ is EtO, $R^6$ is H, and X is CHOH. |
| 139 | $R^4$ is F, $R^5$ is MeO, $R^6$ is F, and X is CHOH. |
| 140 | $R^4$ is F, $R^5$ is MeO, $R^6$ is H, and X is CHOH. |
| 141 | $R^4$ is Cl, $R^5$ is H, $R^6$ is H, and X is CHOH. |
| 142 | $R^4$ is Cl, $R^5$ is H, $R^6$ is Cl, and X is CHOH. |
| 143 | $R^4$ is Cl, $R^5$ is H, $R^6$ is Br, and X is CHOH. |
| 144 | $R^4$ is Cl, $R^5$ is Br, $R^6$ is H, and X is CHOH. |
| 145 | $R^4$ is Cl, $R^5$ is Br, $R^6$ is Br, and X is CHOH. |
| 146 | $R^4$ is Cl, $R^5$ is Br, $R^6$ is Cl, and X is CHOH. |
| 147 | $R^4$ is Cl, $R^5$ is Cl, $R^6$ is H, and X is CHOH. |
| 148 | $R^4$ is Cl, $R^5$ is Cl, $R^6$ is Cl, and X is CHOH. |
| 149 | $R^4$ is Cl, $R^5$ is CN, $R^6$ is Cl, and X is CHOH. |
| 150 | $R^4$ is Cl, $R^5$ is CN, $R^6$ is H, and X is CHOH. |
| 151 | $R^4$ is Cl, $R^5$ is F, $R^6$ is F, and X is CHOH. |
| 152 | $R^4$ is Cl, $R^5$ is F, $R^6$ is H, and X is CHOH. |
| 153 | $R^4$ is Cl, $R^5$ is F, $R^6$ is Cl, and X is CHOH. |
| 154 | $R^4$ is Cl, $R^5$ is I, $R^6$ is H, and X is CHOH. |
| 155 | $R^4$ is Cl, $R^5$ is EtO, $R^6$ is Cl, and X is CHOH. |
| 156 | $R^4$ is Cl, $R^5$ is EtO, $R^6$ is H, and X is CHOH. |
| 157 | $R^4$ is Cl, $R^5$ is MeO, $R^6$ is Cl, and X is CHOH. |
| 158 | $R^4$ is Cl, $R^5$ is MeO, $R^6$ is H, and X is CHOH. |
| 159 | $R^4$ is Br, $R^5$ is H, $R^6$ is H, and X is CHOH. |
| 160 | $R^4$ is Br, $R^5$ is Br, $R^6$ is H, and X is CHOH. |
| 161 | $R^4$ is Br, $R^5$ is Br, $R^6$ is F, and X is CHOH. |
| 162 | $R^4$ is Br, $R^5$ is Cl, $R^6$ is H, and X is CHOH. |
| 163 | $R^4$ is Br, $R^5$ is Cl, $R^6$ is F, and X is CHOH. |
| 164 | $R^4$ is Br, $R^5$ is Cl, $R^6$ is Cl, and X is CHOH. |
| 165 | $R^4$ is Br, $R^5$ is CN, $R^6$ is Br, and X is CHOH. |
| 166 | $R^4$ is Br, $R^5$ is CN, $R^6$ is H, and X is CHOH. |
| 167 | $R^4$ is Br, $R^5$ is F, $R^6$ is F, and X is CHOH. |
| 168 | $R^4$ is Br, $R^5$ is F, $R^6$ is H, and X is CHOH. |
| 169 | $R^4$ is Br, $R^5$ is F, $R^6$ is Cl, and X is CHOH. |
| 170 | $R^4$ is Br, $R^5$ is F, $R^6$ is Br, and X is CHOH. |
| 171 | $R^4$ is Br, $R^5$ is I, $R^6$ is H, and X is CHOH. |
| 172 | $R^4$ is Br, $R^5$ is EtO, $R^6$ is Br, and X is CHOH. |
| 173 | $R^4$ is Br, $R^5$ is EtO, $R^6$ is H, and X is CHOH. |
| 174 | $R^4$ is Br, $R^5$ is MeO, $R^6$ is Br, and X is CHOH. |
| 175 | $R^4$ is Br, $R^5$ is MeO, $R^6$ is H, and X is CHOH. |
| 176 | $R^4$ is I, $R^5$ is H, $R^6$ is H, and X is CHOH. |
| 177 | $R^4$ is I, $R^5$ is Cl, $R^6$ is F, and X is CHOH. |
| 178 | $R^4$ is I, $R^5$ is Cl, $R^6$ is Cl, and X is CHOH. |
| 179 | $R^4$ is I, $R^5$ is F, $R^6$ is H, and X is CHOH. |
| 180 | $R^4$ is I, $R^5$ is F, $R^6$ is F, and X is CHOH. |

Formulation/Utility

A compound selected from compounds of Formula 1, N-oxides, and salts thereof, or a mixture (i.e. composition) comprising the compound with at least one additional fungicidal compound as described in the Summary of the Invention, will generally be used to provide fungicidal active ingredients in further compositions, i.e. formulations, with at least one additional component selected from the group consisting of surfactants, solid diluents and liquid diluents, which serves as a carrier. The formulation or composition ingredients are selected to be consistent with the physical properties of the active ingredients, mode of application and environmental factors such as soil type, moisture and temperature.

The mixtures of component (a) (i.e. at least one compound of Formula 1, N-oxides, or salts thereof) with component (b) (e.g., selected from (b1) to (b46) and salts thereof as described above) and/or one or more other biologically active compound or agent (i.e. insecticides, other fungicides, nematocides, acaricides, herbicides and other biological agents) can be formulated in a number of ways, including:

(i) component (a), component (b) and/or one or more other biologically active compounds or agents can be formulated separately and applied separately or applied simultaneously in an appropriate weight ratio, e.g., as a tank mix; or (ii) component (a), component (b) and/or one or more other biologically active compounds or agents can be formulated together in the proper weight ratio.

Useful formulations include both liquid and solid compositions. Liquid compositions include solutions (including emulsifiable concentrates), suspensions, emulsions (including microemulsions and/or suspoemulsions) and the like, which optionally can be thickened into gels. The general types of aqueous liquid compositions are soluble concentrate, suspension concentrate, capsule suspension, concentrated emulsion, microemulsion and suspo-emulsion. The general types of nonaqueous liquid compositions are emulsifiable concentrate, microemulsifiable concentrate, dispersible concentrate and oil dispersion.

The general types of solid compositions are dusts, powders, granules, pellets, prills, pastilles, tablets, filled films (including seed coatings) and the like, which can be water-dispersible ("wettable") or water-soluble. Films and coatings formed from film-forming solutions or flowable suspensions are particularly useful for seed treatment. Active ingredient can be (micro)encapsulated and further formed into a suspension or solid formulation; alternatively the entire formulation of active ingredient can be encapsulated (or "overcoated"). Encapsulation can control or delay release of the active ingredient. An emulsifiable granule combines the advantages of both an emulsifiable concentrate formulation and a dry granular formulation. High-strength compositions are primarily used as intermediates for further formulation.

Of note is a composition embodiment wherein granules of a solid composition comprising a compound of Formula 1 (or an N-oxide or salt thereof) is mixed with granules of a solid composition comprising component (b). These mixtures can be further mixed with granules comprising additional agricultural protectants. Alternatively, two or more agricultural protectants (e.g., a component (a) (Formula 1) compound, a component (b) compound, an agricultural protectant other than component (a) or (b)) can be combined in the solid composition of one set of granules, which is then mixed with one or more sets of granules of solid compositions comprising one or more additional agricultural protectants. These granule mixtures can be in accordance with the general granule mixture disclosure of PCT Patent Publication WO 94/24861 or more preferably the homogeneous granule mixture teaching of U.S. Pat. No. 6,022,552.

Sprayable formulations are typically extended in a suitable medium before spraying. Such liquid and solid formulations are formulated to be readily diluted in the spray medium, usually water. Spray volumes can range from about from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

The formulations will typically contain effective amounts of active ingredient, diluent and surfactant within the following approximate ranges which add up to 100 percent by weight.

| | Weight Percent | | |
|---|---|---|---|
| | Active Ingredient | Diluent | Surfactant |
| Water-Dispersible and Water-soluble Granules, Tablets and Powders | 0.001-90 | 0-99.999 | 0-15 |
| Oil Dispersions, Suspensions, Emulsions, Solutions (including Emulsifiable Concentrates) | 1-50 | 40-99 | 0-50 |
| Dusts | 1-25 | 70-99 | 0-5 |
| Granules and Pellets | 0.001-99 | 5-99.999 | 0-15 |
| High Strength Compositions | 90-99 | 0-10 | 0-2 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers*, 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide*, 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, Synthetic Detergents, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The compounds of Formula 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2,000 µm can be wet milled using media mills to obtain particles with average diameters below 3 µm. Aqueous slurries can be made into finished suspension concentrates (see, for example, U.S. Pat. No. 3,060,084) or further processed by spray drying to form water-dispersible granules. Dry formulations usually require dry milling processes, which produce average particle diameters in the 2 to 10 µm range. Dusts and powders can be prepared by blending and usually grinding (such as with a hammer mill or fluid-energy mill). Granules and pellets can be prepared by spraying the active material upon preformed granular carriers or by agglomeration techniques. See Browning, "Agglomeration", *Chemical Engineering*, Dec. 4, 1967, pp 147-48, *Perry's Chemical Engineer's Handbook*, 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience, The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4; Klingman, *Weed Control as a Science*, John Wiley and Sons, Inc., New York, 1961, pp 81-96; Hance et al., *Weed Control Handbook*, 8th Ed., Blackwell Scientific Publications, Oxford, 1989; and *Developments in formulation technology*, PJB Publications, Richmond, UK, 2000.

In the following Examples, all percentages are by weight and all formulations are prepared in conventional ways. Compound numbers refer to compounds in Index Table A. Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except where otherwise indicated.

Example A

| High Strength Concentrate | |
|---|---|
| Compound 47 | 49.3% |
| penthiopyrad | 49.2% |
| silica aerogel | 0.5% |
| synthetic amorphous fine silica | 1.0% |

Example B

| Wettable Powder | |
|---|---|
| Compound 81 | 43.0% |
| quinoxyfen | 22.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Example C

| Granule | |
|---|---|
| Compound 136 | 7.5% |
| epoxiconazole | 2.5% |
| attapulgite granules (low volatile matter, 0.71/0.30 mm; U.S.S. No. 25-50 sieves) | 90.0% |

Example D

| Extruded Pellet | |
| --- | --- |
| Compound 144 | 8.0% |
| spiroxamine | 17.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Example E

| Emulsifiable Concentrate | |
| --- | --- |
| Compound 161 | 5.0% |
| azoxystrobin | 5.0% |
| polyoxyethylene sorbitol hexoleate | 20.0% |
| $C_6$-$C_{10}$ fatty acid methyl ester | 70.0% |

Example F

| Microemulsion | |
| --- | --- |
| Compound 195 | 3.3% |
| picoxystrobin | 1.7% |
| polyvinylpyrrolidone-vinyl acetate copolymer | 30.0% |
| alkylpolyglycoside | 30.0% |
| glyceryl monooleate | 15.0% |
| water | 20.0% |

Example G

| Seed Treatment | |
| --- | --- |
| Compound 238 | 4.00% |
| iprodione | 16.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |
| stearyl alcohol (POE 20) | 2.00% |
| polyorganosilane | 0.20% |
| colorant red dye | 0.05% |
| water | 65.75% |

Example H

| Emulsifiable Concentrate | |
| --- | --- |
| Compound 239 | 10.0% |
| polyoxyethylene sorbitol hexoleate | 20.0% |
| $C_6$-$C_{10}$ fatty acid methyl ester | 70.0% |

Formulations such as those in the Formulation Table are typically diluted with water to form aqueous compositions before application. Aqueous compositions for direct applications to the plant or portion thereof (e.g., spray tank compositions) typically comprise at least about 1 ppm or more (e.g., from 1 ppm to 100 ppm) of fungicidally active compounds according to the present invention.

Examples of component (b) fungicidal compounds include acibenzolar-S-methyl, aldimorph, ametoctradin, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, boscalid, bromuconazole, bupirimate, buthiobate, carboxin, carpropamid, captafol, captan, carbendazim, chloroneb, chlorothalonil, chlozolinate, clotrimazole, copper salts such as Bordeaux mixture (tribasic copper sulfate), copper hydroxide and copper oxychloride, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, etaconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, fluazinam, fludioxonil, flumetover, flumorph, fluopicolide (also known as picobenzamid), fluopyram, fluoroimide, fluoxastrobin, fluquinconazole, flusilazole, flusulfamide, flutianil (2-[[2-fluoro-5-(trifluoromethyl)phenyl]thio]-2-[3-(2-methoxyphenyl)-2-thiazolidinylidene]acetonitrile), flutolanil, flutriafol, fluxapyroxad, folpet, fosetyl-aluminum, fuberidazole, furalaxyl, furametpyr, hexaconazole, hymexazol, guazatine, imazalil, imibenconazole, iminoctadine, iodocarb, ipconazole, iprobenfos, iprodione, iprovalicarb, isoprothiolane, isopyrazam, isotianil, kasugamycin, kresoxim-methyl, mancozeb, mandipropamid, maneb, mepronil, meptyldinocap, metalaxyl, metalaxyl-M, metconazole, methasulfocarb, metiram, metominostrobin, mepanipyrim, metrafenone, myclobutanil, naftifine, neo-asozin (ferric methanearsonate), nuarimol, octhilinone, ofurace, orysastrobin, oxadixyl, oxolinic acid, oxpoconazole, oxycarboxin, oxytetracycline, penconazole, pencycuron, penflufen, penthiopyrad, pefurazoate, phosphorous acid and salts thereof, phthalide, picoxystrobin, piperalin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, pyrrolnitrin, quinconazole, quinomethionate, quinoxyfen, quintozene, sedaxane, silthiofam, simeconazole, spiroxamine, streptomycin, sulfur, tebuconazole, tebufloquin, tecloftalam, tecnazene, terbinafine, tetraconazole, thiabendazole, thifluzamide, thiophanate, thiophanate-methyl, thiram, tiadinil, tolclofos-methyl, tolylfluanid, triadimefon, triadimenol, triarimol, triazoxide, tricyclazole, tridemorph, triflumizole, tricyclazole, trifloxystrobin, triforine, trimorphamide, triticonazole, uniconazole, validamycin, valifenalate (valiphenal), vinclozolin, zineb, ziram, zoxamide, N'-[4-[4-chloro-3-(trifluoromethyl)phenoxy]-2,5-dimethylphenyl]-N-ethyl-N-methylmethanimidamide, 5-chloro-6-(2,4,6-trifluorophenyl)-7-(4-methylpiperidin-1-yl)[1,2,4]triazolo[1,5-a]pyrimidine (BAS600), N-[2-[4-[[3-(4-chlorophenyl)-2-propyn-1-yl]oxy]-3-methoxyphenyl]ethyl]-3-methyl-2-[(methylsulfonyl)-amino]butanamide, N-[2-[4-[[3-(4-chlorophenyl)-2-propyn-1-yl]oxy]-3-methoxyphenyl]-ethyl]-3-methyl-2-[(ethylsulfonyl)amino]butanamide, 2-butoxy-6-iodo-3-propyl-4H-1-benzopyran-4-one, 3-[5-(4-chlorophenyl)-2,3-dimethyl-3-isoxazolidinyl]pyridine, 4-fluorophenyl N-[1-[[[1-(4-cyanophenyl)ethyl]sulfonyl]methyl]propyl]

carbamate, N-[[(cyclopropylmethoxy)amino][6-(difluoromethoxy)-2,3-difluorophenyl]methylene]-benzeneacetamide, α-(methoxyimino)-N-methyl-2-[[[1-[3-(trifluoromethyl)phenyl]ethoxy]-imino]methyl]benzeneacetamide, N'-[4-[4-chloro-3-(trifluoromethyl)phenoxy]-2,5-dimethylphenyl]-N-ethyl-N-methylmethanimidamide, N-(4-chloro-2-nitrophenyl)-N-ethyl-4-methylbenzenesulfonamide, 2-[[[[3-(2,6-dichlorophenyl)-1-methyl-2-propen-1-ylidene]amino]-oxy]methyl]-α-(methoxyimino)-N-methylbenzeneacetamide, 1-[(2-propenylthio)carbonyl]-2-(1-methylethyl)-4-(2-methylphenyl)-5-amino-1H-pyrazol-3-one, ethyl-6-octyl-[1,2,4]-triazolo[1,5-a]pyrimidin-7-ylamine, pentyl N-[4-[[[[(1-methyl-1H-tetrazol-5-yl)phenylmethylene]amino]oxy]methyl]-2-thiazolyl]carbamate, pentyl N-[6-[[[[(1-methyl-1H-tetrazol-5-yl)phenylmethylene]amino]oxy]methyl]-2-pyridinyl]carbamate, 2-[(3-bromo-6-quinolinyl)oxy]-N-(1,1-dimethyl-2-butyn-1-yl)-2-(methylthio)acetamide, 2-[(3-ethynyl-6-quinolinyl)oxy]-N-[1-(hydroxymethyl)-1-methyl-2-propyn-1-yl]-2-(methylthio)acetamide, N-(1,1-dimethyl-2-butyn-1-yl)-2-[(3-ethynyl-6-quinolinyl)oxy]-2-(methylthio)acetamide and N'-[4-[[3-[(4-chlorophenyl)methyl]-1,2,4-thiadiazol-5-yl]oxy]-2,5-dimethylphenyl]-N-ethyl-N-methylmethanimidamide. Of note is the preceding list also excluding N'-[4-[[3-[(4-chlorophenyl)methyl]-1,2,4-thiadiazol-5-yl]oxy]-2,5-dimethylphenyl]-N-ethyl-N-methylmethanimidamide. Of further note is the preceding list also excluding buthiobate, etaconazole, quinconazole, triarimol, 2-[(3-bromo-6-quinolinyl)oxy]-N-(1,1-dimethyl-2-butyn-1-yl)-2-(methylthio)acetamide, 2-[(3-ethynyl-6-quinolinyl)oxy]-N-[1-(hydroxymethyl)-1-methyl-2-propyn-1-yl]-2-(methylthio)acetamide and N-(1,1-dimethyl-2-butyn-1-yl)-2-[(3-ethynyl-6-quinolinyl)oxy]-2-(methylthio)acetamide.

Of note as fungicidal compounds in component (b) of the present composition are azoxystrobin, kresoxim-methyl, trifloxystrobin, pyraclostrobin, pyrametostrobin, pyraoxystrobin, picoxystrobin, dimoxystrobin, metominostrobin/fenominostrobin, carbendazim, chlorothalonil, quinoxyfen, metrafenone, pyriofenone, cyflufenamid, fenpropidin, fenpropimorph, bromuconazole, cyproconazole, difenoconazole, epoxiconazole, etaconazole, fenbuconazole, flusilazole, fluxapyroxad, hexaconazole, ipconazole, metconazole, myclobutanil, penconazole, propiconazole, proquinazid, prothioconazole, tebuconazole, triticonazole, famoxadone, prochloraz, penthiopyrad and boscalid (nicobifen).

Generally preferred for better control of plant diseases caused by fungal plant pathogens (e.g., lower use rate or broader spectrum of plant pathogens controlled) or resistance management are mixtures of a compound of Formula 1, an N-oxide, or salt thereof, with a fungicidal compound selected from the group: azoxystrobin, kresoxim-methyl, trifloxystrobin, pyraclostrobin, pyrametostrobin, pyraoxystrobin, picoxystrobin, dimoxystrobin, metominostrobin/fenominostrobin, quinoxyfen, metrafenone, cyflufenamid, fenpropidin, fenpropimorph, cyproconazole, difenoconazole, epoxiconazole, etaconazole, flusilazole, metconazole, myclobutanil, propiconazole, proquinazid, prothioconazole, pyriofenone, tebuconazole, triticonazole, famoxadone and penthiopyrad.

In the fungicidal compositions of the present invention, component (a) (i.e. at least one compound selected from compounds of Formula 1, N-oxides, and salts thereof) and component (b) are present in fungicidally effective amounts. The weight ratio of component (b) (i.e. one or more additional fungicidal compounds) to component (a) is generally between about 1:3000 to about 3000:1, and more typically between about 1:500 and about 500:1. Table B1 lists typical, more typical and most typical ranges of ratios involving particular fungicidal compounds of component (b). Tables A1 through A43 and C1 through C43 exemplify weight ratios for particular combinations of fungicidal compounds. Of note are compositions where in the weight ratio of component (a) to component (b) is from about 125:1 to about 1:125. With many fungicidal compounds of component (b), these compositions are particularly effective for controlling plant diseases caused by fungal plant pathogens. Of particular note are compositions wherein the weight ratio of component (a) to component (b) is from about 25:1 to about 1:25, or from about 5:1 to about 1:5. One skilled in the art can easily determine through simple experimentation the weight ratios and application rates of fungicidal compounds necessary for the desired spectrum of fungicidal protection and control. It will be evident that including additional fungicidal compounds in component (b) may expand the spectrum of plant diseases controlled beyond the spectrum controlled by component (a) alone.

Specific mixtures (compound numbers refer to compounds in Index Table A) are listed in Tables A1 through A43. In Table A1, each line below the column headings "Component (a)" and "Component (b)" specifically discloses a mixture of Component (a), which is Compound 3, with a Component (b) fungicidal compound. The entries under the heading "Illustrative Ratios" disclose three specific weight ratios of Component (b) to Component (a) for the disclosed mixture. For example, the first line of Table A1 discloses a mixture of Compound 3 with acibenzolar-S-methyl and lists weight ratios of acibenzolar-S-methyl to Compound 3 of 1:1, 1:4 or 1:18.

TABLE A1

| Component (a) | Component (b) | Illustrative Ratios(*) | | |
|---|---|---|---|---|
| Compound 3 | acibenzolar-S-methyl | 1:1 | 1:4 | 1:18 |
| Compound 3 | aldimorph | 7:1 | 3:1 | 1:1 |
| Compound 3 | ametoctradin | 3:1 | 1:1 | 1:3 |
| Compound 3 | amisulbrom | 1:1 | 1:2 | 1:6 |
| Compound 3 | anilazine | 22:1 | 8:1 | 4:1 |
| Compound 3 | azaconazole | 2:1 | 1:2 | 1:4 |
| Compound 3 | azoxystrobin | 3:1 | 1:1 | 1:3 |
| Compound 3 | benalaxyl | 1:1 | 1:2 | 1:6 |
| Compound 3 | benalaxyl-M | 1:1 | 1:3 | 1:8 |
| Compound 3 | benodanil | 4:1 | 2:1 | 1:2 |
| Compound 3 | benomyl | 11:1 | 4:1 | 1:1 |
| Compound 3 | benthiavalicarb | 1:1 | 1:4 | 1:12 |
| Compound 3 | benthiavalicarb-isopropyl | 1:1 | 1:4 | 1:12 |
| Compound 3 | bethoxazin | 15:1 | 5:1 | 2:1 |
| Compound 3 | binapacryl | 15:1 | 5:1 | 2:1 |
| Compound 3 | biphenyl | 15:1 | 5:1 | 2:1 |

TABLE A1-continued

| Component (a) | Component (b) | Illustrative Ratios(*) | | |
|---|---|---|---|---|
| Compound 3 | bitertanol | 3:1 | 1:1 | 1:2 |
| Compound 3 | bixafen | 2:1 | 1:1 | 1:3 |
| Compound 3 | blasticidin-S | 1:4 | 1:12 | 1:30 |
| Compound 3 | Bordeaux mixture (tribasic copper sulfate) | 45:1 | 15:1 | 5:1 |
| Compound 3 | boscalid | 4:1 | 2:1 | 1:2 |
| Compound 3 | bromuconazole | 3:1 | 1:1 | 1:3 |
| Compound 3 | bupirimate | 1:3 | 1:10 | 1:30 |
| Compound 3 | captafol | 15:1 | 5:1 | 2:1 |
| Compound 3 | captan | 15:1 | 5:1 | 2:1 |
| Compound 3 | carbendazim | 11:1 | 4:1 | 2:1 |
| Compound 3 | carboxin | 4:1 | 2:1 | 1:2 |
| Compound 3 | carpropamid | 3:1 | 1:1 | 1:3 |
| Compound 3 | chloroneb | 100:1 | 35:1 | 14:1 |
| Compound 3 | chlorothalonil | 15:1 | 5:1 | 2:1 |
| Compound 3 | chlozolinate | 11:1 | 4:1 | 2:1 |
| Compound 3 | clotrimazole | 3:1 | 1:1 | 1:3 |
| Compound 3 | copper hydroxide | 45:1 | 15:1 | 5:1 |
| Compound 3 | copper oxychloride | 45:1 | 15:1 | 5:1 |
| Compound 3 | cyazofamid | 1:1 | 1:2 | 1:6 |
| Compound 3 | cyflufenamid | 1:2 | 1:6 | 1:24 |
| Compound 3 | cymoxanil | 1:1 | 1:2 | 1:5 |
| Compound 3 | cyproconazole | 1:1 | 1:2 | 1:6 |
| Compound 3 | cyprodinil | 4:1 | 2:1 | 1:2 |
| Compound 3 | dichlofluanid | 15:1 | 5:1 | 2:1 |
| Compound 3 | diclocymet | 15:1 | 5:1 | 2:1 |
| Compound 3 | diclomezine | 3:1 | 1:1 | 1:3 |
| Compound 3 | dicloran | 15:1 | 5:1 | 2:1 |
| Compound 3 | diethofencarb | 7:1 | 2:1 | 1:2 |
| Compound 3 | difenoconazole | 1:1 | 1:3 | 1:12 |
| Compound 3 | diflumetorim | 15:1 | 5:1 | 2:1 |
| Compound 3 | dimethirimol | 1:3 | 1:8 | 1:30 |
| Compound 3 | dimethomorph | 3:1 | 1:1 | 1:2 |
| Compound 3 | dimoxystrobin | 2:1 | 1:1 | 1:4 |
| Compound 3 | diniconazole | 1:1 | 1:3 | 1:8 |
| Compound 3 | diniconazole-M | 1:1 | 1:3 | 1:12 |
| Compound 3 | dinocap | 2:1 | 1:1 | 1:3 |
| Compound 3 | dithianon | 5:1 | 2:1 | 1:2 |
| Compound 3 | dodemorph | 7:1 | 3:1 | 1:1 |
| Compound 3 | dodine | 10:1 | 4:1 | 2:1 |
| Compound 3 | edifenphos | 3:1 | 1:1 | 1:3 |
| Compound 3 | enestroburin | 2:1 | 1:1 | 1:4 |
| Compound 3 | epoxiconazole | 1:1 | 1:3 | 1:7 |
| Compound 3 | etaconazole | 1:1 | 1:3 | 1:7 |
| Compound 3 | ethaboxam | 2:1 | 1:1 | 1:3 |
| Compound 3 | ethirimol | 7:1 | 3:1 | 1:1 |
| Compound 3 | etridiazole | 7:1 | 2:1 | 1:2 |
| Compound 3 | famoxadone | 2:1 | 1:1 | 1:4 |
| Compound 3 | fenamidone | 2:1 | 1:1 | 1:4 |
| Compound 3 | fenarimol | 1:2 | 1:7 | 1:24 |
| Compound 3 | fenbuconazole | 1:1 | 1:3 | 1:10 |
| Compound 3 | fenfuram | 4:1 | 1:1 | 1:2 |
| Compound 3 | fenhexamid | 10:1 | 4:1 | 2:1 |
| Compound 3 | fenoxanil | 15:1 | 4:1 | 1:1 |
| Compound 3 | fenpiclonil | 15:1 | 5:1 | 2:1 |
| Compound 3 | fenpropidin | 7:1 | 2:1 | 1:1 |
| Compound 3 | fenpropimorph | 7:1 | 2:1 | 1:1 |
| Compound 3 | fenpyrazamine | 3:1 | 1:1 | 1:3 |
| Compound 3 | fentin salt such as fentin acetate, fentin chloride or fentin hydroxide | 3:1 | 1:1 | 1:3 |
| Compound 3 | ferbam | 30:1 | 10:1 | 4:1 |
| Compound 3 | ferimzone | 7:1 | 2:1 | 1:2 |
| Compound 3 | fluazinam | 3:1 | 1:1 | 1:2 |
| Compound 3 | fludioxonil | 2:1 | 1:1 | 1:4 |
| Compound 3 | flumetover | 3:1 | 1:1 | 1:2 |
| Compound 3 | flumorph | 3:1 | 1:1 | 1:3 |
| Compound 3 | fluopicolide | 1:1 | 1:2 | 1:6 |
| Compound 3 | fluopyram | 3:1 | 1:1 | 1:3 |
| Compound 3 | fluoroimide | 37:1 | 14:1 | 5:1 |
| Compound 3 | fluoxastrobin | 1:1 | 1:2 | 1:6 |
| Compound 3 | fluquinconazole | 1:1 | 1:2 | 1:4 |
| Compound 3 | flusilazole | 3:1 | 1:1 | 1:3 |
| Compound 3 | flusulfamide | 15:1 | 5:1 | 2:1 |
| Compound 3 | flutianil | 1:1 | 1:2 | 1:6 |
| Compound 3 | flutolanil | 4:1 | 1:1 | 1:2 |
| Compound 3 | flutriafol | 1:1 | 1:2 | 1:4 |
| Compound 3 | fluxapyroxad | 2:1 | 1:1 | 1:3 |
| Compound 3 | folpet | 15:1 | 5:1 | 2:1 |
| Compound 3 | fosetyl-aluminum | 30:1 | 12:1 | 5:1 |

TABLE A1-continued

| Component (a) | Component (b) | Illustrative Ratios(*) | | |
|---|---|---|---|---|
| Compound 3 | fuberidazole | 11:1 | 4:1 | 2:1 |
| Compound 3 | furalaxyl | 1:1 | 1:2 | 1:6 |
| Compound 3 | furametpyr | 15:1 | 5:1 | 2:1 |
| Compound 3 | guazatine | 15:1 | 5:1 | 2:1 |
| Compound 3 | hexaconazole | 1:1 | 1:2 | 1:5 |
| Compound 3 | hymexazol | 75:1 | 25:1 | 9:1 |
| Compound 3 | imazalil | 1:1 | 1:2 | 1:5 |
| Compound 3 | imibenconazole | 1:1 | 1:2 | 1:5 |
| Compound 3 | iminoctadine | 15:1 | 4:1 | 1:1 |
| Compound 3 | iodocarb | 15:1 | 5:1 | 2:1 |
| Compound 3 | ipconazole | 1:1 | 1:2 | 1:5 |
| Compound 3 | iprobenfos | 15:1 | 5:1 | 2:1 |
| Compound 3 | iprodione | 15:1 | 5:1 | 2:1 |
| Compound 3 | iprovalicarb | 2:1 | 1:1 | 1:3 |
| Compound 3 | isoprothiolane | 45:1 | 15:1 | 5:1 |
| Compound 3 | isopyrazam | 2:1 | 1:1 | 1:3 |
| Compound 3 | isotianil | 2:1 | 1:1 | 1:3 |
| Compound 3 | kasugamycin | 1:2 | 1:7 | 1:24 |
| Compound 3 | kresoxim-methyl | 2:1 | 1:1 | 1:4 |
| Compound 3 | mancozeb | 22:1 | 7:1 | 3:1 |
| Compound 3 | mandipropamid | 2:1 | 1:1 | 1:4 |
| Compound 3 | maneb | 22:1 | 7:1 | 3:1 |
| Compound 3 | mepanipyrim | 6:1 | 2:1 | 1:1 |
| Compound 3 | mepronil | 1:1 | 1:2 | 1:6 |
| Compound 3 | meptyldinocap | 2:1 | 1:1 | 1:3 |
| Compound 3 | metalaxyl | 1:1 | 1:2 | 1:6 |
| Compound 3 | metalaxyl-M | 1:1 | 1:4 | 1:12 |
| Compound 3 | metconazole | 1:1 | 1:2 | 1:6 |
| Compound 3 | methasulfocarb | 15:1 | 5:1 | 2:1 |
| Compound 3 | metiram | 15:1 | 5:1 | 2:1 |
| Compound 3 | metominostrobin | 3:1 | 1:1 | 1:3 |
| Compound 3 | metrafenone | 2:1 | 1:1 | 1:4 |
| Compound 3 | myclobutanil | 1:1 | 1:3 | 1:8 |
| Compound 3 | naftifine | 15:1 | 5:1 | 2:1 |
| Compound 3 | neo-asozin (ferric methanearsonate) | 15:1 | 5:1 | 2:1 |
| Compound 3 | nuarimol | 3:1 | 1:1 | 1:3 |
| Compound 3 | octhilinone | 15:1 | 4:1 | 1:1 |
| Compound 3 | ofurace | 1:1 | 1:2 | 1:6 |
| Compound 3 | orysastrobin | 3:1 | 1:1 | 1:3 |
| Compound 3 | oxadixyl | 1:1 | 1:2 | 1:6 |
| Compound 3 | oxolinic acid | 7:1 | 2:1 | 1:2 |
| Compound 3 | oxpoconazole | 1:1 | 1:2 | 1:5 |
| Compound 3 | oxycarboxin | 4:1 | 1:1 | 1:2 |
| Compound 3 | oxytetracycline | 3:1 | 1:1 | 1:3 |
| Compound 3 | pefurazoate | 15:1 | 5:1 | 2:1 |
| Compound 3 | penconazole | 1:2 | 1:6 | 1:15 |
| Compound 3 | pencycuron | 11:1 | 4:1 | 2:1 |
| Compound 3 | penflufen | 2:1 | 1:1 | 1:3 |
| Compound 3 | penthiopyrad | 2:1 | 1:1 | 1:3 |
| Compound 3 | phosphorous acid or a salt thereof | 15:1 | 6:1 | 2:1 |
| Compound 3 | phthalide | 15:1 | 6:1 | 2:1 |
| Compound 3 | picoxystrobin | 1:1 | 1:2 | 1:5 |
| Compound 3 | piperalin | 3:1 | 1:1 | 1:3 |
| Compound 3 | polyoxin | 3:1 | 1:1 | 1:3 |
| Compound 3 | probenazole | 3:1 | 1:1 | 1:3 |
| Compound 3 | prochloraz | 7:1 | 2:1 | 1:2 |
| Compound 3 | procymidone | 11:1 | 4:1 | 2:1 |
| Compound 3 | propamocarb or propamocarb-hydrochloride | 10:1 | 4:1 | 2:1 |
| Compound 3 | propiconazole | 1:1 | 1:2 | 1:5 |
| Compound 3 | propineb | 11:1 | 4:1 | 2:1 |
| Compound 3 | proquinazid | 1:1 | 1:3 | 1:12 |
| Compound 3 | prothiocarb | 3:1 | 1:1 | 1:3 |
| Compound 3 | prothioconazole | 1:1 | 1:2 | 1:5 |
| Compound 3 | pyraclostrobin | 2:1 | 1:1 | 1:4 |
| Compound 3 | pyrametostrobin | 2:1 | 1:1 | 1:4 |
| Compound 3 | pyraoxystrobin | 2:1 | 1:1 | 1:4 |
| Compound 3 | pyrazophos | 15:1 | 4:1 | 1:1 |
| Compound 3 | pyribencarb | 4:1 | 1:1 | 1:2 |
| Compound 3 | pyributicarb | 15:1 | 4:1 | 1:1 |
| Compound 3 | pyrifenox | 3:1 | 1:1 | 1:3 |
| Compound 3 | pyrimethanil | 3:1 | 1:1 | 1:2 |
| Compound 3 | pyriofenone | 2:1 | 1:1 | 1:4 |
| Compound 3 | pyroquilon | 3:1 | 1:1 | 1:3 |
| Compound 3 | pyrrolnitrin | 15:1 | 5:1 | 2:1 |
| Compound 3 | quinconazole | 1:1 | 1:2 | 1:4 |
| Compound 3 | quinomethionate | 15:1 | 5:1 | 2:1 |
| Compound 3 | quinoxyfen | 1:1 | 1:2 | 1:6 |
| Compound 3 | quintozene | 15:1 | 5:1 | 2:1 |

TABLE A1-continued

| Component (a) | Component (b) | Illustrative Ratios(*) | | |
|---|---|---|---|---|
| Compound 3 | silthiofam | 2:1 | 1:1 | 1:4 |
| Compound 3 | simeconazole | 1:1 | 1:2 | 1:5 |
| Compound 3 | spiroxamine | 5:1 | 2:1 | 1:2 |
| Compound 3 | streptomycin | 3:1 | 1:1 | 1:3 |
| Compound 3 | sulfur | 75:1 | 25:1 | 9:1 |
| Compound 3 | tebuconazole | 1:1 | 1:2 | 1:5 |
| Compound 3 | tebufloquin | 3:1 | 1:1 | 1:3 |
| Compound 3 | tecloftalam | 15:1 | 5:1 | 2:1 |
| Compound 3 | tecnazene | 15:1 | 5:1 | 2:1 |
| Compound 3 | terbinafine | 15:1 | 5:1 | 2:1 |
| Compound 3 | tetraconazole | 1:1 | 1:2 | 1:5 |
| Compound 3 | thiabendazole | 11:1 | 4:1 | 2:1 |
| Compound 3 | thifluzamide | 3:1 | 1:1 | 1:3 |
| Compound 3 | thiophanate | 11:1 | 4:1 | 2:1 |
| Compound 3 | thiophanate-methyl | 11:1 | 4:1 | 2:1 |
| Compound 3 | thiram | 37:1 | 14:1 | 5:1 |
| Compound 3 | tiadinil | 2:1 | 1:1 | 1:3 |
| Compound 3 | tolclofos-methyl | 37:1 | 14:1 | 5:1 |
| Compound 3 | tolylfluanid | 15:1 | 5:1 | 2:1 |
| Compound 3 | triadimefon | 1:1 | 1:2 | 1:5 |
| Compound 3 | triadimenol | 1:1 | 1:2 | 1:5 |
| Compound 3 | triarimol | 1:2 | 1:7 | 1:24 |
| Compound 3 | triazoxide | 15:1 | 5:1 | 2:1 |
| Compound 3 | tricyclazole | 3:1 | 1:1 | 1:3 |
| Compound 3 | tridemorph | 7:1 | 2:1 | 1:1 |
| Compound 3 | trifloxystrobin | 2:1 | 1:1 | 1:4 |
| Compound 3 | triflumizole | 3:1 | 1:1 | 1:3 |
| Compound 3 | triforine | 3:1 | 1:1 | 1:3 |
| Compound 3 | trimorphamide | 7:1 | 2:1 | 1:2 |
| Compound 3 | triticonazole | 1:1 | 1:2 | 1:5 |
| Compound 3 | uniconazole | 1:1 | 1:2 | 1:5 |
| Compound 3 | validamycin | 3:1 | 1:1 | 1:3 |
| Compound 3 | valifenalate | 2:1 | 1:1 | 1:4 |
| Compound 3 | vinclozolin | 15:1 | 6:1 | 2:1 |
| Compound 3 | zineb | 37:1 | 14:1 | 5:1 |
| Compound 3 | ziram | 37:1 | 14:1 | 5:1 |
| Compound 3 | zoxamide | 2:1 | 1:1 | 1:4 |
| Compound 3 | 5-chloro-6-(2,4,6-trifluorophenyl)-7-(4-methylpiperidin-1-yl)[1,2,4]triazolo[1,5-a]pyrimidine | 1:1 | 1:2 | 1:6 |
| Compound 3 | N-[2-[4-[[3-(4-chlorophenyl)-2-propyn-1-yl]oxy]-3-methoxyphenyl]ethyl]-3-methyl-2-[(methylsulfonyl)amino]-butanamide | 2:1 | 1:1 | 1:4 |
| Compound 3 | N-[2-[4-[[3-(4-chlorophenyl)-2-propyn-1-yl]oxy]-3-methoxyphenyl]ethyl]-3-methyl-2-[(ethylsulfonyl)amino]butanamide | 2:1 | 1:1 | 1:4 |
| Compound 3 | 2-butoxy-6-iodo-3-propyl-4H-1-benzopyran-4-one | 1:1 | 1:3 | 1:12 |
| Compound 3 | 3-[5-(4-chlorophenyl)-2,3-dimethyl-3-isoxazolidinyl]-pyridine | 3:1 | 1:1 | 1:3 |
| Compound 3 | N'-[4-[3-[(4-chlorophenyl)methyl]-1,2,4-thiadiazol-5-yl]oxy]-2,5-dimethylphenyl]-N-ethyl-N-methylmethanimidamide | 3:1 | 1:1 | 1:3 |
| Compound 3 | 4-fluorophenyl N-[1-[[[1-(4-cyanophenyl)ethyl]sulfonyl]-methyl]propyl]carbamate | 2:1 | 1:1 | 1:4 |
| Compound 3 | N-[[(cyclopropylmethoxy)amino][6-(difluoromethoxy)-2,3-difluorophenyl]methylene]benzeneacetamide | 1:2 | 1:7 | 1:24 |
| Compound 3 | α-[methoxyimino]-N-methyl-2-[[[1-[3-(trifluoromethyl)-phenyl]ethoxy]imino]methyl]benzeneacetamide | 3:1 | 1:1 | 1:3 |
| Compound 3 | N'-[4-[4-chloro-3-(trifluoromethyl)phenoxy]-2,5-dimethyl-phenyl]-N-ethyl-N-methylmethanimidamide | 3:1 | 1:1 | 1:3 |
| Compound 3 | N-(4-chloro-2-nitrophenyl)-N-ethyl-4-methylbenzene-sulfonamide | 3:1 | 1:1 | 1:3 |
| Compound 3 | 2-[[[3-(2,6-dichlorophenyl)-1-methyl-2-propen-1-ylidene]-amino]oxy]methyl]-α-(methoxyimino)-N-methylbenzene-acetamide | 3:1 | 1:1 | 1:3 |
| Compound 3 | pentyl N-[4-[[[[(1-methyl-1H-tetrazol-5-yl)phenyl-methylene]amino]oxy]methyl]-2-thiazolyl]carbamate | 3:1 | 1:1 | 1:3 |
| Compound 3 | pentyl N-[6-[[[[(1-methyl-1H-tetrazol-5-yl)phenyl-methylene]amino]oxy]methyl]-2-pyridinyl]carbamate | 3:1 | 1:1 | 1:3 |
| Compound 3 | 2-[(3-bromo-6-quinolinyl)oxy]-N-(1,1-dimethyl-2-butyn-1-yl)-2-(methylthio)acetamide | 2:1 | 1:1 | 1:4 |
| Compound 3 | 2-[(3-ethynyl-6-quinolinyl)oxy]-N-[1-(hydroxymethyl)-1-methyl-2-propyn-1-yl]-2-(methylthio)acetamide | 2:1 | 1:1 | 1:4 |
| Compound 3 | N-(1,1-dimethyl-2-butyn-1-yl)-2-[(3-ethynyl-6-quinolinyl)oxy]-2-(methylthio)acetamide | 2:1 | 1:1 | 1:4 |

(*)Ratios of Component (b) relative to Component (a) by weight.

Tables A2 through A43 are each constructed the same as Table A1 above except that entries below the "Component (a)" column heading are replaced with the respective Component (a) Column Entry shown below. Thus, for example, in Table A2 the entries below the "Component (a)" column heading all recite "Compound 7", and the first line below the column headings in Table A2 specifically discloses a mixture of Compound 7 with acibenzolar-S-methyl. Tables A3 through A43 are constructed similarly.

| Table Number | Component (a) Column Entry |
|---|---|
| A2 | Compound 7 |
| A3 | Compound 8 |
| A4 | Compound 13 |
| A5 | Compound 17 |
| A6 | Compound 40 |
| A7 | Compound 47 |
| A8 | Compound 81 |
| A9 | Compound 82 |
| A10 | Compound 122 |
| A11 | Compound 136 |
| A12 | Compound 143 |
| A13 | Compound 144 |
| A14 | Compound 161 |
| A15 | Compound 195 |
| A16 | Compound 238 |
| A17 | Compound 239 |
| A18 | Compound 240 |
| A19 | Compound 241 |
| A20 | Compound 244 |
| A21 | Compound 245 |
| A22 | Compound 247 |
| A23 | Compound 252 |
| A24 | Compound 253 |
| A25 | Compound 254 |
| A26 | Compound 257 |
| A27 | Compound 258 |
| A28 | Compound 259 |
| A29 | Compound 260 |
| A30 | Compound 261 |
| A31 | Compound 262 |

-continued

| Table Number | Component (a) Column Entry |
|---|---|
| A32 | Compound 263 |
| A33 | Compound 264 |
| A34 | Compound 265 |
| A35 | Compound 266 |
| A36 | Compound 267 |
| A37 | Compound 268 |
| A38 | Compound 269 |
| A39 | Compound 270 |
| A40 | Compound 271 |
| A41 | Compound 273 |
| A42 | Compound 275 |
| A43 | Compound 276 |

Table B1 lists specific combinations of a Component (b) compound with Component (a) illustrative of the mixtures, compositions and methods of the present invention. The first column of Table B1 lists the specific Component (b) compound (e.g., "acibenzolar-S-methyl" in the first line). The second, third and fourth columns of Table B1 lists ranges of weight ratios for rates at which the Component (b) compound is typically applied to a field-grown crop relative to Component (a) (e.g., "2:1 to 1:180" of acibenzolar-S-methyl relative to Component (a) by weight). Thus, for example, the first line of Table B1 specifically discloses the combination of acibenzolar-S-methyl with Component (a) is typically applied in a weight ratio between 2:1 to 1:180. The remaining lines of Table B1 are to be construed similarly. Of particular note is a composition comprising a mixture of any one of the compounds listed in Embodiment 45 as Component (a) with a compound listed in the Component (b) column of Table B1 according to the weight ratios disclosed in Table B1. Table B1 thus supplements the specific ratios disclosed in Tables A1 through A43 with ranges of ratios for these combinations.

TABLE B1

| Component (b) | Typical Weight Ratio | More Typical Weight Ratio | Most Typical Weight Ratio |
|---|---|---|---|
| acibenzolar-S-methyl | 2:1 to 1:180 | 1:1 to 1:60 | 1:1 to 1:18 |
| aldimorph | 30:1 to 1:3 | 10:1 to 1:1 | 7:1 to 1:1 |
| ametoctradin | 9:1 to 1:18 | 3:1 to 1:6 | 3:1 to 1:3 |
| amisulbrom | 6:1 to 1:18 | 2:1 to 1:6 | 1:1 to 1:6 |
| anilazine | 90:1 to 2:1 | 30:1 to 4:1 | 22:1 to 4:1 |
| azaconazole | 7:1 to 1:18 | 2:1 to 1:6 | 2:1 to 1:4 |
| azoxystrobin | 9:1 to 1:12 | 3:1 to 1:4 | 3:1 to 1:3 |
| benalaxyl | 4:1 to 1:18 | 1:1 to 1:6 | 1:1 to 1:6 |
| benalaxyl-M | 4:1 to 1:36 | 1:1 to 1:12 | 1:1 to 1:8 |
| benodanil | 18:1 to 1:6 | 6:1 to 1:2 | 4:1 to 1:2 |
| benomyl | 45:1 to 1:4 | 15:1 to 1:1 | 11:1 to 1:1 |
| benthiavalicarb or benthiavalicarb-isopropyl | 2:1 to 1:36 | 1:1 to 1:12 | 1:1 to 1:12 |
| bethoxazin | 150:1 to 1:36 | 50:1 to 1:12 | 15:1 to 2:1 |
| binapacryl | 150:1 to 1:36 | 50:1 to 1:12 | 15:1 to 2:1 |
| biphenyl | 150:1 to 1:36 | 50:1 to 1:12 | 15:1 to 2:1 |
| bitertanol | 15:1 to 1:5 | 5:1 to 1:2 | 3:1 to 1:2 |
| bixafen | 12:1 to 1:9 | 4:1 to 1:3 | 2:1 to 1:3 |
| blasticidin-S | 3:1 to 1:90 | 1:1 to 1:30 | 1:4 to 1:30 |
| boscalid | 18:1 to 1:6 | 6:1 to 1:2 | 4:1 to 1:2 |
| bromuconazole | 15:1 to 1:9 | 5:1 to 1:3 | 3:1 to 1:3 |
| bupirimate | 3:1 to 1:90 | 1:1 to 1:30 | 1:3 to 1:30 |
| captafol | 90:1 to 1:4 | 30:1 to 1:2 | 15:1 to 2:1 |
| captan | 90:1 to 1:4 | 30:1 to 1:2 | 15:1 to 2:1 |
| carbendazim | 45:1 to 1:4 | 15:1 to 1:2 | 11:1 to 2:1 |
| carboxin | 18:1 to 1:6 | 6:1 to 1:2 | 4:1 to 1:2 |
| carpropamid | 15:1 to 1:9 | 5:1 to 1:3 | 3:1 to 1:3 |
| chloroneb | 300:1 to 2:1 | 100:1 to 4:1 | 100:1 to 14:1 |
| chlorothalonil | 90:1 to 1:4 | 30:1 to 1:2 | 15:1 to 2:1 |
| chlozolinate | 45:1 to 1:2 | 15:1 to 2:1 | 11:1 to 2:1 |
| clotrimazole | 15:1 to 1:9 | 5:1 to 1:3 | 3:1 to 1:3 |
| copper salts such as Bordeaux mixture (tribasic copper sulfate), copper | 450:1 to 1:1 | 150:1 to 4:1 | 45:1 to 5:1 |

TABLE B1-continued

| Component (b) | Typical Weight Ratio | More Typical Weight Ratio | Most Typical Weight Ratio |
|---|---|---|---|
| oxychloride, copper sulfate and copper hydroxide | | | |
| cyazofamid | 4:1 to 1:18 | 1:1 to 1:6 | 1:1 to 1:6 |
| cyflufenamid | 1:1 to 1:90 | 1:2 to 1:30 | 1:2 to 1:24 |
| cymoxanil | 6:1 to 1:18 | 2:1 to 1:6 | 1:1 to 1:5 |
| cyproconazole | 4:1 to 1:18 | 1:1 to 1:6 | 1:1 to 1:6 |
| cyprodinil | 22:1 to 1:9 | 7:1 to 1:3 | 4:1 to 1:2 |
| dichlofluanid | 150:1 to 1:36 | 50:1 to 1:12 | 15:1 to 2:1 |
| diclocymet | 150:1 to 1:36 | 50:1 to 1:12 | 15:1 to 2:1 |
| diclomezine | 15:1 to 1:9 | 5:1 to 1:3 | 3:1 to 1:3 |
| dicloran | 150:1 to 1:36 | 50:1 to 1:12 | 15:1 to 2:1 |
| diethofencarb | 22:1 to 1:9 | 7:1 to 1:3 | 7:1 to 1:2 |
| difenoconazole | 4:1 to 1:36 | 1:1 to 1:12 | 1:1 to 1:12 |
| diflumetorim | 150:1 to 1:36 | 50:1 to 1:12 | 15:1 to 2:1 |
| dimethirimol | 3:1 to 1:90 | 1:1 to 1:30 | 1:3 to 1:30 |
| dimethomorph | 9:1 to 1:6 | 3:1 to 1:2 | 3:1 to 1:2 |
| dimoxystrobin | 9:1 to 1:18 | 3:1 to 1:6 | 2:1 to 1:4 |
| diniconazole | 3:1 to 1:36 | 1:1 to 1:12 | 1:1 to 1:8 |
| diniconazole M | 3:1 to 1:90 | 1:1 to 1:30 | 1:1 to 1:12 |
| dinocap | 7:1 to 1:9 | 2:1 to 1:3 | 2:1 to 1:3 |
| dithianon | 15:1 to 1:4 | 5:1 to 1:2 | 5:1 to 1:2 |
| dodemorph | 30:1 to 1:3 | 10:1 to 1:1 | 7:1 to 1:1 |
| dodine | 30:1 to 1:2 | 10:1 to 2:1 | 10:1 to 2:1 |
| edifenphos | 30:1 to 1:9 | 10:1 to 1:3 | 3:1 to 1:3 |
| enestroburin | 9:1 to 1:18 | 3:1 to 1:6 | 2:1 to 1:4 |
| epoxiconazole | 3:1 to 1:36 | 1:1 to 1:12 | 1:1 to 1:7 |
| etaconazole | 3:1 to 1:36 | 1:1 to 1:12 | 1:1 to 1:7 |
| ethaboxam | 7:1 to 1:9 | 2:1 to 1:3 | 2:1 to 1:3 |
| ethirimol | 30:1 to 1:3 | 10:1 to 1:1 | 7:1 to 1:1 |
| etridiazole | 30:1 to 1:9 | 10:1 to 1:3 | 7:1 to 1:2 |
| famoxadone | 9:1 to 1:18 | 3:1 to 1:6 | 2:1 to 1:4 |
| fenamidone | 6:1 to 1:18 | 2:1 to 1:6 | 2:1 to 1:4 |
| fenarimol | 3:1 to 1:90 | 1:1 to 1:30 | 1:2 to 1:24 |
| fenbuconazole | 3:1 to 1:30 | 1:1 to 1:10 | 1:1 to 1:10 |
| fenfuram | 18:1 to 1:6 | 6:1 to 1:2 | 4:1 to 1:2 |
| fenhexamid | 30:1 to 1:2 | 10:1 to 2:1 | 10:1 to 2:1 |
| fenoxanil | 150:1 to 1:36 | 50:1 to 1:12 | 15:1 to 1:1 |
| fenpiclonil | 75:1 to 1:9 | 25:1 to 1:3 | 15:1 to 2:1 |
| fenpropidin | 30:1 to 1:3 | 10:1 to 1:1 | 7:1 to 1:1 |
| fenpropimorph | 30:1 to 1:3 | 10:1 to 1:1 | 7:1 to 1:1 |
| fenpyrazamine | 100:1 to 1:100 | 10:1 to 1:10 | 3:1 to 1:3 |
| fentin salt such as the acetate, chloride or hydroxide | 15:1 to 1:9 | 5:1 to 1:3 | 3:1 to 1:3 |
| ferbam | 300:1 to 1:2 | 100:1 to 2:1 | 30:1 to 4:1 |
| ferimzone | 30:1 to 1:5 | 10:1 to 1:2 | 7:1 to 1:2 |
| fluazinam | 22:1 to 1:5 | 7:1 to 1:2 | 3:1 to 1:2 |
| fludioxonil | 7:1 to 1:12 | 2:1 to 1:4 | 2:1 to 1:4 |
| flumetover | 9:1 to 1:6 | 3:1 to 1:2 | 3:1 to 1:2 |
| flumorph | 9:1 to 1:18 | 3:1 to 1:6 | 3:1 to 1:3 |
| fluopicolide | 3:1 to 1:18 | 1:1 to 1:6 | 1:1 to 1:6 |
| fluopyram | 15:1 to 1:90 | 5:1 to 1:30 | 3:1 to 1:3 |
| fluoromide | 150:1 to 2:1 | 50:1 to 4:1 | 37:1 to 5:1 |
| fluoxastrobin | 4:1 to 1:18 | 1:1 to 1:6 | 1:1 to 1:6 |
| fluquinconazole | 4:1 to 1:12 | 1:1 to 1:4 | 1:1 to 1:4 |
| flusilazole | 15:1 to 1:9 | 5:1 to 1:3 | 3:1 to 1:3 |
| flusulfamide | 90:1 to 1:2 | 30:1 to 2:1 | 15:1 to 2:1 |
| flutianil | 7:1 to 1:36 | 2:1 to 1:12 | 1:1 to 1:6 |
| flutolanil | 18:1 to 1:6 | 6:1 to 1:2 | 4:1 to 1:2 |
| flutriafol | 4:1 to 1:12 | 1:1 to 1:4 | 1:1 to 1:4 |
| fluxapyroxad | 12:1 to 1:9 | 4:1 to 1:3 | 2:1 to 1:3 |
| folpet | 90:1 to 1:4 | 30:1 to 1:2 | 15:1 to 2:1 |
| fosetyl-aluminum | 225:1 to 2:1 | 75:1 to 5:1 | 30:1 to 5:1 |
| fuberidazole | 45:1 to 1:4 | 15:1 to 1:2 | 11:1 to 2:1 |
| furalaxyl | 15:1 to 1:45 | 5:1 to 1:15 | 1:1 to 1:6 |
| furametpyr | 150:1 to 1:36 | 50:1 to 1:12 | 15:1 to 2:1 |
| guazatine or iminoctadine | 150:1 to 1:36 | 50:1 to 1:12 | 15:1 to 2:1 |
| hexaconazole | 15:1 to 1:36 | 5:1 to 1:12 | 1:1 to 1:5 |
| hymexazol | 225:1 to 2:1 | 75:1 to 4:1 | 75:1 to 9:1 |
| imazalil | 7:1 to 1:18 | 2:1 to 1:6 | 1:1 to 1:5 |
| imibenconazole | 15:1 to 1:36 | 5:1 to 1:12 | 1:1 to 1:5 |
| iodocarb | 150:1 to 1:36 | 50:1 to 1:12 | 15:1 to 2:1 |
| ipconazole | 15:1 to 1:36 | 5:1 to 1:12 | 1:1 to 1:5 |
| iprobenfos | 150:1 to 1:36 | 50:1 to 1:12 | 15:1 to 2:1 |
| iprodione | 120:1 to 1:2 | 40:1 to 2:1 | 15:1 to 2:1 |
| iprovalicarb | 9:1 to 1:9 | 3:1 to 1:3 | 2:1 to 1:3 |
| isoprothiolane | 150:1 to 2:1 | 50:1 to 4:1 | 45:1 to 5:1 |
| isopyrazam | 12:1 to 1:9 | 4:1 to 1:3 | 2:1 to 1:3 |

TABLE B1-continued

| Component (b) | Typical Weight Ratio | More Typical Weight Ratio | Most Typical Weight Ratio |
|---|---|---|---|
| isotianil | 12:1 to 1:9 | 4:1 to 1:3 | 2:1 to 1:3 |
| kasugamycin | 7:1 to 1:90 | 2:1 to 1:30 | 1:2 to 1:24 |
| kresoxim-methyl | 7:1 to 1:18 | 2:1 to 1:6 | 2:1 to 1:4 |
| mancozeb | 180:1 to 1:3 | 60:1 to 2:1 | 22:1 to 3:1 |
| mandipropamid | 6:1 to 1:18 | 2:1 to 1:6 | 2:1 to 1:4 |
| maneb | 180:1 to 1:3 | 60:1 to 2:1 | 22:1 to 3:1 |
| mepanipyrim | 18:1 to 1:3 | 6:1 to 1:1 | 6:1 to 1:1 |
| mepronil | 7:1 to 1:36 | 2:1 to 1:12 | 1:1 to 1:6 |
| meptyldinocap | 7:1 to 1:9 | 2:1 to 1:3 | 2:1 to 1:3 |
| metalaxyl | 15:1 to 1:45 | 5:1 to 1:15 | 1:1 to 1:6 |
| metalaxyl-M | 7:1 to 1:90 | 2:1 to 1:30 | 1:1 to 1:12 |
| metconazole | 3:1 to 1:18 | 1:1 to 1:6 | 1:1 to 1:6 |
| methasulfocarb | 150:1 to 1:36 | 50:1 to 1:12 | 15:1 to 1:1 |
| metiram | 150:1 to 1:36 | 50:1 to 1:12 | 15:1 to 1:1 |
| metominostrobin | 9:1 to 1:12 | 3:1 to 1:4 | 3:1 to 1:3 |
| metrafenone | 6:1 to 1:12 | 2:1 to 1:4 | 2:1 to 1:4 |
| myclobutanil | 5:1 to 1:26 | 1:1 to 1:9 | 1:1 to 1:8 |
| naftifine | 150:1 to 1:36 | 50:1 to 1:12 | 15:1 to 2:1 |
| neo-asozin (ferric methanearsonate) | 150:1 to 1:36 | 50:1 to 1:12 | 15:1 to 2:1 |
| nuarimol | 15:1 to 1:9 | 5:1 to 1:3 | 3:1 to 1:3 |
| octhilinone | 150:1 to 1:36 | 50:1 to 1:12 | 15:1 to 1:1 |
| ofurace | 15:1 to 1:45 | 5:1 to 1:15 | 1:1 to 1:6 |
| orysastrobin | 9:1 to 1:12 | 3:1 to 1:4 | 3:1 to 1:3 |
| oxadixyl | 15:1 to 1:45 | 5:1 to 1:15 | 1:1 to 1:6 |
| oxolinic acid | 30:1 to 1:9 | 10:1 to 1:3 | 7:1 to 1:2 |
| oxpoconazole | 15:1 to 1:36 | 5:1 to 1:12 | 1:1 to 1:5 |
| oxycarboxin | 18:1 to 1:6 | 6:1 to 1:2 | 4:1 to 1:2 |
| oxytetracycline | 15:1 to 1:9 | 5:1 to 1:3 | 3:1 to 1:3 |
| pefurazoate | 150:1 to 1:36 | 50:1 to 1:12 | 15:1 to 2:1 |
| penconazole | 1:1 to 1:45 | 1:2 to 1:15 | 1:2 to 1:15 |
| pencycuron | 150:1 to 1:2 | 50:1 to 2:1 | 11:1 to 2:1 |
| penflufen | 12:1 to 1:9 | 4:1 to 1:3 | 2:1 to 1:3 |
| penthiopyrad | 12:1 to 1:9 | 4:1 to 1:3 | 2:1 to 1:3 |
| phosphorous acid and salts thereof | 150:1 to 1:36 | 50:1 to 1:12 | 15:1 to 2:1 |
| phthalide | 150:1 to 1:36 | 50:1 to 1:12 | 15:1 to 2:1 |
| picoxystrobin | 7:1 to 1:18 | 2:1 to 1:6 | 1:1 to 1:5 |
| piperalin | 15:1 to 1:9 | 5:1 to 1:3 | 3:1 to 1:3 |
| polyoxin | 15:1 to 1:9 | 5:1 to 1:3 | 3:1 to 1:3 |
| probenazole | 15:1 to 1:9 | 5:1 to 1:3 | 3:1 to 1:3 |
| prochloraz | 22:1 to 1:4 | 7:1 to 1:1 | 7:1 to 1:2 |
| procymidone | 45:1 to 1:3 | 15:1 to 1:1 | 11:1 to 2:1 |
| propamocarb or propamocarb-hydrochloride | 30:1 to 1:2 | 10:1 to 2:1 | 10:1 to 2:1 |
| propiconazole | 4:1 to 1:18 | 1:1 to 1:6 | 1:1 to 1:5 |
| propineb | 45:1 to 1:2 | 15:1 to 2:1 | 11:1 to 2:1 |
| proquinazid | 3:1 to 1:36 | 1:1 to 1:12 | 1:1 to 1:12 |
| prothiocarb | 9:1 to 1:18 | 3:1 to 1:6 | 3:1 to 1:3 |
| prothioconazole | 6:1 to 1:18 | 2:1 to 1:6 | 1:1 to 1:5 |
| pyraclostrobin | 9:1 to 1:18 | 3:1 to 1:6 | 2:1 to 1:4 |
| pyrametostrobin | 9:1 to 1:18 | 3:1 to 1:6 | 2:1 to 1:4 |
| pyraoxystrobin | 9:1 to 1:18 | 3:1 to 1:6 | 2:1 to 1:4 |
| pyrazophos | 150:1 to 1:36 | 50:1 to 1:12 | 15:1 to 1:1 |
| pyribencarb | 15:1 to 1:6 | 5:1 to 1:2 | 4:1 to 1:2 |
| pyrifenox | 15:1 to 1:9 | 5:1 to 1:3 | 3:1 to 1:3 |
| pyrimethanil | 30:1 to 1:6 | 10:1 to 1:2 | 3:1 to 1:2 |
| pyriofenone | 6:1 to 1:12 | 2:1 to 1:4 | 2:1 to 1:4 |
| pyroquilon | 15:1 to 1:9 | 5:1 to 1:3 | 3:1 to 1:3 |
| pyrrolnitrin | 150:1 to 1:36 | 50:1 to 1:12 | 15:1 to 2:1 |
| quinconazole | 4:1 to 1:12 | 1:1 to 1:4 | 1:1 to 1:4 |
| quinmethionate | 150:1 to 1:36 | 50:1 to 1:12 | 15:1 to 2:1 |
| quinoxyfen | 4:1 to 1:18 | 1:1 to 1:6 | 1:1 to 1:6 |
| quintozene | 150:1 to 1:36 | 50:1 to 1:12 | 15:1 to 2:1 |
| silthiofam | 7:1 to 1:18 | 2:1 to 1:6 | 2:1 to 1:4 |
| simeconazole | 15:1 to 1:36 | 5:1 to 1:12 | 1:1 to 1:5 |
| spiroxamine | 22:1 to 1:4 | 7:1 to 1:2 | 5:1 to 1:2 |
| streptomycin | 15:1 to 1:9 | 5:1 to 1:3 | 3:1 to 1:3 |
| sulfur | 300:1 to 3:1 | 100:1 to 9:1 | 75:1 to 9:1 |
| tebuconazole | 7:1 to 1:18 | 2:1 to 1:6 | 1:1 to 1:5 |
| tebufloquin | 100:1 to 1:100 | 10:1 to 1:10 | 3:1 to 1:3 |
| tecloftalam | 150:1 to 1:36 | 50:1 to 1:12 | 15:1 to 2:1 |
| tecnazene | 150:1 to 1:36 | 50:1 to 1:12 | 15:1 to 2:1 |
| terbinafine | 150:1 to 1:36 | 50:1 to 1:12 | 15:1 to 2:1 |
| tetraconazole | 15:1 to 1:36 | 5:1 to 1:12 | 1:1 to 1:5 |
| thiabendazole | 45:1 to 1:4 | 15:1 to 1:2 | 11:1 to 2:1 |
| thifluzamide | 15:1 to 1:9 | 5:1 to 1:3 | 3:1 to 1:3 |
| thiophanate | 45:1 to 1:3 | 15:1 to 2:1 | 11:1 to 2:1 |
| thiophanate-methyl | 45:1 to 1:3 | 15:1 to 2:1 | 11:1 to 2:1 |

TABLE B1-continued

| Component (b) | Typical Weight Ratio | More Typical Weight Ratio | Most Typical Weight Ratio |
|---|---|---|---|
| thiram | 150:1 to 1:2 | 50:1 to 2:1 | 37:1 to 5:1 |
| tiadinil | 12:1 to 1:9 | 4:1 to 1:3 | 2:1 to 1:3 |
| tolclofos-methyl | 150:1 to 1:2 | 50:1 to 2:1 | 37:1 to 5:1 |
| tolylfluanid | 150:1 to 1:36 | 50:1 to 1:12 | 15:1 to 2:1 |
| triadimefon | 15:1 to 1:36 | 5:1 to 1:12 | 1:1 to 1:5 |
| triadimenol | 15:1 to 1:36 | 5:1 to 1:12 | 1:1 to 1:5 |
| triarimol | 3:1 to 1:90 | 1:1 to 1:30 | 1:2 to 1:24 |
| triazoxide | 150:1 to 1:36 | 50:1 to 1:12 | 15:1 to 2:1 |
| tricyclazole | 15:1 to 1:9 | 5:1 to 1:3 | 3:1 to 1:3 |
| tridemorph | 30:1 to 1:3 | 10:1 to 1:1 | 7:1 to 1:1 |
| trifloxystrobin | 6:1 to 1:18 | 2:1 to 1:6 | 2:1 to 1:4 |
| triflumizole | 15:1 to 1:9 | 5:1 to 1:3 | 3:1 to 1:3 |
| triforine | 15:1 to 1:9 | 5:1 to 1:3 | 3:1 to 1:3 |
| trimorphamide | 45:1 to 1:9 | 15:1 to 1:3 | 7:1 to 1:2 |
| triticonazole | 15:1 to 1:36 | 5:1 to 1:12 | 1:1 to 1:5 |
| uniconazole | 15:1 to 1:36 | 5:1 to 1:12 | 1:1 to 1:5 |
| validamycin | 150:1 to 1:36 | 50:1 to 1:12 | 3:1 to 1:3 |
| valifenalate | 6:1 to 1:18 | 2:1 to 1:6 | 2:1 to 1:4 |
| vinclozolin | 120:1 to 1:2 | 40:1 to 2:1 | 15:1 to 2:1 |
| zineb | 150:1 to 1:2 | 50:1 to 2:1 | 37:1 to 5:1 |
| ziram | 150:1 to 1:2 | 50:1 to 2:1 | 37:1 to 5:1 |
| zoxamide | 6:1 to 1:18 | 2:1 to 1:6 | 2:1 to 1:4 |
| 5-chloro-6-(2,4,6-trifluorophenyl)-7-(4-methylpiperidin-1-yl)[1,2,4]triazolo-[1,5-a]pyrimidine | 15:1 to 1:36 | 5:1 to 1:12 | 1:1 to 1:6 |
| N-[2-[4-[[3-(4-chlorophenyl)-2-propyn-1-yl]oxy]-3-methoxyphenyl]ethyl]-3-methyl-2-[(methylsulfonyl)amino]-butanamide | 6:1 to 1:18 | 2:1 to 1:6 | 2:1 to 1:4 |
| N-[2-[4-[[3-(4-chlorophenyl)-2-propyn-1-yl]oxy]-3-methoxyphenyl]ethyl]-3-methyl-2-[(ethylsulfonyl)amino]butanamide | 6:1 to 1:18 | 2:1 to 1:6 | 2:1 to 1:4 |
| 2-butoxy-6-iodo-3-propyl-4H-1-benzopyran-4-one | 3:1 to 1:36 | 1:1 to 1:12 | 1:1 to 1:12 |
| 3-[5-(4-chlorophenyl)-2,3-dimethyl-3-isoxazolidinyl]pyridine | 15:1 to 1:9 | 5:1 to 1:3 | 3:1 to 1:3 |
| N'-[4-[[3-[(4-chlorophenyl)methyl]-1,2,4-thiadiazol-5-yl]oxy]-2,5-dimethylphenyl]-N-ethyl-N-methylmethanimidamide | 20:1 to 1:20 | 8:1 to 1:8 | 3:1 to 1:3 |
| 4-fluorophenyl N-[1-[[[1-(4-cyanophenyl)-ethyl]sulfonyl]methyl]propyl]carbamate | 6:1 to 1:18 | 2:1 to 1:6 | 2:1 to 1:4 |
| N-[[(cyclopropylmethoxy)amino][6-(difluoromethoxy)-2,3-difluorophenyl]-methylene]benzeneacetamide | 1:1 to 1:90 | 1:2 to 1:30 | 1:2 to 1:24 |
| α-[methoxyimino]-N-methyl-2-[[[1-[3-(trifluoromethyl)phenyl]ethoxy]imino]-methyl]benzeneacetamide | 9:1 to 1:18 | 3:1 to 1:6 | 3:1 to 1:3 |
| N'-[4-[4-chloro-3-(trifluoromethyl)-phenoxy]-2,5-dimethylphenyl]-N-ethyl-N-methylmethanimidamide | 15:1 to 1:18 | 5:1 to 1:6 | 3:1 to 1:3 |
| N-(4-chloro-2-nitrophenyl)-N-ethyl-4-methylbenzenesulfonamide | 15:1 to 1:18 | 5:1 to 1:6 | 3:1 to 1:3 |
| 2-[[[3-(2,6-dichlorophenyl)-1-methyl-2-propen-1-ylidene]amino]oxy]methyl]-α-(methoxyimino)-N-methylbenzeneacetamide | 9:1 to 1:18 | 3:1 to 1:6 | 3:1 to 1:3 |
| pentyl N-[4-[[[[(1-methyl-1H-tetrazol-5-yl)phenylmethylene]amino]oxy]methyl]-2-thiazolyl]carbamate | 9:1 to 1:18 | 3:1 to 1:6 | 3:1 to 1:3 |
| pentyl N-[6-[[[[(1-methyl-1H-tetrazol-5-yl)phenylmethylene]amino]oxy]methyl]-2-pyridinyl]carbamate | 9:1 to 1:18 | 3:1 to 1:6 | 3:1 to 1:3 |
| 2-[(3-bromo-6-quinolinyl)oxy]-N-(1,1-dimethyl-2-butyn-1-yl)-2-(methylthio)acetamide | 5:1 to 1:22 | 2:1 to 1:8 | 2:1 to 1:4 |
| 2-[(3-ethynyl-6-quinolinyl)oxy]-N-[1-(hydroxymethyl)-1-methyl-2-propyn-1-yl]-2-(methylthio)acetamide | 5:1 to 1:22 | 2:1 to 1:8 | 2:1 to 1:4 |
| N-(1,1-dimethyl-2-butyn-1-yl)-2-[(3-ethynyl-6-quinolinyl)oxy]-2-(methylthio)acetamide | 5:1 to 1:22 | 2:1 to 1:8 | 2:1 to 1:4 |

As already noted, the present invention includes embodiments wherein in the composition comprising components (a) and (b), component (b) comprises at least one fungicidal compound from each of two groups selected from (b1) through (b46). Tables C1 through C43 list specific mixtures (compound numbers refer to compounds in Index Table A) to illustrate embodiments wherein component (b) includes at least one fungicidal compound from each of two groups selected from (b1) through (b46). In Table C1, each line below the column headings "Component (a)" and "Component (b)" specifically discloses a mixture of Component (a), which is Compound 3, with at least two Component (b) fungicidal compounds. The entries under the heading "Illustrative Ratios" disclose three specific weight ratios of Component (a) to each Component (b) fungicidal compound in sequence for the disclosed mixture. For example, the first line discloses a mixture of Compound 3 with cyproconazole and azoxystrobin and lists weight ratios of Compound 3 to cyproconazole to azoxystrobin of 1:1:1, 2:1:1 or 3:1:1.

TABLE C1

| Component (a) | Component (b) | | Illustrative Ratios(*) | | |
|---|---|---|---|---|---|
| Compound 3 | cyproconazole | azoxystrobin | | 1:1:1 | 2:1:1 | 3:1:1 |
| Compound 3 | cyproconazole | kresoxim-methyl | | 1:1:1 | 2:1:1 | 3:1:1 |
| Compound 3 | cyproconazole | picoxystrobin | | 1:1:1 | 2:1:1 | 3:1:1 |
| Compound 3 | cyproconazole | pyraclostrobin | | 1:1:1 | 2:1:1 | 3:1:1 |
| Compound 3 | cyproconazole | pyrametostrobin | | 1:1:1 | 2:1:1 | 3:1:1 |
| Compound 3 | cyproconazole | pyraoxystrobin | | 1:1:1 | 2:1:1 | 3:1:1 |
| Compound 3 | cyproconazole | trifloxystrobin | | 1:1:1 | 2:1:1 | 3:1:1 |
| Compound 3 | cyproconazole | bixafen | | 1:1:2 | 2:1:2 | 3:1:2 |
| Compound 3 | cyproconazole | boscalid | | 1:1:2 | 2:1:2 | 3:1:2 |
| Compound 3 | cyproconazole | cyflufenamid | | 1:2:1 | 2:2:1 | 3:2:1 |
| Compound 3 | cyproconazole | fluopyram | | 1:1:2 | 2:1:2 | 3:1:2 |
| Compound 3 | cyproconazole | isopyrazam | | 1:1:2 | 2:1:2 | 3:1:2 |
| Compound 3 | cyproconazole | metrafenone | | 1:1:2 | 2:1:2 | 3:1:2 |
| Compound 3 | cyproconazole | penthiopyrad | | 1:1:2 | 2:1:2 | 3:1:2 |
| Compound 3 | cyproconazole | proquinazid | | 1:1:1 | 2:1:1 | 3:1:1 |
| Compound 3 | cyproconazole | pyriofenone | | 1:1:2 | 2:1:2 | 3:1:2 |
| Compound 3 | cyproconazole | quinoxyfen | | 1:1:1 | 2:1:1 | 3:1:1 |
| Compound 3 | cyproconazole | sedaxane | | 1:1:2 | 2:1:2 | 3:1:2 |
| Compound 3 | cyproconazole | picoxystrobin | proquinazid | 1:1:1:1 | 2:1:1:1 | 3:1:1:1 |
| Compound 3 | cyproconazole | trifloxystrobin | proquinazid | 1:1:1:1 | 2:1:1:1 | 3:1:1:1 |
| Compound 3 | difenconazole | azoxystrobin | | 1:1:1 | 2:1:1 | 3:1:1 |
| Compound 3 | difenconazole | kresoxim-methyl | | 1:1:1 | 2:1:1 | 3:1:1 |
| Compound 3 | difenconazole | picoxystrobin | | 1:1:1 | 2:1:1 | 3:1:1 |
| Compound 3 | difenconazole | pyraclostrobin | | 1:1:1 | 2:1:1 | 3:1:1 |
| Compound 3 | difenconazole | pyrametostrobin | | 1:1:1 | 2:1:1 | 3:1:1 |
| Compound 3 | difenoconazole | pyraoxystrobin | | 1:1:1 | 2:1:1 | 3:1:1 |
| Compound 3 | difenconazole | trifloxystrobin | | 1:1:1 | 2:1:1 | 3:1:1 |
| Compound 3 | difenconazole | bixafen | | 1:1:2 | 2:1:2 | 3:1:2 |
| Compound 3 | difenconazole | boscalid | | 1:1:2 | 2:1:2 | 3:1:2 |
| Compound 3 | difenconazole | cyflufenamid | | 1:2:1 | 2:2:1 | 3:2:1 |
| Compound 3 | difenconazole | fluopyram | | 1:1:2 | 2:1:2 | 3:1:2 |
| Compound 3 | difenconazole | isopyrazam | | 1:1:2 | 2:1:2 | 3:1:2 |
| Compound 3 | difenconazole | metrafenone | | 1:1:2 | 2:1:2 | 3:1:2 |
| Compound 3 | difenconazole | penthiopyrad | | 1:1:2 | 2:1:2 | 3:1:2 |
| Compound 3 | difenconazole | proquinazid | | 1:1:1 | 2:1:1 | 3:1:1 |
| Compound 3 | difenconazole | pyriofenone | | 1:1:2 | 2:1:2 | 3:1:2 |
| Compound 3 | difenconazole | quinoxyfen | | 1:1:1 | 2:1:1 | 3:1:1 |
| Compound 3 | difenconazole | sedaxane | | 1:1:2 | 2:1:2 | 3:1:2 |
| Compound 3 | difenconazole | picoxystrobin | proquinazid | 1:1:1:1 | 2:1:1:1 | 3:1:1:1 |
| Compound 3 | difenconazole | trifloxystrobin | proquinazid | 1:1:1:1 | 2:1:1:1 | 3:1:1:1 |
| Compound 3 | epoxiconazole | azoxystrobin | | 1:1:1 | 2:1:1 | 3:1:1 |
| Compound 3 | epoxiconazole | kresoxim-methyl | | 1:1:1 | 2:1:1 | 3:1:1 |
| Compound 3 | epoxiconazole | picoxystrobin | | 1:1:1 | 2:1:1 | 3:1:1 |
| Compound 3 | epoxiconazole | pyraclostrobin | | 1:1:1 | 2:1:1 | 3:1:1 |
| Compound 3 | epoxiconazole | pyrametostrobin | | 1:1:1 | 2:1:1 | 3:1:1 |
| Compound 3 | epoxiconazole | pyraoxystrobin | | 1:1:1 | 2:1:1 | 3:1:1 |
| Compound 3 | epoxiconazole | trifloxystrobin | | 1:1:1 | 2:1:1 | 3:1:1 |
| Compound 3 | epoxiconazole | bixafen | | 1:1:2 | 2:1:2 | 3:1:2 |
| Compound 3 | epoxiconazole | boscalid | | 1:1:2 | 2:1:2 | 3:1:2 |
| Compound 3 | epoxiconazole | cyflufenamid | | 1:2:1 | 2:2:1 | 3:2:1 |
| Compound 3 | epoxiconazole | fluopyram | | 1:1:2 | 2:1:2 | 3:1:2 |
| Compound 3 | epoxiconazole | isopyrazam | | 1:1:2 | 2:1:2 | 3:1:2 |
| Compound 3 | epoxiconazole | metrafenone | | 1:1:2 | 2:1:2 | 3:1:2 |
| Compound 3 | epoxiconazole | penthiopyrad | | 1:1:2 | 2:1:2 | 3:1:2 |
| Compound 3 | epoxiconazole | proquinazid | | 1:1:1 | 2:1:1 | 3:1:1 |
| Compound 3 | epoxiconazole | pyriofenone | | 1:1:2 | 2:1:2 | 3:1:2 |
| Compound 3 | epoxiconazole | quinoxyfen | | 1:1:1 | 2:1:1 | 3:1:1 |
| Compound 3 | epoxiconazole | sedaxane | | 1:1:2 | 2:1:2 | 3:1:2 |
| Compound 3 | epoxiconazole | picoxystrobin | proquinazid | 1:1:1:1 | 2:1:1:1 | 3:1:1:1 |
| Compound 3 | epoxiconazole | trifloxystrobin | proquinazid | 1:1:1:1 | 2:1:1:1 | 3:1:1:1 |
| Compound 3 | metconazole | azoxystrobin | | 1:1:1 | 2:1:1 | 3:1:1 |
| Compound 3 | metconazole | kresoxim-methyl | | 1:1:1 | 2:1:1 | 3:1:1 |
| Compound 3 | metconazole | picoxystrobin | | 1:1:1 | 2:1:1 | 3:1:1 |
| Compound 3 | metconazole | pyraclostrobin | | 1:1:1 | 2:1:1 | 3:1:1 |
| Compound 3 | metconazole | pyrametostrobin | | 1:1:1 | 2:1:1 | 3:1:1 |

TABLE C1-continued

| Component (a) | Component (b) | | Illustrative Ratios(*) | | |
|---|---|---|---|---|---|
| Compound 3 | metconazole | pyraoxystrobin | 1:1:1 | 2:1:1 | 3:1:1 |
| Compound 3 | metconazole | trifloxystrobin | 1:1:1 | 2:1:1 | 3:1:1 |
| Compound 3 | metconazole | bixafen | 1:1:2 | 2:1:2 | 3:1:2 |
| Compound 3 | metconazole | boscalid | 1:1:2 | 2:1:2 | 3:1:2 |
| Compound 3 | metconazole | cyflufenamid | 1:2:1 | 2:2:1 | 3:2:1 |
| Compound 3 | metconazole | fluopyram | 1:1:2 | 2:1:2 | 3:1:2 |
| Compound 3 | metconazole | isopyrazam | 1:1:2 | 2:1:2 | 3:1:2 |
| Compound 3 | metconazole | metrafenone | 1:1:2 | 2:1:2 | 3:1:2 |
| Compound 3 | metconazole | penthiopyrad | 1:1:2 | 2:1:2 | 3:1:2 |
| Compound 3 | metconazole | proquinazid | 1:1:1 | 2:1:1 | 3:1:1 |
| Compound 3 | metconazole | pyriofenone | 1:1:2 | 2:1:2 | 3:1:2 |
| Compound 3 | metconazole | quinoxyfen | 1:1:1 | 2:1:1 | 3:1:1 |
| Compound 3 | metconazole | sedaxane | 1:1:2 | 2:1:2 | 3:1:2 |
| Compound 3 | metconazole | picoxystrobin proquinazid | 1:1:1:1 | 2:1:1:1 | 3:1:1:1 |
| Compound 3 | metconazole | trifloxystrobin proquinazid | 1:1:1:1 | 2:1:1:1 | 3:1:1:1 |
| Compound 3 | myclobutanil | azoxystrobin | 1:1:1 | 2:1:1 | 3:1:1 |
| Compound 3 | myclobutanil | kresoxim-methyl | 1:1:1 | 2:1:1 | 3:1:1 |
| Compound 3 | myclobutanil | picoxystrobin | 1:1:1 | 2:1:1 | 3:1:1 |
| Compound 3 | myclobutanil | pyraclostrobin | 1:1:1 | 2:1:1 | 3:1:1 |
| Compound 3 | myclobutanil | pyrametostrobin | 1:1:1 | 2:1:1 | 3:1:1 |
| Compound 3 | myclobutanil | pyraoxystrobin | 1:1:1 | 2:1:1 | 3:1:1 |
| Compound 3 | myclobutanil | trifloxystrobin | 1:1:1 | 2:1:1 | 3:1:1 |
| Compound 3 | myclobutanil | bixafen | 1:1:2 | 2:1:2 | 3:1:2 |
| Compound 3 | myclobutanil | boscalid | 1:1:2 | 2:1:2 | 3:1:2 |
| Compound 3 | myclobutanil | cyflufenamid | 1:2:1 | 2:2:1 | 3:2:1 |
| Compound 3 | myclobutanil | fluopyram | 1:1:2 | 2:1:2 | 3:1:2 |
| Compound 3 | myclobutanil | isopyrazam | 1:1:2 | 2:1:2 | 3:1:2 |
| Compound 3 | myclobutanil | metrafenone | 1:1:2 | 2:1:2 | 3:1:2 |
| Compound 3 | myclobutanil | penthiopyrad | 1:1:2 | 2:1:2 | 3:1:2 |
| Compound 3 | myclobutanil | proquinazid | 1:1:1 | 2:1:1 | 3:1:1 |
| Compound 3 | myclobutanil | pyriofenone | 1:1:2 | 2:1:2 | 3:1:2 |
| Compound 3 | myclobutanil | quinoxyfen | 1:1:1 | 2:1:1 | 3:1:1 |
| Compound 3 | myclobutanil | sedaxane | 1:1:2 | 2:1:2 | 3:1:2 |
| Compound 3 | myclobutanil | picoxystrobin proquinazid | 1:1:1:1 | 2:1:1:1 | 3:1:1:1 |
| Compound 3 | myclobutanil | trifloxystrobin proquinazid | 1:1:1:1 | 2:1:1:1 | 3:1:1:1 |
| Compound 3 | prothioconazole | azoxystrobin | 1:1:1 | 2:1:1 | 3:1:1 |
| Compound 3 | prothioconazole | kresoxim-methyl | 1:1:1 | 2:1:1 | 3:1:1 |
| Compound 3 | prothioconazole | picoxystrobin | 1:1:1 | 2:1:1 | 3:1:1 |
| Compound 3 | prothioconazole | pyraclostrobin | 1:1:1 | 2:1:1 | 3:1:1 |
| Compound 3 | prothioconazole | pyrametostrobin | 1:1:1 | 2:1:1 | 3:1:1 |
| Compound 3 | prothioconazole | pyraoxystrobin | 1:1:1 | 2:1:1 | 3:1:1 |
| Compound 3 | prothioconazole | trifloxystrobin | 1:1:1 | 2:1:1 | 3:1:1 |
| Compound 3 | prothioconazole | bixafen | 1:1:2 | 2:1:2 | 3:1:2 |
| Compound 3 | prothioconazole | boscalid | 1:1:2 | 2:1:2 | 3:1:2 |
| Compound 3 | prothioconazole | cyflufenamid | 1:2:1 | 2:2:1 | 3:2:1 |
| Compound 3 | prothioconazole | fluopyram | 1:1:2 | 2:1:2 | 3:1:2 |
| Compound 3 | prothioconazole | isopyrazam | 1:1:2 | 2:1:2 | 3:1:2 |
| Compound 3 | prothioconazole | metrafenone | 1:1:2 | 2:1:2 | 3:1:2 |
| Compound 3 | prothioconazole | penthiopyrad | 1:1:2 | 2:1:2 | 3:1:2 |
| Compound 3 | prothioconazole | proquinazid | 1:1:1 | 2:1:1 | 3:1:1 |
| Compound 3 | prothioconazole | pyriofenone | 1:1:2 | 2:1:2 | 3:1:2 |
| Compound 3 | prothioconazole | quinoxyfen | 1:1:1 | 2:1:1 | 3:1:1 |
| Compound 3 | prothioconazole | sedaxane | 1:1:2 | 2:1:2 | 3:1:2 |
| Compound 3 | prothioconazole | picoxystrobin proquinazid | 1:1:1:1 | 2:1:1:1 | 3:1:1:1 |
| Compound 3 | prothioconazole | trifloxystrobin proquinazid | 1:1:1:1 | 2:1:1:1 | 3:1:1:1 |
| Compound 3 | tebuconazole | azoxystrobin | 1:1:1 | 2:1:1 | 3:1:1 |
| Compound 3 | tebuconazole | kresoxim-methyl | 1:1:1 | 2:1:1 | 3:1:1 |
| Compound 3 | tebuconazole | picoxystrobin | 1:1:1 | 2:1:1 | 3:1:1 |
| Compound 3 | tebuconazole | pyraclostrobin | 1:1:1 | 2:1:1 | 3:1:1 |
| Compound 3 | tebuconazole | pyrametostrobin | 1:1:1 | 2:1:1 | 3:1:1 |
| Compound 3 | tebuconazole | pyraoxystrobin | 1:1:1 | 2:1:1 | 3:1:1 |
| Compound 3 | tebuconazole | trifloxystrobin | 1:1:1 | 2:1:1 | 3:1:1 |
| Compound 3 | tebuconazole | bixafen | 1:1:2 | 2:1:2 | 3:1:2 |
| Compound 3 | tebuconazole | boscalid | 1:1:2 | 2:1:2 | 3:1:2 |
| Compound 3 | tebuconazole | cyflufenamid | 1:2:1 | 2:2:1 | 3:2:1 |
| Compound 3 | tebuconazole | fluopyram | 1:1:2 | 2:1:2 | 3:1:2 |
| Compound 3 | tebuconazole | isopyrazam | 1:1:2 | 2:1:2 | 3:1:2 |
| Compound 3 | tebuconazole | metrafenone | 1:1:2 | 2:1:2 | 3:1:2 |
| Compound 3 | tebuconazole | penthiopyrad | 1:1:2 | 2:1:2 | 3:1:2 |
| Compound 3 | tebuconazole | proquinazid | 1:1:1 | 2:1:1 | 3:1:1 |
| Compound 3 | tebuconazole | pyriofenone | 1:1:2 | 2:1:2 | 3:1:2 |
| Compound 3 | tebuconazole | quinoxyfen | 1:1:1 | 2:1:1 | 3:1:1 |
| Compound 3 | tebuconazole | sedaxane | 1:1:2 | 2:1:2 | 3:1:2 |
| Compound 3 | tebuconazole | picoxystrobin proquinazid | 1:1:1:1 | 2:1:1:1 | 3:1:1:1 |
| Compound 3 | tebuconazole | trifloxystrobin proquinazid | 1:1:1:1 | 2:1:1:1 | 3:1:1:1 |

(*)Ratios of Component (a) relative to Component (b) in sequence, by weight.

Tables C2 through C43 are each constructed the same as Table C1 above except that entries below the "Component (a)" column heading are replaced with the respective Component (a) Column Entry shown below. Thus, for example, in Table C2 the entries below the "Component (a)" column heading all recite "Compound 7", and the first line in below the column headings in Table C2 specifically discloses a mixture of Compound 7 with cyproconazole and azoxystrobin, and the illustrative weight ratios of 1:1:1, 2:1:1 and 3:1:1 of Compound 7:cyproconazole:azoxystrobin. Tables C3 through C43 are constructed similarly.

| Table Number | Component (a) Column Entry | Table Number | Component (a) Column Entry |
|---|---|---|---|
| C2 | Compound 7 | C23 | Compound 252 |
| C3 | Compound 8 | C24 | Compound 253 |
| C4 | Compound 13 | C25 | Compound 254 |
| C5 | Compound 17 | C26 | Compound 257 |
| C6 | Compound 40 | C27 | Compound 258 |
| C7 | Compound 47 | C28 | Compound 259 |
| C8 | Compound 81 | C29 | Compound 260 |
| C9 | Compound 82 | C30 | Compound 261 |
| C10 | Compound 122 | C31 | Compound 262 |
| C11 | Compound 136 | C32 | Compound 263 |
| C12 | Compound 143 | C33 | Compound 264 |
| C13 | Compound 144 | C34 | Compound 265 |
| C14 | Compound 161 | C35 | Compound 266 |
| C15 | Compound 195 | C36 | Compound 267 |
| C16 | Compound 238 | C37 | Compound 268 |
| C17 | Compound 239 | C38 | Compound 269 |
| C18 | Compound 240 | C39 | Compound 270 |
| C19 | Compound 241 | C40 | Compound 271 |
| C20 | Compound 244 | C41 | Compound 273 |
| C21 | Compound 245 | C42 | Compound 275 |
| C22 | Compound 247 | C43 | Compound 276 |

Of note is a composition of the present invention comprising a compound of Formula 1 (or an N-oxide or salt thereof) with at least one other fungicidal compound that has a different site of action from the compound of Formula 1. In certain instances, a combination with at least one other fungicidal compound having a similar spectrum of control but a different site of action will be particularly advantageous for resistance management. Thus, a composition of the present invention can advantageously comprise at least one fungicidal active compound selected from the group consisting of (b1) through (b46) as described above, having a similar spectrum of control but a different site of action.

Compositions of component (a), or component (a) with component (b), can be further mixed with one or more other biologically active compounds or agents including insecticides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, plant nutrients, other biologically active compounds or entomopathogenic bacteria, virus or fungi to form a multi-component pesticide giving an even broader spectrum of agricultural protection. Thus the present invention also pertains to a composition comprising a fungicidally effective amount of component (a), or a mixture of component (a) with component (b), and a biologically effective amount of at least one additional biologically active compound or agent and can further comprise at least one of a surfactant, a solid diluent or a liquid diluent. The other biologically active compounds or agents can also be separately formulated in compositions comprising at least one of a surfactant, solid or liquid diluent. For compositions of the present invention, one or more other biologically active compounds or agents can be formulated together with one or both of components (a) and (b) to form a premix, or one or more other biologically active compounds or agents can be formulated separately from components (a) and (b) and the formulations combined together before application (e.g., in a spray tank) or, alternatively, applied in succession.

Examples of such biologically active compounds or agents with which compositions of component (a), or component (a) with component (b), can be formulated are: insecticides such as abamectin, acephate, acetamiprid, acetoprole, acrinathrin, aldicarb, amidoflumet, amitraz, avermectin, azadirachtin, azinphos-methyl, bifenthrin, bifenazate, bistrifluoron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyantraniliprole, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, prothiocarb, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulfoxaflor, sulprofos, tebufenozide, tebufenpyrad, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon, triflumuron; nematocides such as aldicarb, imicyafos, oxamyl and fenamiphos; bactericides such as streptomycin; acaricides such as amitraz, chinomethionat, chlorobenzilate, cyenopyrafen, cyhexatin, dicofol, dienochlor, etoxazole, fenazaquin, fenbutatin oxide, fenpropathrin, fenpyroximate, hexythiazox, propargite, pyridaben and tebufenpyrad; and biological agents including entomopathogenic bacteria, such as *Bacillus thuringiensis* subsp. *aizawai*, *Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV, AfNPV; and granulosis virus (GV) such as CpGV.

General references for these agricultural protectants (i.e. insecticides, fungicides, nematocides, acaricides, herbicides and biological agents) include *The Pesticide Manual*, 13*th Edition*, C. D. S. Tomlin, Ed., British Crop Protection Council, Farnham, Surrey, U.K., 2003 and *The BioPesticide Manual*, *2nd Edition*, L. G. Copping, Ed., British Crop Protection Council, Farnham, Surrey, U.K., 2001.

For embodiments where one or more of these various mixing partners are used, the weight ratio of these various mixing partners (in total) to component (a), or a mixture of component (a) with component (b), is generally between about 1:3000 and about 3000:1. Of note are weight ratios between about 1:100 and about 3000:1, or between about 1:30 and about 300:1 (for example ratios between about 1:1 and about 30:1). It will be evident that including these additional components may expand the spectrum of diseases controlled beyond the spectrum controlled by component (a), or a mixture of component (a) with component (b).

Component (a) compounds and/or combinations thereof with component (b) compounds and/or one or more other biologically active compounds or agents can be applied to plants genetically transformed to express proteins toxic to invertebrate pests (such as *Bacillus thuringiensis* delta-endotoxins). The effect of the exogenously applied present component (a) alone or in combination with component (b) may be synergistic with the expressed toxin proteins.

Of note is the combination or the composition comprising component (a), or components (a) and (b), as described in the Summary of the Invention further comprising at least one invertebrate pest control compound or agent (e.g., insecticide, acaricide). Of particular note is a composition comprising component (a) and at least one (i.e. one or more) invertebrate pest control compound or agent, which then can be subsequently combined with component (b) to provide a composition comprising components (a) and (b) and the one or more invertebrate pest control compounds or agents. Alternatively without first mixing with component (b), a biologically effective amount of the composition comprising component (a) with at least one invertebrate pest control agent can be applied to a plant or plant seed (directly or through the environment of the plant or plant seed) to protect the plant or plant seed from diseases caused by fungal pathogens and injury caused by invertebrate pests.

For embodiments where one or more of invertebrate pest control compounds are used, the weight ratio of these compounds (in total) to the component (a) compounds is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity.

Of note is a composition of the present invention which comprises in addition to a component (a) compound, alone or in combination with component (b), at least one invertebrate pest control compound or agent selected from the group consisting of abamectin, acephate, acetamiprid, acetoprole, acrinathrin, aldicarb, amidoflumet, amitraz, avermectin, azadirachtin, azinphos-methyl, bifenthrin, bifenazate, bistrifluoron, buprofezin, carbofuran, cartap, chinomethionat, chlorfenapyr, chlorfluazuron, chlorantraniliprole, chlorpyrifos, chlorpyrifos-methyl, chlorobenzilate, chromafenozide, clothianidin, cyantraniliprole, cyflumetofen, cyfluthrin, beta-cyfluthrin, cyhalothrin, gamma-cyhalothrin, lambda-cyhalothrin, cyhexatin, cypermethrin, cyromazine, deltamethrin, diafenthiuron, diazinon, dicofol, dieldrin, dienochlor, diflubenzuron, dimefluthrin, dimethoate, dinotefuran, diofenolan, emamectin, endosulfan, esfenvalerate, ethiprole, etoxazole, fenamiphos, fenazaquin, fenbutatin oxide, fenothiocarb, fenoxycarb, fenpropathrin, fenpyroximate, fenvalerate, fipronil, flonicamid, flubendiamide, flucythrinate, tau-fluvalinate, flufenerim, flufenoxuron, fonophos, halofenozide, hexaflumuron, hexythiazox, hydramethylnon, imicyafos, imidacloprid, indoxacarb, isofenphos, lufenuron, malathion, meperfluthrin, metaflumizone, metaldehyde, methamidophos, methidathion, methomyl, methoprene, methoxychlor, methoxyfenozide, metofluthrin, milbemycin oxime, monocrotophos, nicotine, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spiridiclofen, spiromesifen, spirotetramat, sulfoxaflor, sulprofos, tebufenozide, tebufenpyrad, teflubenzuron, tefluthrin, terbufos, tetrachlorvinphos, tetramethylfluthrin, thiacloprid, thiamethoxam, thiodicarb, thiosultap-sodium, tolfenpyrad, tralomethrin, triazamate, trichlorfon, triflumuron, *Bacillus thuringiensis* subsp. *aizawai*, *Bacillus thuringiensis* subsp. *kurstaki*, nucleopolyhedro viruses, encapsulated delta-endotoxins of *Bacillus thuringiensis*, baculoviruses, entomopathogenic bacteria, entomopathogenic viruses and entomopathogenic fungi. Of note is the aforedescribed list excluding meperflutrin, sulfoxaflor and tetramethylfluthrin.

In certain instances, combinations of a component (a) compound, alone or in mixture with component (b), with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism of invertebrate pest control active ingredients occurs at application rates giving agronomically satisfactory levels of invertebrate pest control, such combinations can be advantageous for reducing crop production cost and decreasing environmental load.

Table D1 lists specific combinations of invertebrate pest control agents with Compound 3 (identified in Index Table A) as a component (a) compound illustrative of mixtures and compositions comprising these active ingredients and methods using them according to the present invention. The second column of Table D1 lists the specific invertebrate pest control agents (e.g., "Abamectin" in the first line). The third column of Table D1 lists the mode of action (if known) or chemical class of the invertebrate pest control agents. The fourth column of Table D1 lists embodiment(s) of ranges of weight ratios for rates at which the invertebrate pest control agent is typically applied relative to Compound 3 alone or in combination with component (b) (e.g., "50:1 to 1:50" of abamectin relative to a Compound 3 by weight). Thus, for example, the first line of Table D1 specifically discloses the combination of Compound 3 with abamectin is typically applied in a weight ratio between 50:1 to 1:50. The remaining lines of Table D1 are to be construed similarly.

TABLE D1

| Component (a) | Invertebrate Pest Control Agent | Mode of Action or Chemical Class | Typical Weight Ratio |
|---|---|---|---|
| Compound 3 | Abamectin | macrocyclic lactones | 50:1 to 1:50 |
| Compound 3 | Acetamiprid | neonicotinoids | 150:1 to 1:200 |
| Compound 3 | Amitraz | octopamine receptor ligands | 200:1 to 1:100 |
| Compound 3 | Avermectin | macrocyclic lactones | 50:1 to 1:50 |
| Compound 3 | Azadirachtin | ecdysone agonists | 100:1 to 1:120 |
| Compound 3 | Beta-cyfluthrin | sodium channel modulators | 150:1 to 1:200 |
| Compound 3 | Bifenthrin | sodium channel modulators | 100:1 to 1:10 |
| Compound 3 | Buprofezin | chitin synthesis inhibitors | 500:1 to 1:50 |
| Compound 3 | Cartap | nereistoxin analogs | 100:1 to 1:200 |
| Compound 3 | Chlorantraniliprole | ryanodine receptor ligands | 100:1 to 1:120 |
| Compound 3 | Chlorfenapyr | mitochondrial electron transport inhibitors | 300:1 to 1:200 |
| Compound 3 | Chlorpyrifos | cholinesterase inhibitors | 500:1 to 1:200 |
| Compound 3 | Clothianidin | neonicotinoids | 100:1 to 1:400 |
| Compound 3 | Cyantraniliprole | ryanodine receptor ligands | 100:1 to 1:120 |
| Compound 3 | Cyfluthrin | sodium channel modulators | 150:1 to 1:200 |
| Compound 3 | Cyhalothrin | sodium channel modulators | 150:1 to 1:200 |
| Compound 3 | Cypermethrin | sodium channel modulators | 150:1 to 1:200 |
| Compound 3 | Cyromazine | chitin synthesis inhibitors | 400:1 to 1:50 |
| Compound 3 | Deltamethrin | sodium channel modulators | 50:1 to 1:400 |
| Compound 3 | Dieldrin | cyclodiene insecticides | 200:1 to 1:100 |
| Compound 3 | Dinotefuran | neonicotinoids | 150:1 to 1:200 |
| Compound 3 | Diofenolan | molting inhibitor | 150:1 to 1:200 |
| Compound 3 | Emamectin | macrocyclic lactones | 50:1 to 1:10 |
| Compound 3 | Endosulfan | cyclodiene insecticides | 200:1 to 1:100 |
| Compound 3 | Esfenvalerate | sodium channel modulators | 100:1 to 1:400 |
| Compound 3 | Ethiprole | GABA-regulated chloride channel blockers | 200:1 to 1:100 |
| Compound 3 | Fenothiocarb | | 150:1 to 1:200 |
| Compound 3 | Fenoxycarb | juvenile hormone mimics | 500:1 to 1:100 |
| Compound 3 | Fenvalerate | sodium channel modulators | 150:1 to 1:200 |
| Compound 3 | Fipronil | GABA-regulated chloride channel blockers | 150:1 to 1:100 |
| Compound 3 | Flonicamid | | 200:1 to 1:100 |
| Compound 3 | Flubendiamide | ryanodine receptor ligands | 100:1 to 1:120 |
| Compound 3 | Flufenoxuron | chitin synthesis inhibitors | 200:1 to 1:100 |
| Compound 3 | Hexaflumuron | chitin synthesis inhibitors | 300:1 to 1:50 |
| Compound 3 | Hydramethylnon | mitochondrial electron transport inhibitors | 150:1 to 1:250 |
| Compound 3 | Imidacloprid | neonicotinoids | 1000:1 to 1:1000 |
| Compound 3 | Indoxacarb | sodium channel modulators | 200:1 to 1:50 |
| Compound 3 | Lambda-cyhalothrin | sodium channel modulators | 50:1 to 1:250 |
| Compound 3 | Lufenuron | chitin synthesis inhibitors | 500:1 to 1:250 |
| Compound 3 | Meperfluthrin | sodium channel modulators | 100:1 to 1:400 |
| Compound 3 | Metaflumizone | | 200:1 to 1:200 |
| Compound 3 | Methomyl | cholinesterase inhibitors | 500:1 to 1:100 |
| Compound 3 | Methoprene | juvenile hormone mimics | 500:1 to 1:100 |
| Compound 3 | Methoxyfenozide | ecdysone agonists | 50:1 to 1:50 |
| Compound 3 | Nitenpyram | neonicotinoids | 150:1 to 1:200 |
| Compound 3 | Nithiazine | neonicotinoids | 150:1 to 1:200 |
| Compound 3 | Novaluron | chitin synthesis inhibitors | 500:1 to 1:150 |
| Compound 3 | Oxamyl | cholinesterase inhibitors | 200:1 to 1:200 |
| Compound 3 | Pymetrozine | | 200:1 to 1:100 |
| Compound 3 | Pyrethrin | sodium channel modulators | 100:1 to 1:10 |
| Compound 3 | Pyridaben | mitochondrial electron transport inhibitors | 200:1 to 1:100 |
| Compound 3 | Pyridalyl | | 200:1 to 1:100 |
| Compound 3 | Pyriproxyfen | juvenile hormone mimics | 500:1 to 1:100 |
| Compound 3 | Ryanodine | ryanodine receptor ligands | 100:1 to 1:120 |
| Compound 3 | Spinetoram | macrocyclic lactones | 150:1 to 1:100 |
| Compound 3 | Spinosad | macrocyclic lactones | 500:1 to 1:10 |
| Compound 3 | Spirodiclofen | lipid biosynthesis inhibitors | 200:1 to 1:200 |
| Compound 3 | Spiromesifen | lipid biosynthesis inhibitors | 200:1 to 1:200 |
| Compound 3 | Sulfoxaflor | | 200:1 to 1:200 |
| Compound 3 | Tebufenozide | ecdysone agonists | 500:1 to 1:250 |
| Compound 3 | Tetramethylfluthrin | sodium channel modulators | 100:1 to 1:40 |
| Compound 3 | Thiacloprid | neonicotinoids | 100:1 to 1:200 |
| Compound 3 | Thiamethoxam | neonicotinoids | 1250:1 to 1:1000 |
| Compound 3 | Thiodicarb | cholinesterase inhibitors | 500:1 to 1:400 |
| Compound 3 | Thiosultap-sodium | | 150:1 to 1:100 |
| Compound 3 | Tralomethrin | sodium channel modulators | 150:1 to 1:200 |
| Compound 3 | Triazamate | cholinesterase inhibitors | 250:1 to 1:100 |
| Compound 3 | Triflumuron | chitin synthesis inhibitors | 200:1 to 1:100 |
| Compound 3 | *Bacillus thuringiensis* | biological agents | 50:1 to 1:10 |

TABLE D1-continued

| Component (a) | Invertebrate Pest Control Agent | Mode of Action or Chemical Class | Typical Weight Ratio |
|---|---|---|---|
| Compound 3 | *Bacillus thuringiensis* delta-endotoxin | biological agents | 50:1 to 1:10 |
| Compound 3 | NPV (e.g., Gemstar) | biological agents | 50:1 to 1:10 |

Tables D2 through D43 are each constructed the same as Table D1 above except that entries below the "Component (a)" column heading are replaced with the respective Component (a) Column Entry shown below. Thus, for example, in Table D2 the entries below the "Component (a)" column heading all recite "Compound 7", and the first line in below the column headings in Table D2 specifically discloses a mixture of Compound 7 with abamectin. Tables D3 through D43 are constructed similarly.

| Table Number | Component (a) Column Entries |
|---|---|
| D2 | Compound 7 |
| D3 | Compound 8 |
| D4 | Compound 13 |
| D5 | Compound 17 |
| D6 | Compound 40 |
| D7 | Compound 47 |
| D8 | Compound 81 |
| D9 | Compound 82 |
| D10 | Compound 122 |
| D11 | Compound 136 |
| D12 | Compound 143 |
| D13 | Compound 144 |
| D14 | Compound 161 |
| D15 | Compound 195 |
| D16 | Compound 238 |
| D17 | Compound 239 |
| D18 | Compound 240 |
| D19 | Compound 241 |
| D20 | Compound 244 |
| D21 | Compound 245 |
| D22 | Compound 247 |
| D23 | Compound 252 |
| D24 | Compound 253 |
| D25 | Compound 254 |
| D26 | Compound 257 |
| D27 | Compound 258 |
| D28 | Compound 259 |
| D29 | Compound 260 |
| D30 | Compound 261 |
| D31 | Compound 262 |
| D32 | Compound 263 |
| D33 | Compound 264 |
| D34 | Compound 265 |
| D35 | Compound 266 |
| D36 | Compound 267 |
| D37 | Compound 268 |
| D38 | Compound 269 |
| D39 | Compound 270 |
| D40 | Compound 271 |
| D41 | Compound 273 |
| D42 | Compound 275 |
| D43 | Compound 276 |

One embodiment of invertebrate pest control agents (e.g., insecticides and acaricides) for mixing with compounds of component (a) include sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, meperfluthrin, metofluthrin, profluthrin, pyrethrin, tetramethylfluthrin and tralomethrin; cholinesterase inhibitors such as chlorpyrifos, methomyl, oxamyl, thiodicarb and triazamate; neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-regulated chloride channel blockers such as endosulfan, ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin; cyflumetofen; fenothiocarb; flonicamid; metaflumizone; pyrafluprole; pyridalyl; pyriprole; pymetrozine; spirotetramat; and thiosultap-sodium. One embodiment of biological agents for mixing with compounds of component (a) include nucleopolyhedro virus such as HzNPV and AfNPV; *Bacillus thuringiensis* and encapsulated delta-endotoxins of *Bacillus thuringiensis* such as Cellcap, MPV and MPVII; as well as naturally occurring and genetically modified viral insecticides including members of the family Baculoviridae as well as entomophagous fungi. Of note is a composition comprising component (a) and at least one additional biologically active compound or agent selected from the Invertebrate Pest Control Agents listed in Table D1 above.

The compositions of this invention are useful as plant disease control agents. The present invention therefore further comprises a method for controlling plant diseases caused by fungal plant pathogens comprising applying to the plant or portion thereof to be protected, or to the plant seed or vegetative propagation unit to be protected, an effective amount of a composition of the invention (e.g., a composition comprising component (a), or components (a) and (b)). This aspect of the present invention can also be described as a method for protecting a plant or plant seed from diseases caused by fungal pathogens comprising applying a fungicidally effective amount of a composition of the invention to the plant (or portion thereof) or plant seed (directly or through the environment (e.g., growing medium) of the plant or plant seed).

Plant disease control is ordinarily accomplished by applying an effective amount of a composition of the invention (e.g., comprising component (a), or a mixture of components (a) and (b)), typically as a formulated composition, either pre- or post-infection, to the portion of the plant to be protected such as the roots, stems, foliage, fruit, seeds, tubers or bulbs, or to the media (soil or sand) in which the plants to be protected are growing. Component (a) or mixtures thereof can also be applied to seeds to protect the seeds and seedlings developing from the seeds. The mixtures can also be applied through irrigation water to treat plants.

Suitable rates of application (e.g., fungicidally effective amounts) of component (a) (i.e. at least one compound selected from compounds of Formula 1, N-oxides and salts thereof) as well as suitable rates of application (e.g., biologically effective amounts, fungicidally effective amounts or insecticidally effective amounts) for the mixtures and compositions comprising component (a) according to this invention can be influenced by many factors of the environment and should be determined under actual use conditions. Foliage can normally be protected when treated at a rate of from less than about 1 g/ha to about 5,000 g/ha of active ingredients. Seed and seedlings can normally be protected when seed is treated at a rate of from about 0.1 to about 10 g per kilogram of seed; and vegetative propagation units (e.g., cuttings and tubers) can normally be protected when propagation unit is treated at a rate of from about 0.1 to about 10 g per kilogram of propagation unit. One skilled in the art can easily determine through simple experimentation the application rates of component (a), and mixtures and compositions thereof, containing particular combinations of active ingredients according to this invention needed to provide the desired spectrum of plant protection and control of plant diseases and optionally other plant pests.

The compounds of Formula 1, N-oxides, and salts thereof, are particularly efficacious for controlling plant diseases caused by fungal pathogens, particularly in the Basidomycete and Ascomycete classes. Combining these compounds with other fungicidal compounds can provide control of diseases caused by a broad spectrum of fungal plant pathogens in the Basidiomycete, Ascomycete, Oomycete and Deuteromycete classes. Accordingly, mixtures and compositions described herein can control a broad spectrum of plant diseases, foliar pathogens of crops including: cereal grain crops such as wheat, barley, oats, rye, triticale, rice, maize, sorghum and millet; vine crops such as table and wine grapes; field crops such as oilseed rape (canola), sunflower; sugar beets, sugar cane, soybean, peanuts (groundnut), tobacco, alfafa, clover, lespedeza, trefoil and vetch; pome fruits such as apple, pear, crabapple, loquat, mayhaw and quince; stone fruits such as peaches, cherries, plums, apricots, nectarines and almonds; citrus fruits such as lemons, limes, oranges, grapefruit, mandarin (tangerines) and kumquat; root and tuber vegetables and field crops (and their foliage) such as artichoke, garden and sugar beet, carrot, cassaya, ginger, ginseng, horseradish, parsnip, potato, radish, rutabaga, sweet potato, turnip and yam; bulb vegetables such as garlic, leek, onion and shallot; leafy vegetables such as arugula (roquette), celery, celery, cress, endive (escarole), fennel, head and leaf lettuce, parsley, radicchio (red chicory), rhubarb, spinach and Swiss chard; brassica (cole) leafy vegetables such as broccoli, broccoli raab (rapini), Brussels sprouts, cabbage, bok Choy, cauliflower, collards, kale, kohlrabi, mustard and greens; legume vegetables (succulent or dried) such as lupin, bean (*Phaseolus* spp.) (including field bean, kidney bean, lima bean, navy bean, pinto bean, runner bean, snap bean, tepary bean and wax bean), bean (*Vigna* spp.) (including adzuki bean, asparagus bean, blackeyed pea, catjang, Chinese longbean, cowpea, crowder pea, moth bean, mung bean, rice bean, southern pea, urd bean and yardlong bean), broad bean (fava), chickpea (garbanzo), guar, jackbean, lablab bean, lentil and pea (*Pisum* spp.) (including dwarf pea, edible-podded pea, English pea, field pea, garden pea, green pea, snowpea, sugar snap pea, pigeon pea and soybean); fruiting vegetables such as eggplant, groundcherry (*Physalis* spp.), pepino and pepper (including bell pepper, chili pepper, cooking pepper, pimento, sweet pepper; tomatillo and tomato); cucurbit vegetables such as Chayote (fruit), Chinese waxgourd (Chinese preserving melon), citron melon, cucumber, gherkin, edible gourd (including hyotan, cucuzza, hechima, and Chinese okra), *Momordica* spp. (including balsam apple, balsam pear, bittermelon and Chinese cucumber), muskmelon (including cantaloupe and pumpkin), summer and winter squash (including butternut squash, calabaza, hubbard squash, acorn squash, spaghetti squash) and watermelon; berries such as blackberry (including bingleberry, boysenberry, dewberry, lowberry, marionberry, olallieberry and youngberry), blueberry, cranberry, currant, elderberry, gooseberry, huckleberry, loganberry, raspberry and strawberry; tree nuts such as almond, beech nut, Brazil nut, butternut, cashew, chestnut, chinquapin, filbert (hazelnut), hickory nut, macadamia nut, pecan and walnut; tropical fruits and other crops such as bananas, plantains, mangos, coconuts, papaya, guava, avocado, lichee, agave, coffee, cacao, sugar cane, oil palm, sesame, rubber and spices; fiber crops such as cotton, flax and hemp; turfgrasses (including warm- and cool-season turfgrasses) such as bentgrass, Kentucky bluegrass, St. Augustine grass, tall fescue and Bermuda grass.

These pathogens include: Oomycetes, including *Phytophthora* pathogens such as *Phytophthora infestans*, *Phytophthora megasperma*, *Phytophthora parasitica*, *Phytophthora cinnamomi* and *Phytophthora capsici*, *Pythium* pathogens such as *Pythium* aphanidermatum, and pathogens in the Peronosporaceae family such as *Plasmopara viticola*, *Peronospora* spp. (including *Peronospora tabacina* and *Peronospora parasitica*), *Pseudoperonospora* spp. (including *Pseudoperonospora cubensis*) and *Bremia lactucae*; Ascomycetes, including *Alternaria* pathogens such as *Alternaria solani* and *Alternaria brassicae*, *Guignardia* pathogens such as *Guignardia bidwelli*, *Venturia* pathogens such as *Venturia inaequalis*, *Septoria* pathogens such as *Septoria nodorum* and *Septoria tritici*, powdery mildew disease pathogens such as *Blumeria* spp. (including *Blumeria graminis*) and *Erysiphe* spp. (including *Erysiphe* polygoni), *Uncinula necatur*, *Sphaerotheca fuligena* and *Podosphaera leucotricha*, *Pseudocercosporella herpotrichoides*, *Botrytis* pathogens such as *Botrytis cinerea*, *Monilinia fructicola*, *Sclerotinia* pathogens such as *Sclerotinia sclerotiorum*, *Magnaporthe grisea*, *Phomopsis viticola*, *Helminthosporium* pathogens such as *Helminthosporium tritici repentis*, *Pyrenophora teres*, anthracnose disease pathogens such as *Glomerella* or *Colletotrichum* spp. (such as *Colletotrichum graminicola* and *Colletotrichum* orbiculare), and *Gaeumannomyces graminis*; Basidiomycetes, including rust diseases caused by *Puccinia* spp. (such as *Puccinia recondite*, *Puccinia striiformis*, *Puccinia hordei*, *Puccinia graminis* and *Puccinia arachidis*), *Hemileia vastatrix* and *Phakopsora pachyrhizi*; other pathogens including *Rhizoctonia* spp. (such as *Rhizoctonia solani* and *Rhizoctonia oryzae*); *Fusarium* pathogens such as *Fusarium roseum*, *Fusarium graminearum* and *Fusarium oxysporum*; *Verticillium dahliae*; *Sclerotium rolfsii*; *Rynchosporium secalis*; *Cercosporidium personatum*, *Cercospora arachidicola* and *Cercospora beticola*; *Rutstroemia floccosum* (also known as *Sclerontina homoeocarpa*); and other genera and species closely related to these pathogens. Commonly, pathogens are referred to as diseases, and thus in the preceding sentence the word "pathogen" also refers to the plant disease caused by the pathogen. More precisely, plant diseases are caused by pathogens. Therefore, for example, powdery mildew diseases are plant diseases caused by powdery mildew pathogens, *Septoria* diseases are plant diseases caused by *Septoria* pathogens, and rust diseases are plant diseases caused by rust disease pathogens. Certain fungicidal compounds are also bactericidal, and therefore in addition to their fungicidal activity, the compositions or combinations can also have activity against bacteria such as *Erwinia amylovora*, *Xanthomonas campestris*, *Pseudomonas syringae*, and other related species.

Remarkably, 2,6-substituted aniline-pyrazole compounds of Formula 1 (i.e. Formula 1 wherein X is NH, and $R^1$ and $R^3$ are other than H) wherein $R^2$ is H have now been discovered to have significantly improved pharmacokinetic properties compared to corresponding compounds wherein $R^2$ is other than H. In particular in vertebrate animals, compounds wherein $R^2$ is H instead of other than H have been found to have a significantly diminished distribution into fat, thereby reducing the possibility of bioaccumulation. Illustrative of 2,6-substituted aniline-pyrazole compounds of Formula 1 wherein $R^2$ is H are Compounds 239, 240, 241, 244, 245, 247, 252, 253, 254, 257, 258, 259, 260, 261, 262, 263, 264, 265, 266, 267, 268, 269, 270, 271, 273, 275 and 276 identified in Index Table A. Furthermore, in addition to having more favorable pharmacokinetic properties in vertebrate animals, 2,6-substituted anilino-pyrazole compounds of Formula 1 wherein $R^1$ is halogen, or more particularly Cl or Br, and $R^3$ is F or Cl, or more particularly F, have been discovered to retain remarkably high activity when $R^2$ is H against plant fungal diseases, such as caused by *Septoria tritici*.

The pharmacokinetic properties of compounds of Formula 1 can be measured using a wide variety of assay protocols known in the science of pharmacology. In one illustrative method involving a single oral dose, three male and three female rats receive a single dose of a test substance via oral gavage. Approximately 0.25 mL of blood is collected via tail vein immediately prior to dosing, and then at 0.25, 0.5, 1, 2, 4, 8, 12, 24 h and every 24 h thereafter until sacrifice. At sacrifice, fat is also collected to determine the fat:plasma ratio at sacrifice. Blood is collected into tubes that contain ethylenediaminetetracetic acid (EDTA) and centrifuged at 2500×g in order to separate plasma from blood cells. The plasma is then extracted by protein precipitation using, for example, acetonitrile and a protein precipitation plate (e.g., Strata Impact Protein Precipitation Plate, part number CEO-7565 of Phenomenex, Torrance, Calif., U.S.A.) following directions provided for the plate. Alternatively, the plasma is extracted just with acetonitrile, vortexed (i.e. mixed using a vortex mixer), and centrifuged to pellet the proteins. After removal of the proteins, the plasma is analyzed for parent compound and/or metabolites by liquid chromatography-mass spectrometry (LC/MS). The fat is homogenized and extracted by an organic solvent such as acetonitrile. The extract is then analyzed for parent compound and/or metabolites by LC/MS. The plasma pharmacokinetic data is then analyzed using nonlinear modeling software (e.g., WinNonlin™ from Pharsight, Cary, N.C., U.S.A.) to determine half-life of the administered compound in plasma, the time after administration when the maximum plasma concentration is reached ($T_{max}$), the maximum plasma concentration ($C_{max}$) and the area under the plasma concentration curve (AUC). As analysis of fat requires rat sacrifice, fat data is obtained at single time points (i.e. the time of rat sacrifice). However, by using multiple rats sacrificed after different intervals from time of dosing, such parameters as $C_{max}$ for fat are determined. Using the above described method, Compounds 239, 240 and 241 identified in Index Table A are found to have a significantly diminished distribution into fat compared to corresponding compounds wherein $R^2$ is other than H.

In the present fungicidal compositions, the Formula 1 compounds of component (a) can work synergically with the additional fungicidal compounds of component (b) to provide such beneficial results as broadening the spectrum of plant diseases controlled, extending duration of preventative and curative protection, and suppressing proliferation of resistant fungal pathogens. In particular embodiments, compositions are provided in accordance with this invention that comprise proportions of component (a) and component (b) that are especially useful for controlling particular fungal diseases (such as *Alternaria solani*, *Blumeria graminis* f. sp. *tritici*, *Botrytis cinerea*, *Puccinia recondite* f. sp. *tritici*, *Rhizoctonia solani*, *Septoria nodorum*, *Septoria tritici*).

Mixtures of fungicides may also provide significantly better disease control than could be predicted based on the activity of the individual components. This synergism has been described as "the cooperative action of two components of a mixture, such that the total effect is greater or more prolonged than the sum of the effects of the two (or more) taken independently" (see P. M. L. Tames, Neth. *J. Plant Pathology* 1964, 70, 73-80). In methods providing plant disease control in which synergy is exhibited from a combination of active ingredients (e.g., fungicidal compounds) applied to the plant or seed, the active ingredients are applied in a synergistic weight ratio and synergistic (i.e. synergistically effective) amounts. Measures of disease control, inhibition and prevention cannot exceed 100%. Therefore expression of substantial synergism typically requires use of application rates of active ingredients wherein the active ingredients separately provide much less than 100% effect, so that their additive effect is substantially less than 100% to allow the possibility of increase in effect as result of synergism. On the other hand, application rates of active ingredients that are too low may show not show much activity in mixtures even with the benefit of synergism. One skilled in the art can easily identify and optimize through simple experimentation the weight ratios and application rates (i.e. amounts) of fungicidal compounds providing synergy.

The following Tests include tests demonstrating the efficacy of the present compounds for controlling specific pathogens; this efficacy is thus provided to fungicidal mixtures comprising the present compounds. The following Tests also include tests demonstrating the control efficacy of the mixtures of this invention on specific pathogens. The disease control afforded by the present compounds alone or in mixtures is not limited, however, to the pathogenic fungi species exemplified.

See Index Table A for compound descriptions. See Index Table B for melting point data. See Index Table C for $^1$H NMR data. The following abbreviations are used in the Index Tables which follow: Me is methyl, MeO is methoxy, EtO is ethoxy, and —CN is cyano. Because of symmetry, $R^1$ can be interchanged with $R^3$, and $R^4$ can be interchanged with $R^6$, if allowed by the definitions of $R^1$, $R^3$, $R^4$ and $R^6$. The abbreviation "Cmpd." stands for "Compound", and the abbreviation "Ex." stands for "Example" and is followed by a number indicating in which Synthesis Example the compound is prepared. Mass spectra (M.S.) are reported as the molecular weight of the highest isotopic abundance parent ion (M+1) formed by addition of H$^+$ (molecular weight of 1) to the molecule, observed by mass spectrometry using atmospheric pressure chemical ionization (AP$^+$). The presence of molecular ions containing one or more higher atomic weight isotopes of lower abundance (e.g., $^{37}$Cl, $^{81}$Br) is not reported.

INDEX TABLE A

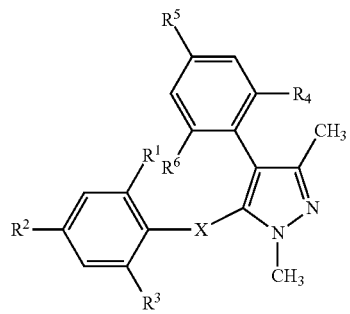

| Cmpd No. | R¹ | R² | R³ | R⁴ | R⁵ | R⁶ | X | M.S. |
|---|---|---|---|---|---|---|---|---|
| 1 | F | H | H | Cl | F | H | NH | 334 |
| 2 | F | F | H | Cl | F | H | NH | 352 |
| 3 (Ex. 1) | F | MeO | F | Cl | F | H | NH | ** |
| 4 | F | F | F | Cl | F | H | NH | 370 |
| 5 | F | MeO | H | Cl | F | H | O | 365 |
| 6 | F | F | H | F | MeO | F | NH | 366 |
| 7 (Ex. 2) | F | F | F | F | MeO | F | NH | ** |
| 8 (Ex. 6) | F | —CN | F | F | F | F | O | ** |
| 9 | Cl | Cl | H | F | F | F | O | 387 |
| 10 | Cl | MeO | H | F | MeO | F | O | 399 |
| 11 | F | F | F | F | F | H | NH | 354 |
| 12 | F | MeO | F | F | F | H | NH | 366 |
| 13 (Ex. 3) | F | —CN | F | Cl | F | H | O | ** |
| 14 | F | —CN | F | F | MeO | H | O | 374 |
| 15 | F | Cl | F | F | MeO | F | O | *** |
| 16 | F | MeO | F | Cl | Cl | H | NH | 398 |
| 17 (Ex. 4) | F | F | H | Cl | Cl | H | NH | ** |
| 18 | F | F | F | Cl | Cl | H | NH | 386 |
| 19 | F | MeO | F | F | F | F | NH | 384 |
| 20 | F | —CN | F | F | MeO | F | NH | 391 |
| 21 | F | MeO | F | F | MeO | F | NH | 396 |
| 22 | F | H | F | F | MeO | F | O | 367 |
| 23 | Cl | F | H | F | MeO | F | NH | 382 |
| 24 | F | Br | F | F | MeO | F | O | 447 |
| 25 | F | —CN | F | Cl | F | H | NH | 377 |
| 26 | F | —CN | F | F | F | H | NH | 379 |
| 27 | F | —CN | H | F | F | F | O | 362 |
| 28 | Cl | —CN | H | F | F | F | O | 378 |
| 29 | F | F | F | Cl | MeO | H | NH | 382 |
| 30 | F | F | H | F | —CN | H | NH | 361 |
| 31 | Cl | F | H | F | —CN | F | NH | * |
| 32 | Cl | —CN | H | F | MeO | F | NH | 389 |
| 33 | F | —CN | H | Cl | F | H | O | 360 |
| 34 | F | —CN | H | F | F | F | NH | 361 |
| 35 | F | F | F | F | —CN | F | NH | * |
| 36 | F | MeO | F | F | —CN | F | NH | * |
| 37 | Cl | —CN | H | Cl | F | H | O | 376 |
| 38 | F | —CN | F | F | MeO | F | O | 392 |
| 39 | F | F | F | F | EtO | F | NH | 380 |
| 40 | F | Cl | H | F | CN | F | NH | * |
| 41 | F | —CN | F | Cl | MeO | H | O | 390 |
| 42 | F | F | H | Cl | MeO | H | NH | 364 |
| 43 | F | H | F | Cl | MeO | H | NH | 364 |
| 44 | Cl | —CN | H | Cl | F | H | NH | 375 |
| 45 | F | —CN | F | F | F | H | O | 362 |
| 46 | F | H | F | Cl | F | H | NH | 352 |
| 47 | Cl | F | H | Cl | F | H | NH | 368 |
| 48 | F | F | H | Cl | H | F | NH | 352 |
| 49 | F | F | H | F | H | F | NH | * |
| 50 | Cl | Cl | H | F | H | F | NH | * |
| 51 | F | MeO | H | F | H | H | NH | * |
| 52 | F | F | H | F | H | H | NH | 318 |
| 53 | F | F | F | F | H | H | NH | 336 |
| 54 | F | MeO | F | H | H | H | NH | 348 |
| 55 | F | MeO | F | Cl | H | F | NH | 382 |
| 56 | F | F | F | Cl | H | F | NH | 369 |
| 57 | F | —CN | F | Cl | H | F | NH | 377 |
| 58 | Cl | F | H | Cl | H | F | NH | 368 |
| 59 | F | —CN | H | F | H | F | NH | 343 |
| 60 | Cl | MeO | H | F | H | F | NH | * |
| 61 | Cl | F | H | F | H | F | NH | * |
| 62 | F | F | H | F | MeO | F | CHOH | 381 |

INDEX TABLE A-continued

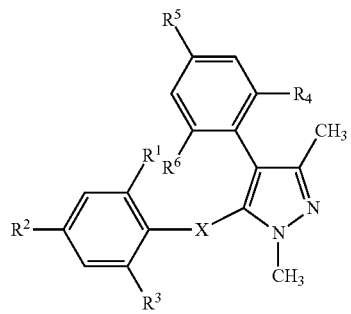

| Cmpd No. | R¹ | R² | R³ | R⁴ | R⁵ | R⁶ | X | M.S. |
|---|---|---|---|---|---|---|---|---|
| 63 | F | MeO | H | F | F | H | NH | * |
| 64 | F | F | H | F | F | H | NH | 336 |
| 65 | F | —CN | F | Br | F | H | O | 423 |
| 66 | Cl | MeO | H | F | F | H | NH | * |
| 67 | Cl | Cl | H | F | F | H | NH | * |
| 68 | F | —CN | H | F | F | H | NH | * |
| 69 | F | H | F | F | H | F | NH | * |
| 70 | F | F | F | Br | H | H | NH | 398 |
| 71 | F | H | F | F | F | H | NH | * |
| 72 | F | MeO | F | F | H | F | NH | * |
| 73 | Br | F | H | Cl | F | H | NH | 413 |
| 74 | F | F | F | Br | F | H | NH | 415 |
| 75 | F | —CN | F | Cl | H | H | O | * |
| 76 | F | —CN | F | Br | H | H | O | * |
| 77 | Cl | Cl | H | Cl | MeO | H | NH | 397 |
| 78 | Cl | Cl | H | Cl | H | F | NH | 386 |
| 79 | F | —CN | H | Br | F | H | O | 406 |
| 80 | Cl | —CN | H | Br | F | H | O | 422 |
| 81 | F | Cl | F | Cl | F | H | NH | 386 |
| 82 | Cl | F | F | Cl | F | H | NH | 386 |
| 83 | F | —CN | F | F | F | H | NH | * |
| 84 | Cl | F | F | Br | F | H | NH | 431 |
| 85 | Cl | MeO | Cl | Cl | F | H | NH | 413 |
| 86 | Cl | F | F | F | H | F | NH | 370 |
| 87 | Cl | F | F | Cl | H | F | NH | 386 |
| 88 | Cl | Cl | H | Cl | H | F | NH | 383 |
| 89 | F | F | F | F | H | F | NH | * |
| 90 | F | —CN | F | F | H | F | NH | * |
| 91 | F | —CN | F | F | H | H | O | * |
| 92 | F | —CN | H | Cl | MeO | H | O | 372 |
| 93 | Cl | —CN | H | Cl | MeO | H | O | 388 |
| 94 | F | F | H | Br | F | H | NH | 398 |
| 95 | Br | F | H | Br | F | H | NH | 458 |
| 96 | Cl | F | H | Br | F | H | NH | 414 |
| 97 | F | F | H | Cl | H | H | NH | 334 |
| 98 | Cl | F | Cl | Br | F | H | NH | 448 |
| 99 | Cl | —CN | H | Br | MeO | H | O | 433 |
| 100 | F | —CN | H | Br | MeO | H | O | 418 |
| 101 | Cl | MeO | H | Cl | F | H | NH | 380 |
| 102 | Cl | MeO | Cl | Br | F | H | NH | 459 |
| 103 | Cl | MeO | H | Br | F | H | NH | 425 |
| 104 | Cl | EtO | H | Cl | F | H | NH | 394 |
| 105 | Cl | Cl | H | Cl | H | H | NH | * |
| 106 | F | —CN | F | Cl | F | F | NH | 395 |
| 107 | F | F | H | Cl | —CN | H | NH | 359 |
| 108 | Cl | F | F | Cl | —CN | H | NH | 393 |
| 109 | Cl | F | H | Cl | H | Cl | NH | * |
| 110 | F | H | F | Cl | —CN | H | NH | 359 |
| 111 | F | Cl | F | Cl | —CN | H | NH | 393 |
| 112 | Cl | F | H | Cl | —CN | H | NH | 375 |
| 113 | F | F | H | Cl | H | Cl | NH | * |
| 114 | Br | F | H | Cl | H | Cl | NH | * |
| 115 | Cl | F | Cl | Cl | H | Cl | NH | * |
| 116 | F | —CN | H | Cl | H | F | O | 360 |
| 117 | Cl | F | F | F | F | H | NH | 369 |
| 118 | Br | F | H | F | F | H | NH | 398 |
| 119 | F | —CN | H | F | Cl | H | O | 360 |
| 120 | Br | F | Cl | F | F | H | NH | 432 |
| 121 | F | F | H | F | H | F | NH | 370 |
| 122 (Ex. 5) | F | F | H | Cl | F | H | CHOH | ** |
| 123 | Cl | F | H | Cl | F | H | CHOH | 383 |
| 124 | F | H | F | Cl | Cl | H | NH | * |

INDEX TABLE A-continued

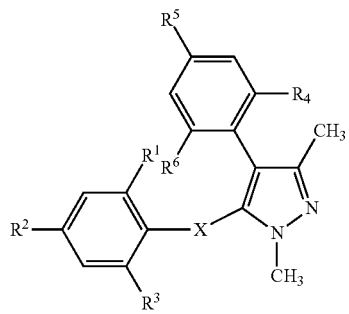

| Cmpd No. | R¹ | R² | R³ | R⁴ | R⁵ | R⁶ | X | M.S. |
|---|---|---|---|---|---|---|---|---|
| 125 | Cl | F | H | Cl | Cl | H | NH | * |
| 126 | F | Cl | F | F | F | H | NH | 370 |
| 127 | Cl | —CN | H | F | H | F | O | 360 |
| 128 | F | —CN | H | F | F | H | O | 376 |
| 129 | F | Cl | F | Br | F | H | NH | 432 |
| 130 | F | —CN | H | F | H | F | O | 344 |
| 131 | Cl | —CN | H | Cl | Cl | H | O | 394 |
| 132 | Cl | F | Cl | Cl | Cl | H | NH | * |
| 133 | F | Br | F | F | F | H | NH | 416 |
| 134 | F | Br | F | Cl | F | H | NH | 432 |
| 135 | F | Br | H | Cl | F | H | NH | 414 |
| 136 | Cl | Cl | F | Cl | F | H | NH | 402 |
| 137 | Cl | F | Cl | F | F | H | NH | 386 |
| 138 | Cl | F | F | Cl | F | H | NH | 404 |
| 139 | Br | —CN | H | F | F | H | O | 406 |
| 140 | Cl | —CN | H | F | F | H | O | 360 |
| 141 | Cl | Cl | F | F | F | H | NH | 386 |
| 142 | Cl | F | F | Cl | H | F | NH | 386 |
| 143 | Br | F | F | F | F | H | NH | 416 |
| 144 | Br | F | F | Cl | F | H | NH | 432 |
| 145 | F | Br | F | F | H | F | NH | 416 |
| 146 | Br | F | F | F | H | F | NH | 416 |
| 147 | Br | F | F | Cl | H | F | NH | |
| 148 | F | Cl | F | Cl | F | H | CHOH | 401‡ |
| 150 | F | Cl | F | F | —CN | H | NH | 377 |
| 151 | Cl | F | F | Cl | F | H | CHOH | |
| 152 | Br | F | H | F | F | H | CHOH | |
| 153 | Br | F | H | Cl | F | H | CHOH | 427† |
| 154 | F | Br | H | F | F | H | NH | 396 |
| 155 | Cl | Br | Cl | F | F | H | NH | 448 |
| 156 | Cl | F | F | Cl | Cl | H | NH | * |
| 157 | F | Cl | F | Cl | Cl | H | NH | * |
| 158 | F | Cl | H | Cl | F | H | O | 369 |
| 159 | F | —CN | H | F | F | H | O | 344 |
| 160 | F | Cl | H | F | F | H | NH | 352 |
| 161 | Cl | Cl | F | F | F | H | NH | 386 |
| 162 | F | Cl | H | F | H | F | NH | 352 |
| 163 | F | Br | F | Br | F | H | NH | 474 |
| 164 | Cl | Br | Cl | Cl | F | H | NH | 464 |
| 165 | Cl | Cl | Cl | F | F | H | NH | 404 |
| 167 | Cl | Br | H | F | F | H | NH | 414 |
| 168 | Cl | Br | Cl | Br | F | H | NH | 508 |
| 169 | F | Br | H | Br | F | H | NH | 458 |
| 170 | Cl | Cl | Cl | Cl | F | H | NH | 420 |
| 172 | Cl | Br | H | Cl | F | H | NH | 430 |
| 173 | Cl | Br | H | Br | F | H | NH | 474 |
| 174 | Cl | Cl | Cl | Br | F | H | NH | 464 |
| 175 | I | F | H | F | F | H | NH | 444 |
| 177 | F | Cl | H | Cl | F | H | CHOH | 384 |
| 178 | F | F | F | Cl | F | H | CHOH | 385 |
| 179 | F | —CN | H | Cl | F | H | CHOH | 374 |
| 180 | F | Cl | I | F | F | H | NH | 478 |
| 181 | I | F | H | Cl | F | H | NH | 460 |
| 182 | F | Cl | I | Cl | F | H | NH | 494 |
| 183 | Br | Br | H | Cl | F | H | NH | 474 |
| 184 | Br | Br | H | F | F | H | NH | 458 |
| 185 | F | Cl | F | F | MeO | H | NH | 382 |
| 186 | F | Cl | Br | Cl | F | H | NH | 448 |
| 187 | F | F | Cl | F | MeO | H | NH | 396 |
| 188 | F | F | Cl | F | EtO | H | NH | 396 |
| 189 | F | Cl | F | F | EtO | H | NH | 396 |
| 190 | F | Cl | Cl | F | EtO | H | NH | 412 |

INDEX TABLE A-continued

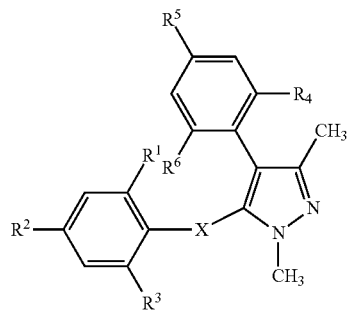

| Cmpd No. | R¹ | R² | R³ | R⁴ | R⁵ | R⁶ | X | M.S. |
|---|---|---|---|---|---|---|---|---|
| 191 | F | Cl | Cl | F | MeO | H | NH | 398 |
| 192 | Cl | F | Cl | F | EtO | H | NH | 412 |
| 193 | F | F | H | F | EtO | H | NH | *** |
| 194 | Cl | F | Cl | F | MeO | H | NH | 398 |
| 195 | Br | F | F | Br | F | H | NH | 476 |
| 196 | F | F | Cl | F | EtO | F | NH | 414 |
| 197 | Cl | Cl | I | Cl | F | H | NH | 512 |
| 198 | Cl | F | F | F | EtO | F | NH | 430 |
| 199 | F | Cl | F | F | EtO | F | NH | 414 |
| 200 | Cl | F | Cl | F | EtO | F | NH | 430 |
| 201 | F | Cl | Cl | Cl | MeO | H | NH | 416 |
| 202 | F | Cl | Cl | Cl | EtO | H | NH | 430 |
| 203 | F | F | Cl | Cl | MeO | H | NH | 398 |
| 204 | F | Cl | F | Cl | MeO | H | NH | 398 |
| 205 | Cl | F | Cl | Cl | MeO | H | NH | 416 |
| 206 | F | F | Cl | Cl | EtO | H | NH | 412 |
| 207 | F | Cl | F | Cl | EtO | H | NH | 412 |
| 208 | Cl | F | Cl | Cl | EtO | H | NH | 430 |
| 209 | F | F | H | Cl | EtO | H | NH | 378 |
| 210 | Cl | Cl | I | F | F | H | NH | 494 |
| 211 | Br | Br | F | F | F | H | NH | 476 |
| 212 | Br | Br | F | Cl | F | H | NH | 492 |
| 213 | F | F | I | Cl | F | H | NH | 478 |
| 214 | F | F | I | F | F | H | NH | 462 |
| 215 | F | F | I | Br | F | H | NH | 524 |
| 216 | F | I | F | F | F | H | NH | 462 |
| 217 | F | I | F | Cl | F | H | NH | 478 |
| 218 | F | I | F | Br | F | H | NH | 524 |
| 219 | I | F | F | Cl | MeO | H | NH | 490 |
| 220 | F | I | F | Cl | MeO | H | NH | 490 |
| 221 | F | F | Br | Cl | MeO | H | NH | 444 |
| 222 | Cl | Cl | F | I | F | H | NH | 494 |
| 223 | Br | Br | F | I | F | H | NH | 584 |
| 224 | F | Cl | F | Cl | MeO | H | CHOH | 413 |
| 225 | F | Cl | F | I | F | H | NH | 478 |
| 226 | Br | F | F | I | F | H | NH | 524 |
| 227 | Cl | F | Cl | F | Cl | H | NH | * |
| 228 | Cl | F | F | F | Cl | H | NH | * |
| 229 | Br | F | F | F | Cl | H | NH | * |
| 230 | F | F | F | F | Cl | H | NH | * |
| 231 | F | Cl | Cl | F | Cl | H | NH | * |
| 232 | Cl | F | H | F | Br | H | NH | * |
| 233 | Cl | F | Cl | F | Br | H | NH | * |
| 234 | Cl | F | F | F | Br | H | NH | * |
| 235 | Br | F | F | F | Br | H | NH | * |
| 236 | F | Cl | F | F | Br | H | NH | * |
| 237 | F | Cl | F | Cl | Br | H | NH | * |
| 238 | Cl | F | F | F | —CN | H | NH | * |
| 239 | Cl | H | F | Cl | F | H | NH | * |
| 240 (Ex. 7) | Cl | H | F | Br | F | H | NH | 414 |
| 241 | Br | H | F | Cl | F | H | NH | 414 |
| 242 | Br | H | H | Br | F | H | NH | 440 |
| 243 | I | H | H | Br | F | H | NH | 488 |
| 244 | Br | H | F | Br | F | H | NH | * |
| 245 | Br | H | F | F | F | H | NH | * |
| 246 | I | H | F | F | F | H | NH | 426 |
| 247 | Br | H | F | F | H | F | NH | * |
| 248 | Cl | F | H | F | —CN | H | NH | *** |
| 249 | Cl | F | Cl | F | —CN | H | NH | * |
| 250 | —CN | F | F | F | —CN | H | NH | * |
| 251 | Cl | H | Cl | F | F | H | NH | 367 |
| 252 | Me | H | F | Cl | F | H | NH | 348 |

INDEX TABLE A-continued

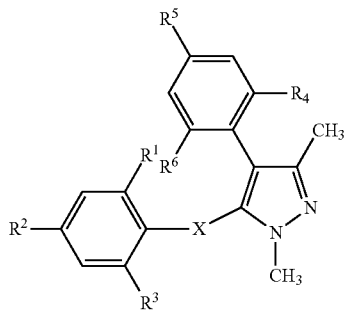

| Cmpd No. | R¹ | R² | R³ | R⁴ | R⁵ | R⁶ | X | M.S. |
|---|---|---|---|---|---|---|---|---|
| 253 | Me | H | Cl | Cl | F | H | NH | 364 |
| 254 | Me | H | Br | Cl | F | H | NH | 410 |
| 255 | Cl | H | Cl | Cl | F | H | NH | * |
| 256 | Cl | H | Cl | Br | F | H | NH | * |
| 257 | Me | H | Cl | F | MeO | H | NH | 360 |
| 258 | Me | H | Br | F | MeO | H | NH | 406 |
| 259 | Me | H | F | F | MeO | H | NH | 344 |
| 260 | Cl | H | F | F | MeO | H | NH | 364 |
| 261 | Br | H | F | F | MeO | H | NH | 410 |
| 262 | Me | H | Cl | Cl | MeO | H | NH | 376 |
| 263 | Me | H | Br | Cl | MeO | H | NH | 422 |
| 264 | Cl | H | F | Cl | MeO | H | NH | 380 |
| 265 | Me | H | Br | F | F | H | NH | 394 |
| 266 | Me | H | Br | Br | F | H | NH | 454 |
| 267 | Me | H | F | Br | F | H | NH | 394 |
| 268 | Me | H | F | F | F | H | NH | 332 |
| 269 | Me | H | Cl | F | F | H | NH | 348 |
| 270 | Me | H | Me | F | F | H | NH | 328 |
| 271 | Me | H | Me | Cl | F | H | NH | 344 |
| 272 | Cl | H | H | Br | F | H | NH | 396 |
| 273 | Br | H | F | Cl | MeO | H | NH | 426 |
| 274 | Br | H | H | Cl | F | H | NH | 396 |
| 275 | Cl | H | F | F | F | H | NH | 352 |
| 276 | Me | H | Cl | Br | F | H | NH | 410 |

*Melting Point (MP) data are listed in Index Table B.
**AP⁺ data or ¹H NMR data are listed in the Synthesis Examples.
***¹H NMR data are listed in Index Table C.
†Parent ion (M), not M + 1, peak was observed.
‡402 (M + 2) peak was also observed.

INDEX TABLE B

| Cmpd No. | Melting Point[a] | Cmpd No. | Melting Point | Cmpd No. | Melting Point |
|---|---|---|---|---|---|
| 31 | 80-82 | 72 | 172-174 | 156 | 181-183 |
| 35 | 160-162 | 75 | 132-135 | 157 | 155-157 |
| 36 | 228-230 | 76 | 132-134 | 227 | 183-184 |
| 40 | 93-95 | 83 | 181-183 | 228 | 180-182 |
| 49 | 110-112 | 89 | 178-180 | 229 | 154-155 |
| 50 | 105-107 | 90 | 168-170 | 230 | 190-191 |
| 51 | 130-132 | 91 | 101-105 | 231 | 154-155 |
| 60 | 109-111 | 114 | 137-139 | 238 | 177-179 |
| 61 | 57-59 | 115 | 151-153 | 239 | 166-168 |
| 63 | 133-135 | 124 | 169-171 | 244 | 154-156 |
| 66 | 91-93 | 125 | 111-113 | 245 | 149-151 |
| 67 | 82-84 | 132 | 229-231 | 247 | 127-129 |
| 68 | 182-184 | 232 | 88-89 | 249 | 200-202 |
| 69 | 156-158 | 233 | 186-187 | 250 | 200-202 |
| 71 | 171-173 | 234 | 182-183 | 255 | 183-185 |
| 105 | 118-120 | 235 | 167-169 | 256 | 199-201 |
| 109 | 117-119 | 236 | 199-201 | | |
| 113 | 135-136 | 237 | 160-162 | | |

[a]Melting point data are ° C.

INDEX TABLE C

| Cmpd No. | ¹H NMR Data (CDCl₃ solution unless indicated otherwise)[a] |
|---|---|
| 15 | δ 6.74 (m, 2H), 6.30 (m, 2H), 3.83 (s, 3H), 3.75 (s, 3H), 2.03 (s, 3H). |
| 193 | δ 7.01 (m, 1 H) 6.79 (ddd, 1H) 6.63 (m, 3 H) 6.34 (td, 1H) 5.34 (br s, 1H) 3.99 (m, 2H) 3.68 (s, 3H) 2.23 (s, 3H) 1.39 (m, 3H). |
| 248 | δ 7.30 (m, 2H), 7.25-7.30 (m, 1H), 7.08 (m, 1H), 6.76 (m, 1H), 6.28 (m, 1H), 5.67 (br s, 1H), 3.69 (s, 3H), 2.27 (s, 3H). |

[a]¹H NMR data are in ppm downfield from tetramethylsilane. Couplings are designated by (s)-singlet, (br s)-broad singlet, (ddd)-doublet of doublets of doublets, (td)-triplet of doublets and (m)-multiplet.

Biological Examples of the Invention

General protocol for preparing test suspensions for Tests A-I: the test compounds were first dissolved in acetone in an amount equal to 3% of the final volume and then suspended at the desired concentration (in ppm) in acetone and purified water (50/50 mix by volume) containing 250 ppm of the surfactant Trem® 014 (polyhydric alcohol esters). The resulting test suspensions were then used in Tests A-I. Each test was conducted in triplicate, and the results were averaged. Spraying a 200 ppm test suspension to the point of run-off on the test plants was the equivalent of a rate of about 800 g/ha. Unless otherwise indicated, the rating values indicate a 200 ppm test suspension was used. (An asterisk "*" next to the rating value indicates a 40 ppm test suspension was used.)

Test A

The test suspension was sprayed to the point of run-off on tomato seedlings. The following day the seedlings were inoculated with a spore suspension of *Botrytis cinerea* (the causal agent of tomato *Botrytis*) and incubated in saturated atmosphere at 20° C. for 48 h, and then moved to a growth chamber at 24° C. for 3 additional days, after which time visual disease ratings were made.

Test B

The test suspension was sprayed to the point of run-off on tomato seedlings. The following day the seedlings were inoculated with a spore suspension of *Alternaria solani* (the causal agent of tomato early blight) and incubated in a saturated atmosphere at 27° C. for 48 h, and then moved to a growth chamber at 20° C. for 5 days, after which time visual disease ratings were made.

Test C

The test suspension was sprayed to the point of run-off on tomato seedlings. The following day the seedlings were inoculated with a spore suspension of *Phytophthora infestans* (the causal agent of tomato late blight) and incubated in a saturated atmosphere at 20° C. for 24 h, and then moved to a growth chamber at 20° C. for 5 days, after which time visual disease ratings were made.

Test D

The test suspension was sprayed to the point of run-off on creeping bent grass (*Agrostis* sp.) seedlings. The following day the seedlings were inoculated with a bran and mycelial slurry of *Rhizoctonia solani* (the causal agent of turf brown patch) and incubated in a saturated atmosphere at 27° C. for 48 h, and then moved to a growth chamber at 27° C. for 3 days, after which time disease ratings were made.

Test E

The test suspension was sprayed to the point of run-off on wheat seedlings. The following day the seedlings were inoculated with a spore suspension of *Septoria nodorum* (the causal agent of *Septoria* glume blotch) and incubated in a saturated atmosphere at 24° C. for 48 h, and then moved to a growth chamber at 20° C. for 9 days, after which time visual disease ratings were made.

Test F

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h. and then the seedlings were moved to a growth chamber at 20° C. for 19 additional days, after which time visual disease ratings were made.

Test G

Wheat seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 2 days. At the end of this time the test suspension was sprayed to the point of run-off, and then the seedlings were moved to a growth chamber at 20° C. for 4 days after which time visual disease ratings were made.

Test H

The test suspension was sprayed to the point of run-off on wheat seedlings. The following day the seedlings were inoculated with a spore suspension of *Puccinia recondita* f. sp. *tritici* (the causal agent of wheat leaf rust) and incubated in a saturated atmosphere at 20° C. for 24 h, and then moved to a growth chamber at 20° C. for 6 days, after which time visual disease ratings were made.

Test I

The test suspension was sprayed to the point of run-off on wheat seedlings. The following day the seedlings were inoculated with a spore dust of *Blumeria graminis* f. sp. *tritici* (also known as *Erysiphe graminis* f. sp. *tritici*, the causal agent of wheat powdery mildew) and incubated in a growth chamber at 20° C. for 8 days, after which time visual disease ratings were made.

Results for Tests A-I are given in Table A. In the Table, a rating of 100 indicates 100% disease control and a rating of 0 indicates no disease control (relative to the controls). A hyphen (-) indicates no test results.

TABLE A

| Cmpd No. | Test A | Test B | Test C | Test D | Test E | Test F | Test G | Test H | Test I |
|---|---|---|---|---|---|---|---|---|---|
| 1 | 99 | 93 | 0 | 99 | 0 | 100 | — | 99 | 100 |
| 2 | 99 | 100 | 0 | 98 | 64 | 100 | — | 100 | 99 |
| 3 | 100 | 100 | — | — | 93 | 97 | 96 | 100 | 100 |
| 4 | 99 | 100 | — | — | 99 | 95 | 99 | 100 | 100 |
| 5 | 98 | 100 | — | — | 97 | 97* | — | 100 | 99 |
| 6 | 98 | 100 | — | — | 99 | 93 | 92 | 100 | 100 |
| 7 | 98 | 100 | — | — | 0 | 94 | 9 | 97 | 100 |
| 8 | 99* | 98* | — | — | 0* | 47* | 15* | 79* | 60* |
| 9 | 99 | 9 | — | — | 0 | 97 | 0 | 99 | 99 |
| 10 | 99 | 0 | — | — | 0 | 94 | 92 | 99 | 99 |
| 11 | 100 | 99 | — | — | 90 | 94 | 0 | 100 | 99 |
| 12 | 100 | 0 | — | — | 0 | 93 | 0 | 94 | 82 |
| 13 | 100 | 100 | — | — | 100 | 100 | 7 | 100 | 100 |
| 14 | 99 | 100 | — | — | 99 | 100 | 37 | 100 | 99 |
| 15 | 98 | 100 | — | — | 89 | 98 | 82 | 100 | 100 |
| 16 | 99 | 98 | — | — | 84 | 98 | 98 | 99 | 99 |
| 17 | 100 | 73 | — | — | 60 | 99 | 91 | 99 | 100 |
| 18 | 100 | 98 | — | — | 98 | 99 | 95 | 99 | 97 |
| 19 | 99 | 82 | — | — | 0 | 98 | 0 | 89 | 91 |
| 20 | 100 | 100 | — | — | 40 | 99 | 0 | 68 | 13 |
| 21 | 100 | 100 | — | — | 89 | 99 | 99 | 96 | 94 |
| 22 | 100 | 100 | — | — | 78 | 100 | 98 | 100 | 99 |
| 23 | 100 | 100 | — | — | 95 | 98 | 85 | 99 | 100 |
| 24 | 99 | 95 | — | — | 84 | 100 | 0 | 98 | 100 |
| 25 | 100 | 99 | — | — | 95 | 99 | 0 | 100 | 100 |
| 26 | 100 | 100 | — | — | 99 | 100 | 41 | 99 | 100 |
| 27 | 99 | 99 | — | — | 99 | 100 | 9 | 99 | 100 |
| 28 | 100 | 17 | — | — | 69 | 100 | 26 | 99 | 99 |
| 29 | 100 | 99 | — | — | 97 | 99 | 99 | 99 | 100 |
| 30 | 100 | 99 | — | — | 90 | 100 | 82 | 99 | 100 |
| 31 | 100 | 98 | — | — | 99 | 99 | 53 | 100 | 100 |
| 32 | 99 | 97 | — | — | 82 | 100 | 11 | 98 | 97 |
| 33 | 100 | 100 | — | — | 98 | 100 | 99 | 100 | 99 |
| 34 | 100 | 99 | 9 | — | 94 | 100 | 0 | 99 | 99 |
| 35 | 100 | 100 | — | — | 60 | 99 | 0 | 100 | 94 |
| 36 | 99 | 0 | — | — | 0 | 99 | 0 | 41 | 0 |
| 37 | 100 | 86 | — | — | 100 | 100 | 69 | 99 | 100 |
| 38 | 99 | 94 | — | — | 87 | 99 | 0 | 96 | 97 |
| 39 | 99 | 99 | — | — | 98 | 100 | 0 | 99 | 100 |
| 40 | 99 | 99 | — | — | 100 | 100 | 63 | 100 | 100 |
| 41 | 100 | 99 | — | — | 100 | 100 | 92 | 100 | 99 |

TABLE A-continued

| Cmpd No. | Test A | Test B | Test C | Test D | Test E | Test F | Test G | Test H | Test I |
|---|---|---|---|---|---|---|---|---|---|
| 42 | 98 | 99 | — | — | 0 | 99 | 8 | 100 | 100 |
| 43 | 98 | 100 | — | — | 0 | 100 | 95 | 100 | 98 |
| 44 | 99 | 0 | — | — | 0 | 99 | 8 | 98 | 94 |
| 45 | 100 | 99 | 0 | — | 99 | 98 | 0 | 100 | 99 |
| 46 | 100 | 100 | — | — | 87 | 100 | 0 | 99 | 100 |
| 47 | 100 | 99 | 0 | — | 82 | 96 | 93 | 99 | 100 |
| 48 | 100 | 100 | — | — | 73 | 98 | 0 | 83 | 100 |
| 49 | 100 | 100 | — | — | 80 | 98 | 0 | 83 | 100 |
| 50 | 100 | 99 | — | — | 73 | 95 | 0 | 93 | 100 |
| 51 | 100 | 99 | — | — | 0 | 98 | 0 | 68 | 100 |
| 52 | 94 | 44 | — | — | 0 | 100 | 0 | 60 | 98 |
| 53 | 97 | 99 | — | — | 87 | 100 | 0 | 95 | 99 |
| 54 | 97 | 100 | — | — | 67 | 99 | 27 | 94 | 99 |
| 55 | 99 | 99 | — | — | 80 | 100 | 94 | 100 | 99 |
| 56 | 98 | 100 | — | — | 0 | 100 | 0 | 97 | 99 |
| 57 | 97 | 100 | — | — | 73 | 100 | 0 | 99 | 99 |
| 58 | 99 | 100 | — | — | 0 | 100 | 32 | 99 | 100 |
| 59 | 99 | 94 | 0 | — | 73 | 100 | 9 | 98 | 98 |
| 60 | 99 | 97 | — | — | 20 | 100 | 18 | 97 | 99 |
| 61 | 100 | 93 | — | — | 64 | 100 | 0 | 99 | 100 |
| 62 | 100 | 100 | — | — | 99 | 100 | 0 | 99 | 99 |
| 63 | 99 | 99 | — | — | 0 | 99 | 0 | 80 | 99 |
| 64 | 99 | 99 | — | — | 0 | 100 | 0 | 97 | 100 |
| 65 | 100 | 99 | — | — | 99 | 100 | 0 | 100 | 100 |
| 66 | 99 | 37 | — | — | 0 | 100 | 0 | 91 | 100 |
| 67 | 100 | 64 | — | — | 0 | 100 | 0 | 97 | 100 |
| 68 | 99 | 51 | — | — | 0 | 100 | 0 | 80 | 100 |
| 69 | 100 | 99 | — | — | 60 | 100 | 0 | 99 | 100 |
| 70 | 99 | 26 | — | — | 73 | 100 | 0 | 99 | 100 |
| 71 | 99 | 99 | — | — | 96 | 100 | 0 | 99 | 100 |
| 72 | 100 | 99 | — | — | 0 | 100 | 0 | 97 | 98 |
| 73 | 100 | 99 | — | — | 78 | 100 | 90 | 100 | 100 |
| 74 | 100 | 100 | — | — | 98 | 100 | 0 | 100 | 100 |
| 75 | 100 | 99 | — | — | 99 | 100 | 0 | 99 | 98 |
| 76 | 100 | 97 | — | — | 99 | 99 | 0 | 99 | 99 |
| 77 | 99 | 98 | — | — | 0 | 99* | 0 | 99 | 100 |
| 78 | 99 | 65 | — | — | 0 | 99* | 9 | 99 | 100 |
| 79 | 99 | 99 | — | — | 100 | 100* | 28 | 100 | 100 |
| 80 | 98 | 0 | — | — | 60 | 100* | 9 | 99 | 99 |
| 81 | 100 | 99 | 0 | — | 90 | 100 | 99 | 100 | 100 |
| 82 | 99 | 100 | 0 | — | 100 | 100 | 97 | 100 | 100 |
| 83 | 100 | 99 | — | — | 87 | 100 | 0 | 100 | 100 |
| 84 | 100 | 99 | — | — | 96 | 100 | 92 | 100 | 100 |
| 85 | 99 | 0 | — | — | 0 | 100 | 0 | 99 | 99* |
| 86 | 100 | 99 | — | — | 90 | 100 | 0 | 100 | 100 |
| 87 | 100 | 93 | — | — | 87 | 100 | 0 | 100 | 100 |
| 88 | 100 | 95 | — | — | 51 | 100* | 41 | 100 | 100 |
| 89 | 100 | 99 | — | — | 82 | 100 | 9 | 99 | 100 |
| 90 | 99 | 87 | — | — | 87 | 100 | 0 | 98 | 99 |
| 91 | 99 | 99 | — | — | 94 | 100 | 0 | 99 | 99 |
| 92 | 100 | 99 | — | — | 99 | 100 | 0 | 99 | 96 |
| 93 | 100 | 0 | — | — | 60 | 100 | 0 | 99 | 91 |
| 95 | 100 | 97 | — | — | 51 | 100 | 91 | 100 | 100 |
| 96 | 100 | 95 | — | — | 0 | 100 | 94 | 100 | 100 |
| 97 | 99 | 99 | — | — | 0 | 100 | 0 | 96 | 100 |
| 98 | 99 | 0 | — | — | 0 | 99 | 9 | 99 | 96 |
| 99 | 99 | 0 | — | — | 0 | 100 | 0 | 97 | 89 |
| 100 | 92 | 88 | — | — | 100 | 100 | 0 | 99 | 95 |
| 101 | 100 | 93 | — | — | 0 | 100 | 99 | 100 | 100 |
| 102 | 98 | 0 | — | — | 0 | 98 | 0 | 94 | 95* |
| 103 | 99 | 83 | — | — | 0 | 100 | 63 | 99 | 99 |
| 104 | 100 | 0 | — | — | 0 | 100 | 0 | 97 | 99 |
| 105 | 99 | 0 | — | — | 0 | 100 | 0 | 96 | 99 |
| 107 | 100 | 80 | — | — | 73 | 100 | 8 | 100 | 97 |
| 109 | 100 | 0 | — | — | 0 | 100 | 0 | 97 | 100 |
| 111 | 100 | 97 | — | — | 95 | 100 | 94 | 100 | 99 |
| 112 | 100 | 37 | — | — | 40 | 100 | 8 | 100 | 99 |
| 113 | 100 | 0 | — | — | 0 | 100 | 0 | 98 | 100 |
| 114 | 99 | 0 | — | — | 0 | 100 | 0 | 91 | 100 |
| 115 | 99 | 0 | — | — | 0 | 99 | 0 | 99 | 93 |
| 116 | 100 | 33 | — | — | 99 | 100 | 0 | 100 | 100 |
| 117 | 100 | 100 | — | — | 97 | 100 | 91 | 100 | 100 |
| 118 | 100 | 93 | — | — | 69 | 100 | 75 | 97 | 99 |
| 119 | 99 | 94 | — | — | 94 | 100 | 0 | 91 | 99 |
| 120 | 100 | 80 | — | — | 94 | 100 | 19 | 100 | 100 |
| 122 | 100 | 99 | — | — | 92 | 100 | 96 | 100 | 99 |
| 123 | 100 | 86 | — | — | 60 | 100 | 6 | 100 | 95 |
| 124 | 97 | 17 | — | — | 0 | 99 | 3 | 99 | 99 |

TABLE A-continued

| Cmpd No. | Test A | Test B | Test C | Test D | Test E | Test F | Test G | Test H | Test I |
|---|---|---|---|---|---|---|---|---|---|
| 125 | 99 | 0 | — | — | 0 | 100 | 82 | 98 | 100 |
| 126 | 100 | 86 | — | — | 87 | 100 | 0 | 99 | 100 |
| 127 | 99 | 0 | — | — | 0 | 100 | 0 | 97 | 97 |
| 128 | 100 | 99 | — | — | 97 | 100 | 0 | 100 | 99 |
| 129 | 100 | 97 | — | — | 95 | 100 | 79 | 100 | 100 |
| 130 | 100 | 90 | — | — | 0 | 100 | 0 | 100 | 100 |
| 131 | 100 | 0 | — | — | 0 | 100 | 0 | 96 | 96 |
| 132 | 93 (Note 1) | 0 | — | — | 0 | 99 | 0 | 96 | 43 |
| 133 | 99 | 97 | — | — | 88 | 100 | 0 | 99 | 100 |
| 134 | 100 | 99 | — | — | 64 | 100 | 74 | 100 | 100 |
| 135 | 100 | 58 | — | — | 0 | 100 | 9 | 99 | 100 |
| 136 | 100 | 100 | 0 | — | 100 | 100 | 100 | 100 | 100 |
| 137 | 100 | 95 | — | — | 87 | 100 | 87 | 99 | 100 |
| 138 | 100 | 66 | 0 | — | 0 | 100 | 17 | 100 | 99 |
| 139 | 82 | 0 | — | — | 0 | 100 | 9 | 89 | 0 |
| 140 | 67 | 0 | — | — | 0 | 100 | 9 | 97 | 97 |
| 141 | 99 | 99 | — | — | 99 | 100 | 97 | 100 | 100 |
| 142 | 100 | 96 | 0 | — | 92 | 100 | 0 | 100 | 100 |
| 143 | 100 | 100 | 0 | — | 100 | 100 | 100 | 100 | 100 |
| 144 | 100 | 99 | — | — | 100 | 100 | 100 | 100 | 100 |
| 145 | 99 | 0 | 0 | — | 0 | 100 | 0 | 28 | 90 |
| 146 | — | 100 | 0 | — | 100 | 100 | 74 | 98 | 100 |
| 148 | 100 | 0 | — | — | 60 | 100 | 0 | 100 | 64 |
| 150 | 100 | — | — | — | — | 100 | — | 100 | 100 |
| 153 | — | 0 | — | — | 0 | 100 | 0 | 96 | 0 |
| 154 | 100 | 9 | — | — | 0 | 100 | 68 | 98 | 99 |
| 155 | 100 | 0 | — | — | 0 | 100 | 94 | 97 | 99 |
| 156 | 100 | 99 | — | — | 73 | 100 | 31 | 99 | 99 |
| 157 | 100 | 97 | 0 | — | 87 | 100 | 27 | 100 | 99 |
| 158 | 100* | 80* | — | — | 0* | 99* | 37* | 98* | 96* |
| 159 | 100* | 97* | — | — | 86* | 100* | 0* | 98* | 96* |
| 160 | 100 | 99 | — | — | 0 | 100 | 0 | 99 | 100 |
| 161 | 100 | 99 | 0 | — | 100 | 99 | 100 | 100 | 100 |
| 162 | 100 | 88 | 0 | — | 0 | 100 | 9 | 100 | 100 |
| 163 | 100* | 77* | — | — | 60* | 100* | 91* | 100* | 100* |
| 164 | 99 | 0 | — | — | 0 | 100 | 99 | 100 | 99 |
| 165 | 100 | 0 | 0 | — | 0 | 100 | 67 | 99 | 99 |
| 167 | 100 | 0 | — | — | 0 | 100 | 6 | 92 | 98 |
| 168 | 0 | 0 | — | — | 0 | 100 | 97 | 91 | 48 |
| 169 | 100 | 0 | — | — | 60 | 100 | 23 | 96 | 99 |
| 170 | 65 | 0 | — | — | 0 | 100 | 79 | 98 | 79 |
| 172 | 100 | 73 | — | — | 60 | 100 | 0 | 100 | 100 |
| 173 | 100 | 0 | — | — | 40 | 100 | 0 | 99 | 99 |
| 174 | 95 | 0 | — | — | 0 | 100 | 0 | 99 | 99* |
| 175 | 100 | 97 | — | — | 73 | 100 | 41 | 100 | 100 |
| 177 | 99 | 0 | — | — | 0 | — | 0 | 0 | 48 |
| 178 | 100 | 33 | — | — | 0 | — | 98 | 100 | 74 |
| 179 | 96 | 16 | — | — | 0 | — | 9 | 99 | 0 |
| 180 | 100 | 100 | 9 | — | 99 | 100 | 98 | 100 | 100 |
| 181 | 100 | 99 | — | — | 99 | 100 | 99 | 99 | 100 |
| 182 | 100 | 100 | — | — | 100 | 100 | 100 | 100 | 100 |
| 183 | 100 | 0 | — | — | 0 | 100 | 54 | 96 | 98 |
| 184 | 100 | 58 | — | — | 60 | 100 | 0 | 98 | 100 |
| 185 | 100 | 99 | 0 | — | 60 | 100 | 0 | 99 | 100 |
| 186 | 100 | 100 | 0 | — | 100 | 100 | 100 | 100 | 100 |
| 187 | 100 | 100 | 0 | — | 89 | — | 32 | 100 | 100 |
| 188 | 100 | 99 | 0 | — | 92 | — | 0 | 98 | 98 |
| 189 | 100 | 88 | 0 | — | 90 | — | 0 | 98 | 98 |
| 190 | 100 | 82 | 0 | — | 0 | — | 9 | 96 | 95 |
| 191 | 100 | 99 | — | — | 92 | — | 46 | 99 | 99 |
| 192 | 33 | 66 | 0 | — | 0 | 100 | 0 | 65 | 35 |
| 193 | — | 58 | — | — | 0 | 100 | 0 | 27 | 92 |
| 194 | — | 93 | — | — | 87 | 100 | 0 | 95 | 63 |
| 195 | 99 | 100 | 0 | — | 99 | 100 | 89 | 100 | 100 |
| 196 | 100 | 100 | 0 | — | 95 | 100 | 0 | 94 | 100 |
| 197 | 100 | 77 | — | — | 0 | 100 | 9 | 97 | 94 |
| 198 | 100 | 100 | — | — | 60 | 100 | 9 | 80 | 96 |
| 199 | 100 | 100 | 68 | — | 69 | 100 | 0 | 83 | 99 |
| 200 | 98 | 97 | 31 | — | 0 | 100 | 0 | 86 | 79 |
| 201 | 100 | 100 | — | — | 99 | 100 | 98 | 100 | 97 |
| 202 | 99 | 77 | — | — | 0 | 100 | 35 | 92 | 95 |
| 203 | 95 | 100 | — | — | 73 | 100 | 79 | 100 | 98 |
| 204 | 99 | 99 | — | — | 99 | 100 | 99 | 100 | 100 |
| 205 | 59 | 31 | — | — | 0 | 100 | 0 | 99 | 21 |
| 206 | 99 | 100 | — | — | 99 | 100 | 0 | 99 | 100 |
| 207 | 94 | 99 | — | — | 86 | 100 | 0 | 94 | 99 |
| 208 | 18 | 0 | — | — | 0 | 99 | 0 | 85 | 27 |

TABLE A-continued

| Cmpd No. | Test A | Test B | Test C | Test D | Test E | Test F | Test G | Test H | Test I |
|---|---|---|---|---|---|---|---|---|---|
| 209 | 98 | 95 | — | — | 0 | 100 | 0 | 92 | 100 |
| 210 | 3 | 0 | — | — | 0 | 100 | 0 | 97 | 0 |
| 211 | 98 | 99 | — | — | 99 | 100 | 82 | 100 | 100 |
| 212 | 98 | 100 | — | — | 100 | 100 | 97 | 100 | 100 |
| 213 | 100 | 100 | — | — | 100 | 100 | 100 | 100 | 100 |
| 214 | 100 | 100 | — | — | 99 | 100 | 99 | 99 | 100 |
| 215 | 100 | 100 | — | — | 99 | 100 | 100 | 100 | 100 |
| 216 | 100 | 0 | — | — | 60 | 100 | 18 | 95 | 99 |
| 217 | 100 | 58 | — | — | 86 | 100 | 41 | 99 | 99 |
| 218 | 100 | 68 | — | — | 86 | 100 | 0 | 99 | 99 |
| 219 | 100 | 100 | — | — | 100 | 100 | 99 | 100 | 99 |
| 220 | 100 | 69 | — | — | 73 | 100 | 0 | 97 | 96 |
| 221 | 100 | 100 | — | — | 97 | 100 | 73 | 99 | 100 |
| 222 | 98 | 77 | — | — | 0 | 100 | 0 | 90 | 96 |
| 223 | 98 | 88 | — | — | 0 | 100 | 0 | 97 | 99 |
| 224 | — | 100 | — | — | 89 | 100 | 54 | 100 | 94 |
| 225 | 99 | 68 | — | — | 0 | 100 | 0 | 99 | 100 |
| 226 | 97 | 97 | — | — | 60 | 100 | 0 | 99 | 100 |
| 227 | 0 | 0 | — | — | 0 | 100 | 0 | 95 | 96 |
| 228 | 68 | 40 | — | — | 0 | 100 | 0 | 96 | 81 |
| 229 | 99 | 99 | — | — | 64 | 100 | 9 | 97 | 98 |
| 230 | 40 | 0 | — | — | 0 | 100 | 0 | 94 | 95 |
| 231 | 33 | 58 | — | — | 0 | 100 | 9 | 94 | 99 |
| 232 | 79 | — | — | — | — | 100 | — | 90 | 99 |
| 233 | 36 | — | — | — | — | 100 | — | 91 | 89 |
| 234 | 97 | — | — | — | — | 100 | — | 91 | 79 |
| 235 | 99 | — | — | — | — | 100 | — | 96 | 90 |
| 236 | 47 | — | — | — | — | 100 | — | 28 | 0 |
| 237 | 99 | — | — | — | — | 100 | — | 92 | 95 |
| 238 | 100 | — | — | — | — | 100 | — | 100 | 100 |
| 239 | 100 | 100 | 0 | — | 99 | 100 | 100 | 100 | 99 |
| 240 | 100 | — | — | — | — | 100 | — | 100 | 100 |
| 241 | 100 | — | — | — | — | 100 | — | 100 | 100 |
| 242 | 99* | — | — | — | — | 100* | — | 96* | 99* |
| 243 | 100 | — | — | — | — | 100 | — | 99 | 100 |
| 244 | 100 | — | — | — | — | 100 | — | 100 | 100 |
| 245 | 100 | — | — | — | — | 100 | — | 100 | 100 |
| 246 | 100 | — | — | — | — | 100 | — | 98 | 99 |
| 247 | 100 | — | — | — | — | 100 | — | 100 | 100 |
| 248 | 99 | — | — | — | — | 100 | — | 99 | 99 |
| 249 | 100 | — | — | — | — | 100 | — | 98 | 92 |
| 250 | 0 | — | — | — | — | 100 | — | 100 | 89 |
| 251 | 100 | — | — | — | — | 100 | — | 100 | 100 |
| 252 | 100 | — | — | — | — | 100 | — | 100 | 100 |
| 253 | 100 | — | — | — | — | 100 | — | 100 | 100 |
| 254 | 100 | — | — | — | — | 100 | — | 100 | 100 |
| 255 | 100* | — | — | — | — | 100* | — | 99* | 81* |
| 256 | 99* | — | — | — | — | 100* | — | 95* | 64* |
| 257 | 100* | — | — | — | 31* | 100* | — | 63* | 27* |
| 258 | 100* | — | — | — | 0* | 100* | — | 9* | 0* |
| 259 | 100* | — | — | — | 0* | 100* | — | 82* | 90* |
| 260 | 100* | — | — | — | 0* | 100* | — | 85* | 90* |
| 261 | — | — | — | — | 0* | 100* | — | 97* | 95* |
| 262 | 97* | — | — | — | 0* | 100* | — | 85* | 79* |
| 263 | 99* | — | — | — | 0* | 100* | — | 79* | 13* |
| 264 | 100* | — | — | — | 0* | 100* | — | 97* | 81* |
| 265 | 100 | — | — | — | — | 100 | — | 99 | 100 |
| 266 | 99 | — | — | — | — | 100 | — | 99 | 99 |
| 267 | 100 | — | — | — | — | 100 | — | 100 | 100 |
| 268 | 100 | — | — | — | — | 100 | — | 99 | 100 |
| 269 | 100 | — | — | — | — | 100 | — | 99 | 100 |
| 270 | 98* | — | — | — | — | 100* | — | 41* | 91* |
| 271 | 99* | — | — | — | — | 100* | — | 97* | 98* |
| 272 | 100 | — | — | — | — | 100 | — | 99 | 100 |
| 275 | 100 | 99 | 0 | — | 60 | 100 | 9 | 95 | 100 |
| 276 | 100* | — | — | — | — | 100* | — | 99* | 92* |

"Cmpd No." means compound number.
(Note 1):
Rating was "65" in earlier test.

Tests K, L and M

The general protocol for preparing test compositions for Tests K, L and M was as follows. Compound 81, bixafen, 5-chloro-6-(2,4,6-trifluorophenyl)-7-(4-methylpiperidin-1-yl)[1,2,4]triazolo[1,5-a]pyrimidine (BAS600), cyproconazole, isopyrazam, penthiopyrad, probenazole, quinoxyfen and spiroxamine were obtained as unformulated, technical-grade materials. Azoxystrobin, boscalid, chlorothalonil, copper hydroxide, cymoxanil, difenoconazole, dimethomorph, epoxiconazole, fenpropimorph, fluazinam, fludioxonil, folpet, iprodione, iprovalicarb, mancozeb, mefenoxam (also known as metalaxyl-M), myclobutanil, picoxystrobin, proquinazid, prothioconazole, pyraclostrobin, tetraconazole and tricyclozole were obtained as formulated products marketed under the trademarks AMISTAR, ENDURA, BRAVO, KOCIDE, CURZATE, SCORE, ACROBAT, OPUS, CORBEL, OMEGA, MAXIM, PHALTAN, ROVRAL, MELODY, MANZATE, RIDOMIL GOLD, NOVA, ACANTO, TALIUS, PROLINE, HEADLINE, DOMARK and BEAM, respectively. Unformulated materials were first dissolved in acetone and then suspended at the desired concentration (in ppm) in acetone and purified water (50/50 mix by volume) containing 250 ppm of the surfactant Trem® 014 (polyhydric alcohol esters). Formulated materials were dispersed in sufficient water to give the desired concentration, and neither organic solvent nor surfactant was added to the suspension. The resulting test mixtures were then used in Tests K, L and M. Spraying a 200 ppm test suspension to the point of run-off on the test plants was the equivalent of a rate of about 800 g/ha. The tests were replicated three times and the results reported as the mean average of the three replicates.

The presence of a synergistic effect between two active ingredients was established with the aid of the Colby equation (see Colby, S. R. "Calculating Synergistic and Antagonistic Responses of Herbicide Combinations", *Weeds*, (1967), 15, 20-22):

$$p = A + B - \left[\frac{A \times B}{100}\right].$$

Using the method of Colby, the presence of a synergistic interaction between two active ingredients is established by first calculating the predicted activity, p, of the mixture based on activities of the two components applied alone. If p is lower than the experimentally established effect, synergism has occurred. In the equation above, A is the fungicidal activity in percentage control of one component applied alone at rate x. The B term is the fungicidal activity in percentage control of the second component applied at rate y. The equation estimates p, the expected fungicidal activity of the mixture of A at rate x with B at rate y if their effects are strictly additive and no interaction has occurred.

Test K (i.e. Tests K1, K2, K3, K4, K5)

The test suspension was sprayed to the point of run-off on wheat seedlings. The following day the seedlings were inoculated with a spore dust of *Blumeria graminis* f. sp. *tritici*, (also known as *Erysiphe graminis* f. sp. *tritici*, the causal agent of wheat powdery mildew) and incubated in a growth chamber at 20° C. for 7 days, after which time visual disease ratings were made.

Test L (i.e. Tests L1, L2, L3, L4, L5)

The test suspension was sprayed to the point of run-off on wheat seedlings. The following day the seedlings were inoculated with a spore suspension of *Puccinia recondite* f. sp. *tritici* (the causal agent of wheat leaf rust) and incubated in a saturated atmosphere at 20° C. for 24 h, and then moved to a growth chamber at 20° C. for 6 days, after which time visual disease ratings were made.

Test M (i.e. Tests M1, M2, M3, M4, M5)

The test suspension was sprayed to the point of run-off on wheat seedlings. The following day the seedlings were inoculated with a spore suspension of *Septoria tritici* (the causal agent of wheat leaf blotch) and incubated in saturated atmosphere at 24° C. for 48 h. and then the seedlings moved to a growth chamber at 20° C. for 19 additional days, after which time visual disease ratings were made.

Results for Tests K-M are presented in the following Tables B through K. A rating of 100 indicates 100% disease control and a rating of 0 indicates no disease control (relative to the controls). A dash (-) indicates no test results. Columns labeled "Obsd" indicate the average of results observed from three replications. Columns labeled "Exp" indicate the expected effect for each treatment mixture calculated using the Colby Equation.

TABLE B

Observed and Expected Effects of Compound 81 Alone and Mixtures with Quinoxyfen, Probenazole, Mancozeb, Iprodione, Boscalid, Copper Hydroxide, Cymoxanil or Proquinazid for Control of Wheat Powder Mildew or Leaf Rust

| Application Rate (ppm) of Compound 81 | Component (b) | Application Rate (ppm) of Component (b) | Test K1 Obsd | Test K1 Exp | Test L1 Obsd | Test L1 Exp |
|---|---|---|---|---|---|---|
| 0 | None | 0 | 0 | | 0 | |
| 1 | None | 0 | 0 | | 88 | |
| 2 | None | 0 | 87 | | 68 | |
| 5 | None | 0 | 99 | | 91 | |
| 10 | None | 0 | 100 | | 98 | |
| 0 | quinoxyfen | 10 | | | 0 | |
| 0 | quinoxyfen | 40 | | | 0 | |
| 0 | quinoxyfen | 200 | | | 0 | |
| 2 | quinoxyfen | 10 | | | 18 | 68 |
| 2 | quinoxyfen | 40 | | | 23 | 68 |
| 2 | quinoxyfen | 200 | | | 38 | 68 |
| 5 | quinoxyfen | 10 | | | 60 | 91 |
| 5 | quinoxyfen | 40 | | | 41 | 91 |
| 5 | quinoxyfen | 200 | | | 47 | 91 |
| 0 | probenazole | 10 | 68 | | 9 | |
| 0 | probenazole | 40 | 21 | | 18 | |
| 0 | probenazole | 200 | 71 | | 18 | |
| 2 | probenazole | 10 | 97 | 96 | 54 | 71 |
| 2 | probenazole | 40 | 99 | 90 | 85 | 74 |
| 2 | probenazole | 200 | 98 | 96 | 74 | 74 |

TABLE B-continued

Observed and Expected Effects of Compound 81 Alone and Mixtures with Quinoxyfen, Probenazole, Mancozeb, Iprodione, Boscalid, Copper Hydroxide, Cymoxanil or Proquinazid for Control of Wheat Powder Mildew or Leaf Rust

| Application Rate (ppm) of Compound 81 | Component (b) | Application Rate (ppm) of Component (b) | Test K1 Obsd | Test K1 Exp | Test L1 Obsd | Test L1 Exp |
|---|---|---|---|---|---|---|
| 5 | probenazole | 10 | 100 | 100 | 92 | 92 |
| 5 | probenazole | 40 | 100 | 99 | 96 | 93 |
| 5 | probenazole | 200 | 100 | 100 | 94 | 93 |
| 0 | mancozeb | 10 | 0 | | 54 | |
| 0 | mancozeb | 40 | 0 | | 88 | |
| 0 | mancozeb | 200 | 0 | | 98 | |
| 2 | mancozeb | 10 | 79 | 87 | 80 | 85 |
| 2 | mancozeb | 40 | 87 | 87 | 91 | 96 |
| 2 | mancozeb | 200 | 84 | 87 | 99 | 99 |
| 5 | mancozeb | 10 | 96 | 99 | 85 | 96 |
| 5 | mancozeb | 40 | 99 | 99 | 98 | 99 |
| 5 | mancozeb | 200 | 99 | 99 | 99 | 100 |
| 0 | iprodione | 10 | 0 | | 0 | |
| 0 | iprodione | 40 | 0 | | 0 | |
| 0 | iprodione | 200 | 21 | | 0 | |
| 2 | iprodione | 10 | 96 | 87 | 27 | 68 |
| 2 | iprodione | 40 | 92 | 87 | 27 | 68 |
| 2 | iprodione | 200 | 94 | 90 | 41 | 68 |
| 5 | iprodione | 10 | 99 | 99 | 68 | 91 |
| 5 | iprodione | 40 | 99 | 99 | 80 | 91 |
| 5 | iprodione | 200 | 99 | 99 | 85 | 91 |
| 0 | boscalid | 10 | 0 | | 0 | |
| 0 | boscalid | 40 | 0 | | 54 | |
| 0 | boscalid | 200 | 0 | | 92 | |
| 2 | boscalid | 10 | 0 | 87 | 76 | 68 |
| 2 | boscalid | 40 | 0 | 87 | 86 | 85 |
| 2 | boscalid | 200 | 64 | 87 | 99 | 97 |
| 5 | boscalid | 10 | 86 | 99 | 89 | 91 |
| 5 | boscalid | 40 | 94 | 99 | 98 | 96 |
| 5 | boscalid | 200 | 97 | 99 | 98 | 99 |
| 0 | copper hydroxide | 10 | 0 | | 0 | |
| 0 | copper hydroxide | 40 | 0 | | 0 | |
| 0 | copper hydroxide | 200 | 0 | | 0 | |
| 2 | copper hydroxide | 10 | 71 | 87 | 9 | 68 |
| 2 | copper hydroxide | 40 | 0 | 87 | 0 | 68 |
| 2 | copper hydroxide | 200 | 0 | 87 | 0 | 68 |
| 5 | copper hydroxide | 10 | 97 | 99 | 41 | 91 |
| 5 | copper hydroxide | 40 | 94 | 99 | 18 | 91 |
| 5 | copper hydroxide | 200 | 93 | 99 | 41 | 91 |
| 0 | cymoxanil | 10 | 0 | | 0 | |
| 0 | cymoxanil | 40 | 0 | | 0 | |
| 0 | cymoxanil | 200 | 50 | | 18 | |
| 2 | cymoxanil | 10 | 73 | 87 | 9 | 68 |
| 2 | cymoxanil | 40 | 89 | 87 | 9 | 68 |
| 2 | cymoxanil | 200 | 91 | 93 | 54 | 74 |
| 5 | cymoxanil | 10 | 96 | 99 | 18 | 91 |
| 5 | cymoxanil | 40 | 98 | 99 | 54 | 91 |
| 5 | cymoxanil | 200 | 97 | 100 | 74 | 93 |
| 0 | proquinazid | 10 | | | 0 | |
| 0 | proquinazid | 40 | | | 0 | |
| 0 | proquinazid | 200 | | | 0 | |
| 2 | proquinazid | 10 | | | 0 | 68 |
| 2 | proquinazid | 40 | | | 18 | 68 |
| 2 | proquinazid | 200 | | | 27 | 68 |
| 5 | proquinazid | 10 | | | 18 | 91 |
| 5 | proquinazid | 40 | | | 27 | 91 |
| 5 | proquinazid | 200 | | | 68 | 91 |

TABLE C

Observed and Expected Effects of Compound 81 Alone and
Mixtures with Chlorothalonil, Tricyclazole, Fluazinam,
Dimethomorph, Fludioxonil, Iprovalicarb, Metalaxyl-M or
Folpet for Control of Wheat Powder Mildew or Leaf Rust

| Application Rate (ppm) of Compound 81 | Component (b) | Application Rate (ppm) of Component (b) | Test K2 Obsd | Test K2 Exp | Test L2 Obsd | Test L2 Exp |
|---|---|---|---|---|---|---|
| 0 | None | 0 | 63 | | 0 | |
| 1 | None | 0 | 91 | | 9 | |
| 2 | None | 0 | 91 | | 27 | |
| 5 | None | 0 | 91 | | 74 | |
| 10 | None | 0 | 100 | | 91 | |
| 0 | chlorothalonil | 10 | 58 | | 0 | |
| 0 | chlorothalonil | 40 | 68 | | 41 | |
| 0 | chlorothalonil | 200 | 79 | | 91 | |
| 2 | chlorothalonil | 10 | 92 | 96 | 18 | 27 |
| 2 | chlorothalonil | 40 | 100 | 97 | 85 | 57 |
| 2 | chlorothalonil | 200 | 97 | 98 | 96 | 93 |
| 5 | chlorothalonil | 10 | 100 | 96 | 66 | 74 |
| 5 | chlorothalonil | 40 | 100 | 97 | 88 | 85 |
| 5 | chlorothalonil | 200 | 100 | 98 | 96 | 98 |
| 0 | tricyclazole | 10 | 0 | | 0 | |
| 0 | tricyclazole | 40 | 29 | | 0 | |
| 0 | tricyclazole | 200 | 79 | | 0 | |
| 2 | tricyclazole | 10 | 99 | 91 | 27 | 27 |
| 2 | tricyclazole | 40 | 99 | 94 | 27 | 27 |
| 2 | tricyclazole | 200 | 98 | 98 | 27 | 27 |
| 5 | tricyclazole | 10 | 100 | 91 | 55 | 74 |
| 5 | tricyclazole | 40 | 100 | 94 | 68 | 74 |
| 5 | tricyclazole | 200 | 100 | 98 | 80 | 74 |
| 0 | fluazinam | 10 | 85 | | 18 | |
| 0 | fluazinam | 40 | 96 | | 41 | |
| 0 | fluazinam | 200 | 100 | | 74 | |
| 2 | fluazinam | 10 | 84 | 99 | 41 | 41 |
| 2 | fluazinam | 40 | 99 | 100 | 68 | 57 |
| 2 | fluazinam | 200 | 99 | 100 | 91 | 81 |
| 5 | fluazinam | 10 | 100 | 99 | 80 | 79 |
| 5 | fluazinam | 40 | 100 | 100 | 80 | 85 |
| 5 | fluazinam | 200 | 100 | 100 | 91 | 93 |
| 0 | dimethomorph | 10 | 82 | | 9 | |
| 0 | dimethomorph | 40 | 71 | | 9 | |
| 0 | dimethomorph | 200 | 82 | | 0 | |
| 2 | dimethomorph | 10 | 99 | 98 | 18 | 34 |
| 2 | dimethomorph | 40 | 100 | 98 | 18 | 34 |
| 2 | dimethomorph | 200 | 99 | 98 | 27 | 27 |
| 5 | dimethomorph | 10 | 100 | 98 | 60 | 76 |
| 5 | dimethomorph | 40 | 100 | 98 | 68 | 76 |
| 5 | dimethomorph | 200 | 100 | 98 | 68 | 74 |
| 0 | fludioxonil | 10 | 82 | | 0 | |
| 0 | fludioxonil | 40 | 92 | | 0 | |
| 0 | fludioxonil | 200 | 96 | | 9 | |
| 2 | fludioxonil | 10 | 100 | 98 | 27 | 27 |
| 2 | fludioxonil | 40 | 99 | 99 | 27 | 27 |
| 2 | fludioxonil | 200 | 100 | 100 | 27 | 34 |
| 5 | fludioxonil | 10 | 100 | 98 | 41 | 74 |
| 5 | fludioxonil | 40 | 100 | 99 | 55 | 74 |
| 5 | fludioxonil | 200 | 100 | 100 | 74 | 76 |
| 0 | iprovalicarb | 10 | 71 | | 0 | |
| 0 | iprovalicarb | 40 | 74 | | 0 | |
| 0 | iprovalicarb | 200 | 56 | | 9 | |
| 2 | iprovalicarb | 10 | 100 | 98 | 27 | 27 |
| 2 | iprovalicarb | 40 | 100 | 98 | 27 | 27 |
| 2 | iprovalicarb | 200 | 99 | 96 | 27 | 34 |
| 5 | iprovalicarb | 10 | 100 | 98 | 74 | 74 |
| 5 | iprovalicarb | 40 | 100 | 98 | 74 | 74 |
| 5 | iprovalicarb | 200 | 100 | 96 | 85 | 76 |
| 0 | metalaxyl-M | 10 | 56 | | 0 | |
| 0 | metalaxyl-M | 40 | 64 | | 0 | |
| 0 | metalaxyl-M | 200 | 21 | | 0 | |
| 2 | metalaxyl-M | 10 | 96 | 96 | 27 | 27 |
| 2 | metalaxyl-M | 40 | 99 | 97 | 27 | 27 |
| 2 | metalaxyl-M | 200 | 99 | 93 | 27 | 27 |
| 5 | metalaxyl-M | 10 | 100 | 96 | 55 | 74 |
| 5 | metalaxyl-M | 40 | 100 | 97 | 55 | 74 |
| 5 | metalaxyl-M | 200 | 100 | 93 | 68 | 74 |
| 0 | folpet | 10 | 0 | | 0 | |
| 0 | folpet | 40 | 0 | | 27 | |

TABLE C-continued

Observed and Expected Effects of Compound 81 Alone and Mixtures with Chlorothalonil, Tricyclazole, Fluazinam, Dimethomorph, Fludioxonil, Iprovalicarb, Metalaxyl-M or Folpet for Control of Wheat Powder Mildew or Leaf Rust

| Application Rate (ppm) of Compound 81 | Component (b) | Application Rate (ppm) of Component (b) | Test K2 Obsd | Test K2 Exp | Test L2 Obsd | Test L2 Exp |
|---|---|---|---|---|---|---|
| 0 | folpet | 200 | 21 |  | 55 |  |
| 2 | folpet | 10 | 93 | 91 | 0 | 27 |
| 2 | folpet | 40 | 96 | 91 | 27 | 47 |
| 2 | folpet | 200 | 66 | 93 | 80 | 67 |
| 5 | folpet | 10 | 100 | 91 | 74 | 74 |
| 5 | folpet | 40 | 100 | 91 | 88 | 81 |
| 5 | folpet | 200 | 100 | 93 | 93 | 88 |

TABLE D

Observed and Expected Effects of Compound 81 Alone and Mixtures with Isopyrazam, BAS600, Bixafen, Penthiopyrad, Spiroxamine, Myclobutanil or Fenpropimorph for Control of Wheat Powdery Mildew or Leaf Rust

| Application Rate (ppm) of Compound 81 | Component (b) | Application Rate (ppm) of Component (b) | Test K3 Obsd | Test K3 Exp | Test L3 Obsd | Test L3 Exp |
|---|---|---|---|---|---|---|
| 0 | None | 0 | 0 |  | 0 |  |
| 1 | None | 0 | 0 |  | 9 |  |
| 2 | None | 0 | 0 |  | 9 |  |
| 5 | None | 0 | 90 |  | 41 |  |
| 10 | None | 0 | 99 |  | 88 |  |
| 0 | isopyrazam | 0.08 | 0 |  |  |  |
| 0 | isopyrazam | 0.4 | 50 |  |  |  |
| 0 | isopyrazam | 2 | 99 |  |  |  |
| 0 | isopyrazam | 10 | 99 |  |  |  |
| 2 | isopyrazam | 0.08 | 0 | 0 |  |  |
| 2 | isopyrazam | 0.4 | 64 | 50 |  |  |
| 2 | isopyrazam | 2 | 94 | 99 |  |  |
| 2 | isopyrazam | 10 | 100 | 99 |  |  |
| 5 | isopyrazam | 0.08 | 99 | 90 |  |  |
| 5 | isopyrazam | 0.4 | 100 | 95 |  |  |
| 5 | isopyrazam | 2 | 100 | 100 |  |  |
| 5 | isopyrazam | 10 | 100 | 100 |  |  |
| 0 | BAS600 | 0.08 | 0 |  | 74 |  |
| 0 | BAS600 | 0.4 | 0 |  | 88 |  |
| 0 | BAS600 | 2 | 96 |  | 99 |  |
| 0 | BAS600 | 10 | 100 |  | 100 |  |
| 2 | BAS600 | 0.08 | 0 | 0 | 74 | 76 |
| 2 | BAS600 | 0.4 | 0 | 0 | 94 | 89 |
| 2 | BAS600 | 2 | 93 | 96 | 100 | 99 |
| 2 | BAS600 | 10 | 99 | 100 | 100 | 100 |
| 5 | BAS600 | 0.08 | 100 | 90 | 92 | 84 |
| 5 | BAS600 | 0.4 | 99 | 90 | 99 | 93 |
| 5 | BAS600 | 2 | 100 | 100 | 100 | 99 |
| 5 | BAS600 | 10 | 100 | 100 | 100 | 100 |
| 0 | bixafen | 0.08 | 0 |  | 9 |  |
| 0 | bixafen | 0.4 | 0 |  | 88 |  |
| 0 | bixafen | 2 | 64 |  | 99 |  |
| 0 | bixafen | 10 | 99 |  | 100 |  |
| 2 | bixafen | 0.08 | 0 | 0 | 18 | 17 |
| 2 | bixafen | 0.4 | 0 | 0 | 80 | 89 |
| 2 | bixafen | 2 | 90 | 64 | 99 | 99 |
| 2 | bixafen | 10 | 99 | 99 | 100 | 100 |
| 5 | bixafen | 0.08 | 99 | 90 | 68 | 46 |
| 5 | bixafen | 0.4 | 100 | 90 | 94 | 93 |
| 5 | bixafen | 2 | 100 | 96 | 100 | 99 |
| 5 | bixafen | 10 | 100 | 100 | 100 | 100 |
| 0 | penthiopyrad | 0.08 | 0 |  |  |  |
| 0 | penthiopyrad | 0.4 | 0 |  |  |  |
| 0 | penthiopyrad | 2 | 99 |  |  |  |
| 0 | penthiopyrad | 10 | 100 |  |  |  |
| 2 | penthiopyrad | 0.08 | 0 | 0 |  |  |
| 2 | penthiopyrad | 0.4 | 42 | 0 |  |  |
| 2 | penthiopyrad | 2 | 99 | 99 |  |  |

TABLE D-continued

Observed and Expected Effects of Compound 81 Alone and Mixtures with Isopyrazam, BAS600, Bixafen, Penthiopyrad, Spiroxamine, Myclobutanil or Fenpropimorph for Control of Wheat Powdery Mildew or Leaf Rust

| Application Rate (ppm) of Compound 81 | Component (b) | Application Rate (ppm) of Component (b) | Test K3 Obsd | Test K3 Exp | Test L3 Obsd | Test L3 Exp |
|---|---|---|---|---|---|---|
| 2 | penthiopyrad | 10 | 100 | 100 | | |
| 5 | penthiopyrad | 0.08 | 99 | 90 | | |
| 5 | penthiopyrad | 0.4 | 100 | 90 | | |
| 5 | penthiopyrad | 2 | 100 | 100 | | |
| 5 | penthiopyrad | 10 | 100 | 100 | | |
| 0 | spiroxamine | 0.4 | 0 | | 0 | |
| 0 | spiroxamine | 2 | 0 | | 0 | |
| 0 | spiroxamine | 10 | 0 | | 0 | |
| 0 | spiroxamine | 40 | 99 | | 91 | |
| 2 | spiroxamine | 0.4 | 0 | 0 | 18 | 9 |
| 2 | spiroxamine | 2 | 0 | 0 | 9 | 9 |
| 2 | spiroxamine | 10 | 0 | 0 | 9 | 9 |
| 2 | spiroxamine | 40 | 100 | 99 | 60 | 92 |
| 5 | spiroxamine | 0.4 | 97 | 90 | 45 | 41 |
| 5 | spiroxamine | 2 | 96 | 90 | 41 | 41 |
| 5 | spiroxamine | 10 | 98 | 90 | 80 | 41 |
| 5 | spiroxamine | 40 | 100 | 100 | 95 | 95 |
| 0 | myclobutanil | 0.4 | 0 | | 0 | |
| 0 | myclobutanil | 2 | 86 | | 0 | |
| 0 | myclobutanil | 10 | 99 | | 41 | |
| 0 | myclobutanil | 40 | 100 | | 99 | |
| 2 | myclobutanil | 0.4 | 42 | 0 | 0 | 9 |
| 2 | myclobutanil | 2 | 93 | 86 | 0 | 9 |
| 2 | myclobutanil | 10 | 100 | 99 | 41 | 46 |
| 2 | myclobutanil | 40 | 100 | 100 | 100 | 99 |
| 5 | myclobutanil | 0.4 | 98 | 90 | 27 | 41 |
| 5 | myclobutanil | 2 | 99 | 99 | 68 | 41 |
| 5 | myclobutanil | 10 | 100 | 100 | 93 | 65 |
| 5 | myclobutanil | 40 | 100 | 100 | 100 | 99 |
| 0 | fenpropimorph | 0.4 | 50 | | 0 | |
| 0 | fenpropimorph | 2 | 96 | | 0 | |
| 0 | fenpropimorph | 10 | 100 | | 88 | |
| 0 | fenpropimorph | 40 | 100 | | 100 | |
| 2 | fenpropimorph | 0.4 | 85 | 50 | 0 | 9 |
| 2 | fenpropimorph | 2 | 97 | 96 | 41 | 9 |
| 2 | fenpropimorph | 10 | 100 | 100 | 97 | 89 |
| 2 | fenpropimorph | 40 | 100 | 100 | 100 | 100 |
| 5 | fenpropimorph | 0.4 | 96 | 95 | 54 | 41 |
| 5 | fenpropimorph | 2 | 100 | 100 | 83 | 41 |
| 5 | fenpropimorph | 10 | 100 | 100 | 99 | 93 |
| 5 | fenpropimorph | 40 | 100 | 100 | 100 | 100 |

TABLE E

Observed and Expected Effects of Compound 81 Alone and Mixtures with Difenoconazole, Azoxystrobin, Tetraconazole, Pyraclostrobin, Prothioconazole, Picoxystrobin or Epoxiconazole for Control of Wheat Powdery Mildew or Leaf Rust

| Application Rate (ppm) of Compound 81 | Component (b) | Application Rate (ppm) of Component (b) | Test K4 Obsd | Test K4 Exp | Test L4 Obsd | Test L4 Exp |
|---|---|---|---|---|---|---|
| 0 | None | 0 | 0 | | 0 | |
| 1 | None | 0 | 0 | | 0 | |
| 2 | None | 0 | 0 | | 27 | |
| 5 | None | 0 | 0 | | 68 | |
| 10 | None | 0 | — | | 88 | |
| 0 | difenoconazole | 0.08 | 0 | | | |
| 0 | difenoconazole | 0.4 | 0 | | | |
| 0 | difenoconazole | 2 | 81 | | | |
| 0 | difenoconazole | 10 | 99 | | | |
| 2 | difenoconazole | 0.08 | 0 | 0 | | |
| 2 | difenoconazole | 0.4 | 21 | 0 | | |
| 2 | difenoconazole | 2 | 90 | 81 | | |
| 2 | difenoconazole | 10 | 100 | 99 | | |
| 5 | difenoconazole | 0.08 | 98 | 0 | | |

TABLE E-continued

Observed and Expected Effects of Compound 81 Alone and Mixtures with Difenoconazole, Azoxystrobin, Tetraconazole, Pyraclostrobin, Prothioconazole, Picoxystrobin or Epoxiconazole for Control of Wheat Powdery Mildew or Leaf Rust

| Application Rate (ppm) of Compound 81 | Component (b) | Application Rate (ppm) of Component (b) | Test K4 Obsd | Test K4 Exp | Test L4 Obsd | Test L4 Exp |
|---|---|---|---|---|---|---|
| 5 | difenoconazole | 0.4 | 97 | 0 | | |
| 5 | difenoconazole | 2 | 98 | 81 | | |
| 5 | difenoconazole | 10 | 100 | 99 | | |
| 0 | azoxystrobin | 0.08 | 0 | | | |
| 0 | azoxystrobin | 0.4 | 0 | | | |
| 0 | azoxystrobin | 2 | 0 | | | |
| 0 | azoxystrobin | 10 | 96 | | | |
| 2 | azoxystrobin | 0.08 | 0 | 0 | | |
| 2 | azoxystrobin | 0.4 | 0 | 0 | | |
| 2 | azoxystrobin | 2 | 0 | 0 | | |
| 2 | azoxystrobin | 10 | 97 | 96 | | |
| 5 | azoxystrobin | 0.08 | 97 | 0 | | |
| 5 | azoxystrobin | 0.4 | 96 | 0 | | |
| 5 | azoxystrobin | 2 | 98 | 0 | | |
| 5 | azoxystrobin | 10 | 100 | 96 | | |
| 0 | tetraconazole | 0.08 | 0 | | 0 | |
| 0 | tetraconazole | 0.4 | 21 | | 0 | |
| 0 | tetraconazole | 2 | 93 | | 27 | |
| 0 | tetraconazole | 10 | 97 | | 99 | |
| 2 | tetraconazole | 0.08 | 0 | 0 | 0 | 27 |
| 2 | tetraconazole | 0.4 | 0 | 21 | 9 | 27 |
| 2 | tetraconazole | 2 | 55 | 93 | 60 | 47 |
| 2 | tetraconazole | 10 | 99 | 97 | 100 | 99 |
| 5 | tetraconazole | 0.08 | 94 | 0 | 74 | 68 |
| 5 | tetraconazole | 0.4 | 94 | 21 | 74 | 68 |
| 5 | tetraconazole | 2 | 97 | 93 | 98 | 77 |
| 5 | tetraconazole | 10 | 100 | 97 | 100 | 100 |
| 0 | pyraclostrobin | 0.08 | 0 | | 9 | |
| 0 | pyraclostrobin | 0.4 | 0 | | 80 | |
| 0 | pyraclostrobin | 2 | 0 | | 98 | |
| 0 | pyraclostrobin | 10 | 93 | | 100 | |
| 2 | pyraclostrobin | 0.08 | 0 | 0 | 27 | 34 |
| 2 | pyraclostrobin | 0.4 | 0 | 0 | 85 | 85 |
| 2 | pyraclostrobin | 2 | 58 | 0 | 97 | 99 |
| 2 | pyraclostrobin | 10 | 94 | 93 | 100 | 100 |
| 5 | pyraclostrobin | 0.08 | 97 | 0 | 74 | 71 |
| 5 | pyraclostrobin | 0.4 | 96 | 0 | 94 | 94 |
| 5 | pyraclostrobin | 2 | 98 | 0 | 100 | 99 |
| 5 | pyraclostrobin | 10 | 99 | 93 | 100 | 100 |
| 0 | prothioconazole | 0.08 | 0 | | 0 | |
| 0 | prothioconazole | 0.4 | 0 | | 0 | |
| 0 | prothioconazole | 2 | 0 | | 9 | |
| 0 | prothioconazole | 10 | 93 | | 9 | |
| 2 | prothioconazole | 0.08 | 0 | 0 | 0 | 27 |
| 2 | prothioconazole | 0.4 | 0 | 0 | 0 | 27 |
| 2 | prothioconazole | 2 | 47 | 0 | 0 | 34 |
| 2 | prothioconazole | 10 | 98 | 93 | 27 | 34 |
| 5 | prothioconazole | 0.08 | 96 | 0 | 80 | 68 |
| 5 | prothioconazole | 0.4 | 96 | 0 | 74 | 68 |
| 5 | prothioconazole | 2 | 97 | 0 | 55 | 71 |
| 5 | prothioconazole | 10 | 98 | 93 | 74 | 71 |
| 0 | picoxystrobin | 0.08 | 0 | | 0 | |
| 0 | picoxystrobin | 0.4 | 0 | | 9 | |
| 0 | picoxystrobin | 2 | 0 | | 82 | |
| 0 | picoxystrobin | 10 | 99 | | 100 | |
| 2 | picoxystrobin | 0.08 | 0 | 0 | 0 | 27 |
| 2 | picoxystrobin | 0.4 | 0 | 0 | 27 | 34 |
| 2 | picoxystrobin | 2 | 42 | 0 | 85 | 87 |
| 2 | picoxystrobin | 10 | 100 | 99 | 100 | 100 |
| 5 | picoxystrobin | 0.08 | 93 | 0 | 60 | 68 |
| 5 | picoxystrobin | 0.4 | 95 | 0 | 80 | 71 |
| 5 | picoxystrobin | 2 | 96 | 0 | 90 | 94 |
| 5 | picoxystrobin | 10 | 100 | 99 | 100 | 100 |
| 0 | epoxiconazole | 0.08 | 0 | | 0 | |
| 0 | epoxiconazole | 0.4 | 90 | | 93 | |
| 0 | epoxiconazole | 2 | 98 | | 99 | |
| 0 | epoxiconazole | 10 | 100 | | 100 | |
| 2 | epoxiconazole | 0.08 | 0 | 0 | 55 | 27 |
| 2 | epoxiconazole | 0.4 | 29 | 90 | 97 | 95 |
| 2 | epoxiconazole | 2 | 99 | 98 | 99 | 99 |

TABLE E-continued

Observed and Expected Effects of Compound 81 Alone and Mixtures with Difenoconazole, Azoxystrobin, Tetraconazole, Pyraclostrobin, Prothioconazole, Picoxystrobin or Epoxiconazole for Control of Wheat Powdery Mildew or Leaf Rust

| Application Rate (ppm) of Compound 81 | Component (b) | Application Rate (ppm) of Component (b) | Test K4 Obsd | Test K4 Exp | Test L4 Obsd | Test L4 Exp |
|---|---|---|---|---|---|---|
| 2 | epoxiconazole | 10 | 100 | 100 | 100 | 100 |
| 5 | epoxiconazole | 0.08 | 93 | 0 | 91 | 68 |
| 5 | epoxiconazole | 0.4 | 98 | 90 | 100 | 98 |
| 5 | epoxiconazole | 2 | 100 | 98 | 100 | 100 |
| 5 | epoxiconazole | 10 | 100 | 100 | 100 | 100 |

TABLE F

Observed and Expected Effects of Compound 81 Alone and Mixtures with Quinoxyfen, Cyproconazole, Penthiopyrad, Isopyrazam, Difenoconazole, Azoxystrobin or Proquinazid for Control of Wheat Powdery Mildew or Leaf Rust

| Application Rate (ppm) of Compound 81 | Component (b) | Application Rate (ppm) of Component (b) | Test K5 Obsd | Test K5 Exp | Test L5 Obsd | Test L5 Exp |
|---|---|---|---|---|---|---|
| 0 | None | 0 | 0 | | 0 | |
| 1 | None | 0 | 0 | | 18 | |
| 2 | None | 0 | 0 | | 27 | |
| 5 | None | 0 | 0 | | 55 | |
| 10 | None | 0 | 100 | | 82 | |
| 0 | quinoxyfen | 0.016 | 21 | | — | |
| 0 | quinoxyfen | 0.08 | 29 | | — | |
| 0 | quinoxyfen | 0.4 | 64 | | — | |
| 0 | quinoxyfen | 2 | 93 | | — | |
| 2 | quinoxyfen | 0.016 | 90 | 21 | — | |
| 2 | quinoxyfen | 0.08 | 87 | 29 | — | |
| 2 | quinoxyfen | 0.4 | 90 | 64 | — | |
| 2 | quinoxyfen | 2 | 99 | 93 | — | |
| 5 | quinoxyfen | 0.016 | 99 | 21 | — | |
| 5 | quinoxyfen | 0.08 | 100 | 29 | — | |
| 5 | quinoxyfen | 0.4 | 100 | 64 | — | |
| 5 | quinoxyfen | 2 | 100 | 93 | — | |
| 0 | cyproconazole | 0.016 | 64 | | 27 | |
| 0 | cyproconazole | 0.08 | 64 | | 80 | |
| 0 | cyproconazole | 0.4 | 79 | | 92 | |
| 0 | cyproconazole | 2 | 96 | | 100 | |
| 2 | cyproconazole | 0.016 | 42 | 64 | 55 | 47 |
| 2 | cyproconazole | 0.08 | 64 | 64 | 74 | 85 |
| 2 | cyproconazole | 0.4 | 96 | 79 | 93 | 94 |
| 2 | cyproconazole | 2 | 100 | 96 | 100 | 100 |
| 5 | cyproconazole | 0.016 | 100 | 64 | 68 | 67 |
| 5 | cyproconazole | 0.08 | 99 | 64 | 97 | 91 |
| 5 | cyproconazole | 0.4 | 100 | 79 | 98 | 96 |
| 5 | cyproconazole | 2 | 100 | 96 | 100 | 100 |
| 0 | penthiopyrad | 0.016 | — | | 9 | |
| 0 | penthiopyrad | 0.08 | — | | 55 | |
| 0 | penthiopyrad | 0.4 | — | | 68 | |
| 0 | penthiopyrad | 2 | — | | 99 | |
| 2 | penthiopyrad | 0.016 | — | | 55 | 34 |
| 2 | penthiopyrad | 0.08 | — | | 68 | 67 |
| 2 | penthiopyrad | 0.4 | — | | 68 | 77 |
| 2 | penthiopyrad | 2 | — | | 99 | 99 |
| 5 | penthiopyrad | 0.016 | — | | 74 | 59 |
| 5 | penthiopyrad | 0.08 | — | | 80 | 79 |
| 5 | penthiopyrad | 0.4 | — | | 88 | 85 |
| 5 | penthiopyrad | 2 | — | | 100 | 100 |
| 0 | isopyrazam | 0.016 | — | | 68 | |
| 0 | isopyrazam | 0.08 | — | | 89 | |
| 0 | isopyrazam | 0.4 | — | | 100 | |
| 0 | isopyrazam | 2 | — | | 100 | |
| 2 | isopyrazam | 0.016 | — | | 74 | 77 |
| 2 | isopyrazam | 0.08 | — | | 88 | 92 |
| 2 | isopyrazam | 0.4 | — | | 100 | 100 |
| 2 | isopyrazam | 2 | — | | 100 | 100 |
| 5 | isopyrazam | 0.016 | — | | 88 | 85 |

TABLE F-continued

Observed and Expected Effects of Compound 81 Alone and Mixtures with Quinoxyfen, Cyproconazole, Penthiopyrad, Isopyrazam, Difenoconazole, Azoxystrobin or Proquinazid for Control of Wheat Powdery Mildew or Leaf Rust

| Application Rate (ppm) of Compound 81 | Component (b) | Application Rate (ppm) of Component (b) | Test K5 Obsd | Test K5 Exp | Test L5 Obsd | Test L5 Exp |
|---|---|---|---|---|---|---|
| 5 | isopyrazam | 0.08 | — | | 99 | 95 |
| 5 | isopyrazam | 0.4 | — | | 100 | 100 |
| 5 | isopyrazam | 2 | — | | 100 | 100 |
| 0 | difenoconazole | 0.016 | — | | 68 | |
| 0 | difenoconazole | 0.08 | — | | 68 | |
| 0 | difenoconazole | 0.4 | — | | 92 | |
| 0 | difenoconazole | 2 | — | | 100 | |
| 2 | difenoconazole | 0.016 | — | | 27 | 77 |
| 2 | difenoconazole | 0.08 | — | | 41 | 77 |
| 2 | difenoconazole | 0.4 | — | | 99 | 94 |
| 2 | difenoconazole | 2 | — | | 100 | 100 |
| 5 | difenoconazole | 0.016 | — | | 74 | 85 |
| 5 | difenoconazole | 0.08 | — | | 80 | 85 |
| 5 | difenoconazole | 0.4 | — | | 100 | 96 |
| 5 | difenoconazole | 2 | — | | 100 | 100 |
| 0 | azoxystrobin | 0.016 | — | | 0 | |
| 0 | azoxystrobin | 0.08 | — | | 68 | |
| 0 | azoxystrobin | 0.4 | — | | 100 | |
| 0 | azoxystrobin | 2 | — | | 100 | |
| 2 | azoxystrobin | 0.016 | — | | 27 | 27 |
| 2 | azoxystrobin | 0.08 | — | | 74 | 77 |
| 2 | azoxystrobin | 0.4 | — | | 100 | 100 |
| 2 | azoxystrobin | 2 | — | | 100 | 100 |
| 5 | azoxystrobin | 0.016 | — | | 74 | 55 |
| 5 | azoxystrobin | 0.08 | — | | 97 | 85 |
| 5 | azoxystrobin | 0.4 | — | | 100 | 100 |
| 5 | azoxystrobin | 2 | — | | 100 | 100 |
| 0 | proquinazid | 0.016 | 0 | | — | |
| 0 | proquinazid | 0.08 | 0 | | — | |
| 0 | proquinazid | 0.4 | 0 | | — | |
| 0 | proquinazid | 2 | 71 | | — | |
| 2 | proquinazid | 0.016 | 0 | 0 | — | |
| 2 | proquinazid | 0.08 | 0 | 0 | — | |
| 2 | proquinazid | 0.4 | 0 | 0 | — | |
| 2 | proquinazid | 2 | 87 | 71 | — | |
| 5 | proquinazid | 0.016 | 87 | 0 | — | |
| 5 | proquinazid | 0.08 | 89 | 0 | — | |
| 5 | proquinazid | 0.4 | 93 | 0 | — | |
| 5 | proquinazid | 2 | 98 | 71 | — | |

TABLE G

Observed and Expected Effects of Compound 81 Alone and Mixtures with Probenazole, Mancozeb, Iprodione, Boscalid, Copper hydroxide, Cymoxanil or Chlorothalonil for Control of Wheat Leaf Blotch

| Application Rate (ppm) of Compound 81 | Component (b) | Application Rate (ppm) of Component (b) | Test M1 Obsd | Test M1 Exp |
|---|---|---|---|---|
| 0 | None | 0 | 0 | |
| 0.01 | None | 0 | 0 | |
| 0.1 | None | 0 | 0 | |
| 1 | None | 0 | 86 | |
| 10 | None | 0 | 100 | |
| 0 | probenazole | 10 | 0 | |
| 0 | probenazole | 40 | 0 | |
| 0 | probenazole | 200 | 0 | |
| 0.1 | probenazole | 10 | 0 | 0 |
| 0.1 | probenazole | 40 | 0 | 0 |
| 0.1 | probenazole | 200 | 25 | 0 |
| 1 | probenazole | 10 | 87 | 86 |
| 1 | probenazole | 40 | 94 | 86 |
| 1 | probenazole | 200 | 87 | 86 |
| 0 | mancozeb | 10 | 0 | |
| 0 | mancozeb | 40 | 55 | |
| 0 | mancozeb | 200 | 91 | |
| 0.1 | mancozeb | 10 | 0 | 0 |

TABLE G-continued

Observed and Expected Effects of Compound 81 Alone and Mixtures with Probenazole, Mancozeb, Iprodione, Boscalid, Copper hydroxide, Cymoxanil or Chlorothalonil for Control of Wheat Leaf Blotch

| Application Rate (ppm) of Compound 81 | Component (b) | Application Rate (ppm) of Component (b) | Test M1 Obsd | Exp |
|---|---|---|---|---|
| 0.1 | mancozeb | 40 | 63 | 55 |
| 0.1 | mancozeb | 200 | 96 | 91 |
| 1 | mancozeb | 10 | 81 | 86 |
| 1 | mancozeb | 40 | 98 | 94 |
| 1 | mancozeb | 200 | 100 | 99 |
| 0 | iprodione | 10 | 0 | |
| 0 | iprodione | 40 | 0 | |
| 0 | iprodione | 200 | 0 | |
| 0.1 | iprodione | 10 | 0 | 0 |
| 0.1 | iprodione | 40 | 0 | 0 |
| 0.1 | iprodione | 200 | 22 | 0 |
| 1 | iprodione | 10 | 88 | 86 |
| 1 | iprodione | 40 | 91 | 86 |
| 1 | iprodione | 200 | 98 | 86 |
| 0 | boscalid | 10 | 77 | |
| 0 | boscalid | 40 | 90 | |
| 0 | boscalid | 200 | 99 | |
| 0.1 | boscalid | 10 | 72 | 77 |
| 0.1 | boscalid | 40 | 98 | 90 |
| 0.1 | boscalid | 200 | 98 | 99 |
| 1 | boscalid | 10 | 99 | 97 |
| 1 | boscalid | 40 | 100 | 99 |
| 1 | boscalid | 200 | 100 | 100 |
| 0 | copper hydroxide | 10 | 0 | |
| 0 | copper hydroxide | 40 | 45 | |
| 0 | copper hydroxide | 200 | 77 | |
| 0.1 | copper hydroxide | 10 | 0 | 0 |
| 0.1 | copper hydroxide | 40 | 25 | 45 |
| 0.1 | copper hydroxide | 200 | 87 | 77 |
| 1 | copper hydroxide | 10 | 72 | 86 |
| 1 | copper hydroxide | 40 | 93 | 92 |
| 1 | copper hydroxide | 200 | 99 | 97 |
| 0 | cymoxanil | 10 | 0 | |
| 0 | cymoxanil | 40 | 0 | |
| 0 | cymoxanil | 200 | 0 | |
| 0.1 | cymoxanil | 10 | 0 | 0 |
| 0.1 | cymoxanil | 40 | 0 | 0 |
| 0.1 | cymoxanil | 200 | 0 | 0 |
| 1 | cymoxanil | 10 | 96 | 86 |
| 1 | cymoxanil | 40 | 85 | 86 |
| 1 | cymoxanil | 200 | 96 | 86 |
| 0 | chlorothalonil | 10 | 0 | |
| 0 | chlorothalonil | 40 | 42 | |
| 0 | chlorothalonil | 200 | 99 | |
| 0.1 | chlorothalonil | 10 | 0 | 0 |
| 0.1 | chlorothalonil | 40 | 75 | 42 |
| 0.1 | chlorothalonil | 200 | 98 | 99 |
| 1 | chlorothalonil | 10 | 72 | 86 |
| 1 | chlorothalonil | 40 | 80 | 92 |
| 1 | chlorothalonil | 200 | 99 | 100 |

TABLE H

Observed and Expected Effects of Compound 81 Alone and Mixtures with BAS600, Isopyrazam, Penthiopyrad, Bixafen or Cyproconazole for Control of Wheat Leaf Blotch

| Application Rate (ppm) of Compound 81 | Component (b) | Application Rate (ppm) of Component (b) | Test M2 Obsd | Exp |
|---|---|---|---|---|
| 0 | None | 0 | 0 | |
| 0.01 | None | 0 | 0 | |
| 0.1 | None | 0 | 0 | |
| 1 | None | 0 | 95 | |
| 10 | None | 0 | 100 | |
| 0 | BAS600 | 0.016 | 0 | |
| 0 | BAS600 | 0.08 | 0 | |
| 0 | BAS600 | 0.4 | 93 | |

TABLE H-continued

Observed and Expected Effects of Compound 81 Alone and Mixtures with BAS600, Isopyrazam, Penthiopyrad, Bixafen or Cyproconazole for Control of Wheat Leaf Blotch

| Application Rate (ppm) of Compound 81 | Component (b) | Application Rate (ppm) of Component (b) | Test M2 Obsd | Test M2 Exp |
|---|---|---|---|---|
| 0 | BAS600 | 2 | 100 | |
| 0.1 | BAS600 | 0.02 | 0 | 0 |
| 0.1 | BAS600 | 0.08 | 38 | 0 |
| 0.1 | BAS600 | 0.40 | 96 | 93 |
| 0.1 | BAS600 | 2 | 100 | 100 |
| 1 | BAS600 | 0.02 | 65 | 95 |
| 1 | BAS600 | 0.08 | 85 | 95 |
| 1 | BAS600 | 0.40 | 97 | 100 |
| 1 | BAS600 | 2 | 99 | 100 |
| 0 | isopyrazam | 0.08 | 0 | |
| 0 | isopyrazam | 0.40 | 77 | |
| 0 | isopyrazam | 2 | 93 | |
| 0 | isopyrazam | 10 | 100 | |
| 0.1 | isopyrazam | 0.08 | 0 | 0 |
| 0.1 | isopyrazam | 0.40 | 72 | 77 |
| 0.1 | isopyrazam | 2 | — | |
| 0.1 | isopyrazam | 10 | — | |
| 1 | isopyrazam | 0.08 | — | |
| 1 | isopyrazam | 0.40 | 80 | 99 |
| 1 | isopyrazam | 2 | — | |
| 1 | isopyrazam | 10 | 100 | 100 |
| 0 | penthiopyrad | 0.08 | 0 | |
| 0 | penthiopyrad | 0.40 | 0 | |
| 0 | penthiopyrad | 2 | — | |
| 0 | penthiopyrad | 10 | — | |
| 0.1 | penthiopyrad | 0.08 | 0 | 0 |
| 0.1 | penthiopyrad | 0.40 | 17 | 0 |
| 0.1 | penthiopyrad | 2 | — | |
| 0.1 | penthiopyrad | 10 | 99 | |
| 1 | penthiopyrad | 0.08 | 83 | 95 |
| 1 | penthiopyrad | 0.40 | 73 | 95 |
| 1 | penthiopyrad | 2 | — | |
| 1 | penthiopyrad | 10 | 99 | |
| 0 | bixafen | 0.08 | 0 | |
| 0 | bixafen | 0.40 | 33 | |
| 0 | bixafen | 2 | 89 | |
| 0 | bixafen | 10 | — | |
| 0.1 | bixafen | 0.08 | 0 | 0 |
| 0.1 | bixafen | 0.40 | 33 | 33 |
| 0.1 | bixafen | 2 | 83 | 89 |
| 0.1 | bixafen | 10 | 100 | |
| 1 | bixafen | 0.08 | — | |
| 1 | bixafen | 0.4 | 85 | 97 |
| 1 | bixafen | 2 | — | |
| 1 | bixafen | 10 | — | |
| 0 | cyproconazole | 0.4 | 0 | |
| 0 | cyproconazole | 2 | 0 | |
| 0 | cyproconazole | 10 | 0 | |
| 0 | cyproconazole | 40 | 98 | |
| 0.1 | cyproconazole | 0.4 | 0 | 0 |
| 0.1 | cyproconazole | 2 | 0 | 0 |
| 0.1 | cyproconazole | 10 | 0 | 0 |
| 0.1 | cyproconazole | 40 | 98 | 98 |
| 1 | cyproconazole | 0.4 | 73 | 95 |
| 1 | cyproconazole | 2 | 63 | 95 |
| 1 | cyproconazole | 10 | 97 | 95 |
| 1 | cyproconazole | 40 | 100 | 100 |

TABLE I

Observed and Expected Effects of Compound 81 Alone and Mixtures with Fludioxonil, Epoxiconazole, Prothioconazole, Difenoconazole or Fenpropimorph for Control of Wheat Leaf Blotch

| Application Rate (ppm) of Compound 81 | Component (b) | Application Rate (ppm) of Component (b) | Test M3 Obsd | Test M3 Exp |
|---|---|---|---|---|
| 0 | None | 0 | 0 | |
| 0.01 | None | 0 | 0 | |
| 0.1 | None | 0 | 0 | |
| 1 | None | 0 | 52 | |
| 10 | None | 0 | 100 | |
| 0 | fludioxonil | 0.08 | 0 | |
| 0 | fludioxonil | 0.4 | 0 | |
| 0 | fludioxonil | 2 | 37 | |
| 0 | fludioxonil | 10 | 67 | |
| 0.1 | fludioxonil | 0.08 | 0 | 0 |
| 0.1 | fludioxonil | 0.4 | 0 | 0 |
| 0.1 | fludioxonil | 2 | 30 | 37 |
| 0.1 | fludioxonil | 10 | 57 | 67 |
| 1 | fludioxonil | 0.08 | 83 | 52 |
| 1 | fludioxonil | 0.4 | 45 | 52 |
| 1 | fludioxonil | 2 | 68 | 69 |
| 1 | fludioxonil | 10 | 78 | 84 |
| 0 | epoxiconazole | 0.4 | 0 | |
| 0 | epoxiconazole | 2 | 0 | |
| 0 | epoxiconazole | 10 | 76 | |
| 0 | epoxiconazole | 40 | 100 | |
| 0.1 | epoxiconazole | 0.4 | 0 | 0 |
| 0.1 | epoxiconazole | 2 | 0 | 0 |
| 0.1 | epoxiconazole | 10 | 75 | 76 |
| 0.1 | epoxiconazole | 40 | 98 | 100 |
| 1 | epoxiconazole | 0.4 | 78 | 52 |
| 1 | epoxiconazole | 2 | 78 | 52 |
| 1 | epoxiconazole | 10 | 97 | 89 |
| 1 | epoxiconazole | 40 | 100 | 100 |
| 0 | prothioconazole | 0.4 | 0 | |
| 0 | prothioconazole | 2 | 0 | |
| 0 | prothioconazole | 10 | 18 | |
| 0 | prothioconazole | 40 | 85 | |
| 0.1 | prothioconazole | 0.4 | 0 | 0 |
| 0.1 | prothioconazole | 2 | 0 | 0 |
| 0.1 | prothioconazole | 10 | 25 | 18 |
| 0.1 | prothioconazole | 40 | — | |
| 1 | prothioconazole | 0.4 | 48 | 52 |
| 1 | prothioconazole | 2 | 25 | 52 |
| 1 | prothioconazole | 10 | 73 | 61 |
| 1 | prothioconazole | 40 | 88 | 93 |
| 0 | difenoconazole | 0.4 | 0 | |
| 0 | difenoconazole | 2 | 0 | |
| 0 | difenoconazole | 10 | 52 | |
| 0 | difenoconazole | 40 | 95 | |
| 0.1 | difenoconazole | 0.4 | 0 | 0 |
| 0.1 | difenoconazole | 2 | 0 | 0 |
| 0.1 | difenoconazole | 10 | 57 | 52 |
| 0.1 | difenoconazole | 40 | 98 | 95 |
| 1 | difenoconazole | 0.4 | 78 | 52 |
| 1 | difenoconazole | 2 | 50 | 52 |
| 1 | difenoconazole | 10 | 88 | 77 |
| 1 | difenoconazole | 40 | 100 | 97 |
| 0 | fenpropimorph | 2 | 0 | |
| 0 | fenpropimorph | 10 | 0 | |
| 0 | fenpropimorph | 40 | 0 | |
| 0 | fenpropimorph | 200 | 0 | |
| 0.1 | fenpropimorph | 2 | 0 | 0 |
| 0.1 | fenpropimorph | 10 | 0 | 0 |
| 0.1 | fenpropimorph | 40 | 0 | 0 |
| 0.1 | fenpropimorph | 200 | 0 | 0 |
| 1 | fenpropimorph | 2 | 85 | 52 |
| 1 | fenpropimorph | 10 | 75 | 52 |
| 1 | fenpropimorph | 40 | 86 | 52 |
| 1 | fenpropimorph | 200 | 98 | 52 |

TABLE J

Observed and Expected Effects of Compound 81 Alone and Mixtures with Pyraclostrobin, Tricyclazole, Fluazinam, Dimethomorph, Iprovalicarb, Metalaxyl-M, Folpet or Myclobutanil for Control of Wheat Leaf Blotch

| Application Rate (ppm) of Compound 81 | Application Rate (ppm) of Component (b) | Component (b) | Test M4 Obsd | Exp |
|---|---|---|---|---|
| 0 | None | 0 | 0 | |
| 0.01 | None | 0 | 0 | |
| 0.1 | None | 0 | 23 | |
| 1 | None | 0 | 66 | |
| 10 | None | 0 | 100 | |
| 0 | pyraclostrobin | 10 | 0 | |
| 0 | pyraclostrobin | 40 | 26 | |
| 0 | pyraclostrobin | 200 | 93 | |
| 0.1 | pyraclostrobin | 10 | 0 | 23 |
| 0.1 | pyraclostrobin | 40 | 32 | 43 |
| 0.1 | pyraclostrobin | 200 | 91 | 94 |
| 1 | pyraclostrobin | 10 | 79 | 66 |
| 1 | pyraclostrobin | 40 | 90 | 75 |
| 1 | pyraclostrobin | 200 | 97 | 98 |
| 0 | tricyclazole | 10 | 0 | |
| 0 | tricyclazole | 40 | 0 | |
| 0 | tricyclazole | 200 | 0 | |
| 0.1 | tricyclazole | 10 | 0 | 23 |
| 0.1 | tricyclazole | 40 | 0 | 23 |
| 0.1 | tricyclazole | 200 | 0 | 23 |
| 1 | tricyclazole | 10 | 74 | 66 |
| 1 | tricyclazole | 40 | 93 | 66 |
| 1 | tricyclazole | 200 | 74 | 66 |
| 0 | fluazinam | 10 | 0 | |
| 0 | fluazinam | 40 | 0 | |
| 0 | fluazinam | 200 | 93 | |
| 0.1 | fluazinam | 10 | 13 | 23 |
| 0.1 | fluazinam | 40 | 60 | 23 |
| 0.1 | fluazinam | 200 | 85 | 95 |
| 1 | fluazinam | 10 | 76 | 66 |
| 1 | fluazinam | 40 | 97 | 66 |
| 1 | fluazinam | 200 | 100 | 98 |
| 0 | dimethomorph | 10 | 0 | |
| 0 | dimethomorph | 40 | 0 | |
| 0 | dimethomorph | 200 | 0 | |
| 0.1 | dimethomorph | 10 | 0 | 23 |
| 0.1 | dimethomorph | 40 | 0 | 23 |
| 0.1 | dimethomorph | 200 | 16 | 23 |
| 1 | dimethomorph | 10 | 93 | 66 |
| 1 | dimethomorph | 40 | 91 | 66 |
| 1 | dimethomorph | 200 | 0 | 66 |
| 0 | iprovalicarb | 10 | 0 | |
| 0 | iprovalicarb | 40 | 0 | |
| 0 | iprovalicarb | 200 | 0 | |
| 0.1 | iprovalicarb | 10 | 0 | 23 |
| 0.1 | iprovalicarb | 40 | 23 | 23 |
| 0.1 | iprovalicarb | 200 | 53 | 23 |
| 1 | iprovalicarb | 10 | 81 | 66 |
| 1 | iprovalicarb | 40 | 96 | 66 |
| 1 | iprovalicarb | 200 | 96 | 66 |
| 0 | metalaxyl-M | 10 | 0 | |
| 0 | metalaxyl-M | 40 | 0 | |
| 0 | metalaxyl-M | 200 | 0 | |
| 0.1 | metalaxyl-M | 10 | 0 | 23 |
| 0.1 | metalaxyl-M | 40 | 0 | 23 |
| 0.1 | metalaxyl-M | 200 | 32 | 23 |
| 1 | metalaxyl-M | 10 | 86 | 66 |
| 1 | metalaxyl-M | 40 | 96 | 66 |
| 1 | metalaxyl-M | 200 | 96 | 66 |
| 0 | folpet | 10 | 0 | |
| 0 | folpet | 40 | 73 | |
| 0 | folpet | 200 | 91 | |
| 0.1 | folpet | 10 | 32 | 23 |
| 0.1 | folpet | 40 | 86 | 79 |
| 0.1 | folpet | 200 | 93 | 93 |
| 1 | folpet | 10 | 91 | 66 |
| 1 | folpet | 40 | 91 | 91 |
| 1 | folpet | 200 | 98 | 97 |
| 0 | myclobutanil | 10 | 0 | |
| 0 | myclobutanil | 40 | 44 | |
| 0 | myclobutanil | 200 | 74 | |

TABLE J-continued

Observed and Expected Effects of Compound 81 Alone and Mixtures with Pyraclostrobin, Tricyclazole, Fluazinam, Dimethomorph, Iprovalicarb, Metalaxyl-M, Folpet or Myclobutanil for Control of Wheat Leaf Blotch

| Application Rate (ppm) of Compound 81 | Component (b) | Application Rate (ppm) of Component (b) | Test M4 Obsd | Test M4 Exp |
|---|---|---|---|---|
| 0.1 | myclobutanil | 10 | 13 | 23 |
| 0.1 | myclobutanil | 40 | 0 | 57 |
| 0.1 | myclobutanil | 200 | 61 | 80 |
| 1 | myclobutanil | 10 | 16 | 66 |
| 1 | myclobutanil | 40 | 91 | 81 |
| 1 | myclobutanil | 200 | 74 | 91 |

TABLE K

Observed and Expected Effects of Compound 81 Alone and Mixtures with Quinoxyfen, Azoxystrobin, Picoxystrobin, Tetraconazole, Spiroxamine or Proquinazid for Control of Wheat Leaf Blotch

| Application Rate (ppm) of Compound 81 | Component (b) | Application Rate (ppm) of Component (b) | Test M5 Obsd | Test M5 Exp |
|---|---|---|---|---|
| 0 | None | 0 | 0 | |
| 0.01 | None | 0 | 0 | |
| 0.1 | None | 0 | 3 | |
| 1 | None | 0 | 90 | |
| 10 | None | 0 | 100 | |
| 0 | quinoxyfen | 10 | 0 | |
| 0 | quinoxyfen | 40 | 0 | |
| 0 | quinoxyfen | 200 | 8 | |
| 0.1 | quinoxyfen | 10 | 0 | 3 |
| 0.1 | quinoxyfen | 40 | 0 | 3 |
| 0.1 | quinoxyfen | 200 | 0 | 11 |
| 1 | quinoxyfen | 10 | 95 | 90 |
| 1 | quinoxyfen | 40 | 99 | 90 |
| 1 | quinoxyfen | 200 | 99 | 91 |
| 0 | azoxystrobin | 10 | 0 | |
| 0 | azoxystrobin | 40 | 20 | |
| 0 | azoxystrobin | 200 | 50 | |
| 0.1 | azoxystrobin | 10 | 0 | 3 |
| 0.1 | azoxystrobin | 40 | 3 | 23 |
| 0.1 | azoxystrobin | 200 | 61 | 52 |
| 1 | azoxystrobin | 10 | 90 | 90 |
| 1 | azoxystrobin | 40 | 94 | 92 |
| 1 | azoxystrobin | 200 | 93 | 95 |
| 0 | picoxystrobin | 10 | 0 | |
| 0 | picoxystrobin | 40 | 0 | |
| 0 | picoxystrobin | 200 | 0 | |
| 0.1 | picoxystrobin | 10 | 0 | 3 |
| 0.1 | picoxystrobin | 40 | 0 | 3 |
| 0.1 | picoxystrobin | 200 | 0 | 3 |
| 1 | picoxystrobin | 10 | 79 | 90 |
| 1 | picoxystrobin | 40 | 70 | 90 |
| 1 | picoxystrobin | 200 | 85 | 90 |
| 0 | tetraconazole | 10 | 0 | |
| 0 | tetraconazole | 40 | 7 | |
| 0 | tetraconazole | 200 | 99 | |
| 0.1 | tetraconazole | 10 | 13 | 3 |
| 0.1 | tetraconazole | 40 | 60 | 10 |
| 0.1 | tetraconazole | 200 | 99 | 99 |
| 1 | tetraconazole | 10 | 87 | 90 |
| 1 | tetraconazole | 40 | 99 | 91 |
| 1 | tetraconazole | 200 | 100 | 100 |
| 0 | spiroxamine | 10 | 0 | |
| 0 | spiroxamine | 40 | 3 | |
| 0 | spiroxamine | 200 | 0 | |
| 0.1 | spiroxamine | 10 | 0 | 3 |
| 0.1 | spiroxamine | 40 | 0 | 7 |
| 0.1 | spiroxamine | 200 | 7 | 3 |
| 1 | spiroxamine | 10 | 88 | 90 |
| 1 | spiroxamine | 40 | 85 | 90 |
| 1 | spiroxamine | 200 | 100 | 90 |
| 0 | proquinazid | 10 | 0 | |
| 0 | proquinazid | 40 | 0 | |
| 0 | proquinazid | 200 | 0 | |
| 0.1 | proquinazid | 10 | 0 | 3 |
| 0.1 | proquinazid | 40 | 0 | 3 |
| 0.1 | proquinazid | 200 | 0 | 3 |
| 1 | proquinazid | 10 | 22 | 90 |
| 1 | proquinazid | 40 | 55 | 90 |
| 1 | proquinazid | 200 | 25 | 90 |

Tables B through K show compositions of the present invention comprising mixtures of a representative Formula 1 compound with a variety of component (b) compounds demonstrating, in some instances, synergistic control of wheat powdery mildew, leaf rust, and leaf blotch. As control cannot exceed 100%, increased activity above expected fungicidal activity was not always observed in mixtures but more likely observed when the separate active ingredient components alone were at application rates providing considerably less than 100% control. Synergy may not be evident at low application rates where the individual active ingredient components alone have little activity. However, in some instances greater activity was observed for combinations wherein individual active ingredients alone at the same application rates had little or no activity. As demonstrated above, this invention provides a method for controlling powdery mildew (*Blumeria graminis* f. sp. *tritici*), leaf rust (*Puccinia recondite* f. sp. *tritici*), and wheat leaf blotch (*Septoria tritici*).

Tests N1 and N2

Tests N1 and N2 involved evaluation of mixtures of Compound 81 with 2-[(3-bromo-8-methyl-6-quinolinyl)oxy]-N-(1,1-dimethyl-2-propyn-1-yl)-2-(methylthio)acetamide (Compound A1) and 2-[(3-bromo-6-quinolinyl)oxy]-N-(1,1-dimethylethyl)butanamide (Compound A2), respectively, for inhibiting the growth of *Septoria tritici* (the causal agent of wheat leaf blotch). The general protocol for preparing test compositions was as follows. Compound 81 (Tests N1 and N2), Compound A1 (Test N1) and Compound A2 (Test N2) were obtained as unformulated, technical-grade materials. Unformulated test compounds were first dissolved in DMSO at the appropriate concentration to provide the desired concentration (in µM) after mixing with the fungal growth medium in the wells of 96-well plates containing 200 µL fungal growth medium per well. The ranges of compound concentrations were chosen to span a range of inhibitory activity from 0 to near 100% to identify any synergistic action when *Septoria tritici* was treated with compounds added in combination. The DMSO solutions of the test compounds were added to the wells prior to addition of the fungal growth medium.

The fungal growth solid medium was prepared by forming an aqueous mixture containing dipotassium hydrogen phosphate (3.0 g/L), potassium dihydrogen phosphate (4.0 g/L), sodium chloride (0.5 g/L), ammonium chloride (1.0 g/L), magnesium sulfate heptahydrate (0.2 g) and calcium chloride dihydrate (0.01 g/L), also containing 1 mL/L of a trace element solution (manganese sulfate hydrate (0.1 mg/mL), zinc sulfate heptahydrate (0.2 mg/mL), copper(II) sulfate pentahydrate (0.2 mg/mL), iron(II) sulfate heptahydrate (0.2 mg/mL), sodium molybdate dihydrate (0.1 mg/mL), cobalt (II) sulfate heptahydrate (0.06 mg/mL), boric acid (0.08 mg/mL)), and supplemented with 50 µL/L of a biotin stock solution (0.1 mg/mL). The pH was adjusted to 6.8 with aqueous 1 M sodium carbonate solution. The mixture was further supplemented with 1 g/L of yeast extract, and GELRITE gellan gum (Kelco) (4 g/L) was added. Sufficient water was added to bring the volume to 90% of final volume (e.g., 900 mL volume for preparation of 1 L of fungal growth medium). The mixture was autoclaved. On cooling to 60° C., 100 mL/L of aqueous dextrose solution (10 g/L), 500 µL/L of aqueous ampicillin solution (100 mg/mL) and 500 µL of rifampicin solution (10 mg/mL in DMSO) were added to provide the final volume of fungal growth medium, which was then dispensed while still warm using a microliter pipette to the wells of the 96-well plates. The dispensed fungal growth medium in each well was agitated using the tip of the dispensing pipette to mix it with the DMSO solution containing the test compounds.

After the fungal growth medium in the wells had cooled to room temperature and solidified, the top surface of the growth medium in each well was inoculated with 20 µL of a suspension of fungus containing $8 \times 10^4$ cells. Following a 2 h period of drying in a sterile hood, plates were placed in a dark incubator at 25° C. for 5 d.

Fungal growth was assessed on a plate reader set to measure absorbance of 600 nm light. The percent growth inhibition observed (Obsd.) in Tests N1 and N2, as well as the percent growth inhibition expected (Exp.) from calculation using the Colby equation, are listed in Tables L and M, respectively.

TABLE L

Observed and Expected Effects of Compound 81 Alone and in Mixtures with Compound A1 as Component (b) for Control of *Septoria tritici*

| Application Rate of Compound 81 | Application Rate of Compound A1 | % inhibition | |
|---|---|---|---|
| (µM) | (µM) | Obsd. | Exp. |
| 0.2 | 0 | 98.0 | |
| 0.04 | 0 | 93.5 | |
| 0.008 | 0 | 10.0 | |
| 0.0016 | 0 | 5.0 | |
| 0.00032 | 0 | 9.0 | |
| 0 | 0 | 0 | |
| 0 | 0.2 | 98.0 | |
| 0 | 0.04 | 97 | |
| 0 | 0.008 | 14.5 | |
| 0 | 0.0016 | 5 | |
| 0 | 0.00032 | 3 | |
| 0 | 0 | 0 | 0 |
| 0.2 | 0.2 | 98 | 98 |
| 0.2 | 0.04 | 98 | 98 |
| 0.2 | 0.008 | 98 | 98 |
| 0.2 | 0.0016 | 98 | 98 |
| 0.2 | 0.00032 | 98 | 98 |
| 0.04 | 0.2 | 98 | 99.0 |
| 0.04 | 0.04 | 98 | 99.0 |
| 0.04 | 0.008 | 98 | 96.0 |
| 0.04 | 0.0016 | 94.2 | 94.0 |
| 0.04 | 0.00032 | 92 | 96.0 |
| 0.008 | 0.2 | 98.0 | 99.0 |
| 0.008 | 0.04 | 97.0 | 99.0 |
| 0.008 | 0.008 | 62.0 | 22.0 |
| 0.008 | 0.0016 | 6.0 | 14.0 |
| 0.008 | 0.00032 | 5.0 | 13.0 |
| 0.016 | 0.2 | 98.0 | 98.0 |
| 0.016 | 0.04 | 97.0 | 96.0 |
| 0.016 | 0.008 | 32.0 | 18.0 |
| 0.016 | 0.0016 | 5.0 | 10.0 |
| 0.016 | 0.00032 | 9.0 | 8.0 |
| 0.0032 | 0.2 | 98.0 | 97.0 |
| 0.0032 | 0.04 | 94.0 | 96.0 |
| 0.0032 | 0.008 | 8.0 | 22.0 |
| 0.0032 | 0.0016 | 8.0 | 14.0 |
| 0.0032 | 0.00032 | 6.0 | 12.0 |

TABLE M

Observed and Expected Effects of Compound 81 Alone and in Mixtures with Compound A2 as Component (b) for Control of *Septoria tritici*

| Application Rate of Compound 81 | Application Rate of Compound A2 | % inhibition | |
|---|---|---|---|
| (µM) | (µM) | Obsd. | Exp. |
| 0.2 | 0 | 96.0 | |
| 0.04 | 0 | 93.5 | |
| 0.008 | 0 | 29.0 | |
| 0.0016 | 0 | 0.0 | |
| 0.00032 | 0 | 0.0 | |
| 0 | 0 | 0 | |
| 0 | 20 | 96.0 | |
| 0 | 4 | 95.0 | |
| 0 | 0.8 | 11.5 | |
| 0 | 0.16 | 6.5 | |
| 0 | 0.032 | 0.0 | |
| 0 | 0 | 0 | |
| 0.2 | 20 | 96 | 100 |
| 0.2 | 4 | 96 | 100 |
| 0.2 | 0.8 | 96 | 96 |
| 0.2 | 0.16 | 96 | 96 |
| 0.2 | 0.032 | 96 | 96 |
| 0.04 | 20 | 96.0 | 100 |
| 0.04 | 4 | 96.0 | 100 |
| 0.04 | 0.8 | 96.0 | 94.2 |
| 0.04 | 0.16 | 95.5 | 93.9 |
| 0.04 | 0.032 | 95.0 | 93.5 |
| 0.008 | 20 | 96.0 | 97.2 |
| 0.008 | 4 | 96.0 | 96.5 |
| 0.008 | 0.8 | 68.0 | 37.2 |
| 0.008 | 0.16 | 0.0 | 33.6 |
| 0.008 | 0.032 | 0.0 | 29.0 |
| 0.016 | 20 | 96.0 | 96.0 |
| 0.016 | 4 | 96.0 | 95.0 |
| 0.016 | 0.8 | 46.5 | 11.5 |

TABLE M-continued

| Observed and Expected Effects of Compound 81 Alone and in Mixtures with Compound A2 as Component (b) for Control of *Septoria tritici* | | | |
|---|---|---|---|
| Application Rate of Compound 81 | Application Rate of Compound A2 | % inhibition | |
| (μM) | (μM) | Obsd. | Exp. |
| 0.016 | 0.16 | 6.5 | 6.5 |
| 0.016 | 0.032 | 0.0 | 0.0 |
| 0.0032 | 20 | 96.0 | 96.0 |
| 0.0032 | 4 | 95.0 | 95.0 |
| 0.0032 | 0.8 | 13.0 | 11.5 |
| 0.0032 | 0.16 | 24.5 | 6.5 |
| 0.0032 | 0.032 | 1.5 | 0.0 |

The observed and expected results from mixtures of Compound 81 with Compound A1 in Test N1 presented in Table L show greater than expected activity (i.e. synergy) at application rates wherein Compound 81 and Compound A1 separately provide much less than 100% inhibition (to allow expression of synergistic increase in inhibition) but also wherein the application rates are not greatly reduced from the application rates providing high inhibition by Compounds 81 and Compound A1 separately (e.g., application rates of 0.008 or 0.016 μM of Compound 81 and an application rate of 0.008 μM of Compound A1). Similarly, the observed and expected results from mixtures of Compound 81 with Compound A2 in Test N2 presented in Table M show greater than expected activity at application rates wherein Compound 81 and Compound A2 separately provide much less than 100% inhibition but also wherein the application rates are not greatly reduced from the application rates providing high inhibition by Compounds 81 and Compound A2 separately (e.g., application rates of 0.008 or 0.016 μM of Compound 81 and an application rate of 0.8 μM of Compound A2).

What is claimed is:

1. A fungicidal composition comprising:

(a) at least one compound selected from the compounds of Formula 1, *N*-oxides, and salts thereof:

1 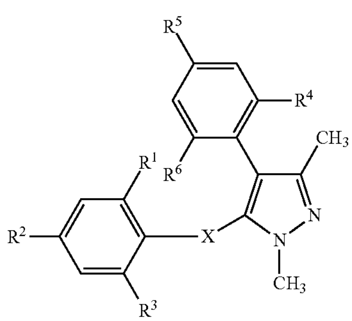 wherein

X is NH;

$R^1$ is halogen;

$R^2$ is H;

$R^3$ is halogen;

$R^4$ is halogen;

$R^5$ is H, cyano, halogen or $C_1$-$C_2$ alkoxy; and $R^6$ is H or halogen; and (b) at least one additional fungicidal compound;

provided that when $R^1$ is F, then $R^3$ is Cl, and when $R^1$ is Cl, then $R^3$ is F.

2. The composition of claim 1 wherein component (a) comprises a compound of Formula 1 or salt thereof, wherein in Formula 1, at most, only one of $R^5$ and $R^6$ is H.

3. The composition of claim 2 wherein in Formula 1, $R^1$ is F, Cl or Br;

$R^2$ is H;

$R^3$ is F or Cl;

$R^4$ is F, Cl or Br;

$R^5$ is H, cyano, F, Cl or methoxy; and $R^6$ is H or F.

4. The composition of claim 3 wherein in Formula 1, $R^3$ is F; and $R^5$ is cyano, F, Cl or methoxy.

5. The composition of claim 1 wherein component (a) comprises a compound selected from the group consisting of 4-(2-chloro-4-fluorophenyl)-N-(2-chloro-6-fluorophenyl)-1,3-dimethyl-1H-pyrazol-5-amine, 4-(2-bromo-4-fluorophenyl)-N-(2-chloro-6-fluorophenyl)-1,3-dimethyl-1H-pyrazol-5-amine, N-(2-bromo-6-fluorophenyl)-4-(2-chloro-4-fluorophenyl)-1,3-dimethyl-1H-pyrazol-5-amine, 4-(2-bromo-4-fluorophenyl)-N-(2-bromo-6-fluorophenyl)-1,3-dimethyl-1H-pyrazol-5-amine, N-(2-bromo-6-fluorophenyl)-4-(2,4-difluorophenyl)-1,3-dimethyl-1H-pyrazol-5-amine, N-(2-bromo-6-fluorophenyl)-4-(2,6-difluorophenyl)-1,3-dimethyl-1H-pyrazol-5-amine, N-(2-chloro-6-fluorophenyl)-4-(2-fluoro-4-methoxyphenyl)-1,3-dimethyl-1H-pyrazol-5-amine, N-(2-bromo-6-fluorophenyl)-4-(2-fluoro-4-methoxyphenyl)-1,3-dimethyl-1H-pyrazol-5-amine, N-(2-bromo-6-fluorophenyl)-4-(2-chloro-4-methoxyphenyl)-1,3-dimethyl-1H-pyrazol-5-amine, and N-(2-chloro-6-fluorophenyl)-4-(2,4-difluorophenyl)-1,3-dimethyl-1H-pyrazol-5-amine.

6. The composition of claim 1 wherein component (b) includes at least one fungicidal compound selected from the group consisting of:

(b1) methyl benzimidazole carbamate fungicides;

(b2) dicarboximide fungicides;

(b3) demethylation inhibitor fungicides;

(b4) phenylamide fungicides;

(b5) amine/morpholine fungicides;

(b6) phospholipid biosynthesis inhibitor fungicides;

(b7) carboxamide fungicides;

(b8) hydroxy(2-amino-)pyrimidine fungicides;

(b9) anilinopyrimidine fungicides;

(b10) N-phenyl carbamate fungicides;

(b11) quinone outside inhibitor fungicides;

(b12) phenylpyrrole fungicides;

(b13) quinoline fungicides;

(b14) lipid peroxidation inhibitor fungicides;

(b15) melanin biosynthesis inhibitors-reductase fungicides;

(b16) melanin biosynthesis inhibitors-dehydratase fungicides;

(b17) hydroxyanilide fungicides;

(b18) squalene-epoxidase inhibitor fungicides;

(b19) polyoxin fungicides;

(b20) phenylurea fungicides;

(b21) quinone inside inhibitor fungicides;

(b22) benzamide fungicides;

(b23) enopyranuronic acid antibiotic fungicides;

(b24) hexopyranosyl antibiotic fungicides;

(b25) glucopyranosyl antibiotic: protein synthesis fungicides;

(b26) glucopyranosyl antibiotic: trehalase and inositol biosynthesis fungicides;
(b27) cyanoacetamideoxime fungicides;
(b28) carbamate fungicides;
(b29) oxidative phosphorylation uncoupling fungicides;
(b30) organo tin fungicides;
(b31) carboxylic acid fungicides;
(b32) heteroaromatic fungicides;
(b33) phosphonate fungicides;
(b34) phthalamic acid fungicides;
(b35) benzotriazine fungicides;
(b36) benzene-sulfonamide fungicides;
(b37) pyridazinone fungicides;
(b38) thiophene-carboxamide fungicides;
(b39) pyrimidinamide fungicides;
(b40) carboxylic acid amide fungicides;
(b41) tetracycline antibiotic fungicides;
(b42) thiocarbamate fungicides;
(b43) benzamide fungicides;
(b44) host plant defense induction fungicides;
(b45) multi-site contact activity fungicides;
(b46) fungicidal compounds other than fungicidal compounds of component (a) and components (b1) through (b45); and salts of compounds of (b1) through (b46).

7. The composition of claim 6 wherein component (b) comprises at least one fungicidal compound from each of two different groups selected from (b1) through (b46).

8. The composition of claim 1 wherein component (b) includes at least one compound selected from acibenzolar-S-methyl, aldimorph, ametoctradin, amisulbrom, anilazine, azaconazole, azoxystrobin, benalaxyl, benalaxyl-M, benodanil, benomyl, benthiavalicarb, benthiavalicarb-isopropyl, bethoxazin, binapacryl, biphenyl, bitertanol, bixafen, blasticidin-S, boscalid, bromuconazole, bupirimate, carboxin, carpropamid, captafol, captan, carbendazim, chloroneb, chlorothalonil, chlozolinate, clotrimazole, copper salts, cyazofamid, cyflufenamid, cymoxanil, cyproconazole, cyprodinil, dichlofluanid, diclocymet, diclomezine, dicloran, diethofencarb, difenoconazole, diflumetorim, dimethirimol, dimethomorph, dimoxystrobin, diniconazole, diniconazole-M, dinocap, dithianon, dodemorph, dodine, edifenphos, enestroburin, epoxiconazole, ethaboxam, ethirimol, etridiazole, famoxadone, fenamidone, fenarimol, fenbuconazole, fenfuram, fenhexamid, fenoxanil, fenpiclonil, fenpropidin, fenpropimorph, fenpyrazamine, fentin acetate, fentin chloride, fentin hydroxide, ferbam, ferimzone, fluazinam, fludioxonil, flumetover, flumorph, fluopicolide, fluopyram, fluoroimide, fluoxastrobin, fluquinconazole, flusilazole, flusulfamide, flutianil, flutolanil, flutriafol, fluxapyroxad, folpet, fosetyl-aluminum, fuberidazole, furalaxyl, furametpyr, hexaconazole, hymexazol, guazatine, imazalil, imibenconazole, iminoctadine, iodocarb, ipconazole, iprobenfos, iprodione, iprovalicarb, isoprothiolane, isopyrazam, isotianil, kasugamycin, kresoxim-methyl, mancozeb, mandipropamid, maneb, mepronil, meptyldinocap, metalaxyl, metalaxyl-M, metconazole, methasulfocarb, metiram, metominostrobin, mepanipyrim, metrafenone, myclobutanil, naftifine, neoasozin (ferric methanearsonate), nuarimol, octhilinone, ofurace, orysastrobin, oxadixyl, oxolinic acid, oxpoconazole, oxycarboxin, oxytetracycline, penconazole, pencycuron, penflufen, penthiopyrad, pefurazoate, phosphorous acid and salts thereof, phthalide, picoxystrobin, piperalin, polyoxin, probenazole, prochloraz, procymidone, propamocarb, propamocarb-hydrochloride, propiconazole, propineb, proquinazid, prothiocarb, prothioconazole, pyraclostrobin, pyrametostrobin, pyraoxystrobin, pyrazophos, pyribencarb, pyributicarb, pyrifenox, pyrimethanil, pyriofenone, pyroquilon, pyrrolnitrin, quinomethionate, quinoxyfen, quintozene, sedaxane, silthiofam, simeconazole, spiroxamine, streptomycin, sulfur, tebuconazole, tebufloquin, tecloftalam, tecnazene, terbinafine, tetraconazole, thiabendazole, thifluzamide, thiophanate, thiophanate-methyl, thiram, tiadinil, tolclofos-methyl, tolylfluanid, triadimefon, triadimenol, triazoxide, tricyclazole, tridemorph, triflumizole, tricyclazole, trifloxystrobin, triforine, trimorphamide, triticonazole, uniconazole, validamycin, valifenalate, vinclozolin, zineb, ziram, zoxamide, N'-[4-[4-chloro-3-(trifluoro-methyl)phenoxy]-2,5-dimethylphenyl]-N-ethyl-N-methylmethanimidamide, 5-chloro-6-(2,4,6-trifluorophenyl)-7-(4-methylpiperidin-1-yl)[1,2,4]triazolo[1,5-a]pyrimidine, N-[2-[4-[[3-(4-chlorophenyl)-2-propyn-1-yl]oxy]-3-methoxyphenyl]ethyl]-3-methyl-2-[(methylsulfonyl)amino]butanamide, N-[2-[4-[[3-(4-chlorophenyl)-2-propyn-1-yl]oxy]-3-methoxyphenyl]ethyl]-3-methyl-2-[(ethylsulfonyl)amino]butanamide, 2-butoxy-6-iodo-3-propyl-4H-1-benzopyran-4-one, 3-[5-(4-chlorophenyl)-2,3-dimethyl-3-isoxazolidinyl]-pyridine, 4-fluorophenyl N-[1-[[[1-(4-cyanophenyl)ethyl]sulfonyl]methyl]propyl]carbamate, N-[[(cyclopropylmethoxy)amino][6-(difluoromethoxy)-2,3-difluorophenyl]methylene]benzeneacetamide, α-(methoxyimino)-N-methyl-2-[[[1-[3-(trifluoro-methyl)phenyl]ethoxy]imino]methyl]benzeneacetamide, N-[4-[4-chloro-3-(trifluoro-methyl)phenoxy]-2,5-dimethylphenyl]-N-ethyl-N-methylmethanimidamide, N-(4-chloro-2-nitrophenyl)-N-ethyl-4-methylbenzenesulfonamide, 2-[[[[3-(2,6-dichlorophenyl)-1-methyl-2-propen-1-ylidene]amino]oxy]methyl]-α-(methoxyimino)-N-methylbenzeneacetamide, 1-[(2-propenylthio)carbonyl]-2-(1-methylethyl)-4-(2-methylphenyl)-5-amino-1H-pyrazol-3-one, 5-ethyl-6-octyl-[1,2,4]triazolo[1,5-a]pyrimidin-7-ylamine, pentyl N-[4-[[[[(1-methyl-1H-tetrazol-5-yl)phenylmethylene]amino]oxy]methyl]-2-thiazolyl]carbamate and pentyl N-[6-[[[[(1-methyl-1H-tetrazol-5-yl)phenylmethylene]amino]oxy]methyl]-2-pyridinyl]carbamate.

9. The composition of claim 1 wherein component (b) includes at least one fungicidal compound selected from compounds of Formula A1 and salts thereof

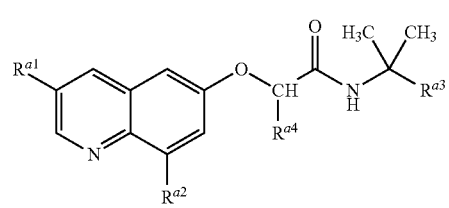

wherein
$R^{a1}$ is halogen, $C_1$-$C_4$ alkoxy or $C_1$-$C_4$ alkynyl;
$R^{a2}$ is H, halogen or $C_1$-$C_4$ alkyl;
$R^{a3}$ is $C_1$-$C_{12}$ alkyl, $C_1$-$C_{12}$ haloalkyl, $C_1$-$C_{12}$ alkoxy, $C_2$-$C_{12}$ alkoxyalkyl, $C_2$-$C_{12}$ alkenyl, $C_2$-$C_{12}$ alkynyl, $C_4$-$C_{12}$ alkoxyalkenyl, $C_4$-$C_{12}$ alkoxyalkynyl, $C_1$-$C_{12}$ alkylthio or $C_2$-$C_{12}$ alkylthioalkyl;
$R^{a4}$ is methyl or $Y^{a1}$—$R^{a5}$;
$R^{a5}$ is $C_1$-$C_2$ alkyl; and
$Y^{a1}$ is $CH_2$, O or S.

10. A composition comprising: (a) at least one compound selected from the compounds of Formula 1 as defined in claim 1, N-oxides, and salts thereof; and at least one invertebrate pest control compound or agent.

11. A composition comprising the composition of claim 1 and at least one additional component selected from the group consisting of surfactants, solid diluents and liquid diluents.

12. A method for protecting a plant or plant seed from diseases caused by fungal pathogens comprising applying a fungicidally effective amount of the composition of claim 1 to the plant or plant seed.

13. A method for protecting a plant from a powdery mildew disease comprising applying to the plant a fungicidally effective amount of the composition of claim 1 wherein component (b) includes at least one fungicidal compound selected from (b11) quinone outside inhibitor fungicides.

14. A method for protecting a plant from a *Septoria* disease comprising applying to the plant a fungicidally effective amount of the composition of claim 9.

15. A compound of Formula 1 or an N-oxide or salt thereof,

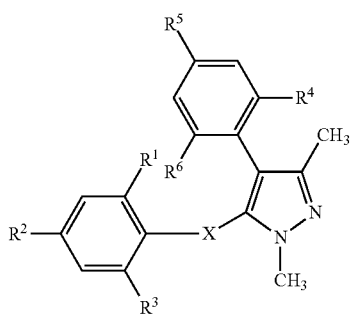

1 wherein
X is NH;
R$^1$ is halogen;
R$^2$ is H;
R$^3$ is halogen;
R$^4$ is halogen;
R$^5$ is H, cyano, halogen or C$_1$-C$_2$ alkoxy; and
R$^6$ is H or halogen;
provided that when R$^1$ is F, then R$^3$ is Cl, and when R$^1$ is Cl, then R$^3$ is F.

16. A compound of claim 15 wherein
R$^3$ is F or Cl.

17. A compound of claim 16 wherein
R$^1$ is Cl or Br; and
R$^3$ is F.

18. A compound of claim 15 selected from the group consisting of
4-(2-chloro-4-fluorophenyl)-N-(2-chloro-6-fluorophenyl)-1,3-dimethyl-1H-pyrazol-5-amine,
4-(2-bromo-4-fluorophenyl)-N-(2-chloro-6-fluorophenyl)-1,3-dimethyl-1H-pyrazol-5-amine, and
N-(2-bromo-6-fluorophenyl)-4-(2-chloro-4-fluorophenyl)-1,3-dimethyl-1H-pyrazol-5-amine.

19. A fungicidal composition comprising: (1) a compound of claim 15; and (2) at least one additional component selected from the group consisting of surfactants, solid diluents and liquid diluents.

20. A method for protecting a plant or plant seed from diseases caused by fungal pathogens comprising applying a fungicidally effective amount of the compound of claim 15 to the plant or plant seed.

21. The composition of claim 1 wherein component (a) is 4-(2-bromo-4-fluorophenyl)-N-(2-chloro-6-fluorophenyl)-1,3-dimethyl-1H-pyrazol-5-amine.

22. A compound of claim 15 which is 4-(2-bromo-4-fluorophenyl)-N-(2-chloro-6-fluorophenyl)-1,3-dimethyl-1H-pyrazol-5-amine.

23. The composition of claim 1 wherein component (a) is 4-(2-bromo-4-fluorophenyl)-N-(2-chloro-6-fluorophenyl)-1,3-dimethyl-1H-pyrazol-5-amine; and component (b) includes at least one compound selected from azoxystrobin, kresoxim-methyl, trifloxystrobin, pyraclostrobin, pyraoxystrobin, pyrametostrobin, picoxystrobin, dimoxystrobin, metominostrobin/ifenominostrobin, carbendazim, chlorothalonil, quinoxyfen, metrafenone, pyriofenone, cyflufenamid, fenpropidin, fenpropimorph, bromuconazole, cyproconazole, difenoconazole, epoxiconazole, fenbuconazole, flusilazole, hexaconazole, ipconazole, metconazole, myclobutanil, penconazole, propiconazole, proquinazid, prothioconazole, tebuconazole, triticonazole, famoxadone, prochloraz, penthiopyrad and boscalid (nicobifen).

24. The composition of claim 1 wherein component (a) is 4-(2-bromo-4-fluorophenyl)-N-(2-chloro-6-fluorophenyl)-1,3-dimethyl-1H-pyrazol-5-amine; and (b) includes at least one compound selected from chlorothalonil, metconazole, prothioconazole and penthiopyrad.

25. The composition of claim 1 wherein component (a) is 4-(2-chloro-4-fluorophenyl)-N-(2-chloro-6-fluorophenyl)-1,3-dimethyl-1H-pyrazol-5-amine.

26. A compound of claim 15 which is 4-(2-chloro-4-fluorophenyl)-N-(2-chloro-6-fluorophenyl)-1,3-dimethyl-1H-pyrazol-5-amine.

* * * * *